(12) United States Patent
Bollu et al.

(10) Patent No.: US 9,040,692 B2
(45) Date of Patent: *May 26, 2015

(54) SUBSTITUTED PYRIDINE AND PYRAZINE COMPOUNDS AS PDE4 INHIBITORS

(71) Applicant: DART NEUROSCIENCE (Cayman), LTD., San Diego, CA (US)

(72) Inventors: Venkataiah Bollu, San Diego, CA (US); James Breitenbucher, Escondido, CA (US); Alan Kaplan, San Diego, CA (US); Robert Lemus, Escondido, CA (US); Andrew Lindstrom, San Diego, CA (US); Troy Vickers, San Diego, CA (US); Mark E. Wilson, Ramona, CA (US); James Zapf, San Diego, CA (US)

(73) Assignee: Dart NeuroScience (Cayman) Ltd. (KY)

( * ) Notice: Subject to any disclaimer, the term of this patent is extended or adjusted under 35 U.S.C. 154(b) by 0 days.

This patent is subject to a terminal disclaimer.

(21) Appl. No.: 14/205,033

(22) Filed: Mar. 11, 2014

(65) Prior Publication Data

US 2014/0275531 A1    Sep. 18, 2014

Related U.S. Application Data

(60) Provisional application No. 61/786,288, filed on Mar. 14, 2013.

(51) Int. Cl.
| | |
|---|---|
| C07D 401/06 | (2006.01) |
| C07D 405/14 | (2006.01) |
| C07D 413/06 | (2006.01) |
| C07D 417/06 | (2006.01) |
| C07D 409/06 | (2006.01) |
| C07D 213/64 | (2006.01) |
| C07D 241/18 | (2006.01) |
| C07D 401/14 | (2006.01) |
| C07D 403/06 | (2006.01) |
| C07D 405/12 | (2006.01) |

(52) U.S. Cl.
CPC ............ *C07D 409/06* (2013.01); *C07D 401/06* (2013.01); *C07D 405/14* (2013.01); *C07D 413/06* (2013.01); *C07D 417/06* (2013.01); *C07D 213/64* (2013.01); *C07D 241/18* (2013.01); *C07D 401/14* (2013.01); *C07D 403/06* (2013.01); *C07D 405/12* (2013.01)

(58) Field of Classification Search
None
See application file for complete search history.

(56) References Cited

U.S. PATENT DOCUMENTS

| | | | |
|---|---|---|---|
| 4,938,949 A | 7/1990 | Borch et al. | |
| 7,087,625 B2 | 8/2006 | Schumacher et al. | |
| 7,399,761 B2 | 7/2008 | Bold et al. | |
| 7,468,370 B2 | 12/2008 | Denholm et al. | |
| 7,511,045 B2 | 3/2009 | Hoenke et al. | |
| 7,674,788 B2 | 3/2010 | Dollinger et al. | |
| 7,829,713 B2 | 11/2010 | Keenan et al. | |
| 7,868,015 B2 | 1/2011 | Tully et al. | |
| 7,947,731 B2 | 5/2011 | Tully et al. | |
| 8,338,405 B2 | 12/2012 | Keenan et al. | |
| 2005/0020587 A1 | 1/2005 | Bailey et al. | |
| 2008/0188525 A1 | 8/2008 | Hallam et al. | |
| 2009/0053140 A1 | 2/2009 | Scott et al. | |
| 2009/0130076 A1 | 5/2009 | Singh et al. | |
| 2009/0131530 A1 | 5/2009 | Singh et al. | |

FOREIGN PATENT DOCUMENTS

| | | |
|---|---|---|
| EP | 1 443 925 B1 | 8/2004 |
| EP | 1 874 781 B1 | 1/2008 |
| JP | 4321737 B2 | 8/2009 |

(Continued)

OTHER PUBLICATIONS

International Search Report and Written Opinion mailed Aug. 29, 2014 for International Patent Application No. PCT/US2014/021426 filed Mar. 6, 2014.

(Continued)

*Primary Examiner* — Timothy R Rozof
(74) *Attorney, Agent, or Firm* — Knobbe Martens Olson & Bear LLP

(57) ABSTRACT

The invention provides a chemical entity of Formula (I)

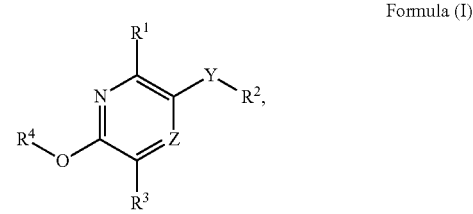

Formula (I)

wherein $R^1$, $R^2$, $R^3$, $R^4$, Y and Z have any of the values described herein, and compositions comprising such chemical entities; methods of making them; and their use in a wide range of methods, including metabolic and reaction kinetic studies, detection and imaging techniques, and radioactive treatments; and therapies, including inhibiting PDE4, enhancing neuronal plasticity, treating neurological disorders, providing neuroprotection, treating a cognitive impairment associated with a CNS disorder, enhancing the efficiency of cognitive and motor training, providing neurorecovery and neurorehabilitation, enhancing the efficiency of non-human animal training protocols, and treating peripheral disorders, including inflammatory and renal disorders.

1 Claim, No Drawings

(56) References Cited

FOREIGN PATENT DOCUMENTS

| | | |
|---|---|---|
| KR | 10-2006-0001207 A | 1/2006 |
| WO | WO 99/31062 A1 | 6/1999 |
| WO | WO 03/039544 A1 | 5/2003 |
| WO | WO 03/050098 A1 | 6/2003 |
| WO | WO 2006/053784 A2 | 5/2006 |
| WO | WO 2007/123953 A2 | 11/2007 |
| WO | WO 2008/040651 A1 | 4/2008 |
| WO | WO 2009/067600 A2 | 5/2009 |
| WO | WO 2009/067621 A1 | 5/2009 |
| WO | WO 2010/003084 A2 | 1/2010 |
| WO | WO 2010/056195 A1 | 5/2010 |
| WO | WO 2010/059836 A1 | 5/2010 |

OTHER PUBLICATIONS

Database Registry Chemical Abstracts Service, Columbus Ohio, Accession No. RN 228096-03-5, Entered STN: Jul. 17, 1999.

Database Registry Chemical Abstracts Service, Columbus Ohio, Accession No. RN 228096-04-6, Entered STN: Jul. 17, 1999.

Database Registry Chemical Abstracts Service, Columbus Ohio, Accession No. RN 544475-12-9, Entered STN: Jul. 8, 2003.

Database Registry Chemical Abstracts Service, Columbus Ohio, Accession No. RN 544475-13-0, Entered STN: Jul. 8, 2003.

Database Registry Chemical Abstracts Service, Columbus Ohio, Accession No. RN 1106203-16-0, Entered STN: Feb. 15, 2009.

Database Registry Chemical Abstracts Service, Columbus Ohio, Accession No. RN 1106203-18-2, Entered STN: Feb. 15, 2009.

SUBSTITUTED PYRIDINE AND PYRAZINE COMPOUNDS AS PDE4 INHIBITORS

INCORPORATION BY REFERENCE TO ANY PRIORITY APPLICATIONS

Any and all priority claims identified in the Application Data Sheet, or any correction thereto, are hereby incorporated by reference under 37 CFR 1.57. For example, this application claims the benefit under 35 U.S.C. §119(e) to U.S. Provisional Application No. 61/786,288, filed on Mar. 14, 2013, which is incorporated herein by reference in its entirety.

BACKGROUND

1. Field

The present invention relates to certain substituted pyridine and pyrazine compounds and derivatives of such compounds; pharmaceutical compositions containing them methods of making them; and their use in various methods, including the inhibition of PDE4 enzymes; detection and imaging techniques; enhancing neuronal plasticity; treating neurological disorders, including psychiatric, neurodegenerative, cerebrovascular, and cognitive disorders; providing neuroprotection; enhancing the efficiency of cognitive and motor training; facilitating neurorecovery and neurorehabilitation; and treating peripheral disorders, including inflammatory and renal disorders.

2. Description of the Related Technology

The mammalian phosphodiesterases (PDEs) are a group of closely related enzymes divided into 11 families (PDE1-11) based on substrate specificity, inhibitor sensitivity and more recently, on sequence homology. The 11 families are coded by 21 genes, providing several of the families with multiple members. All mammalian PDEs share a conserved catalytic domain located in the COOH-terminal portion of the protein. In GAF-containing PDEs, one or both GAFs can provide dimerization contacts. In addition, one of the GAFs in each of these proteins provides for allosteric cGMP binding (PDE2, PDE5, PDE6, PDE11), allosteric cAMP binding (PDE10), and regulation of catalytic site functions (PDE2, PDE5, PDE6). The other families of PDEs have unique complements of various subdomains (UCR, NHR, PAS, membrane association) that contribute to regulation of activity. PDEs 1, 2, 3, and 4 are expressed in many tissues, whereas others are more restricted. In most cells, PDE3 and PDE4 provide the major portion of cAMP-hydrolyzing activity (Francis, *Physiological Reviews*, 2011, 91, 651-690).

The PDE4 family includes four isoforms (PDE4A, B, C and D) with more than 20 splice variants, making it one of the largest PDE subfamilies (Bender and Beavo, *Pharmacol. Rev.*, 2006, 58 (3), 488-520). PDE4 enzymes hydrolyze cAMP with a substrate apparent Km of 1-5 uM for cAMP. The PDE4 enzyme is reported to be regulated by two upstream conserved region (UCR) domains. Depending on differential RNA splicing, PDE4 variants can be distinguished into two major subgroups: long and short forms (Conti et al., *J Biol Chem.*, 2003, 278, 5493-5496). Nine splice variants have been reported. PDE4D1, 4D2 and 4D6 all are shorter forms lacking UCRs. PDE4D3, 4D4, 4D5, 4D7, 4D8 and 4D9 are longer forms that contain both UCRs and N terminal domains important for their subcellular localization (Bender and Beavo, 2006). Long form PDE4D3 activity is increased by PKA phosphorylation via Ser54 in the N-terminal UCR1 (Alvarez et al., *Mol Pharmacol.*, 1995, 48, 616-622; Sette et al., *J Biol Chem.*, 1996, 271, 16526-16534). Conversely, Erk2 phosphorylation of Ser597 in the C-terminus of PDE4D3 causes a reduction in catalytic activity. One or several PDE4D isoforms are expressed throughout most tissues tested, including cortex, hippocampus, cerebellum, heart, liver, kidney, lung and testis (Richter et al., *Biochem. J.*, 2005, 388, 803-811). The localization and regulation of PDE4D isoforms is thought to allow for tight and local regulation of cAMP levels, possibly limiting signal propagation in specific subcellular compartments.

Numerous studies have highlighted a role for PDEs generally, and PDE4 in particular, in modulating intracellular signaling pathways that regulate many physiological processes, including those underling neural plasticity, cognition, and memory. In particular, PDEs play an important role in intracellular signal transduction pathways involving the second messengers. cAMP and cGMP. These cyclic nucleotides function as ubiquitous intracellular signaling molecules in all mammalian cells. PDE enzymes hydrolyze cAMP and cGMP by breaking phosphodiester bonds to form the corresponding monophosphates (Bender and Beavo, *Pharmacol. Rev.*, 2006, 58 (3), 488-520). PDE activities are modulated in coordination with adenylyl cyclase (AC) and guanylyl cyclase (GC) activities through direct effectors and feedback pathways, thereby maintaining cAMP and cGMP levels within optimum ranges for responsiveness to signals. The ability of extracellular signals to modulate the intracellular concentration of cyclic nucleotides allows cells to respond to external stimuli across the boundary of the cell membrane.

The cyclic nucleotide signaling cascades have been adapted to respond to a host of transduction systems including G-protein coupled receptors (GPCRs) and voltage and ligand gated ion channels. Cyclic nucleotides transmit their signal in the cell through a variant of tertiary elements. The best described of these are cAMP dependent protein kinase (PKA) and cGMP dependent protein kinase (PKG). The binding of the cyclic nucleotide to each enzyme enables the phosphorylation of downstream enzymes and proteins functioning as effectors or additional elements in the signaling cascade. Of particular importance to memory formation is cAMP activation of PKA, which phosphorylates cAMP response element-binding protein (CREB). pCREB is an activated transcription factor, which binds to specific DNA loci and initiates transcription of multiple genes involved in neuronal plasticity. Both in vitro and in vivo studies have associated alterations in cyclic nucleotide concentrations with biochemical and physiological process linked to cognitive function (Kelly and Brandon, *Progress in Brain Research*, 2009, 179, 67-73; Schmidt, *Current Topics in Medicinal Chemistry*, 2010, 10, 222-230). Signal intensity and the levels of coincident activity at a synapse are established variables that can result in potentiation of transmission at a particular synapse. Long term potentiation (LTP) is the best described of these processes and is known to be modulated by both the cAMP and cGMP signaling cascades.

Focus on the role of PDE4 in memory stems from the discovery of the PDE4-like *Drosophila* learning mutant dunce (dnc gene), a cyclic nucleotide phosphodiesterase of the PDE4 subtype (Yun and Davis, *Nucleic Acids Research*, 1989, 17(20), 8313-8326). The dnc mutant flies are defective in acquisition and/or short-term memory when tested in several different olfactory associative learning situations, with negative (Dudai et al., *Proc Natl Acad Sci.*, 1976, 73(5), 1684-1688; Dudai Y., *Proc Natl Acad Sci.*, 1983, 80(17), 5445-5448; Tully and Quinn, *Journal of Comparative Physiology*, 1985, 157(2), 263-77) or positive reinforcement (Tempel et al., *Proc Natl Acad Sci.*, 1983, 80(5), 1482-1486). In mammals, PDE4D knockout animals display decreased immobility in the antidepressant tail-suspension and forced swim test models (Zhang et al., *Neuropsychopharmacology*, 2002, 27(4), 587-595), enhanced in vitro LTP in hippocampal CA1 slices (Rutten et al., *Eur. J. Neurosci.*, 2008, 28(3), 625-632), and enhanced memory in radial maze, object recognition, and Morris water maze tasks (Li et al., *J. Neurosci.*, 2011, 31, 172-183).

Such observations highlight the interest in PDE-inhibition, including PDE4-inhibition, as a therapeutic target for numerous disorders and in cognitive enhancement. For example, by increasing cAMP levels, such inhibitors may be useful in treating cognitive deterioration in neurodegenerative disorders such Parkinson's Disease and Alzheimer's Disease, as well as generally improving cognition in normal, diseased, and aging subjects. Various small-molecule PDE4 enzyme inhibitors have been reported e.g., Aza-bridged bicycles (DeCODE Genetics; Intl. Pat. Appl. Publ. WO 2010/059836, May 27, 2010); N-substituted anilines (Memory Pharmaceuticals Corporation; Intl. Pat. Appl. Publ. WO 2010/003084, Jan. 7, 2010); Biaryls (DeCODE Genetics; Intl. Pat. Appl. Publ. WO 2009/067600, May 28, 2009, WO 2009/067621, May 28, 2009); Benzothiazoles and benzoxazoles (DeCODE Genetics; U.S. Pat. Appl. Publ. US 2009/0130076, May 21, 2009); Catechols (DeCODE Genetics; U.S. Pat. Appl. Publ. US 2009/0131530, May 21, 2009), Pteridines (Boehringer Ingelheim International G.m.b.H.; U.S. Pat. No. 7,674,788, Nov. 29, 2007); Heteroaryl pyrazoles (Memory Pharmaceuticals Corporation; Intl. Pat. Appl. Publ. WO 2007/123953, Nov. 1, 2007); Naphthyridines (Glaxo Group Limited; Intl. Pat. Appl. Publ. WO 2006/053784, May 26, 2006); Piperazinyldihydrothienopyrimidines (Boehringer Ingelheim International G.m.b.H.; EP Pat. 1,874,781, Jun. 24, 2009); Nicotinamide derivatives (Pfizer; U.S. Pat. Appl. Publ. US 2005/0020587, Jan. 27, 2005); Heteroarylmethyl phenyl amines (Memory Pharmaceuticals Corporation; U.S. Pat. No. 7,087,625, Aug. 8, 2006); Naphthyridines (Novartis AG; EP Pat. 1,443,925, Dec. 26, 2007; U.S. Pat. No. 7,468,370, Dec. 23, 2008).

However, PDE4 inhibitors have generally been associated with numerous side effects—most notably emesis—that have typically limited their usefulness and tolerability (e.g., Giembycz, *Curr. Opin. Pharm.* 2005, 5, 238-244). It is therefore desirable to develop improved PDE4 inhibitors showing higher potency, greater specificity, and better side effect profiles. The present invention meets these and other needs in the art by disclosing substituted pyridine and pyrazine compounds as potent and well-tolerated PDE4 inhibitors.

SUMMARY

The invention provides a chemical entity of Formula (I):

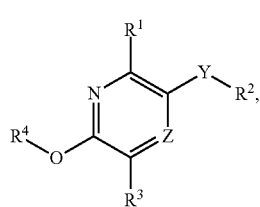

Formula (I)

wherein $R^1$, $R^2$, $R^3$, $R^4$, Y and Z have any of the values described herein.

In one aspect the chemical entity is selected from the group consisting of compounds of Formula (I), pharmaceutically acceptable salts of compounds of Formula (I), pharmaceutically acceptable prodrugs of compounds of Formula (I), and pharmaceutically acceptable metabolites of compounds of Formula (I).

Chemical entities of compounds of Formula (I) are useful in wide range of methods. Isotopically-labeled compounds and prodrugs can be used in metabolic and reaction kinetic studies, detection and imaging techniques, and radioactive treatments. The chemical embodiments of the present invention can be used to inhibit PDE4, in particular; to treat a disorder mediated by PDE4, in particular; to enhance neuronal plasticity; to treat neurological disorders, including neurodegenerative disorders, cognitive disorders, and cognitive deficits associated with CNS disorders; to confer neuroprotection; and to treat peripheral disorders, including inflammatory and renal disorders. The chemical embodiments of the present invention are also useful as augmenting agents to enhance the efficiency of cognitive and motor training, to facilitate neurorecovery and neurorehabilitation, and to increase the efficiency of non-human animal training protocols. The invention is further directed to the general and specific embodiments defined, respectively, by the independent and dependent claims appended hereto, which are incorporated by reference herein.

DETAILED DESCRIPTION

The invention may be more fully appreciated by reference to the following description, including the examples. Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described herein. In addition, the materials, methods, and examples are illustrative only and not intended to be limiting.

For the sake of brevity, all publications, including patent applications, patents, and other citations mentioned herein, are incorporated by reference in their entirety. Citation of any such publication, however, shall not be construed as an admission that it is prior art to the present invention.

ABBREVIATIONS

The specification includes numerous abbreviations, whose meanings are listed in the following Table:

| Abbreviation | Meaning |
| --- | --- |
| ACN | Acetonitrile |
| AcOH | Acetic Acid |
| AIBN | 2,2'-Azobis(2-methylpropionitrile) |
| BOC | tert-Butyl dicarbonate |
| n-BuLi | n-Butyl lithium |
| DCM | Dichloromethane |
| Deoxo-Fluor ® | Bis(2-methoxyethyl)aminosulfur trifluoride |
| Dess-Martin Reagent ® | 1,1,1-Tris(acetyloxy)-1,1-dihydro-1,2-benziodoxol-3(1H)-one |
| DIPEA, Hünig's base | N,N-Ethyl-diisopropylamine or N,N-Diisopropyl-ethyl amine |
| DMA | N, N-Dimethylacetamide |
| DMF | N,N-Dimethylformamide |
| DMSO | Dimethylsulfoxide |
| dppf | 1,1'-Bis(diphenylphosphino)ferrocene |
| EtOAc, or EA | Ethyl Acetate |
| EtOH | Ethanol |
| HOAc or AcOH | Acetic Acid |
| HPLC | High-performance liquid chromatography |
| LAH | Lithium aluminum hydride |
| LCMS, LC/MS | Liquid chromatography-mass spectrometry |
| MeOH | Methanol |
| NBS | n-Bromosuccinimide, |
| $PdCl_2$(dppf)-DCM adduct | [1'1'-Bis(diphenylphosphino)ferrocene]palladium(ll) dichloride dichloromethane adduct |
| $Pd(PPh_3)_4$ | Tetrakis[triphenylphosphine]palladium(0) |
| TBAF | Tetrabutylammonium flouride |
| TEA, $Et_3N$ | Triethylamine |
| TFA | Trifluoroacetic acid |
| THF | Tetrahydrofuran |
| TLC | Thin layer chromatography |
| XtalFluor ® | (Diethylamino)difluorosulfonium tetrafluoroborate |

TERMS AND DEFINITIONS

The use of subheadings such as "General," "Chemistry," "Compositions," "Formulations," etc., in this section, as well as in other sections of this application, are solely for convenience of reference and not intended to be limiting.
General As used herein, the term "about" or "approximately" means within an acceptable range for a particular value as determined by one skilled in the art, and may depend in part on how the value is measured or determined, e.g., the limitations of the measurement system or technique. For example, "about" can mean a range of up to 20%, up to 10%, up to 5%, or up to 1% or less on either side of a given value. Alternatively, with respect to biological systems or processes, the term "about" can mean within an order of magnitude, within 5 fold, or within 2 fold on either side of a value. Numerical quantities given herein are approximate unless stated otherwise, meaning that the term "about" or "approximately" can be inferred when not expressly stated To provide a more concise description, some of the quantitative expressions given herein are not qualified with the term "about". It is understood that, whether the term "about" is used explicitly or not, every quantity given herein is meant to refer to the actual given value, and it is also meant to refer to the approximation of such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity for which that could be obtained under the particular stoichiometric conditions. Concentrations that are given as percentages refer to mass ratios, unless indicated differently.

As used herein, the terms "a," "an," and "the" are to be understood as meaning both singular and plural, unless explicitly stated otherwise. Thus, "a," "an," and "the" (and grammatical variations thereof where appropriate) refer to one or more.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The terms "comprising" and "including" are used herein in their open, non-limiting sense. Other terms and phrases used in this document, and variations thereof, unless otherwise expressly stated, should be construed as open ended as opposed to limiting. As examples of the foregoing: the term "example" is used to provide exemplary instances of the item in discussion, not an exhaustive or limiting list thereof; adjectives such as "conventional," "traditional," "normal," "criterion," "known," and terms of similar meaning should not be construed as limiting the item described to a given time period or to an item available as of a given time, but instead should be read to encompass conventional, traditional, normal, or criterion technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. As will become apparent to one of ordinary skill in the art after reading this document, the illustrated embodiments and their various alternatives may be implemented without confinement to the illustrated examples.

Chemistry

The term "alkyl" refers to a fully saturated aliphatic hydrocarbon group. The alkyl moiety may be a straight- or branched-chain alkyl group having from 1 to 12 carbon atoms in the chain. Examples of alkyl groups include, but are not limited to, methyl (Me, which also may be structurally depicted by the symbol, "▬"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "haloalkyl" refers to the alkyl moiety, which may be a straight- or branched-chain alkyl group having from 1 to 12 carbon atoms in the chain substituted with a halo group. Examples of haloalkyl groups include, but are not limited to, —$CF_3$, —$CHF_2$, —$CH_2F$, —$CH_2CF_3$, —$CH_2CHF_2$, —$CH_2CH_2F$, —$CH_2CH_2Cl$, or —$CH_2CF_2CF_3$.

The term "cyano" refers to the group —CN.

The term "cycloalkyl" refers to a saturated or partially saturated carbocycle, such as monocyclic, fused polycyclic, bridged monocyclic, bridged polycyclic, spirocyclic, or spiro polycyclic carbocycle having from 3 to 12 ring atoms per carbocycle. Where the term cycloalkyl is qualified by a specific characterization, such as monocyclic, fused polycyclic, bridged polycyclic, spirocyclic, and spiro polycyclic, then such term cycloalkyl refers only to the carbocycle so characterized. Illustrative examples of cycloalkyl groups include the following entities, in the form of properly bonded moieties:

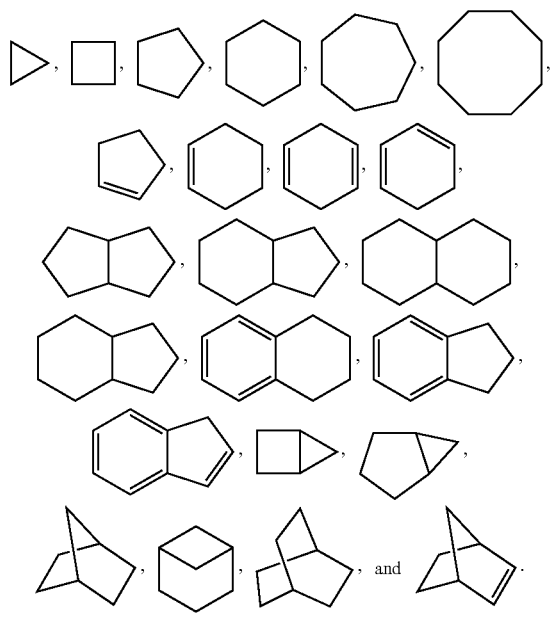

Those skilled in the art will recognize that the species of cycloalkyl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "heteroatom" used herein refers to, for example, O (oxygen), S (sulfur) and N (nitrogen).

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

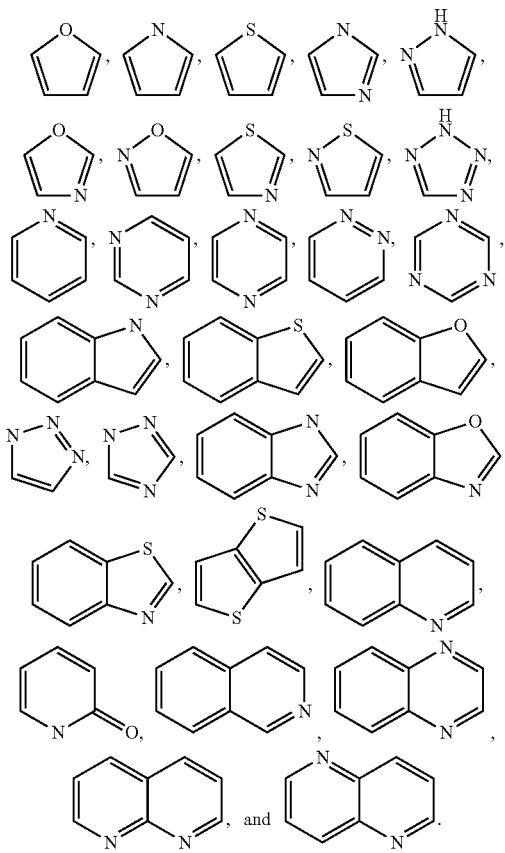

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Formulas

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

The symbols ▬ and ▬ are used as meaning the same spacial arrangement in chemical structures shown herein. Analogously, the symbols ⦀⦀⦀ and ⦀⦀⦀ are used as meaning the same spacial arrangement in chemical structures shown herein.

Compounds

As used herein, a "compound" refers to any one of: (a) the actually recited form of such compound, and (b) any of the forms of such compound in the medium in which the compound is being considered when named. For example, reference herein to a compound such as R—COOH, encompasses reference to any one of, for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered.

As used herein, the term "chemical entity" collectively refers to a compound, along with the derivatives of the compound, including salts, chelates, solvates, conformers, non-covalent complexes, metabolites, and prodrugs.

In one aspect the chemical entity is selected from the group consisting of compounds of Formula (I), pharmaceutically acceptable salts of compounds of Formula (I), pharmaceutically acceptable prodrugs of compounds of Formula (I), and pharmaceutically acceptable metabolites of compounds of Formula (I).

In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As is generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $+H_3NCH_2COO-$. Zwitterions, zwitterionic compounds, inner salts, and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Isotopes may be present in the compounds described. Each chemical element present in a compound either specifically or generically described herein may include any isotope of said element. Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, fluorine, and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of species for the same variable elsewhere in the formula, unless otherwise stated.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$ and "$S^2_{example}$ is one of $S_3$ and $S_4$ is accordingly used herein for the sake of brevity but not by way of limitation. The foregoing first example on substituent terminology, which is stated in generic terms, is meant to illustrate the various substituent assignments described herein. The foregoing convention given herein for substituents extends, when applicable, to members such as $R^1, R^2, R^3, R^4, R^a, R^b, R^c, R^d, R^{d1}, R^e, R^{e1}, R^f, R^g, R^h, R^j, R^k R^m, R^n$ and U, Y, Z, HAL, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$ and $S_3$, the listing refers to embodiments of this invention for which $S_{example}$ is $S_1$; $S_{example}$ is $S_2$; $S_{example}$ is $S^3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$ and $S_3$," is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1, R^2, R^3, R^4 R^a, R^b, R^c, R^d, R^{d1}, R^e, R^{e1}$, Rf, $R^g, R^h, R^j, R^k R^m, R^n$ and U, Y, Z, HAL, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with the total number N of carbon members in the chain that satisfies n≤N≤m, with m>n.

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)).

A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

A "metabolite" means a pharmacologically active product of metabolism in the body of a compound of Formula (I) or salt thereof. Preferably, the metabolite is in an isolated form outside the body.

Compositions

The term "composition," as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula (I) and a pharmaceutically acceptable excipient.

The term "pharmaceutically acceptable," as used in connection with compositions of the invention, refers to molecular entities and other ingredients of such compositions that are physiologically tolerable and do not typically produce untoward reactions when administered to an animal (e.g., human). The term "pharmaceutically acceptable" may also mean approved by a regulatory agency of the Federal or a state government or listed in the U.S. Pharmacopeia or other generally recognized pharmacopeia for use in animals (e.g. mammals), and more particularly in humans.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluents to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable pharmaceutical carriers include those described in Remington: The Science and Practice of Pharmacy, 21st Ed., Lippincott Williams & Wilkins (2005).

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn et al., Trends in Active Pharmaceutical Ingredient Salt Selection based on Analysis of the Orange Book Database, *J. Med. Chem.* 2007, 50, 6665-6672; Berge et al., Pharmaceutical Salts, *J. Pharm. Sci.* 1977, 66, 1-19; Stahl and Wermuth (eds), Pharmaceutical Salts; Properties, Selection, and Use: 2nd Revised Edition, Wiley-VCS, Zurich, Switzerland (2011). Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt bases, and inorganic and organic acids, to form a pharmaceutically acceptable salt.

The term "carrier" refers to an adjuvant, vehicle, or excipients, with which the compound is administered. In preferred embodiments of this invention, the carrier is a solid carrier. Suitable pharmaceutical carriers include those described in Remington: The Science and Practice of Pharmacy, 21st Ed., Lippincott Williams & Wilkins (2005).

The term "dosage form," as used herein, is the form in which the dose is to be administered to the subject or patient.

The drug is generally administered as part of a formulation that includes nonmedical agents. The dosage form has unique physical and pharmaceutical characteristics. Dosage forms, for example, may be solid, liquid or gaseous. "Dosage forms" may include for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the term "inert" refer to any inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

Methods and Uses

As used herein, the term "disorder" is used interchangeably with "disease" or "condition". For example, a CNS disorder also means a CNS disease or a CNS condition.

As used herein, the term "cognitive impairment" is used interchangeably with "cognitive dysfunction" or "cognitive deficit," all of which are deemed to cover the same therapeutic indications.

The terms "treating," "treatment," and "treat" cover therapeutic methods directed to a disease-state in a subject and include: (i) preventing the disease-state from occurring, in particular, when the subject is predisposed to the disease-state but has not yet been diagnosed as having it; (ii) inhibiting the disease-state, e.g., arresting its development (progression) or delaying its onset; and (iii) relieving the disease-state, e.g., causing regression of the disease state until a desired endpoint is reached. Treating also includes ameliorating a symptom of a disease (e.g., reducing the pain, discomfort, or deficit), wherein such amelioration may be directly affecting the disease (e.g., affecting the disease's cause, transmission, or expression) or not directly affecting the disease.

As used in the present disclosure, the term "effective amount" is interchangeable with "therapeutically effective amount" and means an amount or dose of a compound or composition effective in treating the particular disease, condition, or disorder disclosed herein, and thus "treating" includes producing a desired preventative, inhibitory, relieving, or ameliorative effect. In methods of treatment according to the invention, "an effective amount" of at least one compound according to the invention is administered to a subject (e.g., a mammal). An "effective amount" also means an amount or dose of a compound or composition effective to modulate activity of PDE4 or an associated signaling pathway, such as the CREB pathway and thus produce the desired modulatory effect. The "effective amount" will vary, depending on the compound, the disease, the type of treatment desired, and its severity, and age, weight, etc.

The term "animal" is interchangeable with "subject" and may be a vertebrate, in particular, a mammal, and more particularly, a human, and includes a laboratory animal in the context of a clinical trial or screening or activity experiment. Thus, as can be readily understood by one of ordinary skill in the art, the compositions and methods of the present invention are particularly suited to administration to any vertebrate, particularly a mammal, and more particularly, a human.

As used herein, a "control animal" or a "normal animal" is an animal that is of the same species as, and otherwise comparable to (e.g., similar age, sex), the animal that is trained under conditions sufficient to induce transcription-dependent memory formation in that animal.

By "enhance," "enhancing," or "enhancement" is meant the ability to potentiate, increase, improve or make greater or better, relative to normal, a biochemical or physiological action or effect. For example, enhancing long term memory formation refers to the ability to potentiate or increase long term memory formation in an animal relative to the normal long term memory formation of the animal or controls. As a result, long term memory acquisition is faster or better retained. Enhancing performance of a cognitive task refers to the ability to potentiate or improve performance of a specified cognitive task by an animal relative to the normal performance of the cognitive task by the animal or controls.

As used herein, the term "training protocol," or "training," refers to either "cognitive training" or "motor training." The phrase "in conjunction" means that a compound or composition of the present invention enhances CREB pathway function during cognitive or motor training.

Reference will now be made to the embodiments of the present invention, examples of which are illustrated by and described in conjunction with the accompanying drawings and examples. While certain embodiments are described herein, it is understood that the described embodiments are not intended to limit the scope of the invention. On the contrary, the present disclosure is intended to cover alternatives, modifications, and equivalents that can be included within the invention as defined by the appended claims.

Compounds

The present invention provides certain substituted pyridine and pyrazine derivatives, which are useful, for example, as inhibitors of PDE4 enzymatic activity. They are distinct from tri-substituted pyridines are disclosed in the following publications: U.S. Pat. No. 7,399,761 (Novartis AG, Nov. 14, 2002, CAS No. 1106203-18-2, 1106203-.16-0); Intl. Pat. Appl. Publ. WO 2003050098, (Maxia Pharmaceuticals, Jun. 19, 2003, CAS No. 544475-13-0, 544475-12-9) and JP Pat. 4,321,737 (Intl. Pat. Appl. Publ. WO 9931062, Shionogi & Co., Jun. 24, 1999, CAS No. 228096-03-5, 228096-04-6).

In its many embodiments, the invention is directed to a chemical entity of Formula (I):

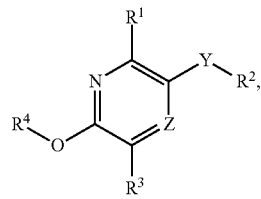

Formula (I)

wherein:

Z is CH or N;

i) wherein when Z is CH, then;

$R^1$ is a member selected from the group consisting of: —H, —$C_{1-3}$alkyl and —$C_{1-3}$haloalkyl;

Y is —$C(R^a)_2$—, where each $R^a$ is independently selected from the group consisting of: —H, —F, —$CH_3$, —OH and —$N(R^b)_2$;

$R^2$ is a member selected from the group consisting of:

A) phenyl unsubstituted or substituted with one or two $R^c$ members, where each $R^c$ is independently selected from the group consisting of: halo, —CN, —$CO_2R^b$, —$CONH_2$, —$SO_2CH_3$, —$C(R^b)_2OH$, —$CH_2NH_2$, —$CH_2CONH_2$, —$CH_2CO_2CH_3$, —$NHCONH_2$, —NH-CONH-oxetane, —CONH-oxetane,

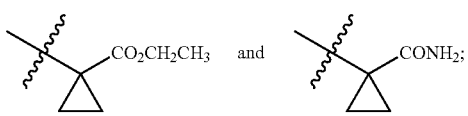

B) six-membered monocyclic heteroaromatic ring containing one or two nitrogen members unsubstituted or substituted with one or two members each independently selected from the group consisting of: halo, —$C_{1-3}$ alkyl, —$C_{1-3}$haloalkyl, —CN, —$C(R^b)_2$OH, —$CH_2NH_2$, —$OC_{1-3}$alkyl, —O—$CH_2$-cyclopropyl, —$CO_2H$, —$CON(R^b)_2$, —$N(R^b)_2$, —$NHCH_2CF_3$, —$NHCH(CH_3)_2$, —$NHCH_2CH_2N(CH_3)_2$, —NHcyclopropyl, and —$NHCOCH_3$;

C) five-membered monocyclic heteroaromatic ring containing two to four nitrogen members unsubstituted or substituted with one or two members each independently selected from the group consisting of halo, —$C_{1-3}$ alkyl, —$C_{1-3}$haloalkyl, —$C(R^b)_2$OH, —$N(R^b)_2$, —$NO_2$, —CN, —$OC_{1-3}$alkyl, —$CH_2OCH_3$, —$CH_2NH_2$, —$CO_2C_{1-3}$alkyl, —$CO_2H$, —$CONH_2$, —$NHCOCH_3$, and cyclopropyl; and D) five or six-membered heteroaromatic ring selected from: 1,2-dihydropyridin-2-one, tetrazole, thiazole or oxazole each unsubstituted or substituted with one or two members each independently selected from the group consisting of —H, —$CH_3$, and —$NH_2$;

$R^3$ is a member selected from the group consisting of: phenyl, pyridyl, thiophene, and pyrazole, each substituted with a member selected from the group consisting of: halo, —$C_{1-3}$ alkyl, —$C_{1-3}$haloalkyl, —$OC_{1-3}$alkyl, —Ocyclopropyl, —$OC_{1-3}$haloalkyl, —CN, —$CH_2$OH and —$SO_2CH_3$;

$R^4$ is a member selected from the group consisting of —$C_{1-3}$ alkyl and —$C_{1-3}$haloalkyl;

where each $R^b$ is independently selected from —H or —$CH_3$; and ii) wherein when Z is N, then;

$R^1$ is —H;

Y is —$CH_2$—;

$R^2$ is a member selected from the group consisting of:

A) phenyl substituted with one or two $R^d$ members, where each $R^d$ is independently selected from the group consisting of: —CN, —$CONH_2$, and —$CO_2C_{1-3}$alkyl;

B) six-membered monocyclic heteroaromatic ring containing one or two nitrogen members unsubstituted or substituted with a member selected from the group consisting of: —CN, —$OC_{1-3}$alkyl, —$CONH_2$, —$N(R^b)_2$, and —NH-cyclopropyl;

C) five-membered monocyclic heteroaromatic ring containing two or three nitrogen members unsubstituted or substituted with one or two members each independently selected from the group consisting of —$C_{1-3}$ alkyl, —$C_{1-3}$haloalkyl, —$CH_2OR^b$, —$N(R^b)_2$, —$NO_2$, —$CO_2CH_3$, and cyclopropyl; and D) oxazole optionally substituted with one or two $R^b$ members;

$R^3$ is phenyl substituted with —Cl, —$OC_{1-3}$alkyl, or —$OC_{1-3}$haloalkyl;

$R^4$ is —$C_{1-3}$ alkyl; and where each $R^b$ is independently selected from —H or —$CH_3$.

In certain embodiments of compounds of Formula (I), Z is CH.

In certain embodiments of compounds of Formula (I), Z is N.

Some embodiments are given by compounds of Formula (I) where Z is CH, and $R^1$—H, —$CH_3$, or —$CF_3$.

In some of these embodiments, $R^1$ is —H.

In certain embodiments of compounds of Formula (I), Y is —$CH_2$—, —CH(F)—, —CH(OH)—, —C(OH)($CH_3$)—, or —CH($CH_3$)—, and Z is CH.

In some of these embodiments, Y is —$CH_2$—.

In certain embodiments of compounds of Formula (I), $R^2$ is

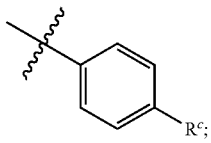

and $R^c$ is —F, —CN, —$CO_2H$, —$CONH_2$, —$SO_2CH_3$, —$C(CH_3)_2OH$, —$CH_2NH_2$, —$CH_2CONH_2$, —$CH_2CO_2CH_3$, —$NHCONH_2$, —NHCONH-oxetane, —CONH-oxetane,

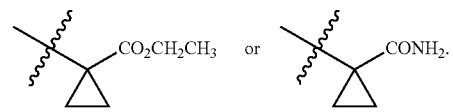

In some of these embodiments, $R^2$ is

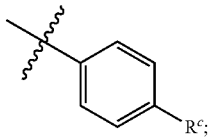

and $R^c$ is —F, —$CONH_2$, —$CH_2CONH_2$, —$CH_2NH_2$, —$C(CH_3)_2OH$, —$SO_2CH_3$, or —$NHCONH_2$.

In certain embodiments of compounds of Formula (I), Z is N and $R^2$ is 4-cyanophenyl, 4-phenylamide or 4-phenylcarboxylic acid methyl ester.

Some embodiments are given by compounds of Formula (I) where $R^2$ is pyridine, unsubstituted or substituted with one or two members each independently selected from: —F, —$C_{1-3}$alkyl, —$C_{1-3}$haloalkyl, —$OC_{1-3}$alkyl, —$OCH_2$cyclopropyl, —CN, —$N(R^b)_2$, —$CH_2NH_2$, —$CO_2H$, —$CON(R^b)_2$, or —$C(CH_3)_2OH$.

In some of these embodiments, $R^2$ is

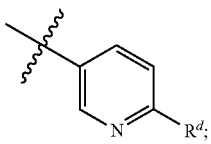

and $R^d$ is —$CH_3$, —$CF_3$, —CN, —$N(R^b)_2$, —$CO_2H$, —$CON(R^b)_2$, —$OC_{1-3}$alkyl, —$CH_2NH_2$, —$C(CH_3)_2OH$, —$OCH_2$cyclopropyl, or —$OCH(CH_3)_2$.

In some of these embodiments, $R^2$ is

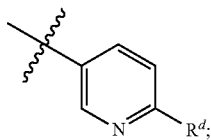

and $R^d$ is —CH$_3$, —CF$_3$, —NH$_2$, —NHCH$_3$, —N(CH$_3$)$_2$, —CONH$_2$, —CONHCH$_3$, —CON(CH$_3$)$_2$, —OC$_{1-3}$alkyl, —C(CH$_3$)$_2$OH, or —OCH$_2$cyclopropyl.

In some of these embodiments, Z is N, and $R^2$ is

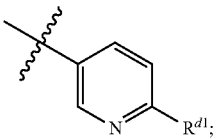

$R^{d1}$ is —CN or —CONH$_2$.

Some embodiments are given by compounds of Formula (I) where $R^2$ is pyrazine, 6-methylpyridazin-3-amine or pyrimidine, where pyrimidine is unsubstituted or substituted with —Cl, —CH$_3$, —CN, —OC$_{1-3}$alkyl, —CO$_2$H, —CON(R$^b$)$_2$, —C(CH$_3$)$_2$OH, —N(R$^b$)$_2$, —NHCH$_2$CF$_3$, —NHCH(CH$_3$)$_2$, —CH$_2$CH$_2$N(CH$_3$)$_2$, —NHcyclopropyl, and —NHCOCH$_3$.

In some of these embodiments, $R^2$ is

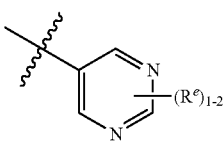

and each $R^e$ is independently —CH$_3$, —CN, —OCH$_3$, —CO$_2$H, —CONH$_2$, —C(CH$_3$)$_2$OH, —N(R$^b$)$_2$, —NHCH$_2$CF$_3$, —NHCH(CH$_3$)$_2$, —CH$_2$CH$_2$N(CH$_3$)$_2$, —NHcyclopropyl, or —NHCOCH$_3$.

In some of these embodiments, $R^2$ is

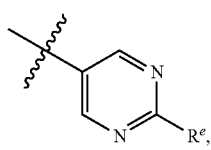

and $R^e$ is —CH$_3$, —CN, —OCH$_3$, —NH$_2$, —NHCH$_3$, —N(CH$_3$)$_2$, —NHCH$_2$CF$_3$, —NHcyclopropyl, —C(CH$_3$)$_2$OH, —CONH$_2$, —CONHCH$_3$, or —CON(CH$_3$)$_2$.

In some of these embodiments, Z is N, and $R^2$ is

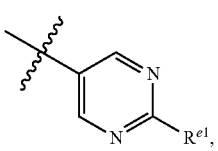

unsubstituted or substituted with $R^{e1}$, where $R^{e1}$ is —CN, —OCH$_3$, —CONH$_2$, —NH$_2$, —NHCH$_3$, or —NHcyclopropyl.

Some embodiments are given by compounds of Formula (I) where $R^2$ is imidazole, pyrazole, and triazole, unsubstituted or substituted with one or two members each independently selected from the group consisting of: —Cl, —CH$_3$, —CF$_3$, —CH$_2$OH, —NH$_2$, —NO$_2$, —CN, —CO$_2$C$_{1-3}$alkyl, —CO$_2$H, —CONH$_2$, or —NHCOCH$_3$.

In some of these embodiments, $R^2$ is

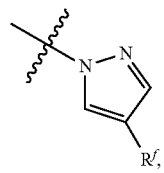

and $R^f$ is —H, —Cl, —CH$_3$, —NO$_2$, —NH$_2$, —NHCOCH$_3$, —CH$_2$OH, —CN, —CONH$_2$, —CO$_2$H, or —CO$_2$CH$_2$CH$_3$.

In some of these embodiments, $R^2$ is

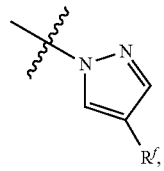

and $R^f$ is —H, —NH$_2$, or —CH$_2$OH.

In some of these embodiments, $R^2$ is

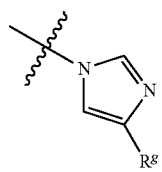

where $R^g$ is —H, —CH$_3$, —CH$_2$OH, or —NH$_2$.

Some embodiments are given by compounds of Formula (I) where $R^2$ is 1H-tetrazole, 2H-tetrazole, 1,2-oxazole, 1,3-thiazole, each independently unsubstituted or substituted with —CH$_3$, or —NH$_2$.

Some embodiments are given by compounds of Formula (I) where $R^2$ is 1,2,3-triazole and 1,2,4-triazole, each unsubstituted or substituted with —CH$_3$, —CH$_2$F, —CHF$_2$, —CF$_3$, —OCH$_3$, —OCH$_2$CH$_3$, —CN, —C(R$^b$)OH, —CH$_2$OCH$_3$, N(R$^b$)$_2$, —NO$_2$, —CO$_2$CH$_3$, —CONH$_2$, cyclopropyl or —CH$_2$NH$_2$.

In some of these embodiments, $R^2$ is

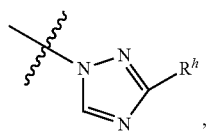

and $R^h$ is —H, —CH$_3$, —CF$_3$, —CH$_2$F, —CHF$_2$, —OCH$_3$, —OCH$_2$CH$_3$, —CH$_2$OH, —C(CH$_3$)$_2$OH, —CH$_2$OCH$_3$, —NO$_2$, —NH$_2$, —NHCH$_3$, —N(CH$_3$)$_2$, —CN, —CONH$_2$, —CO$_2$CH$_3$, or -cyclopropyl.

In some of these embodiments, $R^2$ is

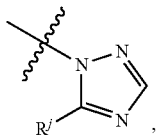

and $R^j$ is —H, —CH$_3$, —CF$_3$, —OCH$_3$, —CH$_2$(OH), —C(CH$_3$)$_2$OH, —CH$_2$OCH$_3$, —CO$_2$CH$_3$, or —NO$_2$.

In some of these embodiments, $R^2$ is

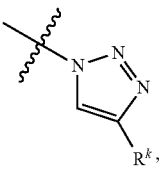

and $R^k$ is —H, —CH$_3$, —CF$_3$, —CH$_2$F, —CHF$_2$, —OCH$_3$, —OCH$_2$CH$_3$, —CH$_2$OH, —C(CH$_3$)$_2$OH, —CH$_2$OCH$_3$, —NO$_2$, —NH$_2$, —NHCH$_3$, —N(CH$_3$)$_2$, —CN, —CONH$_2$, —CO$_2$CH$_3$, or -cyclopropyl.

Some embodiments are given by compounds of Formula (I) where $R^3$ is

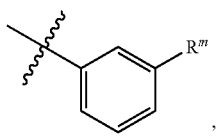

and $R^m$ is —Cl, —F, —CH$_3$, —CHF$_2$, —CN, —OCH$_3$, —CH$_2$OH, —OCH$_2$CH$_3$, —OCF$_3$, —OCHF$_2$, —SO$_2$CH$_3$, —OCH(CH$_3$)$_2$,

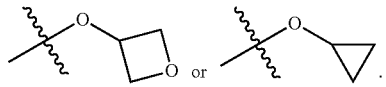

In some of these embodiments, $R^3$ is 3-chlorophenyl, 3-cyanophenyl, 3-fluorophenyl, 3-methylphenyl, 3-methoxyphenyl, 3-ethoxyphenyl, 3-(trifluoromethoxy)phenyl, 3-(difluoromethoxy)phenyl or 3-(difluoromethyl)phenyl.

Some embodiments are given by compounds of Formula (I) where $R^3$ is

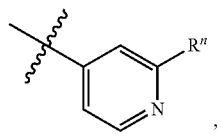

and $R^n$ is H, —Cl, —CH$_3$, —OCH$_3$, —OCH$_2$CH$_3$, —OCHF$_2$, or —OCF$_3$.

In some of these embodiments, $R^3$ is 4-chlorothiophen-2-yl, 4-chloro-1H-pyrazol-1-yl, 1-methyl-1H-pyrazol-4-yl, and 1H-pyrazol-4-yl.

Some embodiments are given by compounds of Formula (I) where $R^4$ is —CH$_3$, —CH$_2$CH$_3$, —CH(CH$_3$)$_2$, or —CHF$_2$.

Further embodiments are provided by pharmaceutically acceptable salts of compounds of Formula (I), pharmaceutically acceptable prodrugs of compounds of Formula (I), and pharmaceutically active metabolites of compounds of Formula (I).

In certain embodiments, a compound, or pharmaceutically acceptable salt thereof, of Formula (I) is selected from the group consisting of:

| Ex | Chemical Name |
|---|---|
| 1 | 5-({6-[3-(Difluoromethoxy)phenyl]-5-ethoxypyrazin-2-yl}methyl)pyrimidine-2-carbonitrile |
| 2 | 2-Chloro-5-{[5-(3-chlorophenyl)-6-methoxypyridin-3-yl]methyl}pyrimidine |
| 3 | {2-[(5-{[5-(3-Chlorophenyl)-6-methoxypyridin-3-yl]methyl}pyrimidin-2-yl)amino]ethyl}dimethylamine |
| 4 | 2-Methoxy-3-(6-methoxypyridin-2-yl)-5-(1H-1,2,4-triazol-1-ylmethyl)pyridine |
| 5 | 2-Methoxy-3-(3-methylphenyl)-5-(1H-1,2,4-triazol-1-ylmethyl)pyridine |
| 6 | 2-Methoxy-3-(5-methylpyridin-3-yl)-5-(1H-1,2,4-triazol-1-ylmethyl)pyridine |
| 7 | 2-Methoxy-3-(2-methylpyridin-4-yl)-5-(1H-1,2,4-triazol-1-ylmethyl)pyridine |
| 8 | {3-[2-Methoxy-5-(1H-1,2,4-triazol-1-ylmethyl)pyridin-3-yl]phenyl}methanol |
| 9 | 3-(3-Methanesulfonylphenyl)-2-methoxy-5-(1H-1,2,4-triazol-1-ylmethyl)pyridine |
| 10 | 2-Methoxy-3-(4-methylpyridin-2-yl)-5-(1H-1,2,4-triazol-1-ylmethyl)pyridine |
| 11 | 2-Methoxy-3-(6-methylpyridin-2-yl)-5-(1H-1,2,4-triazol-1-ylmethyl)pyridine |
| 12 | 2-(Difluoromethoxy)-3-(3-methylphenyl)-5-(1H-1,2,4-triazol-1-ylmethyl)pyridine |
| 13 | 5-({6-[3-(Difluoromethoxy)phenyl]-5-ethoxypyrazin-2-yl}methyl)pyrimidine-2-carboxamide |
| 14 | [5-(3-Chlorophenyl)-6-methoxypyridin-3-yl](4-fluorophenyl)methanol |
| 15 | 1-[5-(3-Chlorophenyl)-6-methoxypyridin-3-yl]-1-(4-fluorophenyl)ethan-1-ol |
| 16 | [5-(3-Chlorophenyl)-6-methoxypyridin-3-yl](5-fluoropyridin-2-yl)methanol |
| 17 | {[5-(3-Chlorophenyl)-6-methoxypyridin-3-yl](4-fluorophenyl)methyl}(methyl)amine |
| 18 | [5-(3-Chlorophenyl)-6-methoxypyridin-3-yl](4-fluorophenyl)methanamine |
| 19 | {[5-(3-Chlorophenyl)-6-methoxypyridin-3-yl](4-fluorophenyl)methyl}dimethylamine |
| 20 | 3-(3-Chlorophenyl)-5-[fluoro(4-fluorophenyl)methyl]-2-methoxypyridine |
| 21 | 4-{[5-(3-Chlorophenyl)-6-methoxypyridin-3-yl]methyl}benzoic acid |
| 22 | 5-{[6-(3-Chlorophenyl)-5-methoxypyrazin-2-yl]methyl}pyrimidine-2-carbonitrile |
| 23 | 5-{[5-(3-Chlorophenyl)-6-methoxypyridin-3-yl]methyl}pyrimidine-2-carboxylic acid |
| 24 | 5-{[5-(3-Chlorophenyl)-6-methoxypyridin-3-yl]methyl}pyrimidine-2-carboxamide |
| 25 | 5-{[5-(3-Chlorophenyl)-6-methoxypyridin-3-yl]methyl}pyrimidin-2-amine |
| 26 | (4-{[5-(3-Chlorophenyl)-6-methoxypyridin-3-yl]methyl}phenyl)urea |

| Ex | Chemical Name |
|---|---|
| 27 | 4-{[5-(3-Chlorophenyl)-6-methoxypyridin-3-yl]methyl}benzamide |
| 28 | 3-(3-Chlorophenyl)-2-(difluoromethoxy)-5-(1H-pyrazol-4-ylmethyl)pyridine |
| 29 | 5-{[6-(Difluoromethoxy)-5-(3-methoxyphenyl)pyridin-3-yl]methyl}pyrimidin-2-amine |
| 30 | 5-{[5-(3-Chlorophenyl)-6-methoxypyridin-3-yl]methyl}pyridin-2-amine |
| 31 | 1-(4-{[5-(3-Chlorophenyl)-6-methoxypyridin-3-yl]methyl}phenyl)-3-(oxetan-3-yl)urea |
| 32 | 3-(3-Chlorophenyl)-2-methoxy-5-[(6-methoxypyridin-3-yl)methyl]pyridine |
| 33 | 5-{[5-(3-Chlorophenyl)-6-(difluoromethoxy)pyridin-3-yl]methyl}pyridin-2-amine |
| 34 | 5-{[5-(3-Chlorophenyl)-6-methoxypyridin-3-yl]methyl}-N,N-dimethylpyridin-2-amine |
| 35 | 5-{[5-(3-Chlorophenyl)-6-(difluoromethoxy)pyridin-3-yl]methyl}pyrimidine-2-carbonitrile |
| 36 | 5-{[5-(3-Chlorophenyl)-6-(difluoromethoxy)pyridin-3-yl]methyl}-1,3-thiazol-2-amine |
| 37 | (2-{[5-(3-Chlorophenyl)-6-methoxypyridin-3-yl]methyl}phenyl)methanol |
| 38 | 5-{[5-(3-Fluorophenyl)-6-methoxypyridin-3-yl]methyl}pyrimidin-2-amine |
| 39 | 5-{[5-(3-Fluorophenyl)-6-methoxypyridin-3-yl]methyl}pyrimidine-2-carbonitrile |
| 40 | 5-{[5-(3-Chlorophenyl)-6-ethoxypyridin-3-yl]methyl}pyrimidin-2-amine |
| 41 | 5-{[5-(3-Chlorophenyl)-6-(propan-2-yloxy)pyridin-3-yl]methyl}pyrimidin-2-amine |
| 42 | 5-{[6-(Difluoromethoxy)-5-[3-(propan-2-yloxy)phenyl]pyridin-3-yl]methyl}pyrimidin-2-amine |
| 43 | 5-{[6-(Difluoromethoxy)-5-[3-(oxetan-3-yloxy)phenyl]pyridin-3-yl]methyl}pyrimidin-2-amine |
| 44 | N-(5-{[5-(3-Chlorophenyl)-6-methoxypyridin-3-yl]methyl}pyrimidin-2-yl)acetamide |
| 45 | 3-(3-Chlorophenyl)-2-(difluoromethoxy)-5-[(4-methanesulfonylphenyl)methyl]pyridine |
| 46 | 5-{[6-(Difluoromethoxy)-5-(2-methoxypyridin-4-yl)pyridin-3-yl]methyl}pyrimidin-2-amine |
| 47 | 5-({5-[2-(Difluoromethoxy)pyridin-4-yl]-6-methoxypyridin-3-yl}methyl)pyrimidin-2-amine |
| 48 | 2-[5-({5-[3-(Difluoromethoxy)phenyl]-6-methoxypyridin-3-yl}methyl)pyrimidin-2-yl]propan-2-ol |
| 49 | 3-(3-Chlorophenyl)-2-methoxy-5-{[6-(trifluoromethyl)pyridin-3-yl]methyl}pyridine |
| 50 | 3-(3-Chlorophenyl)-2-(difluoromethoxy)-5-{[6-(propan-2-yloxy)pyridin-3-yl]methyl}pyridine |
| 51 | 3-(3-Chlorophenyl)-2-(difluoromethoxy)-5-[(6-propoxypyridin-3-yl)methyl]pyridine |
| 52 | 5-{[5-(3-Chlorophenyl)-6-methoxypyridin-3-yl]methyl}-1-methyl-1,2-dihydropyridin-2-one |
| 53 | 3-(3-Chlorophenyl)-2-methoxy-5-(pyridin-4-ylmethyl)pyridine |
| 54 | 5-{[5-(3-Chlorophenyl)-6-(difluoromethoxy)pyridin-3-yl]methyl}pyridine-2-carboxylic acid |
| 55 | 3-(3-Chlorophenyl)-2-methoxy-5-[(2-methoxypyrimidin-5-yl)methyl]pyrazine |
| 56 | 5-{[6-(3-chlorophenyl)-5-methoxypyrazin-2-yl]methyl}-N-methylpyrimidin-2-amine |
| 57 | 5-{[6-(3-chlorophenyl)-5-methoxypyrazin-2-yl]methyl}-N-cyclopropylpyrimidin-2-amine |
| 58 | 3-(3-Chlorophenyl)-2-methoxy-5-[(1-methyl-1H-pyrazol-4-yl)methyl]pyrazine |
| 59 | (4-{[5-(3-Chlorophenyl)-6-methoxypyridin-3-yl]methyl}phenyl)methanamine |
| 60 | 4-{[5-(3-Chlorophenyl)-6-methoxypyridin-3-yl]methyl}pyridin-2-amine |
| 61 | 3-(3-Chlorophenyl)-5-[(2,6-dimethylpyridin-4-yl)methyl]-2-methoxypyridine |
| 62 | 4-{[5-(3-Chlorophenyl)-6-methoxypyridin-3-yl]methyl}pyridine-2-carbonitrile |
| 63 | 4-{[5-(3-Chlorophenyl)-6-methoxypyridin-3-yl]methyl}pyridine-2-carboxamide |
| 64 | 3-(3-Chlorophenyl)-2-methoxy-5-(pyridin-3-ylmethyl)pyridine |
| 65 | 3-(3-Chlorophenyl)-2-methoxy-5-(1,3-thiazol-5-ylmethyl)pyridine |
| 66 | 3-(3-Chlorophenyl)-5-[(dimethyl-1,3-thiazol-5-yl)methyl]-2-methoxypyridine |
| 67 | 3-(3-Chlorophenyl)-2-methoxy-5-[(6-methoxy-5-methylpyridin-3-yl)methyl]pyridine |
| 68 | 3-(3-Chlorophenyl)-2-(difluoromethoxy)-5-(1,3-thiazol-5-ylmethyl)pyridine |
| 69 | 3-(3-Chlorophenyl)-2-(difluoromethoxy)-5-[(dimethyl-1,3-thiazol-5-yl)methyl]pyridine |
| 70 | 5-{[5-(3-Chlorophenyl)-6-(difluoromethoxy)pyridin-3-yl]methyl}pyridine-3-carboxamide |
| 71 | (5-{[5-(3-Chlorophenyl)-6-(difluoromethoxy)pyridin-3-yl]methyl}pyridine-3-yl)methanamine |
| 72 | 3-(3-Chlorophenyl)-2-(difluoromethoxy)-5-[(6-methylpyridin-3-yl)methyl]pyridine |
| 73 | 3-(3-Chlorophenyl)-2-(difluoromethoxy)-5-[(2-methyl-1,3-thiazol-5-yl)methyl]pyridine |
| 74 | 3-(3-Chlorophenyl)-2-(difluoromethoxy)-5-(1,3-thiazol-2-ylmethyl)pyridine |
| 75 | 5-{[5-(3-Chlorophenyl)-6-methoxypyridin-3-yl]methyl}-2-methylpyrimidine |
| 76 | 5-{[5-(3-Chlorophenyl)-6-methoxypyridin-3-yl]methyl}-2-methoxypyrimidine |
| 77 | 5-{[5-(3-Chlorophenyl)-6-methoxypyridin-3-yl]methyl}-N-(propan-2-yl)pyrimidin-2-amine |

| Ex | Chemical Name |
|---|---|
| 78 | 5-{[5-(3-Chlorophenyl)-6-methoxypyridin-3-yl]methyl}pyrimidine |
| 79 | 3-(3-Chlorophenyl)-2-methoxy-5-[(1-methyl-1H-pyrazol-4-yl)methyl]pyridine |
| 80 | 3-(3-Chlorophenyl)-2-methoxy-5-(1H-pyrazol-4-ylmethyl)pyridine |
| 81 | 5-{[5-(3-Chlorophenyl)-6-methoxypyridin-3-yl]methyl}-N-methylpyrimidin-2-amine |
| 82 | 5-{[5-(3-Chlorophenyl)-6-methoxypyridin-3-yl]methyl}-N-cyclopropylpyrimidin-2-amine |
| 83 | 5-{[5-(3-Chlorophenyl)-6-methoxypyridin-3-yl]methyl}-N,N-dimethylpyrimidin-2-amine |
| 84 | 5-{[5-(3-Chlorophenyl)-6-methoxypyridin-3-yl]methyl}-N-(2,2,2-trifluoroethyl)pyrimidin-2-amine |
| 85 | Methyl 4-{[6-(3-chlorophenyl)-5-methoxypyrazin-2-yl]methyl}benzoate |
| 86 | 4-{[6-(3-Chlorophenyl)-5-methoxypyrazin-2-yl]methyl}benzonitrile |
| 87 | 5-{[6-(3-Chlorophenyl)-5-methoxypyrazin-2-yl]methyl}pyrimidin-2-amine |
| 88 | 3-(3-Chlorophenyl)-5-[(4-fluorophenyl)methyl]-2-methoxypyridine |
| 89 | 5-{[5-(3-Chlorophenyl)-6-(difluoromethoxy)pyridin-3-yl]methyl}pyrimidin-2-amine |
| 90 | 5-{[6-(3-Chlorophenyl)-5-methoxypyrazin-2-yl]methyl}pyridine-2-carboxamide |
| 91 | 5-{[5-(3-Chlorophenyl)-6-(difluoromethoxy)pyridin-3-yl]methyl}-N-cyclopropylpyrimidin-2-amine |
| 92 | 5-{[5-(3-Chlorophenyl)-6-(difluoromethoxy)pyridin-3-yl]methyl}-2-methoxypyrimidine |
| 93 | 5-{[5-(3-Chlorophenyl)-6-(difluoromethoxy)pyridin-3-yl]methyl}-N-methylpyrimidin-2-amine |
| 94 | 5-{[5-(3-Chlorophenyl)-6-(difluoromethoxy)pyridin-3-yl]methyl}-N-(2,2,2-trifluoroethyl)pyrimidin-2-amine |
| 95 | 3-(3-Chlorophenyl)-2-methoxy-5-(1,2-oxazol-4-ylmethyl)pyrazine |
| 96 | 3-(3-Chlorophenyl)-2-methoxy-5-(1,2-oxazol-4-ylmethyl)pyridine |
| 97 | 3-(3-Chlorophenyl)-2-(difluoromethoxy)-5-(1,2-oxazol-4-ylmethyl)pyridine |
| 98 | 3-(3-Chlorophenyl)-5-[(dimethyl-1,2-oxazol-4-yl)methyl]-2-methoxypyrazine |
| 99 | 3-(3-Chlorophenyl)-2-(difluoromethoxy)-5-[(dimethyl-1,2-oxazol-4-yl)methyl]pyridine |
| 100 | Methyl 2-(4-{[5-(3-chlorophenyl)-6-(difluoromethoxy)pyridin-3-yl]methyl}phenyl)acetate |
| 101 | Ethyl 1-(4-{[5-(3-chlorophenyl)-6-(difluoromethoxy)pyridin-3-yl]methyl}phenyl)cyclopropane-1-carboxylate |
| 102 | 3-(3-Chlorophenyl)-5-{[6-(cyclopropylmethoxy)pyridin-3-yl]methyl}-2-(difluoromethoxy)pyridine |
| 103 | 5-({6-[3-(Difloromethoxy)phenyl]-5-ethoxypyrazin-2-yl}methyl)pyridine-2-carbonitrile |
| 104 | 5-({6-[3-(Difloromethoxy)phenyl]-5-ethoxypyrazin-2-yl}methyl)pyrimidin-2-amine |
| 105 | 5-{[6-(3-Chlorophenyl)-5-ethoxypyrazin-2-yl]methyl}pyrimidin-2-amine |
| 106 | 5-({6-[3-(Difloromethoxy)phenyl]-5-methoxypyrazin-2-yl}methyl)pyrimidin-2-amine |
| 107 | 5-({6-[3-(Difloromethoxy)phenyl]-5-methoxypyrazin-2-yl}methyl)pyrimidin-2-carbonitrile |
| 108 | 5-{[6-(3-Chlorophenyl)-5-ethoxypyrazin-2-yl]methyl}pyrimidine-2-carbonitrile |
| 109 | 3-(3-Chlorophenyl)-2-(difluoromethoxy)-5-(pyridin-2-ylmethyl)pyridine |
| 110 | 2-{[5-(3-Chlorophenyl)-6-(difluoromethoxy)pyridin-3-yl]methyl}pyrazine |
| 111 | 6-{[5-(3-Chlorophenyl)-6-(difluoromethoxy)pyridin-3-yl]methyl}pyridazin-3-amine |
| 112 | 3-(3-Chlorophenyl)-2-methoxy-6-methyl-5-(1H-1,2,4-triazol-1-ylmethyl)pyridine |
| 113 | 4-{[6-(3-Chlorophenyl)-5-methoxypyrazin-2-yl]methyl}benzamide |
| 114 | 5-{[5-(3-Chlorophenyl)-6-(difluoromethoxy)pyridin-3-yl]methyl}pyridine-2-carboxamide |
| 115 | 5-{[6-(Difluoromethoxy)-5-(3-methoxyphenyl)pyridin-3-yl]methyl}pyrimidine-2-carboxamide |
| 116 | 5-{[5-(3-Chlorophenyl)-6-methoxypyridin-3-yl]methyl}pyridine-2-carboxamide |
| 117 | 5-{[5-(3-Chlorophenyl)-6-(difluoromethoxy)pyridin-3-yl]methyl}pyrimidine-2-carboxamide |
| 118 | 5-{[5-(3-Fluorophenyl)-6-methoxypyridin-3-yl]methyl}pyrimidine-2-carboxamide |
| 119 | 5-({5-[3-(Difluoromethoxy)phenyl]-6-ethoxypyridin-3-yl}methyl)pyrimidine-2-carboxamide |
| 120 | 5-({5-[2-(Difluoromethoxy)pyridin-4-yl]-6-methoxypyridin-3-yl}methyl)pyrimidine-2-carboxamide |
| 121 | 5-({5-[3-(Difluoromethoxy)phenyl]-6-methoxypyridin-3-yl}methyl)pyrimidine-2-carboxamide |
| 122 | 5-({5-[2-(Difluoromethoxy)pyridin-4-yl]-6-ethoxypyridin-3-yl}methyl)pyrimidine-2-carboxamide |
| 123 | 5-{[6-(3-Chlorophenyl)-5-methoxypyrazin-2-yl]methyl}pyrimidine-2-carboxamide |
| 124 | 5-({6-[3-(Difluoromethoxy)phenyl]-5-ethoxypyrazin-2-yl}methyl)pyridine-2-carboxamide |
| 125 | 5-({6-[3-(Difluoromethoxy)phenyl]-5-methoxypyrazin-2-yl}methyl)pyrimidine-2-carboxamide |
| 126 | 5-{[6-(3-Chlorophenyl)-5-ethoxypyrazin-2-yl]methyl}pyrimidine-2-carboxamide |

| Ex | Chemical Name |
|---|---|
| 127 | Methyl 1-{[6-(3-chlorophenyl)-5-methoxypyrazin-2-yl]methyl}-1H-1,2,4-triazole-3-carboxylate |
| 128 | 3-(3-Chlorophenyl)-5-[(3-cyclopropyl-1H-1,2,4-triazol-1-yl)methyl]-2-(difluoromethoxy)pyridine |
| 129 | 3-(3-Fluorophenyl)-2-methoxy-5-(1H-1,2,4-triazol-1-ylmethyl)pyridine |
| 130 | 3-(3-Chlorophenyl)-2-methoxy-5-(1H-1,2,4-triazol-1-ylmethyl)pyrazine |
| 131 | 3-(3-Chlorophenyl)-2-(difluoromethoxy)-5-(1H-1,2,4-triazol-1-ylmethyl)pyridine |
| 132 | 3-(3-Chlorophenyl)-2-methoxy-5-[(3-methyl-1H-1,2,4-triazol-1-yl)methyl]pyrazine |
| 133 | 3-(3-Chlorophenyl)-5-[(3-cyclopropyl-1H-1,2,4-triazol-1-yl)methyl]-2-methoxypyrazine |
| 134 | 3-(3-Chlorophenyl)-2-methoxy-5-(1H-1,2,4-triazol-1-ylmethyl)pyridine |
| 135 | 3-(3-Chlorophenyl)-2-(propan-2-yloxy)-5-(1H-1,2,4-triazol-1-ylmethyl)pyridine |
| 136 | 3-[2-Methoxy-5-(1H-1,2,4-triazol-1-ylmethyl)pyridin-3-yl]benzonitrile |
| 137 | 2-Methoxy-5-(1H-1,2,4-triazol-1-ylmethyl)-3-[3-(trifluoromethoxy)phenyl]pyridine |
| 138 | 3-(3-Chlorophenyl)-2-methoxy-5-[(3-methyl-4H-1,2,4-triazol-4-yl)methyl]pyridine |
| 139 | 3-(3,5-Difluorophenyl)-2-methoxy-5-(1H-1,2,4-triazol-1-ylmethyl)pyridine |
| 140 | Methyl 1-{[5-(3-chlorophenyl)-6-methoxypyridin-3-yl]methyl}-1H-1,2,4-triazole-5-carboxylate |
| 141 | Methyl 1-{[5-(3-chlorophenyl)-6-methoxypyridin-3-yl]methyl}-1H-1,2,4-triazole-3-carboxylate |
| 142 | 3-(4-Chlorothiophen-2-yl)-2-methoxy-5-(1H-1,2,4-triazol-1-ylmethyl)pyridine |
| 143 | 3-(3-Chlorophenyl)-2-methoxy-5-[(3-methyl-1H-1,2,4-triazol-1-yl)methyl]pyridine |
| 144 | 3-[3-(Difluoromethyl)phenyl]-2-methoxy-5-(1H-1,2,4-triazol-1-ylmethyl)pyridine |
| 145 | 3-(3-Chlorophenyl)-2-methoxy-5-(1H-pyrazol-1-ylmethyl)pyridine |
| 146 | 3-(3-Chlorophenyl)-2-methoxy-5-{[3-(trifluoromethyl)-1H-1,2,4-triazol-1-yl]methyl}pyridine |
| 147 | 3-(3-Chlorophenyl)-5-[(3-cyclopropyl-1H-1,2,4-triazol-1-yl)methyl]-2-methoxypyridine |
| 148 | 3-(3-Chlorophenyl)-2-(difluoromethoxy)-5-[(3-methyl-1H-1,2,4-triazol-1-yl)methyl]pyridine |
| 149 | 3-(3-Chlorophenyl)-2-methoxy-5-{[4-(trifluoromethyl)-1H-imidazol-1-yl]methyl}pyridine |
| 150 | 3-(3-Chlorophenyl)-2-(difluoromethoxy)-5-[1-(1H-1,2,4-triazol-1-yl)ethyl]pyridine |
| 151 | 3-(3-Fluorophenyl)-2-methoxy-5-[(3-methyl-1H-1,2,4-triazol-1-yl)methyl]pyridine |
| 152 | 3-(3-Chlorophenyl)-2-ethoxy-5-{[3-(trifluoromethyl)-1H-1,2,4-triazol-1-yl]methyl}pyridine |
| 153 | 3-(3-Chlorophenyl)-2-ethoxy-5-{[5-(trifluoromethyl)-1H-1,2,4-triazol-1-yl]methyl}pyridine |
| 154 | 3-(3-Chlorophenyl)-2-(difluoromethoxy)-5-[(4-methyl-1H-imidazol-1-yl)methyl]pyridine |
| 155 | 3-[3-(Difluoromethoxy)phenyl]-2-methoxy-5-[(3-methyl-1H-1,2,4-triazol-1-yl)methyl]pyridine |
| 156 | 1-{[5-(3-Chlorophenyl)-6-(difluoromethoxy)pyridin-3-yl]methyl}-1H-1,2,4-triazole-3-carbonitrile |
| 157 | 3-(3-Chlorophenyl)-2-(difluoromethoxy)-5-{[3-(methoxymethyl)-1H-1,2,4-triazol-1-yl]methyl}pyridine |
| 158 | 3-(3-Chlorophenyl)-2-(difluoromethoxy)-5-{[5-(methoxymethyl)-1H-1,2,4-triazol-1-yl]methyl}pyridine |
| 159 | 3-[3-(Difluoromethoxy)phenyl]-2-methoxy-5-{[3-(trifluoromethyl)-1H-1,2,4-triazol-1-yl]methyl}pyridine |
| 160 | 3-[3-(Difluoromethoxy)phenyl]-2-methoxy-5-{[5-(trifluoromethyl)-1H-1,2,4-triazol-1-yl]methyl}pyridine |
| 161 | 3-(3-Chlorophenyl)-2-(difluoromethoxy)-5-(1H-1,2,3,4-tetrazol-1-ylmethyl)pyridine |
| 162 | 3-(3-Chlorophenyl)-2-(difluoromethoxy)-5-(2H-1,2,3,4-tetrazol-2-ylmethyl)pyridine |
| 163 | 3-[3-(Difluoromethoxy)phenyl]-2-ethoxy-5-{[3-(trifluoromethyl)-1H-1,2,4-triazol-1-yl]methyl}pyridine |
| 164 | 3-[3-(Difluoromethoxy)phenyl]-2-ethoxy-5-{[5-(trifluoromethyl)-1H-1,2,4-triazol-1-yl]methyl}pyridine |
| 165 | 3-[3-(Difluoromethoxy)phenyl]-2-ethoxy-5-{[3-(methoxymethyl)-1H-1,2,4-triazol-1-yl]methyl}pyridine |
| 166 | 3-[3-(Difluoromethoxy)phenyl]-2-ethoxy-5-{[5-(methoxymethyl)-1H-1,2,4-triazol-1-yl]methyl}pyridine |
| 167 | 5-[(4-Chloro-1H-pyrazol-1-yl)methyl]-3-[3-(difluoromethoxy)phenyl]-2-methoxypyridine |
| 168 | 1-{[5-(3-Chlorophenyl)-6-ethoxypyridin-3-yl]methyl}-1H-pyrazole-3-carboxamide |
| 169 | Ethyl 1-{[5-(3-chlorophenyl)-6-methoxypyridin-3-yl]methyl}-1H-pyrazole-4-carboxylate |
| 170 | 1-{[5-(3-Chlorophenyl)-6-methoxypyridin-3-yl] methyl}-1H-pyrazole-4-carbonitrile |

| Ex | Chemical Name |
|---|---|
| 171 | 2-Methoxy-3-(pyridin-4-yl)-5-(1H-1,2,4-triazol-1-ylmethyl)pyridine |
| 172 | N-(1-{[5-(3-Chlorophenyl)-6-methoxypyridin-3-yl]methyl}-1H-pyrazol-4-yl)acetamide |
| 173 | 3-(3-Chlorophenyl)-5-(1H-imidazol-1-ylmethyl)-2-methoxypyridine |
| 174 | 2-(Difluoromethoxy)-3-(3-fluorophenyl)-5-(1H-1,2,4-triazol-1-ylmethyl)pyridine |
| 175 | 2-(Difluoromethoxy)-3-(3-methoxyphenyl)-5-(1H-1,2,4-triazol-1-ylmethyl)pyridine |
| 176 | 2-(Difluoromethoxy)-5-(1H-1,2,4-triazol-1-ylmethyl)-3-[3-(trifluoromethoxy)phenyl]pyridine |
| 177 | 1-{[5-(3-Chlorophenyl)-6-methoxypyridin-3-yl]methyl}-1,2-dihydropyridin-2-one |
| 178 | 5-[(4-Chloro-1H-pyrazol-1-yl)methyl]-3-(3-chlorophenyl)-2-methoxypyridine |
| 179 | 3-(3-Chlorophenyl)-2-methoxy-5-[(4-methyl-1H-pyrazol-1-yl)methyl]pyridine |
| 180 | 3-(3-Chlorophenyl)-2-methoxy-5-[(4-nitro-1H-pyrazol-1-yl)methyl]pyridine |
| 181 | 3-(3-Chlorophenyl)-2-methoxy-5-[(4-nitro-1H-pyrazol-1-yl)methyl]pyrazine |
| 182 | 3-(3-Chlorophenyl)-2-methoxy-5-(1H-pyrazol-1-ylmethyl)pyrazine |
| 183 | 3-(3-Chlorophenyl)-5-(1H-imidazol-1-ylmethyl)-2-methoxypyrazine |
| 184 | 3-(3-Chlorophenyl)-2-methoxy-5-[(4-methyl-1H-pyrazol-1-yl)methyl]pyrazine |
| 185 | 3-[3-(Difluoromethoxy)phenyl]-2-ethoxy-5-[(3-methyl-1H-1,2,4-triazol-1-yl)methyl]pyrazine |
| 186 | 5-[(3-Cyclopropyl-1H-1,2,4-triazol-1-yl)methyl]-3-[3-(diflurormethoxy)phenyl]-2-ethoxypyrazine |
| 187 | 3-[3-(Difluoromethoxy)phenyl]-2-ethoxy-5-{[3-(trifluoromethyl)-1H-1,2,4-triazol-1-yl]methyl}pyrazine |
| 188 | 3-3-(Difluoromethoxy)phenyl]-2-ethoxy-5-{[5-(trifluoromethyl)-1H-1,2,4-triazol-1-yl]methyl}pyrazine |
| 189 | 3-[3-(Difluoromethoxy)phenyl]-2-ethoxy-5-{[3-(methoxymethyl)-1H-1,2,4-triazol-1-yl]methyl}pyrazine |
| 190 | 3-[3-(Difluoromethoxy)phenyl]-2-ethoxy-5-{[5-(methoxymethyl)-1H-1,2,4-triazol-1-yl]methyl}pyrazine |
| 191 | Methyl 1-((6-(3-(difluoromethoxy)phenyl)-5-ethoxypyrazin-2-yl)methyl)-1H-1,2,4-triazole-3-carboxylate |
| 192 | Methyl 1-((6-(3-(difluoromethoxy)phenyl)-5-ethoxypyrazin-2-yl)methyl)-1H-1,2,4-triazole-5-carboxylate |
| 193 | 3-(3-(Difluoromethoxy)phenyl)-2-ethoxy-5-((3-nitro-1H-1,2,4-triazol-1-yl)methyl)pyrazine |
| 194 | 3-(3-(Difluoromethoxy)phenyl)-2-ethoxy-5-((5-nitro-1H-1,2,4-triazol-1-yl)methyl)pyrazine |
| 195 | Methyl 1-{[6-(3-chlorophenyl)-5-methoxypyrazin-2-yl]methyl}-1H-1,2,4-triazole-5-carboxylate |
| 196 | Methyl 1-({6-[3-difluoromethyoxy)phenyl]-5-methoxypyrazin-2-yl}methyl)-1H-1,2,4-triazole-3-carboxylate |
| 197 | Methyl 1-{[6-(3-chlorophenyl)-5-ethoxypyrazin-2-yl]methyl}-1H-1,2,4-triazole-3-carboxylate |
| 198 | 1-{[5-(3-Chlorophenyl)-6-(difluoromethoxy)pyridin-3-yl]methyl}-1H-imidazole-4-carboxamide |
| 199 | (1-{[6-(3-Chlorophenyl)-5-methoxypyridin-2-yl]methyl}-1H-1,2,4-triazol-3-yl)methanol |
| 200 | (1-{[5-(3-Chlorophenyl)-6-(difluoromethoxy)pyridin-3-yl]methyl}-1H-1,2,4-triazol-3-yl)methanol |
| 201 | [1-({5-[3-Difluoromethoxy)phenyl]-6-ethoxypyridin-3-yl}methyl)-1H-1,2,4-triazol-3-yl]methanol |
| 202 | [1-({5-[3-Difluoromethoxy)phenyl]-6-methoxypyridin-3-yl}methyl)-1H-1,2,4-triazol-3-yl]methanol |
| 203 | (1-((5-(3-Chlorophenyl)-6-ethoxypyridin-3-yl)methyl)-1H-1,2,4-triazol-3-yl)methanol |
| 204 | (1-{[6-(Difluoromethoxy)-5-(3-ethoxyphenyl)pyridin-3-yl]methyl}-1H-1,2,4-triazol-3-yl)methanol |
| 205 | [1-({5-[2-(Difluoromethoxy)pyridin-4-yl]-6-methoxypyridin-3-yl}methyl)-1H-1,2,4-triazol-3-yl]methanol |
| 206 | [1-({5-[2-(Difluoromethoxy)pyridin-4-yl]-6-ethoxypyridin-3-yl}methyl)-1H-1,2,4-triazol-3-yl]methanol |
| 207 | (1-{[6-(Difluoromethoxy)-5-[2-(difluoromethoxy)pyridin-4-yl]pyridin-3-yl]methyl}-1H-1,2,4-triazol-3-yl)methanol |
| 208 | [1-({6-[3-(Difluoromethoxy)phenyl]-5-ethoxypyridin-2-yl}methyl)-1H-1,2,4-triazol-3-yl]methanol |
| 209 | [1-({6-[3-(Difluoromethoxy)phenyl]-5-ethoxypyrazin-2-yl}methyl)-1H-1,2,4-triazol-5-yl]methanol |
| 210 | (1-{[6-(3-Chlorophenyl)-5-methoxypyrazin-2-yl]methyl}-1H-1,2,4-triazol-5-yl)methanol |
| 211 | [1-({6-[3-(Difluoromethoxy)phenyl]-5-methoxypyrazin-2-yl}methyl)-1H-1,2,4-triazol-3-yl]methanol |
| 212 | (1-{[6-(3-Chlorophenyl)-5-ethoxyprazin-2-yl]methyl}-1H-1,2,4-triazol-3-yl)methanol |
| 213 | 3-(3-Chlorophenyl)-2-methoxy-5-[(3-methoxy-1H-1,2,4-triazol-1-yl)methyl]pyridine |
| 214 | 3-(3-Chlorophenyl)-2-(difluoromethoxy)-5-[(3-methoxy-1H-1,2,4-triazol-1-yl)methyl]pyridine |

| Ex | Chemical Name |
|---|---|
| 215 | 3-(3-Chlorophenyl)-2-(difluoromethoxy)-5-[(5-methoxy-1H-1,2,4-triazol-1-yl)methyl]pyridine |
| 216 | 3-(3-Chlorophenyl)-2-(difluoromethoxy)-5-(3-ethoxy-1H-1,2,4-triazol-1-yl)methyl]pyridine |
| 217 | [1-({5-[3-Difluoromethoxy)phenyl]-6-methoxypyridin-3-yl}methyl]-1H-1,2,4-triazol-3-amine |
| 218 | 1-{[5-(3-Chlorophenyl)-6-methoxypyridin-3-yl]methyl}-1H-1,2,4-triazol-3-amine |
| 219 | 1-{[5-(3-Chlorophenyl)-6-(difluoromethoxy)pyridin-3-yl]methyl}-1H-1,2,4-triazol-3-amine |
| 220 | 1-{[5-(3-Fluorophenyl)-6-methoxypyridin-3-yl]methyl}-1H-1,2,4-triazol-3-amine |
| 221 | 1-{[6-Methoxy-5-(3-methoxyphenyl)pyridin-3-yl]methyl}-1H-1,2,4-triazol-3-amine |
| 222 | 1-{[6-Methoxy-5-(3-methylphenyl)pyridin-3-yl]methyl}-1H-1,2,4-triazol-3-amine |
| 223 | 3-{5-[(3-Amino-1H-1,2,4-triazol-1-yl)methyl]-2-methoxypyridin-3-yl}benzonitrile |
| 224 | 1-{[5-(3-Ethoxyphenyl)-6-methoxypyridin-3-yl]methyl}-1H-1,2,4-triazol-3-amine |
| 225 | 1-{[5-(3-Cyclopropoxyphenyl)-6-methoxypyridin-3-yl]methyl}-1H-1,2,4-triazol-3-amine |
| 226 | 1-({5-[3-(Difluoromethoxy)phenyl]-6-ethoxypyrazin-3-yl}methyl)-1H-1,2,4-triazol-3-amine |
| 227 | 1-{[6-(Difluoromethoxy)-5-(3-methoxyphenyl)pyridin-3-yl]methyl}-1H-1,2,4-triazol-3-amine |
| 228 | 1-{[5-(5-Chloropyridin-3-yl)-6-methoxypyridin-3-yl]methyl}-1H-1,2,4-triazol-3-amine |
| 229 | 1-({5-[2-(Difluoromethoxy)pyridin-4-yl]-6-methoxypyridin-3-yl}methyl)-1H-1,2,4-triazol-3-amine |
| 230 | 1-({5-[2-(Difluoromethoxy)pyridin-4-yl]-6-ethoxypyridin-3-yl}methyl)-1H-1,2,4-triazol-3-amine |
| 231 | 1-{[6-(Difluoromethoxy)-5-[2-(difluoromethoxy)pyridin-4-yl]pyridin-3-yl]methyl}-1H-1,2,4-triazol-3-amine |
| 232 | 1-({5-[3-(Difluoromethoxy)phenyl]-6-methoxypyridin-3-yl}methyl)-1H-pyrazol-3-amine |
| 233 | 1-({5-[3-(Difluoromethoxy)phenyl]-6-methoxypyridin-3-yl}methyl)-1H-pyrazol-5-amine |
| 234 | 4-Chloro-1-{[5-(3-chlorophenyl)-6-ethoxypyridin-3-yl]methyl}-1H-pyrazol-3-amine |
| 235 | 4-Chloro-1-{[5-(3-chlorophenyl)-6-ethoxypyridin-3-yl]methyl}-1H-pyrazol-5-amine |
| 236 | 1-{[6-(3-Chlorophenyl)-5-methoxypyrazin-2-yl]methyl}-1H-pyrazol-4-amine |
| 237 | 1-((6-(3-(Difluoromethoxy)phenyl)-5-ethoxypyrazin-2-yl)methyl)-1H-1,2,4-triazol-3-amine |
| 238 | 1-{[5-(3-Chlorophenyl)-6-(difluoromethoxy)pyridin-3-yl]methyl}-N-methyl-1H-1,2,4-triazol-3-amine |
| 239 | 1-{[5-(3-Chlorophenyl)-6-(difluoromethoxy)pyridin-3-yl]methyl}-N,N-dimethyl-1H-1,2,4-triazol-3-amine |
| 240 | (1-{[5-(3-Chlorophenyl)-6-(difluoromethoxy)pyridin-3-yl]methyl}-1H-1,2,4-triazol-3-yl)methanamine |
| 241 | 1-{[5-(3-Chlorophenyl)-6-methoxypyridin-3-yl]methyl}-1H-1,2,4-triazole-3-carboxamide |
| 242 | 2-Methoxy-3-(1H-pyrazol-4-yl)-5-(1H-1,2,4-triazol-1-ylmethyl)pyridine |
| 243 | 4-{[5-(3-Chlorophenyl)-6-methoxypyridin-3-yl]methyl}-N-(oxetan-3-yl)benzamide |
| 244 | 5-{[5-(3-Chlorophenyl)-6-(difluoromethoxy)pyridin-3-yl]methyl}-N-methylpyridine-2-carboxamide |
| 245 | 1-(4-{[5-(3-Chlorophenyl)-6-(difluoromethoxy)pyridin-3-yl]methyl}phenyl)cyclopropane-1-carboxamide |
| 246 | 2-(4-{[5-(3-Chlorophenyl)-6-(difluoromethoxy)pyridin-3-yl]methyl}phenyl)acetamide |
| 247 | 2-(1-{[5-(3-Chlorophenyl)-6-methoxypyridin-3-yl]methyl}-1H-1,2,4-trizaol-3-yl)propan-2-ol |
| 248 | 2-Methoxy-3-(1-methyl-1H-pyrazol-4-yl)-5-(1H-1,2,4-triazol-1-ylmethyl)pyridine |
| 249 | 2-(1-{[5-(3-Chlorophenyl)-6-methoxypyridin-3-yl]methyl}-1H-1,2,4-trizaol-5-yl)propan-2-ol |
| 250 | 2-(4-{[5-(3-Chlorophenyl)-6-methoxypyridin-3-yl]methyl}phenyl)propan-2-ol |
| 251 | 2-(5-{[5-(3-Chlorophenyl)-6-methoxypyridin-3-yl]methyl}pyridin-2-yl)propan-2-ol |
| 252 | 2-(5-{[5-(3-Chlorophenyl)-6-(difluoromethoxy)pyridin-3-yl]methyl}pyridin-2-yl)propan-2-ol |
| 253 | 3-[3-(Difluoromethoxy)phenyl]-5-{[3-(fluoromethyl)-1H-1,2,4-triazol-1-yl]methyl}-2-methoxypyridine |
| 254 | 3-[3-(Difluoromethoxy)phenyl]-2-ethoxy-5-{[4-(fluoromethyl)-1H-1,2,3-triazol-1-yl]methyl}pyridine |
| 255 | 2-(Difluoromethoxy)-3-(3-ethoxyphenyl)-5-{[3-(fluoromethyl)-1H-1,2,4-triazol-1-yl]methyl}pyridine |
| 256 | 3-[2-(Difluoromethoxy)pyridin-4-yl]-5-{[3-(fluoromethyl)-1H-1,2,4-triazol-1-yl]methyl}-2-methoxypyridine |

-continued

| Ex | Chemical Name |
|---|---|
| 257 | 3-[3-(Difluoromethoxy)phenyl]-2-ethoxy-5-{[3-(fluoromethyl)-1H-1,2,4-triazol-1-yl]methyl}pyrazine |
| 258 | 3-(3-Chlorophenyl)-5-{[3-(fluoromethyl)-1H-1,2,4-triazol-1-yl]methyl}-2-methoxypyrazine |
| 259 | 3-(3-Chlorophenyl)-2-(difluoromethoxy)-5-{[3-(difluoromethyl)-1H-1,2,4-triazol-1-yl]methyl}pyridine |
| 260 | 3-[3-(Difluoromethoxy)phenyl]-5-{[3-(difluoromethyl)-1H-1,2,4-triazol-1-yl]methyl}-2-ethoxypyridine |
| 261 | 3-[2-(Difluoromethoxy)pyridin-4-yl]-5-{[3-(difluoromethyl)-1H-1,2,4-triazol-1-yl]methyl}-2-methoxypyridine |
| 262 | 3-(3-Chlorophenyl)-2-methoxy-5-(1H-1,2,3-triazol-1-ylmethyl)pyridine |
| 263 | [1-({5-[3-(Difluoromethoxy)phenyl]-6-ethoxypyridin-3-yl}methyl)-1H-1,2,3-triazol-4-yl]methanol |
| 264 | (1-((6-(Difluoromethoxy)-5-(3-ethoxyphenyl)pyridin-3-yl)methyl)-1H-1,2,3-triazol-4-yl)methanol |
| 265 | (1-({6-[3-(Difluoromethoxy)phenyl]-5-ethoxypyrazin-2-yl}methyl)-1H-1,2,3-triazol-4-yl]methanol |
| 266 | (1-{[6-(3-Chlorophenyl)-5-methoxypyrazin-2-yl]methyl}-1H-1,2,3-triazol-4-yl)methanol |
| 267 | [1-({6-[3-(Difluoromethoxy)phenyl]-5-methoxypyrazin-2-yl}methyl)-1H-1,2,3-triazol-4-yl]methanol |
| 268 | (1-{[6-(3-Chlorophenyl)-5-ethoxypyrazin-2-yl]methyl}-1H-1,2,3-triazol-4-yl)methanol |
| 269 | 3-[3-(Difluoromethoxy)phenyl]-5-{[4-(difluoromethyl)-1H-1,2,3-triazol-1-yl]methyl}-2-ethoxypyridine |
| 270 | 1-{[5-(3-Chlorophenyl)-6-methoxypyridin-3-yl]methyl}-1H-pyrazole-4-carboxylic acid |
| 271 | 1-{[5-(3-Chlorophenyl)-6-methoxypyridin-3-yl]methyl}-1H-pyrazole-4-carboxamide |
| 272 | [1-({5-[3-(Difluoromethoxy)phenyl]-6-methoxypyridin-3-yl}methyl)-1H-pyrazol-4-yl]methanol |
| 273 | (1-{[5-(3-Chlorophenyl)-6-(difluoromethoxy)pyridin-3-yl]methyl}-1H-imidazol-5-yl)methanol |
| 274 | (1-{[5-(3-Chlorophenyl)-6-(difluoromethoxy)pyridin-3-yl]methyl}-1H-imidazol-4-yl)methanol |
| 275 | [1-({5-[3-(Difluoromethoxy)phenyl]-6-methoxypyridin-3-yl}methyl)-1H-pyrazol-3-yl]methanol |
| 276 | 1-{[5-(3-Chlorophenyl)-6-ethoxypyridin-3-yl]methyl}-1H-pyrazole-4-yl)methanol |
| 277 | (4-Chloro-1-{[5-(3-chlorophenyl)-6-ethoxypyridin-3-yl]methyl}-1H-pyrazol-3-yl)methanol |
| 278 | (4-Chloro-1-{[5-(3-chlorophenyl)-6-ethoxypyridin-3-yl]methyl}-1H-pyrazol-5-yl)methanol |
| 279 | 3-(4-Chloro-1H-pyrazol-1-yl)-2-methoxy-5-(1H-1,2,4-triazol-1-ylmethyl)pyridine |
| 280 | 4-{[5-(3-Chlorophenyl)-6-(difluoromethoxy)pyridin-3-yl]methyl}benzoic acid |

Isotopically-Labeled Compounds

The invention also includes isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of carbon, chlorine, fluorine, hydrogen, iodine, nitrogen, oxygen, phosphorous, sulfur, and technetium, including $^{11}C$, $^{13}C$, $^{14}C$, $^{36}Cl$, $^{18}F$, $^{2}H$, $^{3}H$, $^{123}I$, $^{125}I$, $^{13}N$, $^{15}N$, $^{15}O$, $^{17}O$, $^{18}O$, $^{31}P$, $^{32}P$, $^{35}S$, and $^{99m}Tc$.

Compounds of the present invention (and derivatives of such compounds, such as pharmaceutically acceptable salts and prodrugs) that contain the aforementioned isotopes or other isotopes of other atoms are within the scope of the invention. Isotopically-labeled compounds of the present invention are useful in drug and substrate tissue distribution and target occupancy assays. For example, isotopically labeled compounds are particularly useful in SPECT (single photon emission computed tomography) and in PET (positron emission tomography), as discussed further herein.

Derivatives

The present invention also provides derivatives of a chemical entity of Formula (I), which include, but are not limited to, any salt, solvate, conformer, crystalline or form/polymorph.

Salts

Accordingly, in one embodiment the invention includes pharmaceutically acceptable salts of the compounds represented by Formula (I), and methods using such salts.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, borate, nitrate, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methane-sulfonates, propane sulfonates, naphthalene-1-sulfonates, naphthalene-2-sulfonates, besylate, mesylate and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-O-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

Solvates

In other embodiments, the invention provides a solvate of a compound of Formula (I), and the use of such solvates in methods of present invention. Certain compounds of Formula (I) or pharmaceutically acceptable salts of compounds of Formula (I) may be obtained as solvates. In some embodiments, the solvent is water and the solvates are hydrates.

More particularly, solvates include those formed from the interaction or complexes of compounds of the invention with one or more solvents, either in solution or as a solid or crystalline form. Such solvent molecules are those commonly used in the pharmaceutical art, which are known to be innocuous to the recipient, e.g., water, ethanol, ethylene glycol, and the like. Other solvents may be used as intermediate solvates in the preparation of more desirable solvates, such as MeOH, methyl t-butyl ether, ethyl acetate, methyl acetate, (S)-propylene glycol, (R)-propylene glycol, 1,4-butyne-diol, and the like. Hydrates include compounds formed by an incorporation of one or more water molecules.

Conformers and Crystalline Forms/Polymorphs

In other embodiments, the invention provides conformer and crystalline form of a compound of Formula (I), and the use of these derivatives in methods of present invention. A conformer is a structure that is a conformational isomer. Conformational isomerism is the phenomenon of molecules with the same structural formula but different conformations (conformers) of atoms about a rotating bond.

A polymorph is a composition having the same chemical formula, but a different solid state or crystal structure. In certain embodiments of the invention, compounds of Formula (I) were obtained in crystalline form. In addition, certain crystalline forms of compounds of Formula (I) or pharmaceutically acceptable salts of compounds of Formula (I) may be obtained as co-crystals. In still other embodiments, compounds of Formula (I) may be obtained in one of several polymorphic forms, as a mixture of crystalline forms, as a polymorphic form, or as an amorphous form.

Prodrugs

The invention also relates to prodrugs of the compounds of Formula (I), and the use of such pharmaceutically acceptable prodrugs in methods of the present invention, particularly therapeutic methods. Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$ alkyl primary amines, and di($C_{1-2}$alkyl)amines. Examples of esters of the invention include $C_{1-6}$alkyl, $C_{1-6}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130.

Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J. Med. Chem.* 1996, 39, 10-18. Free amines can also be derivatized as amides, sulfonamides or phosphonamides. All of these prodrug moieties may incorporate groups including ether, amine, and carboxylic acid functionalities.

Prodrugs may be determined using routine techniques known or available in the art (e.g., Bundgard (ed.), 1985, Design of prodrugs, Elsevier; Krogsgaard-Larsen et al., (eds.), 1991, Design and Application of Prodrugs, Harwood Academic Publishers).

Metabolites

The present invention also relates to a metabolite of a compound of Formula (I), as defined herein, and salts thereof. The present invention further relates to the use of such metabolites, and salts thereof, in methods of present invention, including therapeutic methods.

Metabolites of a compound may be determined using routine techniques known or available in the art. For example, isolated metabolites can be enzymatically and synthetically produced (e.g., Bertolini et al., *J. Med. Chem.* 1997, 40, 2011-2016; Shan et al., *J. Pharm. Sci.* 1997, 86, 765-767;

Bagshawe, *Drug Dev. Res.* 1995, 34, 220-230; and Bodor, *Adv Drug Res.* 1984, 13, 224-231).

Compositions

In some embodiments compounds of Formula (I) and pharmaceutically acceptable salts thereof are used, alone or in combination with one or more additional active ingredients, to formulate pharmaceutical compositions. A pharmaceutical composition of the invention comprises: (a) an effective amount of at least one active agent in accordance with the invention; and (b) a pharmaceutically acceptable excipient.

Formulations and Administration

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Osol, ed.), 1980, 1553-1593.

Any suitable route of administration may be employed for providing an animal, especially a human, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent, or excipient used will depend upon the means and purpose for which the compound of the present invention is being applied. Solvents are generally selected based on solvents recognized by persons skilled in the art as safe (GRAS) to be administered to an animal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., a compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable and appropriate dosage of the drug.

The pharmaceutical composition (or formulation) for application may be packaged in a variety of ways, depending upon the method used to administer the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with a variety of the other ingredients enumerated above, as required, followed by filter sterilization. In the case of sterile powders for the preparation of sterile injectable solutions, common methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of the compounds of Formula (I) can be determined by comparing their in vitro activity and in vivo activity in animal models. Methods for the extrapolation of effective dosages in mice, and other animals, to humans are known to the art. Useful dosages of the compounds of formula I can be determined by comparing their in vitro activity, and in vivo activity in animal models. Methods for the extrapolation of effective dosages in mice, and other animals, to humans are known to the art (e.g., U.S. Pat. No. 4,938,949). Useful dosages of PDE4 inhibitors are known to the art (e.g., U.S. Pat. No. 7,829,713; U.S. Pat. No. 8,338,405).

Optimal dosages to be administered in the therapeutic methods of the present invention may be determined by those skilled in the art and will depend on multiple factors, including the particular composition in use, the strength of the preparation, the mode and time of administration, and the advancement of the disease or condition. Additional factors may include characteristics on the subject being treated, such as age, weight, gender, and diet.

In general, however, a suitable dose will be in the range from about 0.01 to about 100 mg/kg, more specifically from about 0.1 to about 100 mg/kg, such as 10 to about 75 mg/kg of body weight per day, 3 to about 50 mg per kilogram body weight of the recipient per day, 0.5 to 90 mg/kg/day, or 1 to 60 mg/kg/day (or any other value or range of values therein). The compound is conveniently administered in a unit dosage form; for example, containing about 1 to 1000 mg, particularly about 10 to 750 mg, and more particularly, about 50 to 500 mg of active ingredient per unit dosage form.

Preferably, the active ingredient should be administered to achieve peak plasma concentrations of the active compound of from about 0.5 to about 75 µM, preferably, about 1 to 50 µM, and more preferably, about 2 to about 30 µM. This may be achieved, for example, by the intravenous injection of a 0.05 to 5% solution of the active ingredient, optionally in saline, or orally administered as a bolus containing about 1 to 100 mg of the active ingredient. Desirable blood levels may be maintained by continuous infusion to provide about 0.01 to 5.0 mg/kg/hr or by intermittent infusions containing about 0.4 to 15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of temporally-distinct administrations used according to the compositions and methods of the present invention.

Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. Such compositions and preparations should contain at least 0.1% of active compound. The percentage of the compositions and preparations may, of course, be varied and may conveniently be between 2 to about 60% of the weight of a given unit dosage form. The amount of active compound in such therapeutically useful composition is such that an effective dosage level will be obtained. An exemplary dose is in the range from about 0.001 to about 200 mg of active agent per kg of subject's body weight per day, preferably about 0.05 to 100 mg/kg/day, or about 1 to 35 mg/kg/day, or about 0.1 to 10 mg/kg/daily in single or divided dosage units (e.g., BID, TID, QID). For a 70-kg human, an illustrative range for a suitable dosage amount is from 1 to 200 mg/day, or about 5 to 50 mg/day.

Methods and Uses

Uses of Isotopically-Labeled Compounds

In one aspect, the present invention provides a method of using isotopically labeled compounds and prodrugs of the present invention in: (i) metabolic studies (preferably with $^{14}C$), reaction kinetic studies (with, for example $^{2}H$ or $^{3}H$); (ii) detection or imaging techniques [such as positron emission tomography (PET) or single-photon emission computed tomography (SPECT)] including drug or substrate tissue distribution assays; or (iii) in radioactive treatment of patients.

Isotopically labeled compounds and prodrugs of the invention thereof can generally be prepared by carrying out the procedures disclosed in the schemes or in the examples and preparations described below by substituting a readily available isotopically labeled reagent for a non-isotopically labeled reagent. An $^{18}F$ or $^{11}C$ labeled compound may be particularly preferred for PET, and an $I^{123}$ labeled compound may be particularly preferred for SPECT studies. Further substitution with heavier isotopes such as deuterium (i.e., $^{2}H$) may afford certain therapeutic advantages resulting from greater metabolic stability, for example increased in vivo half-life or reduced dosage requirements.

Therapeutic Methods

Generally

In certain embodiments the present invention provides therapeutic methods of using a compound of Formula (I) and its pharmaceutically acceptable salts, pharmaceutically acceptable prodrugs, and pharmaceutically active metabolites, whether alone or in combination (collectively, "active agents") of the present invention are useful as inhibiting PDE4 in the methods of the invention. Such methods for inhibiting PDE4 comprising administering to an animal an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Embodiments of this invention inhibit PDE4. The invention further includes the use compositions of such chemical entities in the methods described herein. In one aspect of such methods disclosed herein, the animal is healthy. In another aspect of such methods, the animal has a disorder. In another aspect of all such methods the animal is an aged animal. In preferred embodiments of such methods, the animal is a human.

Chemical entities of the present invention may be administered as a mono-therapy or as part of a combination therapy. In one aspect, one or more of the compounds (or salts, prodrugs, or metabolites thereof) of the present invention may be co-administered or used in combination with one or more additional therapies known in the art.

Compounds of the present invention may also be used as adjunct therapy, for example, with other PDE inhibitors.

The present invention also includes methods of treating a disease, disorder, or condition mediated by PDE4. Accordingly, in one embodiment, the invention provides a method of treating a disorder mediated by PDE4 in particular, comprising administering to an animal in need of such treatment an effective amount of a chemical entity of Formula (I) or composition of the present invention.

In certain embodiments, the present invention includes the use of a chemical entity of Formula (I) in the manufacture of a medicament for treating a disease, condition, or disorder by inhibiting PDE4 The present invention further provides a method of administering a therapeutically effective amount of a medicament of the present invention to a patient in need of such treatment to treat the disorder.

In one aspect, the compounds of the present invention are useful in enhancing neuronal plasticity—an essential property of the brain that can be augmented in healthy animals and can be impaired in numerous CNS disorders. For example, by inhibiting PDE4, a compound of the present invention can increase levels of cAMP, modulating cyclic nucleotide signaling cascades.

More particularly, the ability of extracellular signals to modulate the intracellular concentration of cyclic nucleotides allows cells to respond to external stimuli across the boundary of the cell membrane. The cyclic nucleotide signaling cascades have been adapted to respond to a host of transduction systems including G-protein coupled receptors (GPCRs) and voltage and ligand gated ion channels. Cyclic nucleotides transmit their signal in the cell through a variant of tertiary elements. The best described of these are cAMP dependent protein kinase (PKA) and cGMP dependent protein kinase (PKG). The binding of the cyclic nucleotide to each enzyme enables the phosphorylation of downstream enzymes and proteins functioning as effectors or additional elements in the signaling cascade. Of particular importance to memory formation is cAMP-dependent activation of PKA, which phosphorylates CREB. pCREB is an activated transcription factor, which binds to specific DNA loci and initiates transcription of multiple genes involved in neuronal plasticity (e.g., Tully et al., *Nat. Rev. Drug. Discov.* 2003, 2, 267-277; and Alberini, *Physiol Rev.* 2009, 89, 121-145).

Consistent with these observations, both in vitro and in vivo studies have associated alterations in cyclic nucleotide concentrations with biochemical and physiological process linked to cognitive function (Kelly and Brandon, *Progress in Brain Research,* 2009, 179, 67-73; Schmidt, *Current Topics in Medicinal Chemistry,* 2010, 10, 222-230). Moreover, signal intensity and the levels of coincident activity at a synapse are established variables that can result in potentiation of transmission at a particular synapse. Long term potentiation (LTP) is the best described of these processes and is known to be modulated by both the cAMP and cGMP signaling cascades.

Accordingly, the present invention provides a method of enhancing neuronal plasticity, comprising administering to an animal in need thereof an effective amount of a chemical entity or composition of the present invention.

In another embodiment, the present invention provides a method of treating a disease mediated by PDE4, comprising administering to an animal in need of such treatment an effective amount of a compound or composition of the present invention. PDE4-related indications that can be treated by compounds and compositions of the present invention include, but are not limited to neurological disorders, inflammatory disorder, renal disorder, and other disorders involving PDE4.

Chemical entities and compositions of the present invention are also useful as neuroprotective agents, as described in greater detail herein. Accordingly, the present invention provides a method of neuroprotection, comprising administering to an animal in need thereof an effective amount of at least one chemical entity or composition of the present invention.

Chemical entities and compositions of the present invention are also useful as agents in neurorehabilitation and neurorecovery, as described in greater detail herein. Accordingly, the present invention provides a method of neurorehabilitation or neurorecovery, comprising administering to an animal in need thereof an effective amount of at least one chemical entity or composition of the present invention.

In addition, such compounds can be administered in conjunction with training protocols to treat cognitive or motor deficits associated with CNS disorders, as described in more detail herein. In addition, such compounds can be used to enhance the efficiency of training protocols in non-human animals, in particular healthy non-human animals, as described herein.

Neurological Disorders

In some embodiments, the present invention provides a method of treating a neurological disorder, comprising administering to an animal in need of such treatment an effective amount of a compound or composition described herein.

A neurological disorder (or condition or disease) is any disorder of the body's nervous system. Neurological disorders can be categorized according to the primary location affected, the primary type of dysfunction involved, or the primary type of cause. The broadest division is between central nervous system (CNS) disorders and peripheral nervous system (PNS) disorders.

Neurological disorders include structural, biochemical, or electrical abnormalities in the brain, spinal cord or other nerves, abnormalities that can result in a range of symptoms.

Examples of such symptoms include paralysis, muscle weakness, poor coordination, loss of sensation, seizures, confusion, pain, altered levels of consciousness, and cognitive deficits, including memory impairments. There are many recognized neurological disorders, some relatively common, but many rare. They may be assessed by neurological examination, and studied and treated within the specialties of neurology and clinical neuropsychology.

Neurological disorders and their sequalae (direct consequences) affect as many as one billion people worldwide, as estimated by the World Health Organization in 2006. Interventions for neurological disorders may include, in addition to medications, preventative measures, lifestyle changes, physiotherapy or other therapies, neurorehabilitation, pain management, and surgery.

Neurological disorders include, but are not limited to the following (which are not necessarily mutually exclusive): psychiatric disorders, such as mood disorders, psychotic disorders, and anxiety disorders; personality disorders; substance-related disorders; dissociative disorders; eating disorders; sleep disorders; developmental disorders; neurodegenerative disorders, including movement disorders; trauma-related disorders; pain disorders; and cognitive disorders, a category that includes memory disorders such as AAMI and MCI, as well as cognitive deficits (particularly memory deficits) associated with CNS disorders.

Psychiatric Disorders

In one embodiment, the invention provides a method of treating a psychiatric disorder, comprising administering to an animal in need of such treatment an effective amount of a compound or pharmaceutical composition described herein. Psychiatric disorders include mood (or affective) disorders, psychotic disorders, and anxiety (or neurotic) disorders.

Mood Disorders

In some embodiments, the psychiatric disorder is a mood (or affective) disorder. Accordingly, the present invention provides a method of treating a mood disorder, comprising administering to an animal in need of such treatment an effective amount of a compound or pharmaceutical composition described herein. In a specific aspect, the mood disorder is a depressive disorder, including a dysthymic disorder, major depressive disorder (recurrent and single episode), mania, bipolar disorders (I and II), and cyclothymic disorder. Long-standing research underscores a role for PDE4 in mood disorders, including depressive disorders, bipolar disorders, and substance induced mood disorders is known in the literature.

A specific embodiment of the invention is a method of treating a substance induced mood disorder, comprising administering to an animal in need of such treatment a therapeutically effective amount of a compound or pharmaceutical composition described herein. The utility of PDE4 inhibitors in the treatment of substance induced mood disorders is known in the literature.

Psychotic Disorders

In some embodiments, the psychiatric disorder is a psychotic disorder. Accordingly, the present invention provides a method of treating a psychotic disorder, comprising an animal in need of such treatment an effective amount of a compound or pharmaceutical composition described herein. In a specific aspect, the psychotic disorder is one or more of the following: schizophrenia; schizophreniform disorder; schizoaffective disorder; delusional disorder; brief psychotic disorder; shared psychotic disorder; substance-induced psychotic disorders, such as a psychosis induced by alcohol, amphetamine, cannabis, cocaine, hallucinogens, inhalants, opioids, or phencyclidine; and personality disorders at times of stress (including paranoid personality disorder, schizoid personality disorder, and borderline personality disorder).

A specific embodiment of the invention is a method of treating a delusional disorder, comprising administering to an animal in need of such treatment a therapeutically effective amount of a compound or pharmaceutical composition described herein. The utility of PDE4 inhibitors in the treatment of delusional disorders is known in the literature.

A particular embodiment of the invention is a method of treating schizophrenia, comprising administering to an animal in need of such treatment a therapeutically effective amount of a compound or pharmaceutical composition described herein. The utility of PDE4 inhibitors in the treatment of schizophrenia, including schizophreniform disorder and schizoaffective disorder, is known in the literature.

Anxiety Disorders

In some embodiments, the psychiatric disorder is an anxiety (or neurotic) disorder. Accordingly, the present invention provides a method of treating an anxiety disorder, comprising administering to an animal in need of such treatment an effective amount of a compound or pharmaceutical composition described herein. More particularly, the anxiety disorder is one or more of the following: panic disorder, specific phobia, social phobia, obsessive-compulsive disorder, generalized anxiety disorder, post-traumatic stress disorder; and acute stress disorder. The use of PDE4 inhibitors in the treatment of anxiety is known in the literature.

Personality Disorders

In some embodiments, the neurological disorder is a personality disorder. Accordingly, the present invention provides a method of treating a personality disorder, comprising administering to an animal in need of such treatment an effective amount of a compound or pharmaceutical composition described herein. In particular embodiments, the personality disorder is one or more of the following: includes those of Cluster A (odd or eccentric), such as paranoid or schizoid personality disorder; those of Cluster B (dramatic, emotional, or erratic), such as antisocial, borderline, or narcissistic personality disorder; and those of Cluster C (anxious or fearful), such as avoidant, dependent, or obsessive-compulsive personality disorder.

Substance Related Disorders

In some embodiments, the neurological disorder is a substance-related disorder. Accordingly, a specific embodiment of the invention is a method of treating a substance-related disorder, comprising administering to an animal in need of such treatment an effective amount of a compound or pharmaceutical composition described herein.

More particularly, the substance-related disorder includes one or more of the following: an alcohol-related disorder, such as abuse, dependence, and withdrawal; an amphetamine (or amphetamine-related) disorder, such as abuse, dependence and withdrawal, a cocaine-related disorder, such as abuse, dependence and withdrawal; a hallucinogen-related disorder, such as abuse, dependence and withdrawal; an inhalant-related disorder, such as dependent and withdrawal; a nicotine-related disorder, such as dependence and withdrawal; an opioid-related disorder, such as abuse, dependence and withdrawal; a phencyclidine (or phencyclidine-like) related disorder, such as abuse and dependence; and a sedative-, hypnotic-, or anxiolytic-related disorder, such as abuse, dependence, and withdrawal.

In a specific embodiment, the compounds and compositions of the present invention are useful as an aid to a treatment of smoking cessation. Accordingly, the present invention provides a method of treating smoking addiction, comprising administering to an animal in need thereof an effective amount of a compound or composition of the present invention.

Dissociative Disorders

In some embodiments, the neurological disorder is a dissociative disorder. Accordingly, a specific embodiment of the invention is a method of treating a dissociative disorder, comprising administering to an animal in need of such treatment an effective amount of a compound or pharmaceutical composition described herein. More particularly, the dissociative disorder includes one or more of the following: depersonalization disorder, dissociative amnesia, and dissociative identity disorder.

Eating Disorders

In some embodiments, the neurological disorder is an eating disorder. Accordingly, a specific embodiment of the invention is a method of treating an eating disorder, comprising administering to an animal in need of such treatment an effective amount of a compound or pharmaceutical composition described herein. More particularly, the eating disorder is anorexia nervosa or bulimia nervosa. The utility of PDE4 inhibitors in the treatment of eating disorders is known in the literature.

Sleep Disorders

In some embodiments, the neurological disorder is a sleep disorder. Accordingly, a specific embodiment of the invention is a method of treating a sleep disorder, comprising administering to an animal in need of such treatment an effective amount of a compound or pharmaceutical composition described herein. More particularly, the sleep disorder includes a primary sleep disorder, such as primary hypersomnia, primary insomnia, and narcolepsy; a parasomnia, such as a nightmare or sleep tenor disorder; and other sleep disorders. The utility of PDE4 inhibitors in the treatment of sleep disorders is known in the literature.

In other embodiments, the sleep disorder is restless leg syndrome. Restless legs syndrome (RLS) is a disorder of the part of the nervous system that affects the legs and causes an urge to move them. People with restless legs syndrome have uncomfortable sensations in their legs (and sometimes arms or other parts of the body) and an irresistible urge to move their legs to relieve the sensations. The sensations are usually worse at rest, especially when lying or sitting. The sensations can lead to sleep deprivation and stress. Because it usually interferes with sleep, it also is considered a sleep disorder. Accordingly, the present invention provides a method of treating restless leg syndrome, comprising administering to an animal in need thereof an effective amount of a compound or composition of the present invention.

Developmental Disorders

In some embodiments, the neurological disorder is a developmental disorder. Accordingly, a specific embodiment of the invention is a method of treating a developmental disorder, comprising administering to an animal in need of such treatment an effective amount of a compound or pharmaceutical composition described herein.

More particularly, the developmental disorder is one or more of the following: mental retardation, including mild, moderate, and severe forms; a learning disorder, such as that affecting reading, mathematics, or written expression; a motor skill disorder, such as developmental coordination disorder; a communication disorder; a pervasive developmental disorder, such as an autistic disorder, Rhett's disorder, childhood disintegrative disorder, and Asperger's disorder; an attention-deficit or disruptive disorder, such as attention-deficit hyperactivity disorder; and a tic disorder, such as Tourette's disorder, chronic motor disorder, or vocal tic disorder.

A specific embodiment of the invention is a method of treating an autistic disorder, comprising administering to an animal in need of such treatment an effective amount of a compound or pharmaceutical composition described herein. In another embodiment, the invention provides a method of treating an attention-deficit hyperactivity disorder, comprising administering to an animal in need of such treatment a therapeutically effective amount of a compound or pharmaceutical composition described herein. The utility of PDE4 inhibitors in the treatment of attention-deficit hyperactivity disorder is known in the literature.

Neurodegenerative Disorders

In particular embodiments, the invention provides a method of treating a neurodegenerative disorder, comprising administering to an animal in need of such treatment an effective amount of a compound or pharmaceutical composition described herein.

In one aspect, neurodegenerative disorders include Alzheimer's disease, Amyotrophic lateral sclerosis, corticobasal degeneration, chronic traumatic encephalopathy, and a disorder associated with repetitive head injury.

Alzheimer's Disease

In a specific embodiment, the invention provides a method of treating Alzheimer's disease, comprising administering to an animal in need of such treatment an effective amount of a compound or pharmaceutical composition described herein. A detailed set of criteria for the diagnosis of Alzheimer's is set forth in the Diagnostic and Statistical Manual of Mental Disorders (Fourth Edition, text revision (2000), also known as the DSM-IV-TR). First, multiple cognitive deficits must be present, one of which must be memory impairment. Second, one or more of the following must be present: aphasia (deterioration of language abilities); apraxia (difficulty executing motor activities—even though movement, senses, and the ability to understand what is being asked are still intact); or agnosia (impaired ability to recognize or identify objects—even though sensory abilities are intact).

Amyotrophic Lateral Sclerosis

In another specific embodiment, the invention provides a method of treating amyotrophic lateral sclerosis, comprising administering to an animal in need of such treatment an effective amount of a compound or pharmaceutical composition described herein.

Amyotrophic lateral sclerosis (ALS), often referred to as "Lou Gehrig's Disease," is a progressive neurodegenerative disease that affects nerve cells. Motor neurons reach from the brain to the spinal cord and from the spinal cord to the muscles throughout the body. As motor neurons degenerate, they can no longer send impulses to the muscle fibers that normally result in muscle movement.

Early symptoms of ALS often include increasing muscle weakness, especially involving the arms and legs, speech, swallowing or breathing. The progressive degeneration of the motor neurons in ALS eventually leads to their death. When the motor neurons die, the ability of the brain to initiate and control muscle movement is lost. With voluntary muscle action progressively affected, patients in the later stages of the disease may become totally paralyzed.

Movement Disorders

In other embodiments, the invention provides a method of treating a movement disorder, comprising administering to an animal in need of such treatment an effective amount of a compound or pharmaceutical composition described herein. In one aspect, the movement disorder includes one or more of the following: Huntington's disease, Parkinson's disease, an essential tremor, a Lewy body disease, hypokinetic disease, Multiple Sclerosis, various types of Peripheral Neuropathy, dystonia, a basal ganglia disorder, hypokinesia (including akinesia), and dyskinesia. In addition, Tourette's syndrome and other tic disorders can be included as categories of movement disorders. The utility of PDE4 inhibitors in the treatment of movement disorders is known in the literature.

In related embodiment, the invention provides a method of treating chorea, comprising administering to an animal in need of such treatment an effective amount of a compound or pharmaceutical composition described herein. Chorea can occur in a variety of conditions and disorders, and is a primary feature of Huntington's disease, a progressive neurological disorder.

Huntington's Disease

In a specific embodiment, the present invention provides a method of treating Huntington's disease, comprising administering to an animal in need of such treatment an effective amount of a compound or pharmaceutical composition described herein.

Huntington's Disease (HD, or Huntington chorea) is a disorder passed down through families in which nerve cells in certain parts of the brain waste away, or degenerate. It is caused by a genetic defect on chromosome 4, causing a CAG repeat, to occur many more times than normal. The CAG element is normally repeated 10 to 28 times, but in persons with Huntington's disease, is repeated 36 to 120 times.

There are two forms of Huntington's disease: adult-onset Huntington's disease—which is the most common form and usually begins in the mid 30s and 40s; and early-onset Huntington's disease, which accounts for a small number of cases and begins in childhood or adolescence.

Symptoms of Huntington's disease include behavioral changes, abnormal and unusual movements, and worsening dementia. Behavioral changes may include behavioral disturbances, hallucinations, irritability, moodiness, restlessness or fidgeting, paranoia, and psychosis. Abnormal and unusual movements include facial movements, such as grimaces; head turning to shift eye position; quick, sudden, sometimes wild jerking movements of the arms, legs, face, and other body parts; slow, uncontrolled movements; and unsteady gait. Worsening dementia includes; disorientation or confusion; loss of judgment; loss of memory; personality changes; and speech changes (e.g., Dumas et al., "A review of cognition in Huntington's disease", *Front Biosci* (Schol Ed) 2013, 5, 1-18). The utility of PDE4 inhibitors in treating Huntington's disease is known in the art.

Parkinson's Disease

In a specific embodiment, the present invention provides a method of treating Parkinson's disease, comprising administering to an animal in need of such treatment an effective amount of a compound or pharmaceutical composition described herein.

In another embodiment, the invention provides a method of treating myoclonus, Gilles de Ia Tourette's syndrome, dystonia, or tics, comprising administering to an animal in need of such treatment an effective amount of a compound or pharmaceutical composition described herein. The utility of PDE4 inhibitors in the treatment of myoclonus, Tourette's syndrome, dystonia and tics is known in the art.

In a specific aspect, a movement disorder also includes multiple sclerosis, basal ganglia disorders, hypokinesia, and dyskinesia.

Lewy Body Diseases

In one embodiment, the present embodiment, the invention provides a method of treating a Lewy Body Disease, comprising administering to an animal in need of such treatment an effective amount of a compound or composition of the present invention. Lewy bodies appear as spherical masses that displace other cell components. The two morphological types are classical (brain stem) Lewy bodies and cortical Lewy bodies. A classical Lewy body is an eosinophilic cytoplasmic inclusion consisting of a dense core surrounded by a halo of 10-nm-wide radiating fibrils, the primary structural component of which is alpha-synuclein. In contrast, a cortical Lewy body is less well defined and lacks the halo. Nonetheless, it is still made up of alpha-synuclein fibrils. Cortical Lewy bodies are a distinguishing feature of Dementia with Lewy bodies (DLB), but may occasionally be seen in ballooned neurons characteristic of Pick's disease and corticobasal degeneration, as well as in patients with other tauopathies.

More particularly, the Lewy Body disorder is selected from the group consisting of multiple system atrophy, particularly the Parkinsonian variant; Parkinson disease without or with dementia (PDD); dementia with LBs (DLB) alone or in association with Alzheimer disease (AD); multiple system atrophy, particularly the Parkinsonian variant, as well as Pick's disease and corticobasal degeneration.

Multiple Sclerosis

In one embodiment, the present invention provides a method of treating a motor symptom associated with multiple sclerosis (MS), comparing administering to animal in need of such treatment an effective amount of a compound or composition of the present invention. MS is an autoimmune, demyelinating disease that affects the brain and spinal cord of the CNS. It affects women more than men and is most commonly diagnosed between ages 20 and 40, but can be seen at any age.

MS is caused by damage to the myelin sheath, the protective covering that surrounds nerve cells. When this nerve covering is damaged, nerve signals slow down or stop. Because nerves in any part of the brain or spinal cord may be damaged, patients with multiple sclerosis can have symptoms in many parts of the body. Symptoms vary, because the location and severity of each attack can be different. Episodes can last for days, weeks, or months. These episodes alternate with periods of reduced or no symptoms (remissions).

Muscle symptoms associated with MS include loss of balance; muscle spasms; numbness, tingling, or abnormal sensation in any area; problems moving arms or legs; problems walking; problems with coordination and making small movements; tremor in one or more arms or legs; and weakness in one or more arms or legs.

Basal Ganglia Disorders

In particular embodiments, the present invention provides a method of treating a basal ganglia disorder. Basal ganglia disorders refer to a group of physical dysfunctions that occur when the group of nuclei in the brain known as the basal ganglia fail to properly suppress unwanted movements or to properly prime upper motor neuron circuits to initiate motor function (Leisman and Mello, *Rev. Neurosci.* 2013, 24, 9-25).

Increased output of the basal ganglia inhibits thalamocortical projection neurons. Proper activation or deactivation of these neurons is an integral component for proper movement. If something causes too much basal ganglia output, then the thalamocortical projection neurons become too inhibited and one cannot initiate voluntary movement. These disorders are known as hypokinetic disorders. However, a disorder leading to abnormally low output of the basal ganglia leads to relatively no inhibition of the thalamocortical projection neurons. This situation leads to an inability to suppress unwanted movements. These disorders are known as hyperkinetic disorders (Wichmann and DeLong, *Curr. Opin. Neurobiol* 1996, 6, 751-758).

Hypokinesia

In particular embodiments, the present invention provides a method of treating hypokinesia. Hypokinesia refers to decreased bodily movements, and they may be associated with basal ganglia diseases (such as Parkinson's disease), mental health disorders and prolonged inactivity due to illness, amongst other diseases.

More generally, hypokinesia describes a spectrum of disorders, including: (i) Akinesia, which refers to the inability to initiate movement due to difficulty selecting or activating motor programs in the central nervous system. Akinesia is a result of severely diminished dopaminergic cell activity in the direct pathway of movement and is common in severe cases of Parkinson's disease; (ii) Bradykinesia, which is characterized by slowness of movement and has been linked to Parkinson's disease and other disorders of the basal ganglia. Rather than being a slowness in initiation (akinesia), bradykinesia describes a slowness in the execution of movement. It is one of the 3 key symptoms of parkinsonism, which are bradykinesia, tremor and rigidity. Bradykinesia is also the cause of what is normally referred to as "stone face" (expressionless face) among those with Parkinson's; (iii) Freezing, which is characterized by an inability to move muscles in any desired direction; and (iv) Rigidity, which is characterized by an increase in muscle tone causing resistance to externally imposed joint movements; and (v) Postural instability, which is the loss of ability to maintain an upright posture.

Dyskinesia

In particular embodiments, the present invention provides a method of treating dyskinesia. Dyskinesia is a movement disorder which consists of adverse effects including diminished voluntary movements and the presence of involuntary movements, similar to tics or chorea.

Dyskinesia can be anything from a slight tremor of the hands to uncontrollable movement of, most commonly, the upper body but can also be seen in the lower extremities. Discoordination can also occur internally especially with the respiratory muscles and it often goes unrecognized. Dyskinesia is a symptom of several medical disorders, distinguished by the underlying cause and generally corresponding to one of three types: acute dyskinesia, chronic (or tardive) dyskinesia, and non-motor dyskinesia.

More specifically, a dyskinesia can include one or more the following: paroxysmal dyskinesias, e.g., primary and secondary paroxysmal dyskinesias; paroxysmal kinesigenic dyskinesias (PKD); paroxysmal non-kinesigenic dyskinesias (PNKD); paroxysmal exercise-induced (exertion-induced) dyskinesias (PED); and paroxysmal hypnogenic dyskinesias (PHD).

Trauma-Related Disorders

In specific embodiments, the present invention provides a method of treating a trauma-related disorder, comprising administering to an animal in need of such treatment an effective amount of a compound or pharmaceutical composition of the present invention.

In specific embodiments, trauma-related disorders comprise brain trauma; head trauma (closed and penetrating); head injury; tumors, especially cerebral tumors affecting the thalamic or temporal lobe head injuries; cerebrovascular disorders (diseases affecting the blood vessels in the brain), such as stroke, ischemia, hypoxia, and viral infection (e.g., encephalitis); excitotoxicity; and seizures.

Conditions within the scope of the invention that are amenable to neuroprotection include: Stroke; traumatic brain injury (TB); Dementia; Alzheimer's disease; Parkinson's disease; Huntington's disease; Cerebral palsy; Post-polio syndrome; Guillain-Barre syndrome, and Multiple Sclerosis; and other developmental syndromes, genetic conditions, and progressive CNS diseases affecting cognitive function, such as autism spectrum disorders, fetal alcohol spectrum disorders (FASD), Rubinstein-Taybi syndrome, Down syndrome, and other forms of mental retardation.

Pain Disorders

In specific embodiments, the invention provides methods of treating pain, comprising administering to an animal in need of such treatment an effective amount of a compound or pharmaceutical composition described herein. The utility of PDE4 inhibitors in the treatment of pain is known in the literature.

In particular embodiments, the pain disorder includes one or more of the following: dental pain, cancer pain, myofascial pain, perioperative pain, acute pain, chronic pain, posttraumatic pain, trigeminal neuralgia, migraine severe pain, intractable pain, neuropathic pain, post-traumatic pain, cancer pain, non-cancer pain. Pain also encompasses a pain disorder associated with psychological factors, a pain disorder associated with a general medical condition, and a pain disorder associated with both psychological factors and a general medical condition.

Cognitive Disorders

In particular embodiments of the invention, the neurological disorder is a cognitive disorder. Accordingly, the present invention provides a method of treating a cognitive disorder, comprising administering to an animal in need of such treatment an effective amount of a compound or pharmaceutical composition described herein. The utility of PDE4 inhibitors in the treatment of cognitive disorders is known in the literature (e.g., U.S. Pat. No. 7,829,713; U.S. Pat. No. 8,338,405).

Cognitive disorders can significantly impair social and occupational functioning, adversely impacting the autonomy and quality of life of the affected individual. An estimated four to five million Americans (about 2% of all ages and 15% of those older than 65) have some form and degree of cognitive impairment (Abrams et al., *Merck Manual of Geriatrics*, 1995, Whitehouse Station (NJ), Medical Services).

Cognitive disorders reflect problems in cognition, i.e., the general processes by which knowledge is acquired, retained and used. Accordingly, cognitive disorders can encompass impairments in such functions as concentration, perception, attention, information processing, learning, memory, or language. Cognitive disorders can also encompass impairments in psychomotor learning abilities, which include physical skills, such as movement and coordination; fine motor skills such as the use of precision instruments or tools; and gross motor skills, such as dance, musical, or athletic performance.

Cognitive disorders also encompass impairments in executive functions, which include abilities underlying the planning and execution of goal-oriented behaviors. Such abilities include flexibility, i.e., the capacity for quickly switching to the appropriate mental mode; anticipation and prediction based on pattern recognition; reasoning and problem-solving; decision making; working memory, i.e., the capacity to hold and manipulate internally- or externally-derived information in real time; emotional self-regulation, including the ability to recognize and manage one's emotions for good performance; sequencing, such as the ability to dissect complex actions into manageable units and prioritize them in the right order; and self-inhibition, i.e., the ability to withstand distraction and internal urges.

Cognitive disorders also comprise cognitive impairments (deficits or dysfunctions) that are associated with (due to) to CNS disorders. In one aspect, a cognitive impairment can be a direct result of a CNS disorder. For example, impairments in speech and language can directly result from a stroke or head-injury that damages the brain regions controlling speech and language, as in aphasia.

In another aspect, a cognitive impairment is associated with a complex CNS disorder, condition, or disease. For example, a cognitive impairment can comprise a deficit in executive control that accompanies autism or mental retardation; a deficit in memory associated with schizophrenia or Parkinson's disease; or a cognitive deficit arising from multiple sclerosis. In the case of multiple sclerosis (MS), for example, about one-half of MS patients will experience problems with cognitive function, such as slowed thinking, decreased concentration, or impaired memory. Such problems typically occur later in the course of MS—although in some cases they can occur much earlier, if not at the onset of disease.

Cognitive impairments can be due to many, non-exclusive categories of CNS disorders, including the following (and as described herein):

(1) dementias, such as those associated with Alzheimer's disease, Parkinson's disease; Huntington's disease, Pick's disease, Creutzfeldt-Jakob, AIDS Dementia, and other neurodegenerative disorders; and cognitive disabilities associated with progressive diseases involving the nervous system, such as multiple sclerosis.

(2) psychiatric disorders, which include affective (mood) disorders, such as depression and bipolar disorders; psychotic disorders, such as schizophrenia and delusional disorder; and neurotic and anxiety disorders, such as phobias, panic disorders, obsessive-compulsive disorder, generalized anxiety disorder; eating disorders; and posttraumatic stress disorders.

(3) developmental syndromes, genetic conditions, and progressive CNS diseases affecting cognitive function, such as autism spectrum disorders; fetal alcohol spectrum disorders (FASD); Rubinstein-Taybi syndrome; Down syndrome, and other forms of mental retardation; and multiple sclerosis.

(4) trauma-dependent losses of cognitive functions, i.e., impairments in memory, language, or motor skills resulting from brain trauma; head trauma (closed and penetrating); head injury; tumors, especially cerebral tumors affecting the thalamic or temporal lobe; cerebrovascular disorders (diseases affecting the blood vessels in the brain), such as stroke, ischemia, hypoxia, and viral infection (e.g., encephalitis); excitotoxicity; and seizures. Such trauma-dependent losses also encompass cognitive impairments resulting from extrinsic agents such as alcohol use, long-term drug use, and neurotoxins, e.g., lead, mercury, carbon monoxide, and certain insecticides (e.g., Duncan et al., "Monoamine oxidases in major depressive disorder and alcoholism", *Drug Discover. Ther.* 2012, 6, 112-122).

(5) age-associated cognitive deficits, including age-associated memory impairment (AAMI; also referred to herein as age-related memory impairment (AMI)), and deficits affecting patients in early stages of cognitive decline, as in Mild Cognitive Impairment (MCI); and (6) learning, language, or reading disabilities, such as perceptual handicaps, dyslexia, and attention deficit disorders.

Accordingly, the invention provides a method of treating a cognitive impairment associated with a CNS disorder selected from one or more of the group comprising: dementias, including those associated with neurodegenerative disorders; psychiatric disorders; developmental syndromes, genetic conditions, and progressive CNS diseases and genetic conditions; trauma-dependent losses of cognitive function, age-associated cognitive deficits; and learning, language, or reading disorders.

Dementias

In a specific embodiment, the invention provides a method of treating a cognitive deficit associated with dementia, comprising administering to an animal in need of such treatment an effective amount of a compound or pharmaceutical composition described herein.

Dementias are neurodegenerative diseases characterized by learning and cognitive deficiencies and are typically accompanied by behavioral symptoms, psychological symptoms and motor symptoms. More particularly, dementia symptoms can include difficulty with many areas of mental function, including emotional behavior or personality, language, memory, perception, and thinking and judgment.

Dementias include, but are not limited to, the following: dementia due to Alzheimer's disease (with early or late onset), dementia due to Parkinson's disease, dementia due to Pick's disease, dementia due to Creutzfeldt-Jakob disease, dementia due to HIV disease, dementia due to head trauma; dementia due to a vascular disease ("vascular dementia"), Lewy body dementia, fronto-temporal dementia, Pick's disease and corticobasal degeneration.

In one embodiment, dementia is due to Alzheimer's disease. Accordingly, the present invention provides a method of treating dementia due to Alzheimer's disease, comprising administering to an animal in need of such treatment a therapeutically effective amount of a compound or pharmaceutical composition described herein. The utility of PDE4 inhibitors in the treatment of Alzheimer's disease is known in the literature. Accordingly, the invention provides a method of treating dementia due to Alzheimer's disease, comprising administering to an animal in need of such treatment a therapeutically effective amount of a compound or pharmaceutical composition described herein.

In another embodiment, dementia is due to Parkinson's disease. Accordingly, the invention provides a method of treating dementia due to Parkinson's disease, comprising administering to an animal in need of such treatment a therapeutically effective amount of a compound or pharmaceutical composition described herein. Dementia has been reported to occur in approximately 20%-60% of individuals with Parkinson's disease and is more likely to be present in older individuals or those with more severe or advanced disease. The dementia associated with Parkinson's disease is characterized by cognitive and motoric slowing; problems with executive functioning, such as planning tasks, organizing projects, or carrying out goals in the proper sequence; and impairment in memory retrieval. Declining cognitive performance in individuals with Parkinson's disease is frequently exacerbated by depression. The utility of PDE4 inhibitors in treating Parkinson's disease is known in the literature.

Dementia has been reported to occur in approximately 20%-60% of individuals with Parkinson's disease and is more likely to be present in older individuals or those with more severe or advanced disease. The dementia associated with Parkinson's disease is characterized by cognitive and motoric slowing, executive dysfunction, and impairment in memory retrieval. Declining cognitive performance in individuals with Parkinson's disease is frequently exacerbated by depression. For a review, Davie, "A review of Parkinson's disease", *Br. Med. Bull.* 2008, 86, 109-127. The motor symptoms of Parkinson's disease result from the death of dopamine-generating cells in the substantia nigra, a region of the midbrain;

the cause of this cell death is unknown. Early in the course of the disease, the most obvious symptoms are movement-related. Four motor symptoms are considered cardinal in PD: shaking (tremors), rigidity, slowness of movement, and postural instability, i.e., difficulty with walking and gait (e.g., Jankovic, "Parkinson's disease: clinical features and diagnosis", *J. Neurol. Neurosurg. Psychiatr.* 2008, 79, 368-376). Later, cognitive and behavioral problems may arise, with dementia commonly occurring in the advanced stages of the disease. Other symptoms include sensory, sleep and emotional problems. PD is more common in the elderly, with most cases occurring after the age of 50.

In another aspect, a cognitive impairment is associated with a complex CNS syndrome, condition, or disease. For example, a cognitive impairment can comprise a deficit in executive control that accompanies autism or mental retardation; a deficit in memory associated with schizophrenia or Parkinson's disease; or a cognitive deficit arising from multiple sclerosis. In the case of multiple sclerosis (MS), for example, about one-half of MS patients will experience problems with cognitive function, such as slowed thinking, decreased concentration, or impaired memory. Such problems typically occur later in the course of MS—although in some cases they can occur much earlier, if not at the onset of disease.

In one aspect, a cognitive impairment can be a direct result of a CNS disorder. For example, impairments in speech and language can directly result from a stroke or head-injury that damages the brain regions controlling speech and language, as in aphasia.

Psychiatric Disorders

In a specific embodiment, the invention provides a method of treating a cognitive deficit associated with a psychiatric disorder, comprising administering to an animal in need of such treatment an effective amount of a compound or pharmaceutical composition described herein. Psychiatric disorders include affective disorders (mood disorders), such as depression and bipolar disorders; psychotic disorders, such as schizophrenia and delusional disorder; and neurotic and anxiety disorders, such as phobias, panic disorders, obsessive-compulsive disorder, generalized anxiety disorder, eating disorders, and posttraumatic stress disorders.

Developmental Syndromes, Genetic Disorders, and Progressive Diseases

In a specific embodiment, the invention provides a method of treating a cognitive deficit associated with a developmental syndrome, genetic disorder, or progressive disease, comprising administering to an animal in need of such treatment an effective amount of a compound or pharmaceutical composition described herein. In a specific aspect, the cognitive deficit is associated with an autism spectrum disorder; a fetal alcohol spectrum disorder (FASD); Rubinstein-Taybi syndrome; Down syndrome, and other forms of mental retardation; and multiple sclerosis.

Trauma-Related Disorders

In a specific embodiment, the invention provides a method of treating a cognitive deficit associated with trauma. Such trauma-dependent losses of cognitive function include, but are not limited to, those due to cerebrovascular diseases, including stroke and ischemia; brain trauma, including subdural hematoma and brain tumor; traumatic brain injury (TBI) and head injury.

Such trauma-dependent losses also encompass cognitive impairments resulting from extrinsic agents such as alcohol use, long-term drug use, and neurotoxins such as lead, mercury, carbon monoxide, and certain insecticides.

Age-Associated Cognitive Deficits

AAMI

In a specific embodiment, the invention provides a method of treating an age-associated cognitive deficit. In one aspect, the age-associated cognitive deficit is age-related memory impairment (AAMI). Accordingly, the invention provides a method of treating age-associated memory impairment (AAMI), comprising administering to an animal in need of such treatment an effective amount of a compound or pharmaceutical composition described herein.

AAMI is a decline in various cognitive abilities, in particular memory abilities, associated with normal aging. For example, AAMI subjects show a decline in the ability to encode new memories of events or facts, as well as working memory (Hedden and Gabrieli, "Insights into the aging mind: a view from cognitive neuroscience", *Nat. Rev. Neurosci.* 2004, 5, 87-96). In addition, AAMI subjects, when compared with age-matched controls, appeared to be impaired in tests of executive functions associated with frontal lobe function. These and other studies suggest an important role for frontal lobe dysfunction in the memory loss of elderly people. (More generally, studies comparing the effects of aging on episodic memory, semantic memory, short-term memory and priming find that episodic memory is especially impaired in normal aging; but some types of short-term memory can also be impaired (Nilsson, "Memory function in normal aging", *Acta Neurol. Scand. Suppl.* 2003, 179, 7-13)

In general, an AAMI diagnosis identifies persons with subjectively and objectively evidenced memory loss without cognitive decline impaired enough to warrant the diagnosis of dementia. According to criteria established by the NIH working group (Crook et al., "Age-associated memory impairment: proposed diagnostic criteria and measures of clinical damage—report of a National Institute of Mental Health work group", *Devel. Neuropsychol.* 1986, 2, 261-276) a diagnosis of AAMI includes the following in a person aged 50 or older:

(i) the presence of subjective memory decline, e.g., complaints of memory loss reflected in such everyday problems as difficulty remembering names of individuals introduced to the subject, misplacing objects, difficulty remembering a list of items to be purchased or a list of tasks to be performed;

(ii) objective evidence of memory loss (e.g., a score at least one standard deviation below the mean of younger adults in a well standardized memory test);

(iii) evidence of adequate intellectual function (e.g., a raw score of at least 32) on the Vocabulary subtest of the Wechsler Adult Intelligence Scale., and (iv) the absence of dementia (or other memory-affecting disease, such as stroke), e.g., based on the Global Deterioration Scale for assessment of dementia, individuals with AAMI have very mild cognitive decline (level 2) (Reisberg et al., "The global deterioration Scale for assessment of primary degenerative dementia", *Am. J. Psych.* 1982, 139,1136-1139).

Individuals with AAMI have been shown to have a three-fold greater risk for development of dementia than individuals who do not meet AAMI criteria (Goldman and Morris, "Evidence that age-associated memory impairment is not a normal variant of aging" *Alzheimer Dis. Assoc. Disord.* 2002, 15:72-79).

MCI

In a specific embodiment, the invention provides a method of treating mild cognitive impairment (MCI), comprising administering to an animal in need of such treatment an effective amount of a compound or pharmaceutical composition described herein.

MCI may be diagnosed when an individual's memory declines below the level considered normal for that age group. In other words, MCI is a condition in which people face memory problems more often than that of the average person their age. These symptoms, however, do not prevent them from carrying out normal activities and are not as severe as the symptoms for Alzheimer's disease. Symptoms often include misplacing items, forgetting events or appointments, and having trouble thinking of desired words.

According to recent research, MCI has been called the transitional state between cognitive changes of normal aging and Alzheimer's disease (AD). Many people who experience mild cognitive impairment are at a high risk of developing Alzheimer's disease. Indeed, research suggests that: about 12% of people aged 65 or older diagnosed with MCI go on to develop Alzheimer's disease within a year; and that about 40% develop Alzheimer's within three years. This is a much higher rate than in the general population, wherein only about 1% of people aged 65 or older develop Alzheimer's each year.

Thus, people with MCI are considered at heightened risk to develop Alzheimer's disease. These symptoms, however, do not prevent them from carrying out normal activities and are not as severe as the symptoms for Alzheimer's disease. Symptoms often include misplacing items, forgetting events or appointments, and having trouble thinking of desired words (e.g., Arnáiz and Almkvist, "Neuropsychological features of mild cognitive impairment and preclinical Alzheimer's disease" *Acta Neurol. Scand. Suppl.* 2003, 179, 34-41). Some patients with MCI, however, never progress to AD.

Learning and Related Disabilities

In a specific embodiment, the invention provides a method of treating a learning, language, or reading disability, comprising administering to an animal in need of such treatment an effective amount of a compound or pharmaceutical composition described herein.

Neuroprotection

In specific embodiments, the invention provides a method of neuroprotection, comprising administering to animal in need thereof an effective amount of a chemical entity or composition of the present invention.

Like neuroplasticity, neuroprotection reflects an endogenous neurobiological process that is central to protection of the nervous system. More specifically, neuroprotection refers to the ability to halt or slow the loss of neurons, thereby preventing or slowing disease progression and secondary injuries. In a particular aspect, neuroprotection targets neuronal damage arising from oxidative stress and excitotoxicity—both of which are highly associated with CNS disorders, despite differences in symptoms or injuries.

The utility of PDE4 inhibitors in the treatment of neuronal damage is known in the literature. In addition to neurodegenerative diseases, neuronal damage can also result from other sources of trauma, such as cerebrovascular diseases, including stroke and ischemia; brain trauma, including subdural hematoma and brain tumor; and head injury.

Augmented Cognitive and Motor Training

In certain embodiments, a compound or composition herein is used as an augmenting agent in methods to enhance the efficiency of cognitive or motor training (collectively "training"). Such enhancement methods are collectively known as "augmented training," comprising "augmented cognitive training" or "augmented motor training."

Training generally requires multiple sessions to attain the desired benefits, for example, to rehabilitate a motor deficit or language deficit following stroke. This can be costly and time-consuming, deterring subject compliance and the realization of real world benefits that endure over time. The efficiency of such training protocols can be improved by administering certain agents (known as augmenting agents) in conjunction with the training protocol (e.g., U.S. Pat. No. 7,868,015; U.S. Pat. No. 7,947,731; US 2008-0188525). Augmented training comprises a specific training protocol for a particular brain function, such as that underlying declarative memory, performance of a fine motor skill, locomotion, language acquisition, an executive function, etc., and a general administration of CREB pathway-enhancing drugs. The training protocol (cognitive or motor training) induces neuronal activity in specific brain regions and produces improved performance of a specific brain (cognitive or motor) function.

In some embodiments, the invention provides methods of treating a cognitive disorder, and more particularly, methods for improving a cognitive deficit associated with a central nervous system (CNS) disorder or condition in an animal, comprising treating the animal with an augmenting agent that enhances CREB pathway function in conjunction with cognitive training, wherein the augmenting agent is a compound or composition of the present invention. Exemplary compounds of the present inventions, for example, have been shown to activate CREB in cell-based assays.

In one aspect, the method comprises: (a) providing cognitive training to a subject in need of treatment of a cognitive deficit under conditions sufficient to produce an improvement in performance by said animal of a cognitive function whose impairment is associated with said cognitive deficit; (b) administering a compound or composition of the present invention to the animal in conjunction with said cognitive training; repeating steps (a) and (b) one or more times; and (d) reducing the number of training sessions sufficient to produce the improvement in performance, relative to the same improvement in performance produced by cognitive training alone.

In another aspect, the method comprises: (a) providing cognitive training to a subject in need of treatment of a cognitive deficit under conditions sufficient to produce an improvement in performance by said animal of a cognitive function whose impairment is associated with said cognitive deficit; (b) administering a compound or composition of the present invention to the animal in conjunction with said cognitive training; repeating steps (a) and (b) one or more times; and (d) producing a long-lasting improvement in performance of said function relative to the improvement in performance of said function produced by cognitive training alone.

In one aspect, a compound or composition of the present invention can be used as an augmenting agent in conjunction with any psychotherapeutic approach intended to modulate cognitive function in the brain, thereby enhancing the efficacy of such therapy by reducing the number of sessions necessary to attain benefits.

In another aspect, the cognitive deficit treated by these methods is or includes memory impairment, and more particularly, a defect in long-term memory. Long-term memory (LTM) generally comprises two main biological properties. First, formation of long-term memory requires synthesis of new proteins. Second, it involves cAMP-responsive transcription and is mediated through the cAMP-response element binding protein (CREB) family transcription factors. Compounds of the present invention can act as CREB-augmenting agents and are therefore useful in enhancing memory formation in an animal, and more particularly, transcription-dependent memory. Indeed, exemplary compounds of the present invention activate CREB in cell-based assays.

In some embodiments, the invention provides methods of treating a motor disorder, and more particularly, methods for improving a motor deficit associated with a central nervous system (CNS) disorder or condition in an animal comprising treating the animal with an augmenting agent that enhances CREB pathway function in conjunction with motor training. Methods are also provided herein for providing sustained improvement in a motor deficit associated with a central nervous system (CNS) disorder or condition in an animal in need of said treatment comprising administering to the animal a compound or composition of the present invention; and detecting said sustained improvement In one aspect, the method comprises: (a) providing motor training to a subject in need of treatment of a motor deficit under conditions sufficient to produce an improvement in performance by said animal of a motor function whose impairment is associated with said cognitive deficit; (b) administering a compound or composition of the present invention to the animal in conjunction with said motor training; repeating steps (a) and (b) one or more times; and (d) reducing the number of training sessions sufficient to produce the improvement in performance, relative to the same improvement in performance produced by motor training alone.

In another aspect, the method comprises: (a) providing motor training to a subject in need of treatment of a motor deficit under conditions sufficient to produce an improvement in performance by said animal of a motor function whose impairment is associated with said cognitive deficit; (b) administering a compound or composition of the present invention to the animal in conjunction with said motor training; repeating steps (a) and (b) one or more times; and (d) producing a long-lasting improvement in performance of said function relative to the improvement in performance of said function produced by motor training alone.

In other embodiments, the invention provides methods for enhancing a specific aspect of cognitive performance in an otherwise healthy animal (particularly in a human or other mammal or vertebrate) comprising (a) administering to the animal an augmenting agent of the present invention; and (b) training the animal under conditions sufficient to produce an improvement in performance of a particular cognitive task by the animal. In other embodiments, the present invention provides methods of enhancing cognitive or motor performance, as well as methods for repeated stimulation of neuronal activity or a pattern of neuronal activity, such as that underlying a specific neuronal circuit(s).

Augmenting Agents

Augmenting agents, including the compounds and compositions herein, are able to enhance CREB pathway function. By enhancing CREB pathway function in conjunction with training, such augmented training can decrease the number of training sessions required to improve performance of a cognitive or motor function, relative to the improvement observed by training alone (e.g., U.S. 2007-0203154, U.S. 2011-0160248, U.S. 2010-0317648, and U.S. Pat. No. 8,222, 243).

The augmenting agent can be administered before, during or after one or more of the training sessions. In a particular embodiment, the augmenting agent is administered before and during each training session. Treatment with an augmenting agent in connection with each training session is also referred to as the "augmenting treatment".

Training Protocols

Training protocols are generally employed in rehabilitating individuals who have some form and degree of cognitive or motor dysfunction. For example, training protocols are commonly employed in stroke rehabilitation and in age-related memory loss rehabilitation. Because multiple training sessions are often required before an improvement or enhancement of a specific aspect of cognitive (or motor) performance (ability or function) is obtained in the individuals, training protocols are often very costly and time-consuming. Augmented training methods are more efficacious and therefore more cost-effective.

For example, human brain injury often results in motor and cognitive impairments. While advances in critical care medicine and patient management have led to improvements in patient outcome following traumatic brain injury (TBI), there is currently no known treatment to prevent the neuronal cell death and dysfunction that follows TBI. Although multiple treatments have proven neuroprotective in pre-clinical models of TBI, most have failed to show efficacy in humans.

Once a patient is stabilized following TBI, the standard of care dictates extensive motor or cognitive rehabilitation. During this rehabilitation the patient often regains lost skills, finally resulting in improved functional outcome. It would be beneficial if pharmaceutical treatments could be developed to enhance motor or cognitive rehabilitation following TBI, and thus improve functional outcome.

Cognitive and motor training protocols and the underlying principles are well known in the art (e.g., Allen et al., *Parkinsons Dis.* 2012, 1-15; Jaeggi et al., *Proc. Natl. Acad. Sci. USA* 2011, 108, 10081-10086; Chein et al., *Psychon. Bull. Rev.* 2010, 17, 193-199; Klingberg, *Trends Cogn. Sci.* 2010, 14, 317-324; Owen et al., *Nature* 2010, 465, 775-778; Tsao et al., *J. Pain* 2010, 11, 1120-1128; Lustig et al., *Neuropsychol. Rev.* 2009, 19, 504-522; Park and Reuter-Lorenz, *Ann. Rev. Psych.* 2009, 60, 173-196; Oujamaa et al., *Ann. Phys. Rehabil. Med.* 2009, 52, 269-293; Frazzitta et al., *Movement Disorders* 2009, 8, 1139-1143; Jaeggi et al., *Proc. Natl. Acad. Sci. USA* 2008, 105, 6829-6833; Volpe et al., *Neurorehabil. Neural Repair* 2008, 22, 305-310; Fischer et al., *Top. Stroke Rehab.* 2007, 14, 1-12; Jonsdottir et al., *Neurorehabil. Neural Repair* 2007, 21, 191-194; Stewart et al., *J. Neurol. Sci.* 2006, 244, 89-95; Krakauer, *Curr. Opin. Neurol.* 2006, 19, 84-90; Belleville et al., *Dement. Geriatr. Cogn. Disord.* 2006, 22, 486-499; Klingberg et al., *J. Am. Acad. Child. Adolesc. Psychiatry* 2005, 44, 177-186; Dean et al., *Arch. Phys. Med. Rehabil.* 2000, 81, 409-417; Whitall et al., *Stroke* 2000, 31, 2390-2395; Hummelsheim and Eickhof, *Scand. J. Rehabil. Med.* 1999, 31, 250-256; Merzenich et al., *Science* 1996, 271, 77-81; Merzenich et al., *Cold Spring Harb. Symp. Quant. Biol.* 1996, 61, 1-8; Rider and Abdulahad, *Percept. Mot. Skills* 1991, 73, 219-224; Wek and Husak, *Percept. Mot. Skills,* 1989, 68, 107-113;

Cognitive training protocols are directed to numerous cognitive dimensions, including memory, concentration and attention, perception, learning, planning, sequencing, and judgment. Motor training protocols can be directed to numerous motor domains, such as the rehabilitation of arm or leg function after a stroke or head injury. One or more protocols (or modules) underlying a training program can be provided to a subject.

In some embodiments, the protocols can be used to treat, or rehabilitate, cognitive or motor impairments in afflicted subjects. Such protocols may be restorative or remedial, intended to reestablish prior skills and functions, or they may be focused on delaying or slowing cognitive or motor decline due to neurological disease. Other protocols may be compensatory, providing a means to adapt to a cognitive or motor deficit by enhancing function of related and uninvolved brain domains. In other embodiments, the protocols can be used to improve particular skills or cognitive or motor functions in otherwise healthy individuals. For example, a cognitive training program might include modules focused on delaying or preventing cognitive decline that normally accompanies aging; here the program is designed to maintain or improve cognitive health.

In general, a training protocol (or module) comprises a set of distinct exercises that can be process-specific or skill-based: Process-specific training focuses on improving a particular domain such as attention, memory, language, executive function, or motor function. Here the goal of training is to obtain a general improvement that transfers from the trained activities to untrained activities associated with the same cognitive or motor function or domain. For example, an auditory cognitive training protocol can be used to treat a student with impaired auditory attention. At the end of training, the student should show a generalized improvement in auditory attention, manifested by an increased ability to attend to and concentrate on verbal information presented in class—and therefore to remember to write down and complete homework assignments. Similarly, a cognitive training protocol may be directed to impaired executive function in an autistic subject, preventing the subject from carrying out instructions to complete an activity, such as making a meal, cleaning one's room, or preparing for school in the morning. Cognitive training allows the subject to focus his attention and concentration and as a result, complete the sequence of tasks required for such activities.

Skill-based training is aimed at improving performance of a particular activity or ability. Here the goal of training is to obtain a general improvement in the skill or ability. For example, a training protocol may focus on learning a new language, performing a musical instrument, improving memory, or learning a fine motor skill. The different exercises within such a protocol will focus on core components underlying the skill Modules for increasing memory, for example, may include tasks directed to the recognition and use of fact, and the acquisition and comprehension of explicit knowledge rules.

Some rehabilitation programs may rely on a single strategy (such as computer-assisted cognitive training) targeting either an isolated cognitive function or multiple functions concurrently. For example, the CogState testing method comprises a customizable range of computerized cognitive tasks able to measure baseline and change in cognitive domains underlying attention, memory, executive function, as well as language and social-emotional cognition (e.g., Yoshida et al., *PloS ON*, 2011, 6, e20469; Frederickson et al., *Neuroepidemiology* 2010, 34, 65-75). Other rehabilitation programs may use an integrated or interdisciplinary approach. Cognitive and motor training programs may involve computer games, handheld game devices, interactive exercises, and may employ feedback and adaptive models.

Neurorehabilitation and Neurorecovery

In other embodiments, the invention further relates to the use of compounds and compositions of the present invention in neurorecovery and neurorehabilitation—endogenous neurobiological processes that are central to recovery of cognitive and motor impairments of the nervous system (e.g., Harkema et al., "Locomotor training: as a treatment of spinal cord injury and in the progression of neurologic rehabilitation", *Arch. Phys. Med. Rehabil.* 2012, 93, 1588-1597; Muresanu et al., "Towards a roadmap in brain protection and recovery", *J. Cell. Mol. Med.* 2012, 16, 2861-2871).

Neurorehabilitation or neurorecovery generally refers to a collection process that focuses on aiding a person's recovery from a neurological disorder, or helping that individual to live a more normal, active, and independent life. For example, the quality of life of a person can be greatly affected by a brain or spinal cord injury, or a medical condition which affects the mobility, cognitive functions, or other physical or psychological processes that have been affected by changes in the nervous system. The goal of neurorehabilitation is to combat those changes and improve quality of life by various therapies.

Conditions within the scope of the invention that are treated by neurorehabilitation and neurorecovery include: Stroke; traumatic brain injury (TB); Dementia; Alzheimer's disease; Parkinson's disease; Huntington's disease; Cerebral palsy; Post-polio syndrome; Guillain-Barre syndrome, and Multiple Sclerosis; and other developmental syndromes, genetic conditions, and progressive CNS diseases affecting cognitive function, such as autism spectrum disorders, fetal alcohol spectrum disorders (FASD), Rubinstein-Taybi syndrome, Down syndrome, and other forms of mental retardation.

By focusing on all aspects of a person's well-being, neurorehabilitation or neurorecovery offers a series of therapies from the psychological to occupational, teaching or re-training patients on mobility skills, communication processes, and other aspects of that person's daily routine. Neurorehabilitation or neurorecovery also provides focuses on nutrition, psychological, and creative parts of a person's recovery.

In one embodiment, the present invention provides a method of augmenting neurorehabilitation or neurorecovery from a cognitive impairment, comprising (a) providing cognitive training to a subject in need of treatment of a cognitive deficit under conditions sufficient to produce an improvement in performance by said animal of a cognitive function whose impairment is associated with said cognitive deficit; (b) administering a compound or composition of the present invention to the animal in conjunction with said cognitive training; repeating steps (a) and (b) one or more times; and (d) producing a long-lasting improvement in performance of said function relative to the improvement in performance of said function produced by cognitive training alone.

In another embodiment, the present invention provides a method of augmenting neurorehabilitation or neurorecovery from a motor impairment, comprising: (a) providing motor training to a subject in need of treatment of a motor deficit under conditions sufficient to produce an improvement in performance by said animal of a motor function whose impairment is associated with said cognitive deficit; (b) administering a compound or composition of the present invention to the animal in conjunction with said motor training; repeating steps (a) and (b) one or more times; and (d) reducing the number of training sessions sufficient to produce the improvement in performance, relative to the same improvement in performance produced by motor training alone.

Non-Human Animal Training Protocols

Aside from applications for humans, compounds and compositions of the present invention have additional uses for non-human animals, namely in enhancing (augmenting) the efficiency of training protocols directed to numerous cognitive and motor functions.

Conditions, under which non-human animals would benefit, include enhanced (augmented) training procedures for specific purposes, (e.g. hunting dogs, guide dogs, police dogs etc, or animals used in movie industry).

Enhanced training protocols can also benefit animals that have been exposed to stressful or traumatic conditions and are in need of training to treat the resulting cognitive impairments. Such a need may arise, for example, after such an animal has been captured or transported, subjected to new housing conditions (as in a change of domicile or owner), or has developed analogous disorders and is distressed or aggressive, or displays stereotypic behavior, obsessive-compulsive behavior, or anxiety. Animals which are subject to stress would also include animals used in racing (eg. dogs, horses, camels) or other sports, performing animals (such as circus animals and those appearing on stage, television or in the movies) and horses that perform dressage and other highly disciplined routines.

Compounds of the present invention can also enhance the efficiency of rehabilative protocols following physical injury to a non-human animal, such as limb amputation. For example, administering an augmenting agent of the present invention in conjunction with a training protocol can increase the efficiency of a rehabilitative program by decreasing the number of training sessions necessary to achieve an improvement in motor function.

In particular embodiments, compounds and compositions of the present invention are used in methods of training service animals. By combining augmenting agents of the present invention with training protocols, the efficiency of training non-human animals for service in both the public and private sectors will be enhanced. Service animals are typically dogs. However, other non-human animals can also be trained to perform services, such as assisting blind or disabled people. For example, miniature horses can be trained to guide the blind, to pull wheelchairs, or to provide support for Parkinson's patients. As another example, capuchin monkeys can be trained to assist disabled perform manual tasks, such as grasping items, operating knobs and switches, turning the pages of a book.

In specific embodiments, augmented training with compounds and compositions of the present invention can be used to reduce the number of training sessions necessary to teach an animal skills that are useful in public service, such as in law enforcement. In dogs, for example, such skills include, but are not limited to, the following: (i) public order maintenance, e.g., chasing, holding, or detaining suspects; (ii) search and rescue, e.g., locating suspects, missing persons, or objects; and (iii) contraband detection, e.g., detecting illicit substances such as drugs, narcotics, explosives, weapons, and even human remains. Such methods can therefore be applied to police dogs, bomb-sniffing dogs, drug-sniffing dogs, search and rescue dogs, etc.

In other embodiments, augmented training (with compounds and compositions of the present invention) can be used to reduce the number of training sessions required to teach animals skills that are useful in the private sector, such as security and medical care. In dogs, for example, such skills can include, but are not limited to, the following: (i) private security, e.g., guarding property or protecting an individual; (ii) handicap assistance, e.g., providing eyes for the visually impaired, ears for the hearing-impaired, arms and legs for the physically-disabled; (iii) health care, e.g., detecting cancer or altering a caregiver to seizures in a subject; (iv) psychiatric assistance, e.g., calming a phobic person under stress-triggering conditions, or alerting an autistic person to distracting repetitive movements such as hand flapping; and (v) pest control, e.g., identifying source of infestations by bedbugs or termites.

In some embodiments, the training protocol can be directed to a single skill or task, such as the detection of a single drug. In other embodiments, the training protocol can be directed to a complex set of skills, such as those underlying search and rescue. For a complex set of skills, training will therefore comprise more than one task.

In another aspect, when training is carried out with a wide enough scope of tasks, a generalized "rehabilitation" effect is expected, resulting in generalized improved function of one or more cognitive domains. This results in improved performance of the animal of related tasks (involving the same cognitive domains) that are not specifically part of the training protocol.

Accordingly, the present invention provides a method of reducing the time necessary to teach an animal one or more skills, wherein said reducing comprising: a) administering an augmenting agent of the present invention to the animal; b) providing a training protocol to said dog under conditions to improve performance of one or more tasks, wherein said training protocol comprises multiple training sessions; and c) decreasing the number of training sessions required to improve performance of said one or more tasks relative to the number of said training sessions required to produce said improvement in performance by the training protocol alone.

The training protocol can be provided to the animal under conditions to improve performance of a single task; a complex set of tasks; or a wide scope of tasks, resulting in generalized improved function of one or more cognitive domains. The tasks can relate to a skill involved in public service, such as public order maintenance, search and rescue, and contraband detection. The tasks can also relate to a skill involved in private service, such as private security, handicap assistance, health care, psychiatric assistance, and pest control.

Peripheral Disorders

PDE4 enzymes are located in a number of peripheral tissues. For example, one or several PDE4D isoforms are expressed throughout most tissues tested, including cortex, hippocampus, cerebellum, heart, liver, kidney, lung and testis (Richter et al., *Biochem. J.*, 2005, 388, 803-811). The localization and regulation of PDE4D isoforms is thought to allow for tight and local regulation of cAMP levels, possibly limiting signal propagation in specific subcellular compartments.

Thus, in one embodiment, the invention provides a method of treating a peripheral disorder associated with PDE4, by administering to an animal in need thereof a therapeutically effective amount of a compound or pharmaceutical composition described herein.

The peripheral disorder may include, but is not limited to, such PDE4-associated disorders as inflammatory bowel disease (Banner and Trevethick, 2004, *Trends Pharmacol. Sci.* 25, 430-436); rheumatoid arthritis (Kobayashi et al., 2007, *Mediators Inflamm.* 2007, 58901); chronic obstructive pulmonary disease (COPD), asthma, allergic rhinitis, pulmonary artery hypertension (DeFranceschi et al., 2008, *FASEB J.*, 22, 1849-1860); renal diseases (Conti et al., 2003, *J. Biol. Chem.*, 278, 5493); allergic skin diseases and psoriasis (Baumer et al., 2007, *Inflamm. Allergy Drug Targets*, 6, 17-26).

Examples

The present disclosure will be further illustrated by the following non-limiting Examples. These Examples are understood to be exemplary only, and they are not to be construed as limiting the scope of the invention herein, and as defined by the appended claims.

Preparative Examples

Exemplary compounds useful in methods of the invention will now be described by reference to the illustrative synthetic schemes for their general preparation below and the specific examples to follow.

Synthetic Schemes

One skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between −78° C. and the reflux temperature of the solvent. Reactions may be heated employing conventional heating or microwave heating. Reactions may also be conducted in sealed pressure vessels above the normal reflux temperature of the solvent.

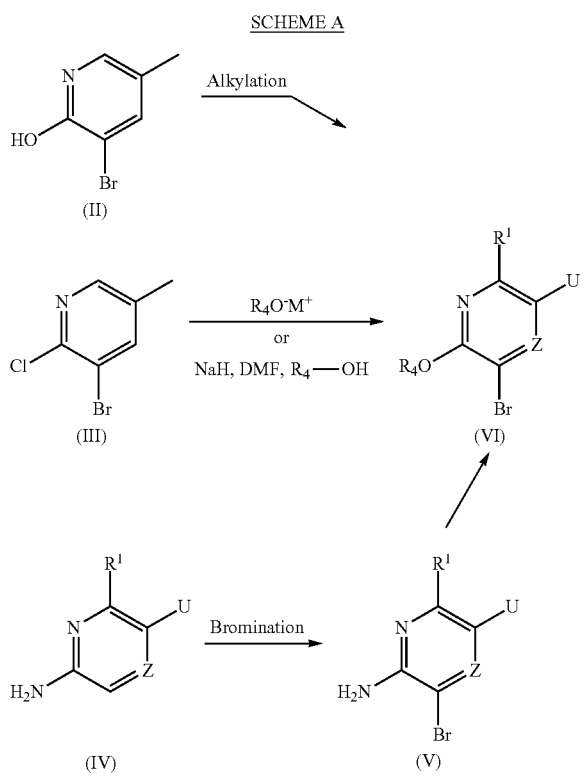

According to Scheme A, commercially available or synthetically accessible 3-bromo-5-methylpyridin-2-ol (II) is difluoromethylated with 2,2-difluoro-2-(fluorosulfonyl)acetic acid or the silyl ester of 2-fluorosulfonyldifluoroacetate, preferably 2,2-difluoro-2-(fluorosulfonyl)acetic acid, in an aprotic solvent, such as ACN, a base, such as $Na_2CO_3$, NaH, and the like, preferably $Na_2CO_3$, at temperatures ranging from room temperature to the reflux temperature of the solvent, preferably room temperature, to afford a compound of formula (VI) where Z is CH and $R_4$ is $CHF_2$ (Chen et al., J. Flourine Chem., 1989, 44, 433-440).

According to Scheme A, compounds of formula (VI), where Z is CH, $R^4$ is —$C_{1-3}$alkyl or —$C_{1-3}$haloalkyl, are prepared from commercially available or synthetically accessible 3-bromo-2-chloro-5-methylpyridine (III). Reaction of 3-bromo-2-chloro-5-methylpyridine (III), with an alkoxide, such as sodium ethoxide, sodium methoxide and the like, in a suitable solvent, such as the alcohol used to generate the alkoxide, at temperatures ranging from room temperature to the reflux temperature of the solvent, for a period of 4 to 48 h provides bromopyridyl ethers of formula (VI). Alternatively, compounds of formula (VI), where $R^4$ is —$C_{1-3}$alkyl or —$C_{1-3}$haloalkyl, may be prepared by reaction of 3-bromo-2-chloro-5-methylpyridine with a suitably substituted primary or secondary alcohol, in the presence of a base such as NaH, in a solvent, such as DMA, 1,4-dioxane, THF, and the like, at temperatures ranging from room temperature to the reflux temperature of the solvent.

According to Scheme A, commercially available or synthetically accessible 5-methylpyrazin-2-amine (IV), where $R^1$ is H, U is $CH_3$, and Z is N), is brominated under conditions known to one skilled in the art, for example, by reaction with a suitable halogenating agent such as NBS, $Br_2$, and the like, in an appropriate solvent such as DCM, 1,4-dioxane, THF, $CHCl_3$, preferably DCM, at temperatures ranging from 0° C. to room temperature, for a period of 8 to 16 h to afford 3-bromo-5-methylpyrazin-2-amine. Subsequent reaction of 3-bromo-5-methylpyrazin-2-amine (V) with an oxidizing agent, such as, but not limited to, tert-butyl nitrite, in the presence of an anhydrous acid source, for example, HCl in 1,4-dioxane, in an alcoholic solvent such as MeOH, EtOH, and the like, at temperatures ranging from 0° C. to 60° C., for a period of 8 to 16 h affords compounds of formula (VI), where Z is N, U is —$CH_3$, and $R_4$ is —$C_{1-3}$alkyl. According to Scheme A, commercially available or synthetically accessible 6-amino-2-methylnicotinonitrile (IV), where $R^1$ is —$CH_3$, U is —CN, and Z is CH is prepared in two steps (bromination and diazotization/alcohol addition) by the methods previously described to provide compounds of formula (VI) where $R^1$ is —$CH_3$, U is —CN, and Z is CH.

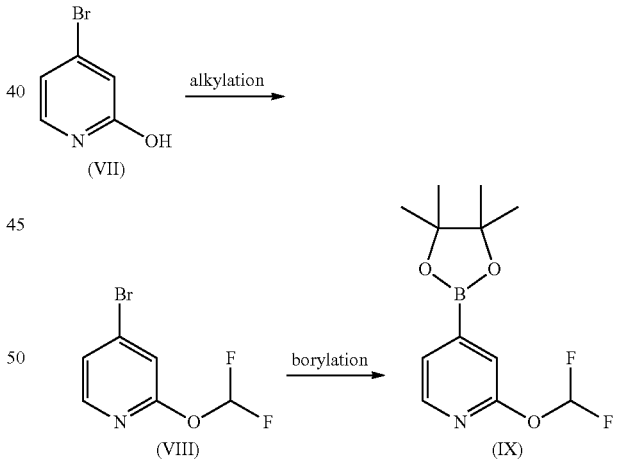

According to Scheme B, 2-(difluoromethoxy)-4-(4,4,5,5-tetramethyl-1,3,2-dioxoborolan-2-yl)pyridine (IX) is obtained in 2 steps from commercially available 4-bromo-2-hydroxypyridine (VII). Alkylation of 4-bromo-2-hydroxypyridine (VII), with 2-chloro-2,2-difluoroacetate in a solvent such as ACN, THF, 1,4-dioxane, or a mixture thereof, at temperatures ranging from room temperature to the reflux temperature of the solvent, for a period of 6-12 h (also described in WO2010/056195, May 20, 2010) provides 4-bromo-2-(difluoromethoxy)pyridine (VIII). Boronate esters are prepared using methods known to one skilled in the art, for example, 2-difluoromethoxy-4-(4,4,5,5-tetramethyl-

[1,3,2]dioxaborolan-2-yl)-pyridine (IX) is prepared from 4-bromo-2-(difluoromethoxy)pyridine (VIII) by reaction with KOAc, $K_3PO_4$, and the like, a catalyst such as Pd(dppf)$Cl_2$, $Pd(PPh_3)_4$, and the like, bis(pinacolato)diboron, and the like, in a solvent such as 1,4-dioxane, 1-2-dimethoxyethane, DMF, DMSO, and the like, at temperatures ranging from 60 to 150° C., for a period of 6-24 h.

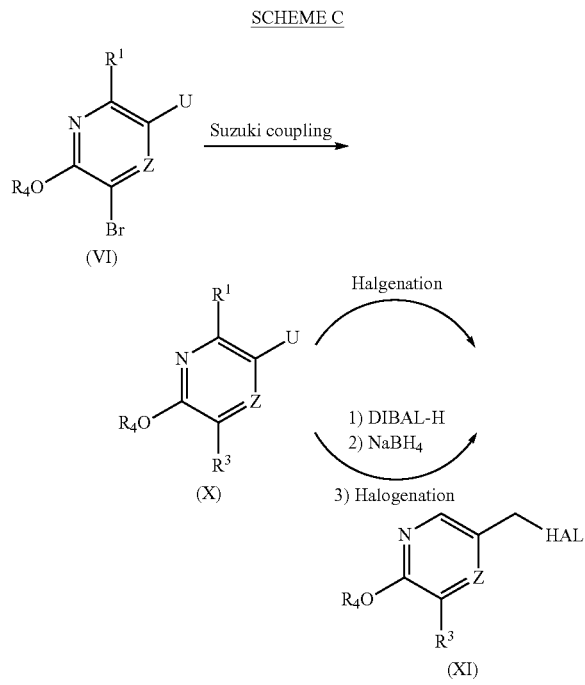

SCHEME C

As shown in Scheme C, compounds of formula (VI), where U is —$CH_3$, —CN or —$NH_2$, Z is CH or N; $R^1$ is H or —$CH_3$, and $R^4$ is —$C_{1-3}$alkyl or —$C_{1-3}$haloalkyl; under Suzuki reaction conditions known to one skilled in the art, are reacted with commercially available or synthetically accessible aromatic or heteroaromatic boronic acids or esters, or synthetically accessible heteroaromatic boronic esters, such as compound (IX), in a solvent such as ACN, toluene, EtOH, $H_2O$, or a mixture thereof, in the presence of a base such as, $NaHCO_3$, $Na_2CO_3$, $K_2CO_3$, $Cs_2CO_3$, and the like, and a palladium catalyst such as, $Pd(dppf)_2$, $Pd(Ph_3)_4$, and the like, using conventional or microwave heating, at temperatures ranging from 80 to 120° C. provides compounds of formula (X). Compounds of formula (X) where $R^3$ is aryl or heteroaryl optionally substituted with —OH, under standard alkylating conditions known to one skilled in the art, are treated with commercially available or synthetically accessible alkyl groups with appropriate leaving groups, such as halides, for example —Cl, —Br or —I, or sulfonates, such as methanesulfonyl, p-toluenesulfonyl and the like, in the presence of a base, such as but not limited to, NaH, $K_2CO_3$, $Cs_2CO_3$, and the like, in a solvent such as DMF, DMSO, 1,4-dioxane, and the like, at temperatures ranging from 60° C. to the reflux temperature of the solvent for a period of 8 to 24 h, to provide aryl or heteroaryl O-alkyl compounds of formula (X).

Halogenation of compounds of formula (X), where U is —$CH_3$, Z is CH or N; $R^1$ is H or —$CH_3$, $R_3$ is aryl or heteroaryl, and $R^4$ is —$C_{1-3}$alkyl or —$C_{1-3}$haloalkyl, under standard halogenation conditions, for example, NBS, a radical initiator such as AIBN or benzoyl peroxide, in a solvent such as $CCl_4$, at temperatures ranging from 60° C. to the reflux temperature of the solvent, for a period of 4 to 24 h, provides compounds of formula (XI), where HAL is —Br.

Nitrile compounds of formula (X), where U is —CN, Z is CH; $R^1$ is —$CH_3$, $R_3$ is aryl or heteroaryl, and $R^4$ is —$CH_3$, are reduced to the corresponding aldehyde with a reducing agent such as diisobutylaluminum hydride, and the like, in a solvent such as DCM, THF, toluene, and the like, at low temperature, preferably −78° C., for a period of 1 to 3 h. Subsequent reduction of the aldehyde moiety to the corresponding alcohol, is accomplished with a reducing agent, such as sodium or lithium borohydride, and the like, in a solvent such as MeOH, THF, and the like, at temperatures ranging from 0° C. to room temperature. Activation of the alcohol using methanesulfonyl chloride, in a suitable solvent, such as DCM, in the presence of an alkylamine base, such as Hünig's base, TEA, and the like, provides compounds of formula (XI), where U is —CN, Z is CH; $R^1$ is —$CH_3$, $R^4$ is —$CH_3$ and HAL is —Cl.

According to Scheme C, 5-bromo-6-methoxypyridin-3-amine, where U is —$NH_2$, Z is CH; $R^1$ is H, $R^4$ is —$CH_3$, is reacted under standard Suzuki reaction conditions as previously described, to provide compounds of formula (X), where U is —$NH_2$, Z is CH; $R^1$ is H, $R^3$ is aryl or heteroaryl, and $R^4$ is —$CH_3$. Alternately, compounds of formula (X), may be prepared from commercially available or synthetically accessible suitably substituted pyridine amines, such as, 5-bromo-6-ethoxypyridin-3-amine, as outlined in the procedures described above, where U is —$NH_2$, Z is CH; $R^1$ is H, $R^3$ is aryl or heteroaryl, and $R^4$ is —$C_{1-3}$alkyl.

SCHEME D

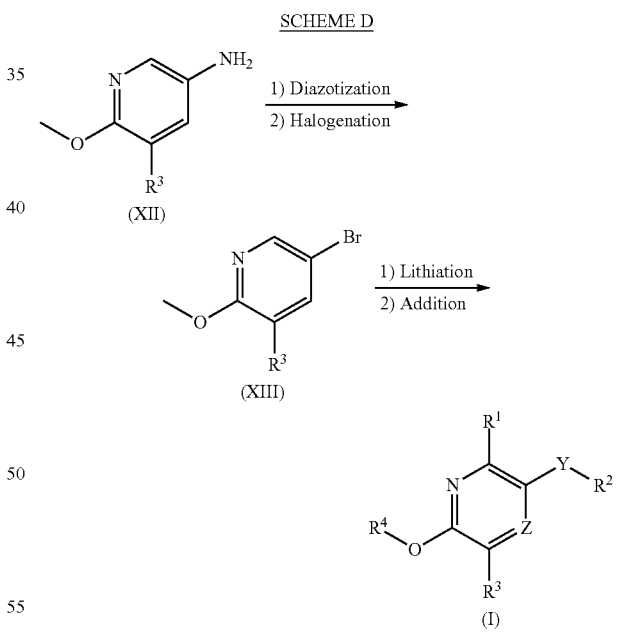

According to Scheme D, compounds of formula (XII), under Sandmeyer conditions known to one skilled in the art, are reacted with an oxidizing agent, such as, but not limited to, tert-butyl nitrite, in the presence of a halogenating agent, for example copper(II)bromide, in an appropriate solvent, such as ACN and the like, at a suitable temperature, preferably 60° C., affords compounds of formula (XIII) Lithiation of compounds of formula (XIII) with a suitable metallo-base, such as n-BuLi or the like, in a non-protic solvent, such as THF, $Et_2O$ or the like, at a low temperature, preferably −78° C., for a period of 30-60 minutes, prior to addition of an appropriate aryl or heteroarylcarbonyl compound, followed by additional stirring at temperatures ranging from −78° C. to ambient temperature, provides compounds of Formula (I), where Y is CHOH, Z is CH, $R^2$ and $R^3$ are monocyclic aromatic or heteroaromatic rings, and $R^4$ is —$CH_3$.

Fluoro compounds of Formula (I), where Y is —$C(R^a)_2$—, and $R^a$ is —H or —F; are prepared by the reaction of alcohols of Formula (I), where Y is CH(OH), employing fluorinating conditions such, but not limited to, reaction with Deoxo-Fluor® , XtalFluor® and the like, in a solvent such as DCM and the like, at room temperature, for a period of 1 to 24 h.

Compounds of Formula (I), where Y is —$C(R^a)_2$—, and $R^a$ is —H are prepared by treating the alcohols of Formula (I), where Y is CH(OH), with a reducing agent, such as but not limited to triethylsilane in the presence of an acid source, such as trifluoroacetic acid, triflic acid and the like, in a solvent such as DCM and the like, at room temperature, for a period up to 24 h.

Amine compounds of Formula (I), where Y is —$CHNH_2$—, —$CHNH(CH_3)$—, or —$CHN(CH_3)_2$—, are prepared in two steps by the reaction of alcohols of Formula (I), where Y is —CH(OH), with a chlorinating agent, such as thionyl chloride, oxalyl chloride and the like, with or without a catalytic amount of DMF, in a solvent such as DCM, and the like, at temperatures ranging from 0° C. to room temperature to provide the chloro intermediate which is then reacted with the appropriate amine, such as, but not limited to ammonia, methylamine and the like, with or without a catalytic amount of sodium iodide, in solvent such as ACN, at a temperature ranging from room temperature to 80° C.

SCHEME E

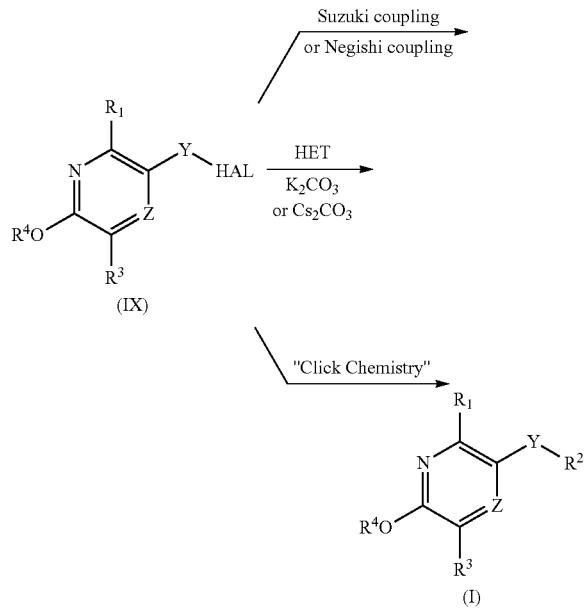

As described in Scheme E, compounds of Formula (I) can be obtained from compounds of formula (IX) thru reactions such as, but not limited to, Suzuki or Negishi coupling reactions, and substitution reactions with nitrogen heteroaryls, Compounds of formula (IX) are reacted, employing standard Suzuki coupling conditions, known to those skilled in the art and previously described herein, with commercially available aromatic or heteroaromatic boronic acids or esters, or synthetically accessible heteroaromatic boronic esters, such as compound (IV), to give compounds of Formula (I).

Compounds of formula (IX) are reacted, employing standard Negishi coupling conditions, known to those skilled in the art. An example of Negishi reaction conditions are: coupling commercially available halogen containing aromatic or heteroaromatic intermediates, with a preformed zincate obtained from reacting compounds of formula (IX) with zinc, pretreated with activators such as trimethylsilyl chloride and 1,2-dibromoethane, in an appropriate solvent, such as THF, 1,4-dioxane, and the like, at a temperature ranging from room temperature to reflux temperature, preferably reflux temperature, for a period of 12 to 24 h. Combining the zincate intermediate with commercially available halogen containing aromatic or heteroaromatic compounds in the presence of a palladium catalyst, such as $Pd(PPh_3)_4$ and the like, in a suitable solvent, such as THF, 1,4-dioxane, and the like, at temperatures ranging from 50° C. to the reflux temperature of the solvent, for a period of 12 to 48 h, affords compounds of Formula (I), where $R^2$ is a six membered heteroaryl ring containing one to two nitrogen members.

Compounds of formula (IX) when combined with the appropriate heterocycle (HET) with an acidic proton, such as but not limited to, 1H-1,2,4-triazole or imidazole, in an aprotic solvent, for example DMF, acetone, ACN, and the like, with a suitable base, such as $Cs_2CO_3$, $K_2CO_3$, and the like, at temperatures ranging from room temperature to 60° C., for period of 2 to 24 h, provides compounds of Formula (I), where $R^2$ is a five membered heteroaryl ring containing two to three nitrogen members.

Compounds of Formula (I), where Y is —$CH_2$, and $R^2$ is an optionally substituted 1,2,3-triazole are obtained using "Click Chemistry" (for example, copper-catalyzed azide-alkyne cycloaddition) under conditions known to one skilled in the art, for example, by treating compounds of formula (IX) with sodium azide in a suitable solvent, such as DMF, acetone, DMSO, and the like, and base such as $K_2CO_3$, and the like, at temperatures ranging from room temperature to 100° C., affords the azido intermediate which is then combined with a commercially available or synthetically accessible alkyne, such as but not limited to ethynyltrimethylsilane, and the like, in a solvent such as DMSO, 1,4-dioxane, THF, ACN, t-butanol, and water or a mixture thereof, in the presence of a catalyst, for example copper(II)iodide, copper (II)bromide, copper(I)sulfate, and the like, and base, such as Hünig's base, and the like, at temperatures ranging from room temperature to 100° C., for a period of 2 to 12 h, provides compounds of Formula (I), where $R^2$ is an optionally substituted 1,2,3-triazole.

Compounds of Formula (I), where $R^2$ is substituted with an amide (—$CONH_2$), are prepared from the corresponding nitriles (—CN) or esters (—$CO_2C_{1-3}$alkyl) using methods known to those skilled in the art. For example, amides of Formula (I) are obtained by reaction of nitrile compounds of Formula (I) with a base, such as NaOH or KOH, preferably NaOH, and a peroxide, such as hydrogen peroxide, in a solvent such as MeOH, and the like, at a temperatures ranging from 0 to 50° C., for a period of 8 to 24 h. Optionally, carboxylic acid compounds of Formula (I) are obtained when nitrile compounds of Formula (I) are treated as described above at a temperature of 50° C., for a period of 2 to 4 h. Ester compounds of Formula (I) are converted to amides of Formula (I) by treating with an appropriate amine, such as ammonia, methylamine or the like, in a solvent, such as MeOH, 1,4-dioxane, and the like, at temperatures ranging from room temperature to the reflux temperature of the solvent.

Compounds of Formula (I), where $R^2$ is substituted with a primary (—$CH_2OH$) or tertiary (—$C(CH_3)_2OH$) alcohol were prepared from the corresponding aldehyde or ester compounds of Formula (I), using methods known to those skilled in the art. Reduction of aldehyde compounds of Formula (I) with a reducing agent, such as $NaBH_4$ or sodium cyanoborohydride, and the like, in a solvent such as MeOH, THF, DMF and the like, at temperatures ranging from 0° C. to room temperature, for a period of 0.2 to 2 h, affords primary alcohol compounds of Formula (I), where $R^2$ is substituted with —$CH_2OH$. Compounds of Formula (I), where $R^2$ is substituted with an ester moiety, are reduced, with a reducing agent, such as lithium borohydride, lithium aluminum hydride, and the like, in a solvent such as MeOH, THF, $Et_2O$ and the like, at temperatures ranging from 0° C. to room temperature, for a period of 2 to 24 h, affords primary alcohol compounds of Formula (I), where $R^2$ is substituted with —$CH_2OH$.

Compounds of Formula (I), where $R^2$ is substituted with —$CH_2OH$ or —CHO, are fluorinated, employing fluorinating conditions such as, but not limited to, reaction with Deoxo-Fluor®, XtalFluor® and the like, in a solvent such as DCM and the like, room temperature, for a period of 2 to 24 h, to provide fluoroalkyl compounds of Formula (I), where $R^2$ is substituted with —$CH_2F$ or —$CHF_2$.

Compounds of Formula (I), where $R^2$ is substituted with an ester moiety, are reacted under Grignard conditions known to one skilled in the art, with a Grignard reagent such as, but not limited to, methylmagnesium bromide, in a solvent such as THF, $Et_2O$, and the like, at temperatures ranging from 0° C. to room temperature, for a period of 0.3 to 2 h, to provide compounds of Formula (I), where $R^2$ is substituted with a tertiary alcohol (—$C(CH_3)_2OH$).

Compounds of Formula (I), where $R^2$ is substituted with —CN, are reduced with a reducing agent, such as diisobutylaluminum hydride and the like, in a solvent such as $Et_2O$, THF, and the like, at low temperatures, preferably −78° C., for a period of 1 to 4 h, to provide primary amine compounds of Formula (I), where $R^2$ is substituted with primary amine (—$CH_2NH_2$).

Compounds of Formula (I), where $R^2$ is substituted with an ester moiety, are reacted under standard hydrolysis conditions known to one skilled in the art, with a base such as, but not limited to, KOH, LiOH, NaOH and the like, in a solvent such as THF, 1,4-dioxane, MeOH, $H_2O$ or a mixture thereof, at temperatures ranging from room temperature to the reflux temperature of the solvent, for a period of 1 to 4 h, to provide compounds of Formula (I), where $R^2$ is substituted with carboxylic acid (—$CO_2H$).

Compounds of Formula (I), where $R^2$ is an optionally substituted pyrimidine with —Cl are reacted with an amine, such as N1,N1-dimethylethane-1,2-diamine, and the like, in a solvent such as ACN, a base such as N-ethyl-N-isopropylpropan-2-amine, and the like, at temperature ranging from 80 to 180° C., using conventional or microwave heating conditions, for a period of 1 to 4 h, to provide amine substituted compounds of Formula (I), where $R^2$ is substituted with (—$NHCH_2CH_2N(CH_3)_2$).

Compounds of Formula (I), where $R^2$ is substituted with —$NO_2$, are reduced with a reducing agent, such as, but not limited to zinc or iron, in a solvent such as acetic acid, water, or a mixture thereof, at temperatures ranging from room temperature to 50° C., for a period of 1 to 4 h, to provide primary amine compounds of Formula (I), where $R^2$ is substituted with primary amine (—$NH_2$).

Compounds of Formula (I), where $R^2$ is substituted with (—$NHR^b$) or (—$N(R^b)_2$) are prepared from the corresponding amine compounds of Formula (I), employing methods known to one skilled in the art, such as but not limited to reductive amination reactions. For example, compounds of Formula (I) where $R^2$ is substituted with (—$NH_2$), are reacted with an appropriate carbonyl intermediate, such as but not limited to, formaldehyde and the like, in a solvent such as THF, DCM, MeOH and the like, with a reducing agent, such as sodium triacetoxyborohydride, sodium cyanoborohydride and the like, at temperatures ranging from 0 to 50° C., for a period of 1 to 4 h, provides alkyl amine compounds of Formula (I), where $R^b$ is —$CH_3$.

Compounds of Formula (I), where $R^2$ is substituted with (—$NHCOCH_3$) are prepared from the corresponding amine compounds of Formula (I), employing methods known to one skilled in the art, such as but not limited to, treatment with an acyl chloride or anhydride. For example, compounds of Formula (I) where $R^2$ is substituted with (—$NH_2$), are treated with an appropriately activated acylating agent, such as but not limited to, acetyl chloride, acetic anhydride and the like, in a solvent such as, DCM, DMF and the like, with a base, such as TEA, Hünig's base, and the like, at temperatures ranging from 0° C. to room temperature, for a period of up to 24 h, provides acyl substituted amine compounds of Formula (I), where $R^2$ is (—$NHCOCH_3$)

Compounds of Formula (I), where $R^2$ is substituted with (—$NHCONH_2$) are prepared from the corresponding amine compounds of Formula (I), employing methods known to one skilled in the art, such as but not limited to, treatment with potassium cyanate and the like, in a solvent such as, acetic acid and water or a mixture thereof, at temperatures ranging from room temperature to 60° C., for 0.2 to 4 h, to provide urea substituted compounds of Formula (I), where $R^2$ is (—$NHCONH_2$). Optionally, compounds of Formula (I), where $R^2$ is substituted with (—NHCONH-oxetane) are prepared from the corresponding carboxylic acid compounds of Formula (I), using the Curtius rearrangement employing methods known to one skilled in the art. For example, compounds of Formula (I) where $R^2$ is substituted with (—$CO_2H$), are treated with, but not limited to, diphenylphosphoryl azide and the like, in the presence of a base, such as TEA, Hünig's base, and the like, in an appropriate solvent such as, toluene, 1,-4-dioxane, and the like, at the reflux temperature of the solvent, for a period of up to 1 h. The intermediate acyl azide is then reacted with an appropriate amine, in the presence of a base, such as TEA, Hünig's base, and the like, to afford the compounds of Formula (I) where $R^2$ is substituted with (—NHCONH-oxetane)

Compounds of Formula (I), where $R^2$ is substituted with —$NO_2$, are reacted with a commercially available or synthetically accessible metallo-alkoxide, for example, sodium methoxide, sodium ethoxide and the like, in a solvent such as, but not limited to, MeOH, EtOH, 1,4-dioxane and the like, at temperatures ranging from room temperature to the reflux temperature of the solvent, for a period of 24 h, to provide compounds of Formula (I) where $R^2$ is substituted with (—$OC_{1-3}$alkyl).

Compounds of Formula (I), wherein $R^2$ is 1,2,3-triazole optionally substituted with —H, are synthesized from the corresponding 4-(trimethylsilyl)-1H-1,2,3-triazol-1-yl) compounds of Formula (I), by reacting with a desilylating agent, such as but not limited to, tetrabutylammonium fluoride, in a solvent such as THF, DMF, and the like, at temperatures ranging from room temperature to 50° C., for a period of 8 to 24 h.

Compounds of Formula (I), where $R^2$ is substituted with —CHO, are prepared from the corresponding alcohols or esters, previously described using methods known to those skilled in the art. For example, treating an alcohol of Formula (I) with an oxidizing agent, such as but not limited to Dess-Martin® reagent, in an appropriate solvent, such as DCM or THF and the like, at room temperature for 3 to 8 h give the desired aldehyde. The desired aldehydes of Formula (I) are also obtained by treating the corresponding ester of Formula (I) with a reducing agent, such as diisobutylaluminum hydride, in an appropriate solvent, such as THF, Et$_2$O and the like, at low temperature, preferably −78° C., for 1 to 4 h.

Removal of the terl-butylcarbamate (BOC) in compounds of Formula (I) where R$^2$ is optionally substituted with (—NH—BOC) or (—HET-N—BOC) is accomplished by using methods known to one skilled in the art, such as, HCl, TFA, or p-toluenesulfonic acid, in a solvent such as CH$_3$OH, dioxane, or CH$_2$Cl$_2$. In a preferred embodiment, a compound of formula is treated with TFA in DCM or HCl to afford a compound of Formula (I) where R$^2$ is optionally substituted with (—NH$_2$) or (—HET-NH$_2$)

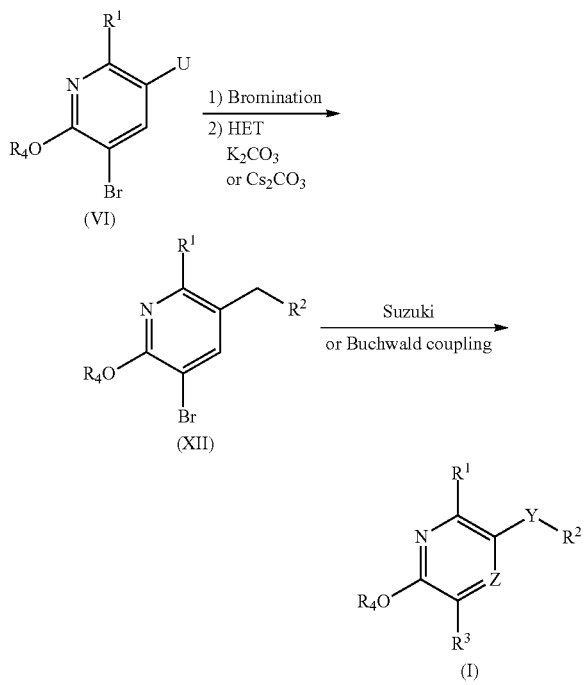

According to Scheme F, compounds of formula (VI) where U is —CH$_3$; R$^1$ is H, R$^4$ is —C$_{1-3}$alkyl or —C$_{1-3}$haloalkyl, are halogenated according to methods previously described to provide the corresponding alkylbromide compounds. Subsequent reaction with HET, where HET is a five membered heteroaryl ring selected from the group consisting of 1H-1,2,4-triazole or imidazole, according to methods previously described, provides compounds of formula (XII) where R$^2$ is 1H-1,2,4-triazole or imidazole.

Compounds of formula (XII) are reacted, employing standard Suzuki coupling conditions, known to those skilled in the art and previously described herein, with commercially available aromatic or heteroaromatic boronic acids or esters, or synthetically accessible heteroaromatic boronic esters, such as compound (1V), to give compounds of Formula (I).

Optionally, compounds of Formula (I), where R$^3$ is substituted with pyrazole are prepared from the corresponding compounds of formula (XII), employing methods known to one skilled in the art, such as but not limited to, Buchwald coupling conditions. For example, compounds of formula (XII) are reacted with the appropriate heterocycle (HET) with an acidic proton, such as but not limited to, pyrazole, in a solvent, such as toluene, 1,4-dioxane, and the like, with a suitable base, such as sodium tert-butoxide, sodium methoxide, a palladium catalyst such as but not limited to, tris(dibenzylideneacetone)dipalladium(0), palladium(II)acetate and the like, and a phosphine ligand, such as (2-dicyclohexylphosphino-2'-(N,N-dimethylamino)biphenyl, tri(tert-butyl)phosphine and the like, at temperatures ranging from room temperature to the reflux temperature of the solvent, for period of 4 to 48 h, provides compounds of Formula (I), where insert R$^3$ is an optionally substituted pyrazole.

Compounds of Formula (I) may be converted to their corresponding salts using methods known to those skilled in the art. For example, compounds of Formula (I) may be treated with TFA, HCl, maleic acid, or citric acid in a solvent such as Et$_2$O, DCM, THF, or MeOH to provide the corresponding salt forms.

Compounds prepared according to the schemes described above may be obtained as single enantiomers, diastereomers, or regioisomers, by enantio-, diastereo-, or regiospecific synthesis, or by resolution. Where compounds according to this invention have at least one chiral center, they may accordingly exist as enantiomers. Where compounds possess two or more chiral centers, they may additionally exist as diastereomers. It is to be understood that all such isomers and mixtures thereof are encompassed within the scope of the present invention. Compounds prepared according to the schemes above may alternately be obtained as racemic (1:1) or non-racemic (not 1:1) mixtures of mixtures as diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following examples are provided to further illustrate the invention and various preferred embodiments.

EXAMPLES

Chemistry

In obtaining the compounds described in the examples below, and the corresponding analytical data, the following experimental and analytical protocols were followed unless otherwise indicated.

Unless otherwise stated, reaction mixtures were magnetically stirred at room temperature (rt) under nitrogen atmosphere. Where solutions were "dried", they were generally dried over a drying agent such as Na$_2$SO$_4$ or MgSO$_4$. Where mixtures, solutions, and extracts were "concentrated", they were typically concentrated on a rotary evaporator under reduced pressure.

Reactions under microwave irradiation conditions were carried out in a CEM Discover-SP with Activent microwave reaction apparatus, model number 909150, or Biotage Initiator, model number 355302.

Normal-phase flash column chromatography (FCC) was performed on silica gel (SiO$_2$) using packed or prepackaged cartridges, eluting with the indicated solvents.

LC/MS were obtained on a Waters 2695 Separations Unit, 2487 Dual Absorbance Detector, Micromass ZQ fitted with ESI Probe, or a Waters Acquity™ Ultra performance LC (UPLC) with PDA eλ and SQ detectors.

Nuclear magnetic resonance (NMR) spectra were obtained in a Varian 400 MHz or Bruker 400 MHz NMR. Samples were analyzed in either deuterated chloroform (CDCl$_3$), methanol-d$_4$ (CD$_3$OD), or dimethyl sulfoxide-d$_6$ (DMSO-d$_6$). For CDCl$_3$ samples, tetramethylsilane (TMS) was used as an internal standard with the TMS resonance set to a chemical shift of 0.00 ppm for $^1$H NMR spectra. For CD$_3$OD the residual central resonance peak at 3.31 for $^1$H was used for chemical shift assignment and for DMSO-d$_6$ the residual central resonance peak at 2.50 ppm for $^1$H was used for chemical shift assignment. The format of the $^1$H NMR data below is: chemical shift in ppm downfield the tetramethylsilane reference (multiplicity, coupling constant J in Hz, integration).

Chemical names were generated using ChemDraw Ultra 12.0 (CambridgeSoft Corp., Cambridge, Mass.) or ChemAxon.

Intermediate 1

5-(Bromomethyl)-3-(3-(difluoromethoxy)phenyl)-2-ethoxypyrazine

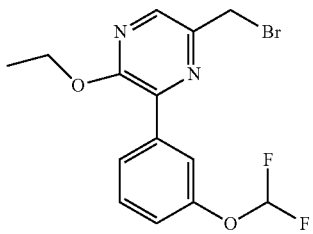 [SMILES: CCOc1ncc(CBr)nc1-c1cccc(OC(F)F)c1]

Step 1. 3-Bromo-5-methylpyrazin-2-amine. To a cooled, 0° C., solution of 5-methylpyrazin-2-amine (5.00 g, 0.05 mol) in DCM (230 mL) was added 1-bromopyrrolidine-2,5-dione (8.97 g, 0.05 mol) all at once. The reaction mixture was allowed to warm to room temperature and stirred for 12 h. The reaction was quenched with 1 N sodium thiosulfate (50 mL), the layers were separated and the organic phase was extracted with water (2×50 mL). The combined organic layers were dried (Na$_2$SO$_4$), and the solvent was removed under reduced pressure. Purification (FCC, SiO$_2$, 0-50%, EtOAc/hexanes) afforded the title compound as a yellow solid (8.61 g, 65%). [M+H]=188.9/190.11

Step 2. 3-Bromo-2-ethoxy-5-methylpyrazine. To a solution of 3-bromo-5-methylpyrazin-2-amine (4.00 g, 21.27 mmol) in EtOH (42 mL), at 0° C., was added tert-butyl nitrite (7.65 mL, 63.82 mmol) followed by 4 N hydrochloric acid in 1,4-dioxane (1.91 mL, 7.66 mmol). The reaction mixture was allowed to warm to room temperature and stirred for 8 h. The mixture was concentrated under reduced pressure. The residue was diluted with aq. NaHCO$_3$ and extracted into DCM. The combined organic layers were dried, and the solvent was removed under reduced pressure. Purification (FCC, SiO$_2$, 0-20%, EtOAc/hexanes) afforded the title compound as a white solid (2.5 g, 54%). [M+H]=217.06/219.05.

Step 3. 3-(3-(Difluoromethoxy)phenyl)-2-ethoxy-5-methylpyrazine. A solution of 3-bromo-2-ethoxy-5-methylpyrazine (1.80 g, 8.29 mmol), 3-(difluoromethoxy)phenyl)boronic acid (2.03 g, 10.78 mmol), tetrakis(triphenylphosphine) palladium(0) (958.25 mg, 0.83 mmol), sodium carbonate (21.63 mL, 1.15 mol/L, 24.88 mmol), in EtOH (22 mL) and toluene (118 mL), under nitrogen, was heated at 88° C. for 1 h. The reaction mixture was extracted with EtOAc. The combined organic layers were dried (Na$_2$SO$_4$), and the solvent was removed under reduced pressure. Purification (FCC, SiO$_2$, 0-50%, EtOAc/hexanes) afforded the title compound as a colorless oil (2.09 g, 90%). [M+H]=281.19.

Step 4. 5-(Bromomethyl)-3-(3-(difluoromethoxy)phenyl)-2-ethoxypyrazine. To a solution of 3-(3-(difluoromethoxy)phenyl)-2-ethoxy-5-methylpyrazine (2.00 g, 0.01 mol), 1-bromopyrrolidine-2,5-dione (1.27 g, 0.01 mol) in carbon tetrachloride (24 mL), was added benzoylperoxide (0.26 g, 1.07 mmol). The mixture was heated at 88° C. for 8 h. The reaction mixture was diluted with water and extracted with DCM. The combined organic layers were dried (Na$_2$SO$_4$) and the solvent was removed under reduced pressure. Purification (FCC, SiO$_2$, 0-5%, EtOAc/hexanes) afforded the title compound contaminated with ~10% starting material (1.5 g, 59%). [M−H]=459.13/361.13.

Intermediates 2-3 were prepared in a manner analogous to Intermediate 1, Steps 3-4, with the appropriated starting material substitutions.

Intermediate 2

5-(Bromomethyl)-3-(3-chlorophenyl)-2-methoxypyridine

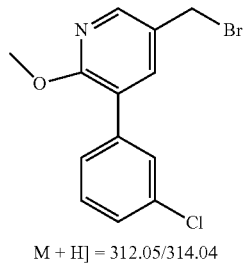 [SMILES: COc1ncc(CBr)cc1-c1cccc(Cl)c1]

M + H] = 312.05/314.04

Intermediate 3

5-(Bromomethyl)-3-(3-chlorophenyl)-2-methoxypyrazine

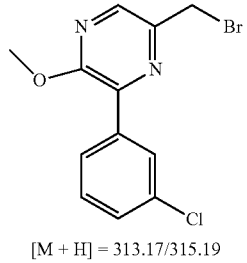 [SMILES: COc1ncc(CBr)nc1-c1cccc(Cl)c1]

[M + H] = 313.17/315.19

Intermediate 4

3-Bromo-2-(difluoromethoxy)-5-methylpyridine

3-Bromo-2-(difluoromethoxy)-5-methylpyridine. To a solution of 3-bromo-5-methylpyridin-2-ol (25.0 g, 0.13 mol) in ACN (100 mL) was added 2,2-difluoro-2-(fluorosulfonyl)acetic acid (23.7 g, 0.13 mol) and sodium carbonate (28.2 g, 0.270 mol). The reaction mixture was stirred at room temperature overnight. Water was added to the reaction mixture, and the reaction mixture was extracted with DCM. The combined organic layers were dried ($Na_2SO_4$), and the solvent was removed under reduced pressure. Purification (FCC, $SiO_2$, 0-10%, EtOAc/hexanes) afforded the title compound as an off-white solid (22 g, 70%). M+H]=238.09/240.09.

Intermediate 5

5-((1H-1,2,4-Triazol-1-yl)methyl)-3-bromo-2-(difluoromethoxy)pyridine

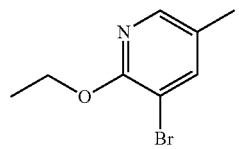

Step 1. 3-Bromo-5-(bromomethyl)-2-(difluoromethoxy)pyridine. To a solution of 3-bromo-2-(difluoromethoxy)-5-methylpyridine (0.50 g, 2.1 mmol) in carbon tetrachloride (13 mL), was added 1-bromopyrrolidine-2,5-dione (0.521 g, 2.93 mmol), and azobisisobutyronitrile (44 mg, 0.26 mmol). The reaction mixture was stirred at 80° C. for 8 h. The reaction mixture was diluted with water and extracted with DCM. The combined organic layers were dried ($Na_2SO_4$), and the solvent was removed under reduced pressure. Purification (FCC, $SiO_2$, 10-90%, EtOAc/hexanes) afforded the title compound (400 mg, 60%). [M+H]=317.88.

Step 2. 5-((1H-1,2,4-Triazol-1-yl)methyl)-3-bromo-2-(difluoromethoxy)pyridine. To a solution of 3-bromo-5-(bromomethyl)-2-(difluoromethoxy)pyridine (Intermediate 4, 0.50 g, 1.57 mmol) in acetone (12 mL), was added 1H-1,2,4-triazole (202 mg, 2.9 mmol), and potassium carbonate (650 mg, 4.7 mmol). The reaction mixture stirred at room temperature for 2 h, then filtered and concentrated under reduced pressure. Purification (FCC, $SiO_2$, 30-70%, EtOAc/hexanes) afforded the title compound (431 mg, 90%). [M+H]=304.91/306.91.

Intermediate 6

3-Bromo-2-ethoxy-5-methylpyridine

To a solution of 3-bromo-2-chloro-5-methylpyridine (4.00 g, 19.37 mmol) in ethanol (100 mL) was added sodium ethoxide (6.59 g, 96.9 mmol) in three portions. The mixture was stirred under nitrogen at 100° C. for 2 days. The reaction was cooled to room temperature, diluted with water and extracted with DCM. The combined organic layers were dried ($Na_2SO_4$), and the solvent was removed under reduced pressure. Purification (FCC, $SiO_2$, 20%, EtOAc/hexanes) afforded the title compound (3.00 g, 72%). $^1$H NMR (400 MHz, DMSO-$d_6$) δ 7.94 (dd, J=0.8, 2.3 Hz, 1H), 7.89-7.82 (m, 1H), 4.31 (q, J=7.0 Hz, 2H), 2.18 (t, J=0.8 Hz, 3H), 1.30 (t, J=7.0 Hz, 3H).

Intermediate 7

5-Bromo-3-(3-chlorophenyl)-2-methoxypyridine

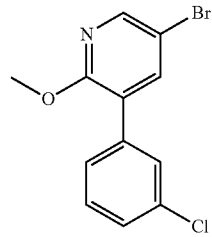

Step 1. 5-(3-Chlorophenyl)-6-methoxypyridin-3-amine. A 10 mL microwave vial was charged with 5-bromo-6-methoxypyridin-3-amine (2.00 g, 10 mmol) (3-chlorophenyl)boronic acid (1.87 g, 12 mmol), 1,1'-bis(diphenylphosphino)ferrocene-palladium(II)dichloride DCM complex (365 mg, 0.45 mmol), ACN (6 mL) and saturated aq. sodium bicarbonate (3 mL). The vial was sealed, purged with nitrogen and heated at 110° C. for 15 min. The layers were separated and the aq. phase extracted with EtOAc. The combined organic layers were dried ($Na_2SO_4$), and the solvent was removed under reduced pressure. Purification (FCC, $SiO_2$, 0-50%, EtOAc/hexanes) afforded the title compound (1.95 g, 84%) which was taken on directly to the next step.

Step 2. 5-Bromo-3-(3-chlorophenyl)-2-methoxypyridine. A solution of 5-(3-chlorophenyl)-6-methoxypyridin-3-amine (1.95 g, 8.39 mmol), copper (II) bromide (3.72 g, 16.7 mmol), tert-butyl nitrite (1.7 g, 16.7 mmol) in ACN (50 mL), under nitrogen, was heated at 60° C. for 12 h. The reaction mixture was concentrated under reduced pressure. Purification (FCC, SiO₂, 0-10%, EtOAc/hexanes) afforded the title compound as an orange solid (1.53 g, 61%). [M+H]=298.20/300.21.

Intermediate 8

3-(Chloromethyl)-5-(3-chlorophenyl)-6-methoxy-2-methylpyridine

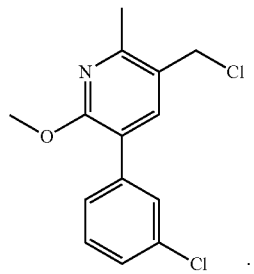 [SMILES: COc1nc(C)c(CCl)cc1-c1cccc(Cl)c1]

Step 1. 6-Amino-5-bromo-2-methylnicotinonitrile. A solution of 6-amino-2-methylnicotinonitrile (5 g, 37.6 mmol), NBS (7.36 g, 41.3 mmol) and DCM (100 mL) was stirred at room temperature for 1 hr. The reaction mixture was concentrated under reduced pressure. Purification (FCC, SiO₂, 1:1 EtOAc/DCM) afforded the title compound as tan solid (4.5 g, 56%). [M+H]=211.95/213.96.

Step 2. 5-Bromo-6-methoxy-2-methylnicotinonitrile. A solution of 6-amino-5-bromo-2-methylnicotinonitrile (4.5 g, 21.2 mmol), HCl (2 mL 4 N HCl in 1,4-dioxane), tert-butyl nitrite (6.56 g, 63.7 mmol) and methanol (50 mL) was heated at 60° C. for 12 h. The solvent was removed under reduced pressure. Purification (FCC, SiO₂, 0-25%, EtOAc/hexanes) afforded the title compound (2.5 g, 51%). [M+H]=226.96/228.96.

Step 3. 5-(3-Chlorophenyl)-6-methoxy-2-methylnicotinonitrile. A 20 mL microwave vial was charged with 5-bromo-6-methoxy-2-methylnicotinonitrile (1.2 g, 5.28 mmol), (3-chlorophenyl)boronic acid (990 mg, 6.3 mmol), 1,1'-bis(diphenylphosphino)ferrocene-palladium(II)dichloride DCM complex (191 mg, 0.26 mmol), ACN (10 mL) and saturated aq. sodium bicarbonate (3 mL). The vial was sealed, purged with nitrogen and heated at 100° C. under microwave irradiation for 10 min. The layers were separated and the aq. phase extracted with EtOAc. The combined organic layers were dried (Na₂SO₄), and the solvent was removed under reduced pressure. Purification (FCC, SiO₂, 0-50%, EtOAc/hexanes) afforded the title compound as an off white solid (995 mg, 74%). [M+H]=259.06.

Step 4. 5-(3-Chlorophenyl)-6-methoxy-2-methylnicotinaldehyde. To a cooled solution, −78° C., of 5-(3-chlorophenyl)-6-methoxy-2-methylnicotinonitrile (500 mg, 1.9 mmol) in DCM (15 mL), under nitrogen, was added diisobutylaluminum hydride (1 M in hexanes, 4.8 mL, 4.8 mmol) dropwise, over 3 minutes. The reaction mixture was stirred at −78° C. for 1 h. The reaction was carefully quenched by addition of saturated sodium fluoride (1 mL). After stirring for 30 minutes the suspension was filtered and the filtrate concentrated under reduced pressure. Purification (FCC, SiO₂, 0-50%, EtOAc/hexanes) afforded the title compound (358 mg, 72%). [M+H]=262.05.

Step 5. (5-(3-Chlorophenyl)-6-methoxy-2-methylpyridin-3-yl)methanol. To a solution of 5-(3-chlorophenyl)-6-methoxy-2-methylnicotinaldehyde (350 mg, 1.34 mmol) in methanol (3 mL) was added sodium borohydride (52 mg, 1.3 mmol). The solution was stirred at room temperature for 20 minutes then concentrated under reduced pressure. Purification (FCC, SiO₂, 0-50%, EtOAc/hexanes) afforded the title compound (322 mg, 91%). [M+H]=264.06.

Step 6. 3-(Chloromethyl)-5-(3-chlorophenyl)-6-methoxy-2-methylpyridine. Into a scintillation vial containing (5-(3-chlorophenyl)-6-methoxy-2-methylpyridin-3-yl)methanol (340 mg, 1.29 mmol) in DCM (5 mL), was added diisopropylethylamine (199 mg, 1.54 mmol), and methanesulfonyl chloride (147 mg, 1.29 mmol). The solution was stirred at room temperature for 1 h. The reaction mixture was extracted with water (3×). The combined organic layers were dried (Na₂SO₄), and the solvent was removed under reduced pressure. Purification (FCC, SiO₂, 0-30%, EtOAc/hexanes) afforded the title compound (87 mg, 24%). [M+H]=282.03

Intermediate 9

2-Difluoromethoxy-4-(4,4,5,5-tetramethyl-[1,3,2]dioxaborolan-2-yl)-pyridine

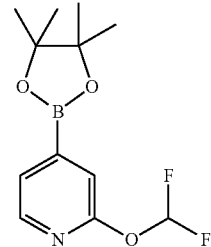 [SMILES: CC1(C)OB(c2ccnc(OC(F)F)c2)OC1(C)C]

Step 1. 4-Bromo-2-(difluoromethoxy)pyridine. To a stirring solution of 2-chloro-2,2-difluoroacetate (6.00 g, 39.4 mmol) in ACN (200 mL) was added 4-bromopyridin-2(1H)-one (4.90 g, 28.1 mmol). The mixture was refluxed for 8 h. The resulting mixture was filtered and the filtrate was extracted with hexane (6×20 mL). The combined organic layers were dried (Na₂SO₄), and concentrated at room temperature to give the title compound as a liquid (2.60 g, 42% yield). ¹H NMR (400 MHz, DMSO-d₆) δ 8.19-8.20 (s, 1H), 7.48 (s, 1H), 7.52 (s, 1H), 7.54-7.88 (m, 1H).

Step 2. 2-Difluoromethoxy-4-(4,4,5,5-tetramethyl-[1,3,2]dioxaborolan-2-yl)-pyridine. To a solution of 4-bromo-2-(difluoromethoxy)pyridine (7.20 g, 32.1 mmol), in 1,4-dioxane (230 mL), was added bis(pinacolato)diboron (8.80 g, 34.6 mmol), and potassium acetate (7.10 g, 71.9 mmol). The flask was fitted with a reflux condenser and vacuum/nitrogen inlet, and it was degassed/backfilled with nitrogen (3×). The catalyst, [1,1'-bis(diphenylphosphino)ferrocene]dichloropalladium(II) (2.35 g, 3.2 mmol) was added, and the reaction mixture was refluxed for 8 h. The resulting mixture was filtered, and concentrated under reduced pressure. Purification (FCC, SiO₂, 1:1 petroleum ether/hexanes) afforded the title compound (6.10 g, 70%) as a liquid. ¹H NMR (400 MHz, DMSO-d₆) δ 8.31-8.32 (d, J=4.8 Hz, 1H), 7.52-7.89 (m, 1H), 7.42-7.44 (d, J=4.8 Hz, 1H), 7.156 (s, 1H), 1.32 (s, 12H).

Intermediate 10

5-(Bromomethyl)-2-(difluoromethoxy)-3-(3-(oxetan-3-yloxy)phenyl)pyridine

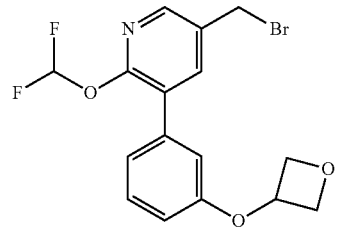 [SMILES: FC(F)Oc1ncc(CBr)cc1-c1cccc(OC2COC2)c1]

Step 1. 3-(2-(Difluoromethoxy)-5-methylpyridin-3-yl)phenol. A 20 mL microwave vial was charged with 3-bromo-2-(difluoromethoxy)-5-methylpyridine (intermediate 4, 1.90 g, 7.98 mmol), 3-hydroxyphenylboronic acid (1.32 g, 9.58 mmol), [1,1'-bis(diphenylphosphino)ferrocene]dichloropalladium(II) (330 mg, 0.40 mmol), sodium carbonate (2.12 g, 19.96 mmol), water (4.0 mL), and ACN (12 mL). The vial was sealed, purged with nitrogen, and heated under microwave irradiation at 100° C. for 15 min. The reaction mixture was diluted with water and extracted with DCM (3×). The combined organic phase was dried (Na₂SO₄), filtered, and concentrated under reduced pressure. Purification (FCC, SiO₂, 0-40% EtOAc/hexanes) afforded the title compound (1.81 g, 91%) as a colorless waxy solid. [M+H]=252.12.

Step 2. 2-(Difluoromethoxy)-5-methyl-3-(3-(oxetan-3-yloxy)phenyl)pyridine. To a solution of 3-(2-(difluoromethoxy)-5-methylpyridin-3-yl)phenol (502.5 mg, 2.0 mmol), in DMF, was added oxetan-3-yl 4-methylbenzenesulfonate (685 mg, 3.0 mmol), and potassium carbonate (553 mg, 4.00 mmol). The reaction mixture was stirred at 60° C. for 8 h. LC-MS suggested about 50% conversion. The temperature was raised to 90° C. and the reaction mixture was stirred an additional 4 h. Sat. aq. NaCl was added, and the mixture was extracted with DCM (3×). The combined organic layers were dried (Na₂SO₄), filtered and concentrated under reduced pressure. Purification (FCC, SiO₂, 10-30% EtOAc/hexanes) afforded the title compound (310 mg, 50%) as a colorless solid. [M+H]=308.11

Step 3. 5-(Bromomethyl)-2-(difluoromethoxy)-3-(3-(oxetan-3-yloxy)phenyl)pyridine. To a solution of 2-(difluoromethoxy)-5-methyl-3-(3-(oxetan-3-yloxy)phenyl)pyridine (310 mg, 1.0 mmol) in carbon tetrachloride (10 mL), was added 1-bromopyrrolidine-2,5-dione (180 mg, 1.0 mmol), and benzoylperoxide (37 mg, 0.15 mmol). The reaction mixture was stirred at 80° C. for 8 h. The reaction mixture was diluted with water and extracted with DCM. The combined organic layers were dried (Na₂SO₄), and the solvent was removed under reduced pressure. Purification (FCC, SiO₂, 10-30%, EtOAc/hexanes) afforded the title compound (140 mg, 36%). [M+H]=387.21

Intermediate 11

5-(Bromomethyl)-2-(difluoromethoxy)-3-(3-isopropoxyphenyl)pyridine

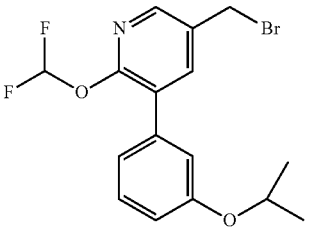 [SMILES: CC(C)Oc1cccc(-c2cc(CBr)cnc2OC(F)F)c1]

The title compound was prepared in a manner analogous to Intermediate 10, using 2-bromopropane for step 2, followed by bromination according to step 3. [M-FI-1]=373.24.

Intermediate 12

5-(Bromomethyl)-3-(3-chlorophenyl)-2-(difluoromethoxy)pyridine

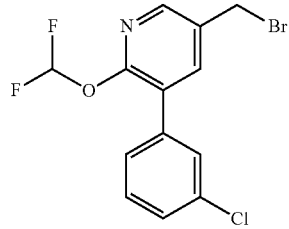 [SMILES: FC(F)Oc1ncc(CBr)cc1-c1cccc(Cl)c1]

The title compound was prepared in a manner analogous to Intermediate 10, using Intermediate 4 and 3-chlorophenyl boronic acid in Step 1, followed by bromination according to Step 3. [M+H]=348.17/350.15

Intermediate 13

5-((1H-1,2,4-Triazol-1-yl)methyl)-3-bromo-2-methoxypyridine

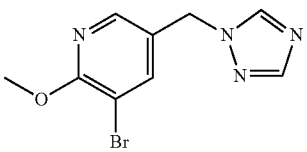

The title compound was prepared in a manner analogous to Intermediate 5, with the appropriate starting material substitutions. [M+H]=269.21/271.23

EXAMPLES

Example 1

5-({6-[3-(Difluoromethoxy)phenyl]-5-ethoxypyrazin-2-yl}methyl)pyrimidine-2-carbonitrile

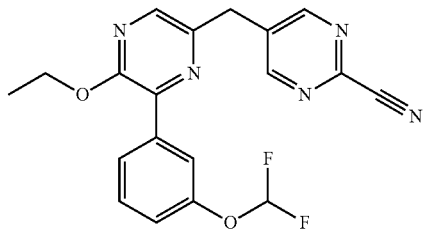 [SMILES: CCOc1ncc(Cc2cnc(C#N)nc2)nc1-c1cccc(OC(F)F)c1]

Into a 5 mL microwave vial was combined 5-(bromomethyl)-3-(3-(difluoromethoxy)phenyl)-2-ethoxypyrazine (Intermediate 1, 176.00 mg, 0.49 mmol), 5-(4,4,5,5-tetramethyl-1,3,2-dioxaborolan-2-yl)pyrimidine-2-carbonitrile (124.55 mg, 0.54 mmol), EtOH (2.45 mL), benzene (7.00 mL), tetrakis(triphenylphosphine)palladium(0) (56.63 mg, 0.05 mmol), and sodium bicarbonate (1.38 mL, 1.15 mol/L; 1.59 mmol). The vial was sealed, purged with nitrogen and heated to 125° C. under microwave conditions for 15 minutes. Water was removed from the reaction with a pipette, and the crude reaction mixture was filtered thru CELITE®, and washed with EtOAc (3×5 mL). The combined organic layers were dried ($Na_2SO_4$), and the solvent was removed under reduced pressure. Purification (FCC, $SiO_2$, 0-30%, EtOAc/hexanes) afforded the title compound as a white solid (100 mg, 53%). $^1$H NMR (400 MHz, $CD_3OD$) δ 8.94 (s, 2H), 8.17 (s, 1H), 7.95-7.90 (m, 1H), 7.85 (t, J=1.8 Hz, 1H), 7.46 (t, J=8.2 Hz, 1H), 7.19 (dd, J=2.3, 7.8 Hz, 1H), 7.04-6.61 (m, 1H), 4.49 (q, J=7.0 Hz, 2H), 4.30-4.25 (m, 2H), 1.44 (t, J=7.0 Hz, 3H). [M+H]=384.15.

Example 2

2-Chloro-5-{[5-(3-chlorophenyl)-6-methoxypyridin-3-yl]methyl}pyrimidine

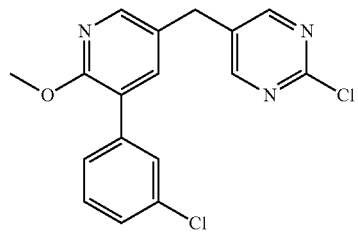 [SMILES: COc1ncc(Cc2cnc(Cl)nc2)cc1-c1cccc(Cl)c1]

To a solution of 5-(bromomethyl)-3-(3-chlorophenyl)-2-methoxypyridine (Intermediate 2, 100 mg, 0.321 mmol), (2-chloropyrimidin-5-yl)boronic acid (76 mg, 0.481 mmol) in ACN (3.2 mL) was added $NaHCO_3$ (417 mg, 1.282 mmol) and $PdCl_2$(dppf)-DCM (23 mg, 0.032 mmol). The reaction was heated under microwave conditions, at 120° C. for 12 minutes. Water was removed from the reaction with a pipette, and the crude reaction mix was filtered thru CELITE®, and washed with EtOAc. The combined organics were dried ($Na_2SO_4$), filtered and concentrated onto silica. Purification (FCC, $SiO_2$, 30-70% EtOAc/hexanes) afforded the title compound (61 mg, 55%). $^1$H NMR (400 MHz, DMSO-$d_6$) δ 8.34 (s, 2H), 8.11 (d, J=2.0 Hz, 1H), 7.70 (d, J=2.0 Hz, 1H), 7.58 (t, J=1.8 Hz, 1H), 7.53-7.36 (m, 3H), 3.83 (s 2H), 3.73 (s, 3H). [M+H]=346.11.

Example 3

{2-[(5-{[5-(3-Chlorophenyl)-6-methoxypyridin-3-yl]methyl}pyrimidin-2-yl)amino]ethyl}dimethylamine

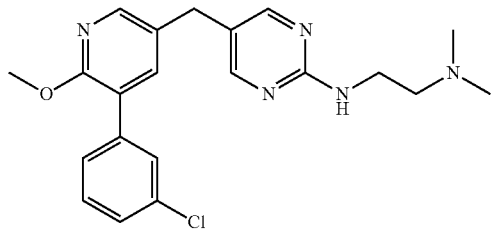

A 5 mL microwave vial was charged with 2-chloro-5-{[5-(3-chlorophenyl)-6-methoxypyridin-3-yl]methyl}pyrimidine (Example 2, 50.00 mg, 0.14 mmol), ACN (1.44 mL), N1,N1-dimethylethane-1,2-diamine (0.03 mL, 0.29 mmol), and N-ethyl-N-isopropylpropan-2-amine (77.13 µL, 0.43 mmol). The vial was sealed, and the reaction mixture was heated at 180° C. for 15 minutes. EtOAc (5 mL) was added to the reaction mixture, and the reaction mixture was extracted with water (3×). The combined organic layers were dried ($Na_2SO_4$), and the solvent was removed under reduced pressure. Purification (FCC, $SiO_2$, 0-15% MeOH/DCM) afforded the title compound (15.6 mg, 28%). $^1$H NMR (400 MHz, DMSO-$d_6$) δ 8.21 (s, 2H), 8.09 (s, 1H), 7.67 (br s, 2H), 7.58 (s, 1H), 7.51-7.34 (m, 2H), 6.79 (br s, 1H), 3.84 (s, 3H), 3.72 (s, 2H), 2.42-2.37 (m, 4H), 2.17 (s, 6H). [M+H]=398.20.

Example 4

2-Methoxy-3-(6-methoxypyridin-2-yl)-5-(1H-1,2,4-triazol-1-ylmethyl)pyridine

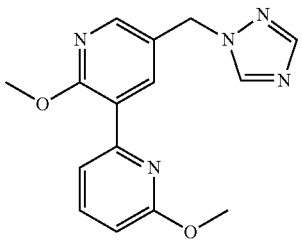 [SMILES: COc1cccc(-c2cc(Cn3cncn3)cnc2OC)n1]

A solution of 5-((1H-1,2,4-triazol-1-yl)methyl)-3-bromo-2-(difluoromethoxy)pyridine (Intermediate 13, 50 mg, 0.16 mmol), (6-methoxypyridin-2-yl)boronic acid (46 mg, 0.30 mmol), in EtOH (2.45 mL), benzene (7.00 mL), was combined with tetrakis(triphenylphosphine)palladium(0) (27 mg, 0.02 mmol), and 4 M aqueous sodium carbonate (3 mL) in a microwave vial. The vial was sealed, purged with nitrogen and heated under microwave conditions to 120° C. for 12 minutes. Water was removed from the reaction with a pipette, and the crude reaction mix was filtered thru CELITE®, and washed with EtOAc (3×5 mL). The combined organic layers were dried (Na$_2$SO$_4$), and the solvent was removed under reduced pressure. Purification (FCC, SiO$_2$, 30-70% EtOAc/hexanes) afforded the title compound (11.9 mg, 25%). $^1$H NMR (400 MHz, DMSO-d$_6$) δ 7.88 (s, 1H), 7.58 (d, J=2.7 Hz, 1H), 7.41 (d, J=2.3 Hz, 1H), 7.24 (s, 1H), 6.91-6.84 (m, 2H), 5.93 (d, J=4.3 Hz, 1H), 4.69 (s, 2H), 3.97 (s, 3H), 3.14 (s, 3H). [M+H]=298.02.

Examples 5-12 were prepared analogous to procedures described in Examples 1 or 2, with the appropriate starting materials and reagent substitutions.

Example 5

2-Methoxy-3-(3-methylphenyl)-5-(1H-1,2,4-triazol-1-ylmethyl)pyridine

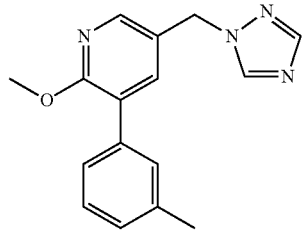 [SMILES: COc1ncc(Cn2cncn2)cc1-c1cccc(C)c1]

$^1$H NMR (400 MHz, DMSO-d$_6$) δ 8.65 (s, 1H), 8.18-8.15 (m, 1H), 7.95 (s, 1H), 7.70 (d, J=2.3 Hz, 1H), 7.31-7.27 (m, 3H), 7.19-7.14 (m, 1H), 5.41 (s, 2H), 3.85 (s, 3H), 2.33 (s, 3H). [M+H]=281.36.

Example 6

2-Methoxy-3-(5-methylpyridin-3-yl)-5-(1H-1,2,4-triazol-1-ylmethyl)pyridine $^1$H NMR (400 MHz, DMSO-d$_6$) δ 8.93 (s, 1H), 8.77 (s, 2H), 8.57 (s, 1H), 8.35 (d, J=2.0 Hz, 1H), 8.04 (s, 2H), 5.45 (s, 2H), 3.91 (s, 3H), 2.50 (s, 3H). [M+H]=282.09.

Example 7

2-Methoxy-3-(2-methylpyridin-4-yl)-5-(1H-1,2,4-triazol-1-ylmethyl)pyridine

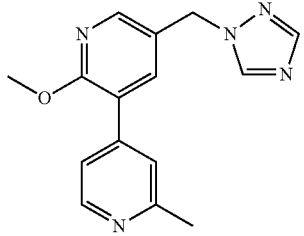 [SMILES: COc1ncc(Cn2cncn2)cc1-c1ccnc(C)c1]

$^1$H NMR (400 MHz, DMSO-d$_6$) δ 8.77-8.63 (m, 2H), 8.37 (d, J=2.3 Hz, 1H), 8.04 (d, J=2.0 Hz, 1H), 8.00-7.85 (m, 2H), 7.58-7.43 (m, 1H), 5.45 (s, 2H), 3.92 (s, 3H), 2.68 (s, 3H). [M+H]=282.20.

Example 8

{3-[2-Methoxy-5-(1H-1,2,4-triazol-1-ylmethyl)pyridin-3-yl]phenyl}methanol

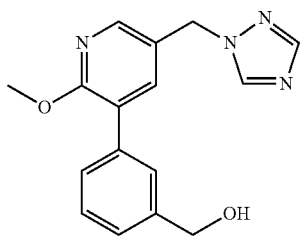 [SMILES: COc1ncc(Cn2cncn2)cc1-c1cccc(CO)c1]

$^1$H NMR (400 MHz, DMSO-d$_6$) δ 8.65 (s, 1H), 8.18 (d, J=2.0 Hz, 1H), 7.95 (s, 1H), 7.70 (d, J=2.3 Hz, 1H), 7.45-7.26

(m, 4H), 5.41 (s, 2H), 5.22 (t, J=5.7 Hz, 1H), 4.51 (d, J=5.9 Hz, 2H), 3.85 (s, 3H). [M+H]=297.23.

Example 9

3-(3-Methanesulfonylphenyl)-2-methoxy-5-(1H-1,2,4-triazol-1-ylmethyl)pyridine

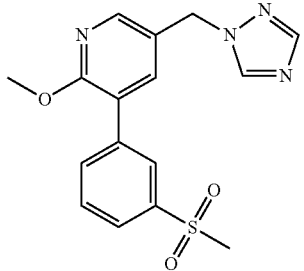 [SMILES: COc1ncc(Cn2cncn2)cc1-c1cccc(S(C)(=O)=O)c1]

¹H NMR (400 MHz, CD₃OD) δ 8.61 (s, 1H), 8.24 (d, J=1.96 Hz, 1H), 8.12 (s, 1H), 8.00 (s, 1H), 7.94 (d, J=7.83 Hz, 1H), 7.89 (d, J=7.83 Hz, 1H), 7.83 (d, J=1.56 Hz, 1H), 7.65-7.72 (m, 1H), 5.46 (s, 2H), 3.96 (s, 3H), 3.15 (s, 3H). [M+H]=345.21.

Example 10

2-Methoxy-3-(4-methylpyridin-2-yl)-5-(1H-1,2,4-triazol-1-ylmethyl)pyridine

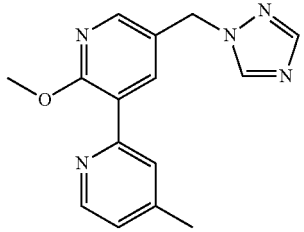 [SMILES: COc1ncc(Cn2cncn2)cc1-c1cc(C)ccn1]

¹H NMR (400 MHz, CD₃OD) δ 8.60 (s, 1H), 8.44 (d, J=5.1 Hz, 1H), 8.26 (d, J=2.3 Hz, 1H), 8.01 (d, J=2.3 Hz, 1H), 7.98 (s, 1H), 7.70 (s, 1H), 7.22 (d, J=5.1 Hz, 1H), 5.46 (s, 2H), 3.99 (s, 3H), 2.42 (s, 3H). [M+H]=282.31.

Example 11

2-Methoxy-3-(6-methylpyridin-2-yl)-5-(1H-1,2,4-triazol-1-ylmethyl)pyridine

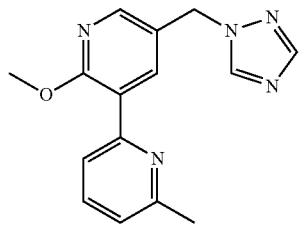 [SMILES: COc1ncc(Cn2cncn2)cc1-c1cccc(C)n1]

¹H NMR (400 MHz, CD₃OD) δ 8.50 (s, 1H), 8.32-8.27 (m, 1H), 8.22 (d, J=2.3 Hz, 1H), 7.89 (s, 1H), 7.68-7.62 (m, 1H), 7.56 (d, J=2.7 Hz, 1H), 7.26 (dd, J=5.1, 7.8 Hz, 1H), 5.37 (s, 2H), 3.82 (s, 3H), 2.04 (s, 3H). [M+H]=282.39.

Example 12

2-(Difluoromethoxy)-3-(3-methylphenyl)-5-(1H-1,2,4-triazol-1-ylmethyl)pyridine

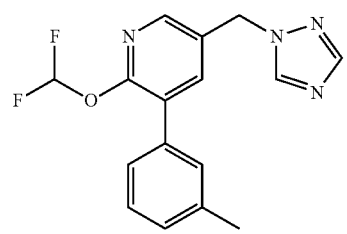 [SMILES: Cc1cccc(-c2cc(Cn3cncn3)cnc2OC(F)F)c1]

As a mixture of compounds, ¹H NMR (400 MHz, DMSO-d₆) δ 8.72-8.61 (m, 1H), 8.00-7.96 (m, 1H), 7.94-7.86 (m, 1H), 7.73-7.68 (m, 1H), 7.55-7.51 (m, 1H), 7.40-7.33 (m, 1H), 7.32-7.27 (m, 1H), 7.24 (d, J=7.8 Hz, 1H), 5.75 (s, 1H), 5.49 (s, 1H), 5.44 (s, 1H), 2.35 (s, 3H). [M+H]=317.15.

Example 13

5-({6-[3-(Difluoromethoxy)phenyl]-5-ethoxypyrazin-2-yl}methyl)pyrimidine-2-carboxamide

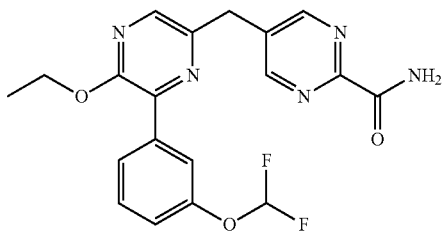 [SMILES: CCOc1ncc(Cc2cnc(C(N)=O)nc2)nc1-c1cccc(OC(F)F)c1]

To a solution of 5-(6-(3-(difluoromethoxy)phenyl)-5-ethoxypyrazin-2-yl)methyl)pyrimidine-2-carbonitrile (Example 1, 100.00 mg, 0.26 mmol) in MeOH (1.3 mL) was added aq. NaOH (0.78 mL, 0.78 mmol), followed by hydrogen peroxide (0.78 mL, 0.79 mmol) The reaction mixture was stirred at room temperature for 8 h. The reaction mixture was concentrated, and the precipitate filtered and washed with water to obtain the title compound as a white solid (70 mg, 67%). ¹H NMR (400 MHz, DMSO-d₆) δ 8.93 (s, 2H), 8.27 (s, 1H), 8.12 (br s, 1H), 7.91-7.84 (m, 1H), 7.81 (t, J=1.8 Hz, 1H), 7.72 (br s, 1H), 7.52 (s, 1H), 7.44-7.02 (m, 2H), 4.42 (q, J=7.0 Hz, 2H), 4.25 (s, 2H), 1.35 (t, J=7.0 Hz, 3H). [M+H]=402.26.

Example 14

[5-(3-Chlorophenyl)-6-methoxypyridin-3-yl](4-fluorophenyl)methanol

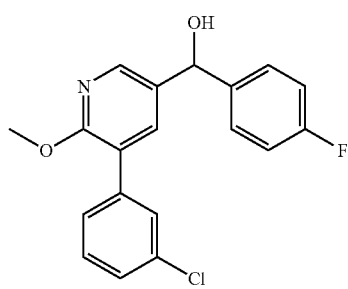 [SMILES: COc1ncc(C(O)c2ccc(F)cc2)cc1-c1cccc(Cl)c1]

To a cooled solution, −78° C., of 5-bromo-3-(3-chlorophenyl)-2-methoxypyridine (Intermediate 7, 1.5 g, 5 mmol) in THF (25 mL), under nitrogen, was added nBuLi (4.8 mL, 5.5 mmol) drop-wise over 2 minutes. The reaction mixture was stirred at −78° C. for 40 min. A solution of 4-fluorobenzaldehyde (744 mg, 6 mmol) in THF (2 mL) was added, and the reaction mixture was stirred an additional 30 min at −78° C. The reaction was quenched with saturated sodium sulfate, filtered, and concentrated under reduced pressure. Purification (FCC, SiO$_2$, 0-25% EtOAc/hexanes) afforded the title compound as a colorless solid (1.65 g, 96%). $^1$H NMR (400 MHz, CD$_3$OD) δ 8.11 (d, J=2.3 Hz, 1H), 7.63 (d, J=2.0 Hz, 1H), 7.51 (s, 1H), 7.47-7.29 (m, 5H), 7.07 (t, J=8.6 Hz, 2H), 5.84 (s, 1H), 3.93 (s, 3H). [M+H]=344.18.

Examples 15-16 were prepared in a manner analogous to Example 14, with the appropriate starting materials and reagent substitutions.

Example 15

1-[5-(3-Chlorophenyl)-6-methoxypyridin-3-yl]-1-(4-fluorophenyl)ethan-1-ol

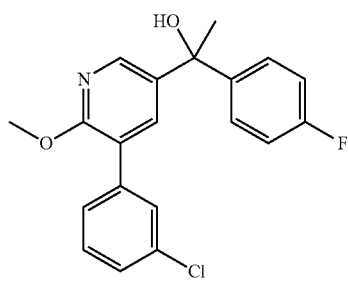 [SMILES: COc1ncc(C(C)(O)c2ccc(F)cc2)cc1-c1cccc(Cl)c1]

$^1$H NMR (400 MHz, CD$_3$OD) δ 8.16 (d, J=2.7 Hz, 1H), 7.68 (d, J=2.7 Hz, 1H), 7.53-7.43 (m, 3H), 7.42-7.28 (m, 3H), 7.04 (t, J=8.8 Hz, 2H), 3.93 (s, 3H), 1.94 (s, 3H). [M+H]=358.21.

Example 16

[5-(3-Chlorophenyl)-6-methoxypyridin-3-yl](5-fluoropyridin-2-yl)methanol

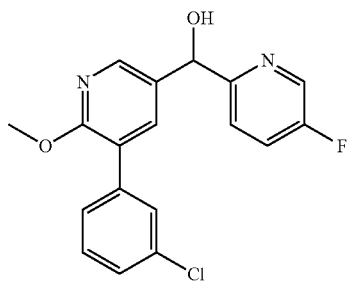 [SMILES: COc1ncc(C(O)c2ccc(F)cn2)cc1-c1cccc(Cl)c1]

$^1$H NMR (400 MHz, CD$_3$OD) δ 8.38 (d, J=2.7 Hz, 1H), 8.16 (d, J=2.3 Hz, 1H), 7.77-7.58 (m, 3H), 7.52 (s, 1H), 7.45-7.28 (m, 3H), 5.87 (s, 1H), 3.93 (s, 3H). [M+H]=345.19.

Example 17

{[5-(3-Chlorophenyl)-6-methoxypyridin-3-yl](4-fluorophenyl)methyl}(methyl)amine

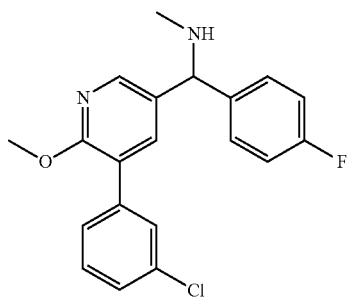 [SMILES: CNC(c1ccc(F)cc1)c1cnc(OC)c(-c2cccc(Cl)c2)c1]

Step 1. 5-(Chloro(4-fluorophenyl)methyl)-3-(3-chlorophenyl)-2-methoxypyridine. To a cooled solution, 0° C., of [5-(3-chlorophenyl)-6-methoxypyridin-3-yl](4-fluorophenyl)methanol (Example 14, 1.43 g, 4.17 mmol), in DCM (10 mL), was added thionyl chloride (744 mg, 6.25 mmol) drop-wise. The solution was allowed to warm up to room temperature, and stirred for 1 h. The reaction mixture was concentrated under reduced pressure. Purification (FCC, SiO$_2$, 0-10% EtOAc/hexanes) afforded the title compound, which was used directly for the next step.

Step 2. {[5-(3-chlorophenyl)-6-methoxypyridin-3-yl](4-fluorophenyl)methyl}(methyl)amine. To a solution of 5-(chloro(4-fluorophenyl)methyl)-3-(3-chlorophenyl)-2-methoxypyridine (70 mg, 0.193 mmol) in ACN (2 mL) was added potassium carbonate (53 mg, 0.39 mmol), sodium Iodide (5 mg, 0.03 mmol), and methylamine (0.5 mL, 0.97 mmol). The reaction was sealed and heated at 45° C. for 12 h. The reaction mixture was concentrated. Purification (FCC, SiO$_2$, 0-10% MeOH/DCM) afforded the title compound (23 mg, 33%). $^1$H NMR (400 MHz, CD$_3$OD) δ 8.20 (d, J=2.3 Hz, 1H), 7.71 (s, 1H), 7.50-7.42 (m, 3H), 7.40-7.27 (m, 3H), 7.18 (t, J=8.8 Hz, 2H), 5.54-5.49 (m, 1H), 3.90 (s, 3H), 2.63 (s, 3H). [M⁺; loss of NHMe]=326.14.

Examples 18-19 were prepared in a manner analogous to Example 17, with the appropriate starting materials and reagent substitutions.

Example 18

[5-(3-Chlorophenyl)-6-methoxypyridin-3-yl](4-fluorophenyl)methanamine

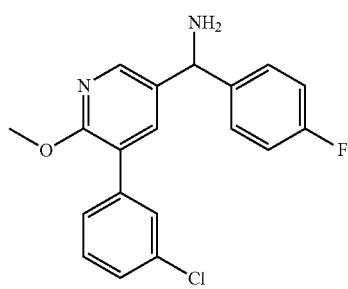 [SMILES: COc1ncc(C(N)c2ccc(F)cc2)cc1-c1cccc(Cl)c1]

¹H NMR (400 MHz, CD₃OD) δ 8.17 (d, J=2.3 Hz, 1H), 7.72 (d, J=2.7 Hz, 1H), 7.55 (s, 1H), 7.49-7.34 (m, 5H), 7.18 (m, 2H), 5.58 (s, 1H), 3.96 (s, 3H). [M⁺; loss of NH₂]=326.14.

Example 19

{[5-(3-Chlorophenyl)-6-methoxypyridin-3-yl](4-fluorophenyl)methyl}dimethylamine

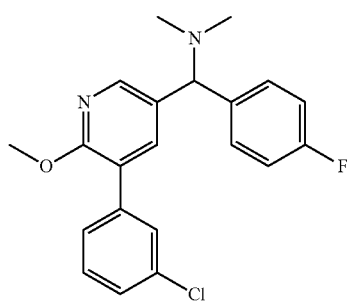 [SMILES: COc1ncc(C(c2ccc(F)cc2)N(C)C)cc1-c1cccc(Cl)c1]

¹H NMR (400 MHz, CD₃OD) δ 8.28 (d, J=2.3 Hz, 1H), 7.86 (s, 1H), 7.57 (dd, J=5.1, 8.6 Hz, 2H), 7.50 (t, J=1.6 Hz, 1H), 7.43-7.28 (m, 3H), 7.18 (m, 2H), 5.51-5.38 (m, 1H), 3.90 (s, 3H), 2.88-2.74 (m, 6H). [M+H]=371.20.

Example 20

3-(3-Chlorophenyl)-5-[fluoro(4-fluorophenyl)methyl]-2-methoxypyridine

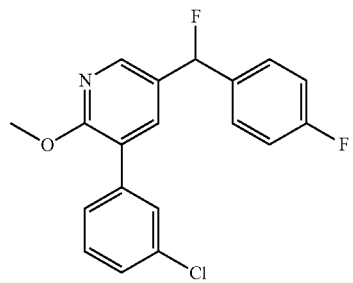 [SMILES: COc1ncc(C(F)c2ccc(F)cc2)cc1-c1cccc(Cl)c1]

To a solution of [5-(3-chlorophenyl)-6-methoxypyridin-3-yl](4-fluorophenyl)methanol (Example 14, 70 mg, 0.18 mmol) in DCM (1 mL) was added Deoxo-Fluor® (79 mg, 0.36 mmol). The solution was stirred at room temperature for 1 h then concentrated under reduced pressure. Purification (FCC, SiO₂, 0-10% EtOAc/hexanes) afforded the title compound (21 mg, 34%). ¹H NMR (400 MHz, CD₃OD) δ 8.13 (s, 1H), 7.62 (d, J=2.0 Hz, 1H), 7.52 (s, 1H), 7.47-7.31 (m, 5H), 7.15 (t, J=8.8 Hz, 2H), 6.70-6.52 (m, 1H), 3.96 (s, 3H). [M+H]=346.17.

Example 21

4-{[5-(3-Chlorophenyl)-6-methoxypyridin-3-yl]methyl}benzoic acid

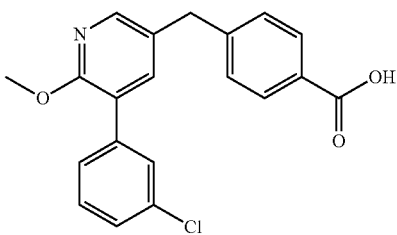 [SMILES: COc1ncc(Cc2ccc(C(=O)O)cc2)cc1-c1cccc(Cl)c1]

Step 1. Methyl 4-((5-(3-chlorophenyl)-6-methoxypyridin-3-yl)methyl)benzoate was prepared in a manner analogous to Example 2 with the appropriate starting material substitution. Purification (FCC, SiO₂, 0-50% EtOAc/hexanes) afforded the title compound. [M+H]=368.11

Step 2. 4-{[5-(3-Chlorophenyl)-6-methoxypyridin-3-yl]methyl}benzoic acid. To a solution of methyl 4-((5-(3-chlorophenyl)-6-methoxypyridin-3-yl)methyl)benzoate (91 mg, 0.248 mmol) in MeOH (2 mL) was added 2 N aq. NaOH (2.0 mL). The reaction mixture was stirred at rt for 2 hr. Solvent was removed under reduced pressure, and the resulting solid was triturated with diethyl ether. The resulting white solid was dissolved in DCM and filtered to remove inorganic solids. The filtrated was concentrated under reduced pressure to afford the title compound (74 mg, 85%). ¹H NMR (400 MHz, CD₃OD) δ 8.03 (d, J=2.0 Hz, 1H), 7.96 (d, J=7.8 Hz, 2H), 7.60 (d, J=2.3 Hz, 1H), 7.52 (s, 1H), 7.43-7.30 (m, 5H), 4.05 (s, 2H), 3.95 (s, 3H). [M+H]=354.13.

Example 22

5-{[6-(3-Chlorophenyl)-5-methoxypyrazin-2-yl]methyl}pyrimidine-2-carbonitrile

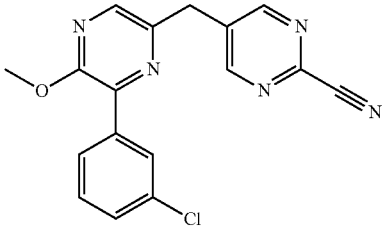 [SMILES: COc1ncc(Cc2cnc(C#N)nc2)nc1-c1cccc(Cl)c1]

Example 22 was prepared in a manner analogous to Example 1, with the appropriate starting materials and reagent substitutions. [M+H]=338.10

Example 23

5-{[5-(3-Chlorophenyl)-6-methoxypyridin-3-yl]methyl}pyrimidine-2-carboxylic acid

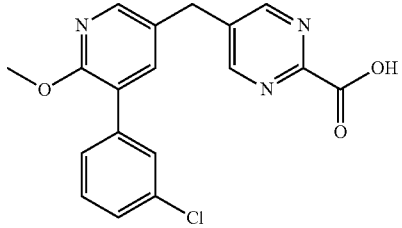 [SMILES: COc1ncc(Cc2cnc(C(=O)O)nc2)cc1-c1cccc(Cl)c1]

A solution of 5-{[6-(3-chlorophenyl)-5-methoxypyrazin-2-yl]methyl}pyrimidine-2-carbonitrile (Example 22, 30 mg, 0.0845 mmol) in MeOH (1.54 mL) was heated to 50° C. until the starting material dissolved. 1 N aq. NaOH (0.23 mL, 0.23 mmol) was added followed by hydrogen peroxide (0.23 mL, 1.00 mol/L, 0.23 mmol) and the solution was heated at 50° C. for an additional 2 h. Water (5 mL) was added and the reaction was filtered and washed with water (3×5 mL). A mixture of products were observed; 5-{[5-(3-chlorophenyl)-6-methoxypyridin-3-yl]methyl}pyrimidine-2-carboxylic acid (the title compound) and 5-{[5-(3-chlorophenyl)-6-methoxypyridin-3-yl]methyl}pyrimidine-2-carboxamide (Example 24, 4 mg, 13%). The filtrated contained the acid, and the water layer was acidified with concentrated HCl (3 drops) and extracted with DCM (3×20 mL). The organic layers were combined, dried (Na$_2$SO$_4$), and concentrated under reduced pressure to afford the title compound (23 mg, 74%). $^1$H NMR (400 MHz, CD$_3$OD) δ 8.86 (br s, 2H), 8.11 (d, J=1.96 Hz, 1H), 7.66 (d, J=1.96 Hz, 1H), 7.55 (s, 1H), 7.49-7.27 (m, 3H), 4.14 (br s, 2H), 3.94 (s, 3H). [M+H]=356.13

Example 24

5-{[5-(3-Chlorophenyl)-6-methoxypyridin-3-yl]methyl}pyrimidine-2-carboxamide

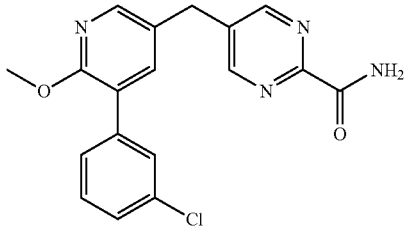 [SMILES: COc1ncc(Cc2cnc(C(N)=O)nc2)cc1-c1cccc(Cl)c1]

The title compound was made in a manner analogous to Example 13. $^1$H NMR (400 MHz, CD$_3$OD) δ 8.83 (s, 2H), 8.11 (d, J=2.0 Hz, 1H), 7.65 (d, J=2.3 Hz, 1H), 7.54 (s, 1H), 7.47-7.29 (m, 3H), 4.12 (s, 2H), 3.94 (s, 3H). [M+H]=355.21.

Examples 25, 27-30, 32-35, 37-43. 45-89, 91-108 were prepared analogous to procedures described in Examples 1 or 2, with the appropriate starting materials and reagent substitutions.

Example 25

5-{[5-(3-Chlorophenyl)-6-methoxypyridin-3-yl]methyl}pyrimidin-2-amine

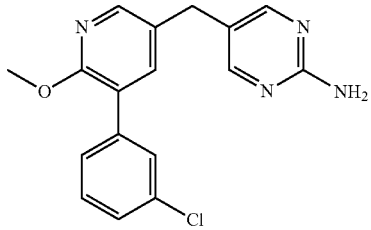 [SMILES: COc1ncc(Cc2cnc(N)nc2)cc1-c1cccc(Cl)c1]

$^1$H NMR (400 MHz, CD$_3$OD) δ 8.18 (s, 2H), 8.02 (d, J=2.3 Hz, 1H), 7.58-7.51 (m, 2H), 7.44-7.31 (m, 3H), 3.93 (s, 3H), 3.82 (s, 2H). [M+H]=327.21.

Example 26

(4-{[5-(3-Chlorophenyl)-6-methoxypyridin-3-yl]methyl}phenyl)urea

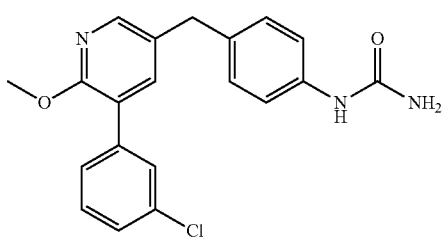 [SMILES: COc1ncc(Cc2ccc(NC(N)=O)cc2)cc1-c1cccc(Cl)c1]

Step 1. 3-(3-Chlorophenyl)-2-methoxy-5-(4-nitrobenzyl)pyridine. The title compound was prepared in a manner analogous to Example 1, from Intermediate 2 and 4-nitrophenyl boronic acid to afford a tan solid. [M+H]=355.07.

Step 2. 4-((5-(3-Chlorophenyl)-6-methoxypyridin-3-yl)methyl)aniline. A solution of 3-(3-chlorophenyl)-2-methoxy-5-(4-nitrobenzyl)pyridine (162 mg, 0.45 mmol), HOAc (3 mL), water (1 mL), and zinc (292.5 mg, 4.5 mmol) was heated at 60° C. for 1 h, then filtered hot through a 1 cm pad of Celite® and used directly for the next step.

Step 3. (4-{[5-(3-Chlorophenyl)-6-methoxypyridin-3-yl]methyl}phenyl)urea. 4-((5-(3-chlorophenyl)-6-methoxypyridin-3-yl)methyl)aniline solution from Step 2 was added potassium cyanate (73 mg, 0.9 mmol). The mixture was sonicated for 20 min to afford a gummy ppt. The reaction mixture was diluted with water, neutralized with aq. sodium carbonate to pH 7, then extracted with EtOAc (3×5 mL). The combined organic layers were concentrated under reduced pressure to afford a solid, which was triturated with DCM to give (55 mg, 34%) of the title compound as a white solid. $^1$H NMR (400 MHz, DMSO-$d_6$) δ 8.41 (s, 1H), 8.06 (d, J=2.3 Hz, 1H), 7.64-7.53 (m, 2H), 7.49-7.37 (m, 3H), 7.28 (d, J=8.2 Hz, 2H), 7.10 (d, J=8.6 Hz, 2H), 5.75 (s, 2H), 3.85-3.81 (m, 5H). [M+H]=368.27.

Example 27

4-{[5-(3-Chlorophenyl)-6-methoxypyridin-3-yl]methyl}benzamide

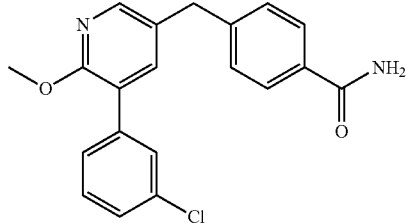

$^1$H NMR (400 MHz, CD$_3$OD) δ 8.02 (d, J=2.0 Hz, 1H), 7.81 (d, J=8.2 Hz, 2H), 7.56-7.49 (m, 2H), 7.42-7.29 (m, 5H), 4.03 (s, 2H), 3.92 (s, 3H). [M+H]=353.13.

Example 28

5-((1H-Pyrazol-4-yl)methyl)-3-(3-chlorophenyl)-2-(difluoromethoxy)pyridine

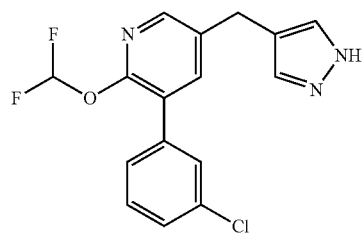 [SMILES: FC(F)Oc1ncc(Cc2cn[nH]c2)cc1-c1cccc(Cl)c1]

$^1$H NMR (400 MHz, DMSO-$d_6$) δ 12.61 (br s, 1H), 7.92-7.43 (m, 9H), 3.84 (s, 2H). [M+H]=336.18.

Example 29

5-{[6-(Difluoromethoxy)-5-(3-methoxyphenyl)pyridin-3-yl]methyl}pyrimidin-2-amine

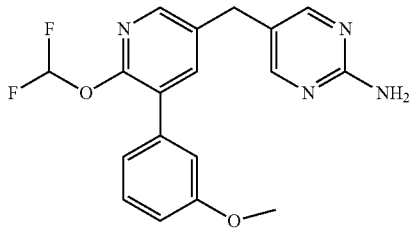 [SMILES: COc1cccc(-c2cc(Cc3cnc(N)nc3)cnc2OC(F)F)c1]

$^1$H NMR (400 MHz, CD$_3$OD) δ 8.19 (s, 2H), 8.07 (d, J=2.35 Hz, 1H), 7.71 (d, J=1.96 Hz, 1H), 7.57 (s, 1H), 7.30-7.38 (m, 1H), 7.02-7.10 (m, 2H), 6.95 (dd, J=8.22, 1.57 Hz, 1H), 3.82 (s, 3H), 3.87 (s, 2H). [M+H]=359.28.

Example 30

5-{[5-(3-Chlorophenyl)-6-methoxypyridin-3-yl]methyl}pyridin-2-amine

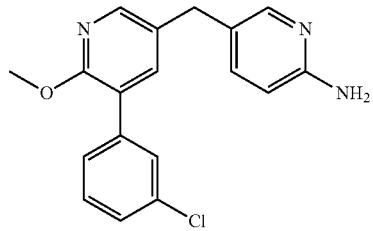 [SMILES: COc1ncc(Cc2ccc(N)nc2)cc1-c1cccc(Cl)c1]

$^1$H NMR (400 MHz, CD$_3$OD) δ 7.99 (d, J=2.0 Hz, 1H), 7.80 (d, J=2.0 Hz, 1H), 7.52 (d, J=2.0 Hz, 2H), 7.43-7.29 (m, 4H), 6.55 (d, J=8.6 Hz, 1H), 3.92 (s, 3H), 3.81 (s, 2H). [M+H]=326.26.

Example 31

1-(4-{[5-(3-Chlorophenyl)-6-methoxypyridin-3-yl]methyl}phenyl)-3-(oxetan-3-yl)urea

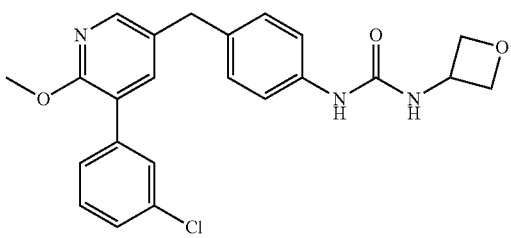 [SMILES: COc1ncc(Cc2ccc(NC(=O)NC3COC3)cc2)cc1-c1cccc(Cl)c1]

To a solution of 4-((5-(3-chlorophenyl)-6-methoxypyridin-3-yl)methyl)benzoic acid (Example 21, 90 mg, 0.25 mmol) in toluene (5 mL) was added N,N-diisopropylethylamine (33 mg, 0.25 mmol) and diphenylphosphoryl azide (77 mg, 0.28 mmol). The mixture was stirred at 80° C. for 30 minutes. The LCMS confirmed the disappearance of the starting acid. A solution of oxetan-3-amine hydrochloride (41.5 mg, 0.38 mmol), N,N-diisopropylethylamine (49 mg, 0.38 mmol) and DCM (2 mL) was added to the reaction mixture and stirred at room temperature for 2 h. The LCMS confirmed the presence of the product. All solvents were removed under reduced pressure. Purification (FCC, SiO$_2$, 0-5%, MeOH/DCM) afforded the title compound (50 mg, 46%). $^1$H NMR (400 MHz, CD$_3$OD) δ 7.99 (d, J=2.3 Hz, 1H), 7.49 (d, J=2.3 Hz, 2H), 7.41-7.24 (m, 5H), 7.14 (d, J=8.6 Hz, 2H), 4.87 (br s, 3H), 4.55 (s, 2H), 3.91 (s, 3H), 3.90 (s, 2H). [M+H]=424.20.

Example 32

3-(3-Chlorophenyl)-2-methoxy-5-[(6-methoxypyridin-3-yl)methyl]pyridine

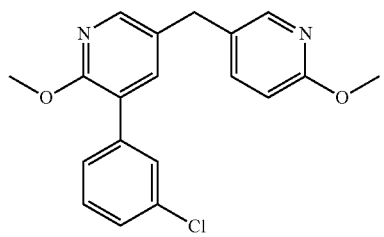

$^1$H NMR (400 MHz, DMSO-d$_6$) δ 8.10 (dd, J=2.0, 6.3 Hz, 2H), 7.67 (d, J=2.3 Hz, 1H), 7.61-7.54 (m, 2H), 7.50-7.36 (m, 3H), 6.72 (d, J=8.2 Hz, 1H), 3.86 (s, 2H), 3.84 (s, 3H), 3.78 (s, 3H). [M+H]=341.19.

Example 33

5-{[5-(3-Chlorophenyl)-6-(difluoromethoxy)pyridin-3-yl]methyl}pyridin-2-amine

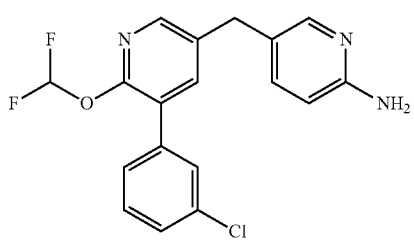 [SMILES: Nc1ccc(Cc2cnc(OC(F)F)c(-c3cccc(Cl)c3)c2)cn1]

$^1$H NMR (400 MHz, CD$_3$OD) δ 8.06 (d, J=2.3 Hz, 1H), 7.77 (dd, J=2.0, 9.4 Hz, 1H), 7.73-7.64 (m, 2H), 7.51-7.30 (m, 5H), 6.89 (d, J=9.4 Hz, 1H), 3.88 (s, 2H). [M+H]=362.31.

Example 34

5-{[5-(3-Chlorophenyl)-6-methoxypyridin-3-yl]methyl}-N,N-dimethylpyridin-2-amine

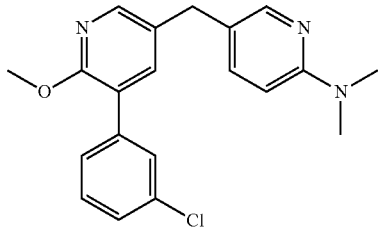

$^1$H NMR (400 MHz, CD$_3$OD) δ 8.00 (d, J=2.0 Hz, 1H), 7.94 (d, J=2.0 Hz, 1H), 7.51 (d, J=1.6 Hz, 2H), 7.43-7.29 (m, 4H), 6.63 (d, J=9.0 Hz, 1H), 3.92 (s, 3H), 3.84 (s, 2H), 3.04 (s, 6H). [M+H]=354.22.

Example 35

5-{[5-(3-Chlorophenyl)-6-(difluoromethoxy)pyridin-3-yl]methyl}pyrimidine-2-carbonitrile

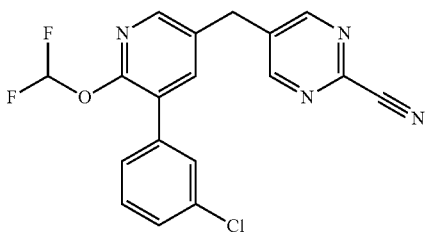 [SMILES: N#Cc1ncc(Cc2cnc(OC(F)F)c(-c3cccc(Cl)c3)c2)cn1]

¹H NMR (400 MHz, CD₃OD) δ 8.85 (s, 2H), 8.18 (s, 1H), 7.85 (d, J=2.3 Hz, 1H), 7.80-7.38 (m, 5H), 4.21-4.17 (m, 2H). [M+H]=373.14.

Example 36

5-{[5-(3-Chlorophenyl)-6-(difluoromethoxy)pyridin-3-yl]methyl}-1,3-thiazol-2-amine

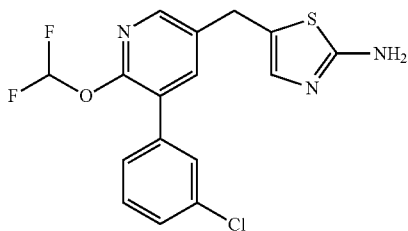 [SMILES: Nc1ncc(Cc2cnc(OC(F)F)c(-c3cccc(Cl)c3)c2)s1]

Step 1. 3-(3-Chlorophenyl)-5-(dibromomethyl)-2-(difluoromethoxy)pyridine was prepared in a manner analogous to Intermediate 1, Steps 4, with the appropriate starting material substitutions. [M+H]=426.1, 428.1, 430.1.

Step 2. 5-(3-Chlorophenyl)-6-(difluoromethoxy)nicotinaldehyde. To a solution of 3-(3-chlorophenyl)-5-(dibromomethyl)-2-(difluoromethoxy)pyridine (700 mg, 1.65 mmol) in ACN (2 mL) was added a solution of sodium carbonate (525 mg, 5.0 mmol) in water (4 mL) and the mixture was stirred at 70° C. for 16 h. The LCMS showed complete conversion. All solvents were removed under reduced pressure. The residue was dissolved in DCM, washed with water, dried (Na₂SO₄), filtered and the solvent was removed under reduced pressure. Purification (FCC, SiO₂, 0-20%, EtOAc/hexanes) afforded 5-(3-chlorophenyl)-6-(difluoromethoxy)nicotinaldehyde (355 mg, 76%). [M+H]=284.1.

Step 3. tert-Butyl (5-((5-(3-chlorophenyl)-6-(difluoromethoxy)pyridin-3-yl)(hydroxy)methyl)thiazol-2-yl)carbamate. A solution of tert-butyl (5-bromothiazol-2-yl)carbamate (100 mg, 0.36 mmol) in THF (2 mL) was cooled to −78° C. and n-butyllithium (0.51 mL of 1.4 M solution in hexanes, 0.72 mmol) was added dropwise and the mixture was stirred for 30 minutes at −78° C. A solution of 5-(3-chlorophenyl)-6-(difluoromethoxy)nicotinaldehyde (112 mg, 0.39 mmol) in THF (2 mL) was added dropwise to the reaction and this mixture was stirred for 30 minutes at −78° C. The LCMS confirmed the product. A saturated aqueous solution of ammonium chloride was added and the mixture was extracted into EtOAc. The combined extracts were dried (Na₂SO₄), filtered and solvent was removed under reduced pressure. Purification (FCC, SiO₂, 10-80%, EtOAc/hexanes) afforded tert-butyl (5-((5-(3-chlorophenyl)-6-(difluoromethoxy)pyridin-3-yl)(hydroxy)methyl)thiazol-2-yl)carbamate (73 mg, 42%). [M(-tBu)+H]=428.1.

Step 4. 5-{[5-(3-Chlorophenyl)-6-(difluoromethoxy)pyridin-3-yl]methyl}-1,3-thiazol-2-amine. To a solution of tert-butyl (5-((5-(3-chlorophenyl)-6-(difluoromethoxy)pyridin-3-yl)(hydroxy)methyl)thiazol-2-yl)carbamate (73 mg, 0.15 mmol) in DCM (3 mL) was added triethylsilane (52.2 mg, 0.45 mmol) and TFA (102 mg, 0.90 mmol) and the mixture was stirred at room temperature for 16 h. The LCMS showed complete conversion. All solvents were removed in vacuo. The residue was dissolved in DCM and a saturated aqueous solution of sodium bicarbonate, the layers shaken and separated and the aqueous layer extracted into DCM. The combined organic extracts were washed with brine, dried (Na₂SO₄), filtered and solvent under reduced pressure. Purification (FCC, SiO₂, 20-100%, EtOAc/hexanes) gave the title compound (34.4 mg, 62%). ¹H NMR (400 MHz, CD₃OD) δ 8.02 (d, J=2.3 Hz, 1H), 7.71-7.30 (m, 6H), 6.68 (s, 1H), 3.94 (s, 2H). [M+H]=368.06.

Example 37

(2-{[5-(3-Chlorophenyl)-6-methoxypyridin-3-yl]methyl}phenyl)methanol

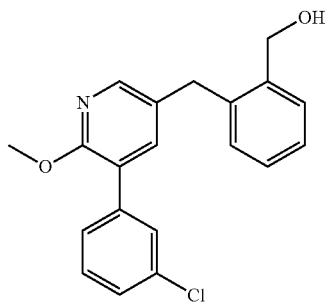 [SMILES: COc1ncc(Cc2ccccc2CO)cc1-c1cccc(Cl)c1]

¹H NMR (400 MHz, CD₃OD) δ 7.94 (d, J=2.3 Hz, 1H), 7.49 (m, 2H), 7.44-7.14 (m, 7H), 4.63 (s, 2H), 4.07 (s, 2H), 3.91 (s, 3H). [M+H]=340.13.

Example 38

5-{[5-(3-Fluorophenyl)-6-methoxypyridin-3-yl]methyl}pyrimidin-2-amine

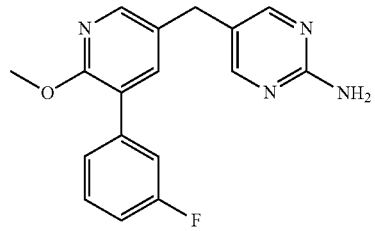 [SMILES: COc1ncc(Cc2cnc(N)nc2)cc1-c1cccc(F)c1]

¹H NMR (400 MHz, CD₃OD) δ 8.17 (s, 2H), 8.02 (d, J=2.3 Hz, 1H), 7.57 (d, J=2.3 Hz, 1H), 7.43-7.25 (m, 3H), 7.09-7.02 (m, 1H), 3.93 (s, 3H), 3.81 (s, 2H). [M+H]=311.00.

Example 39

5-{[5-(3-Fluorophenyl)-6-methoxypyridin-3-yl]methyl}pyrimidine-2-carbonitrile

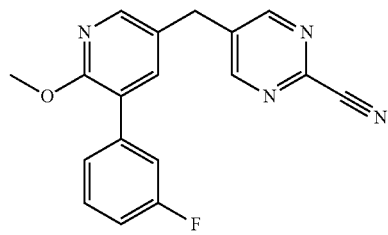 [SMILES: COc1ncc(Cc2cnc(C#N)nc2)cc1-c1cccc(F)c1]

¹H NMR (400 MHz, CDCl₃) δ 8.71 (s, 2H), 8.06 (d, J=2.3 Hz, 1H), 7.55 (s, 1H), 7.42-7.35 (m, 2H), 7.26-7.23 (m, 1H), 7.10-7.03 (m, 1H), 4.05 (s, 2H), 3.98 (s, 3H). [M+H]=321.17.

Example 40

5-{[5-(3-Chlorophenyl)-6-ethoxypyridin-3-yl]methyl}pyrimidin-2-amine

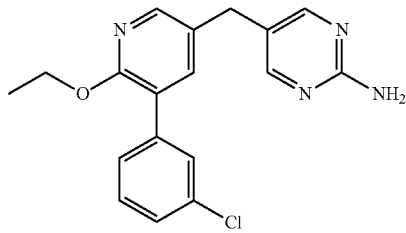 [SMILES: CCOc1ncc(Cc2cnc(N)nc2)cc1-c1cccc(Cl)c1]

¹H NMR (400 MHz, CD₃OD) δ 8.18 (s, 2H), 7.99 (d, J=2.3 Hz, 1H), 7.56 (d, J=2.3 Hz, 2H), 7.47-7.30 (m, 3H), 4.38 (d, J=7.0 Hz, 2H), 3.81 (s, 2H), 1.33 (t, J=7.0 Hz, 3H). [M+H]=341.04.

Example 41

5-{[5-(3-Chlorophenyl)-6-(propan-2-yloxy)pyridin-3-yl]methyl}pyrimidin-2-amine

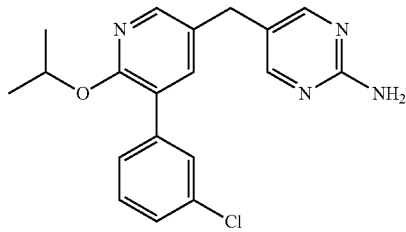 [SMILES: CC(C)Oc1ncc(Cc2cnc(N)nc2)cc1-c1cccc(Cl)c1]

¹H NMR (400 MHz, CD₃OD) δ 8.18 (s, 2H), 8.01-7.98 (m, 1H), 7.58-7.53 (m, 2H), 7.46-7.29 (m, 3H), 5.35 (m, 1H), 3.80 (s, 2H), 1.30 (d, J=6.3 Hz, 6H). [M+H]=355.21.

Example 42

5-{[6-(Difluoromethoxy)-5-[3-(propan-2-yloxy)phenyl]pyridin-3-yl]methyl}pyrimidin-2-amine

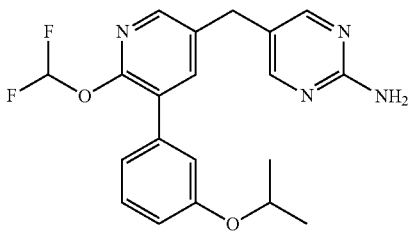 [SMILES: CC(C)Oc1cccc(-c2cc(Cc3cnc(N)nc3)cnc2OC(F)F)c1]

¹H NMR (400 MHz, CD₃OD) δ 8.19 (s, 2H), 8.06 (d, J=2.3 Hz, 1H), 7.78-7.29 (m, 3H), 7.06-7.00 (m, 2H), 6.95-6.90 (m, 1H), 4.68-4.55 (m, 1H), 3.86 (s, 2H), 1.32 (d, J=6.3 Hz, 6H). [M+H]=387.25.

Example 43

5-{[6-(Difluoromethoxy)-5-[3-(oxetan-3-yloxy)phenyl]pyridin-3-yl]methyl}pyrimidin-2-amine

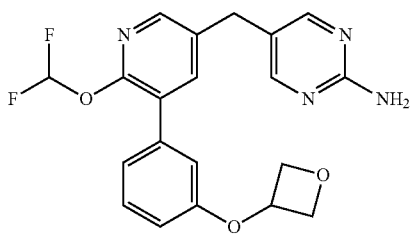

¹H NMR (400 MHz, CD₃OD) δ 8.10 (s, 2H), 7.99 (d, J=2.3 Hz, 1H), 7.69-7.24 (m, 3H), 7.04-6.99 (m, 1H), 6.84-6.80 (m, 1H), 6.75-6.70 (m, 1H), 5.21 (m, 1H), 4.92 (t, J=7.0 Hz, 2H), 4.64-4.59 (m, 2H), 3.78 (s, 2H). [M+H]=401.22.

Example 44

N-(5-{[5-(3-Chlorophenyl)-6-methoxypyridin-3-yl]methyl}pyrimidin-2-yl)acetamide

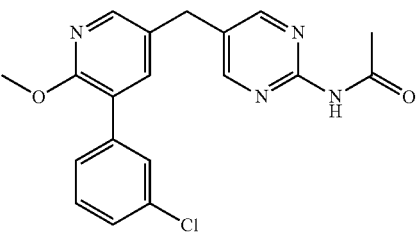 [SMILES: COc1ncc(Cc2cnc(NC(C)=O)nc2)cc1-c1cccc(Cl)c1]

Step 1: To a solution of 5-{[5-(3-chlorophenyl)-6-methoxypyridin-3-yl]methyl}pyrimidin-2-amine (Example 25, 50.0 mg, 0.15 mmol), in DCM (10 mL), was added and diisopropylethylamine (40 mg, 0.31 mmol). The solution was cooled to 0° C. and acetyl chloride (230 μL, (0.23 mmol) was added dropwise. The reaction mixture was allowed warm up to room temperature overnight, then concentrated to afford the corresponding imide (bis-acylated adduct), which was used crude in the next step.

Step 2: N-(5-{[5-(3-Chlorophenyl)-6-methoxypyridin-3-yl]methyl}pyrimidin-2-yl)acetamide. A solution of the crude product from step 1 in added ammonia (7N in methanol) was stirred at room temperature for 1 h. Purification (FCC, SiO₂, 0-100% EtOAc/hexanes) afforded the title compound (11.4 mg, 21%) as an off white solid. ¹H NMR (400 MHz, DMSO-d₆) δ 10.44 (s, 1H), 8.59 (s, 2H), 8.14 (d, J=2.7 Hz, 1H), 7.74

(d, J=2.3 Hz, 1H), 7.61-7.54 (m, 1H), 7.51-7.38 (m, 3H), 3.90 (s, 2H), 3.85 (s, 3H), 2.12 (s, 3H). [M+H]=369.20.

Example 45

3-(3-Chlorophenyl)-2-(difluoromethoxy)-5-[(4-methanesulfonylphenyl)methyl]pyridine

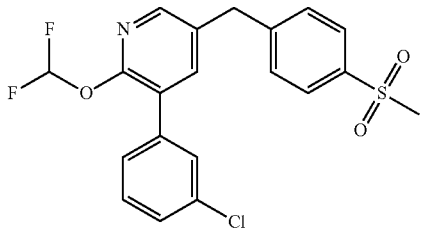 [SMILES: CS(=O)(=O)c1ccc(Cc2cnc(OC(F)F)c(-c3cccc(Cl)c3)c2)cc1]

¹H NMR (400 MHz, CD₃OD) δ 8.13 (s, 1H), 7.89 (d, J=8.2 Hz, 2H), 7.78-7.37 (m, 8H), 4.16 (s, 2H), 3.08 (s, 3H). [M+H]= 424.16.

Example 46

5-{[6-(Difluoromethoxy)-5-(2-methoxypyridin-4-yl)pyridin-3-yl]methyl}pyrimidin-2-amine

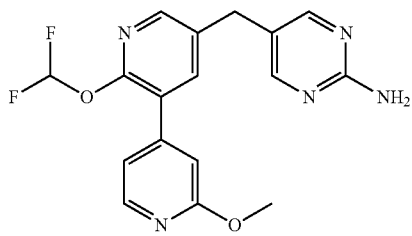 [SMILES: COc1cc(-c2cc(Cc3cnc(N)nc3)cnc2OC(F)F)ccn1]

¹H NMR (400 MHz, CD₃OD) δ 8.27-8.16 (m, 4H), 7.85 (d, J=2.3 Hz, 1H), 7.63 (t, J=1.0 Hz, 1H), 7.16-6.96 (m, 2H), 3.96 (s, 3H), 3.89 (s, 2H). [M+H]=360.23.

Example 47

5-({5-[2-(Difluoromethoxy)pyridin-4-yl]-6-methoxypyridin-3-yl}methyl)pyrimidin-2-amine

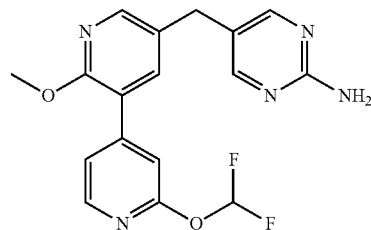 [SMILES: COc1ncc(Cc2cnc(N)nc2)cc1-c1ccnc(OC(F)F)c1]

¹H NMR (400 MHz, CD₃OD) δ 8.23-8.20 (m, 1H), 8.18 (s, 2H), 8.11 (d, J=2.3 Hz, 1H), 7.71 (d, J=2.3 Hz, 1H), 7.56 (s, 1H), 7.41-7.36 (m, 1H), 7.20-7.16 (m, 1H), 3.96 (s, 3H), 3.84 (s, 2H). [M+H]=360.23

Example 48

2-[5-({5-[3-(Difluoromethoxy)phenyl]-6-methoxypyridin-3-yl}methyl)pyrimidin-2-yl]propan-2-ol

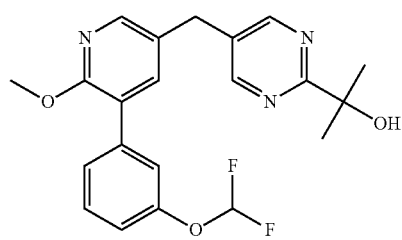 [SMILES: COc1ncc(Cc2cnc(C(C)(C)O)nc2)cc1-c1cccc(OC(F)F)c1]

¹H NMR (400 MHz, CD₃OD) δ 8.69 (s, 2H), 8.09 (d, J=2.3 Hz, 1H), 7.63 (d, J=2.3 Hz, 1H), 7.46-7.35 (m, 2H), 7.31 (t, J=1.8 Hz, 1H), 7.12 (td, J=1.0, 7.4 Hz, 1H), 7.03-6.64 (m, 1H), 4.04 (s, 2H), 3.94 (s, 3H), 1.20 (s, 6H). [M+H]=402.26.

Example 49

3-(3-Chlorophenyl)-2-methoxy-5-{[6-(trifluoromethyl)pyridin-3-yl]methyl}pyridine

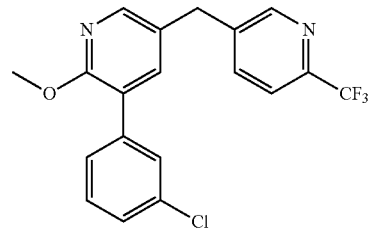 [SMILES: COc1ncc(Cc2ccc(C(F)(F)F)nc2)cc1-c1cccc(Cl)c1]

¹H NMR (400 MHz, CD₃OD) δ 8.66 (d, J=2.0 Hz, 1H), 8.08 (d, J=2.3 Hz, 1H), 7.93-7.89 (m, 1H), 7.75 (d, J=8.6 Hz, 1H), 7.62 (d, J=2.3 Hz, 1H), 7.55 (t, J=1.6 Hz, 1H), 7.45-7.32 (m, 3H), 4.13 (s, 2H), 3.94 (s, 3H). [M+H]=379.15.

Example 50

3-(3-Chlorophenyl)-2-(difluoromethoxy)-5-{[6-(propan-2-yloxy)pyridin-3-yl]methyl}pyridine

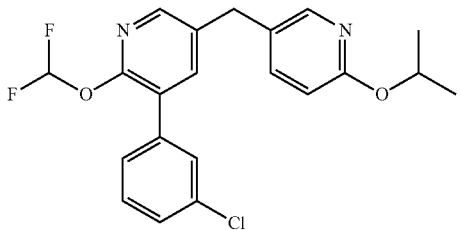 [SMILES: CC(C)Oc1ccc(Cc2cnc(OC(F)F)c(-c3cccc(Cl)c3)c2)cn1]

¹H NMR (400 MHz, CDCl₃) δ 8.03 (dd, J=2.15, 10.37 Hz, 2H), 7.31-7.72 (m, 7H), 6.64 (d, J=8.61 Hz, 1H), 5.27 (m, 1H), 3.90 (s, 2H), 1.34 (d, J=6.26 Hz, 6H). [M+H]=405.22.

Example 51

3-(3-Chlorophenyl)-2-(difluoromethoxy)-5-[(6-propoxypyridin-3-yl)methyl]pyridine

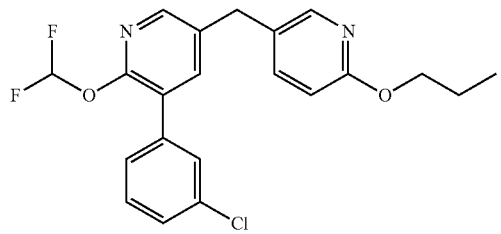 [SMILES: CCCOc1ccc(Cc2cnc(OC(F)F)c(-c3cccc(Cl)c3)c2)cn1]

¹H NMR (400 MHz, CDCl₃) δ 8.06-8.00 (m, 2H), 7.71-7.31 (m, 7H), 6.70 (d, J=9.00 Hz, 1H), 4.23 (t, J=6.85 Hz, 2H), 3.91 (s, 2H), 1.80 (q, J=6.65 Hz, 2H), 1.02 (t, J=7.43 Hz, 3H).

Example 52

5-{[5-(3-Chlorophenyl)-6-methoxypyridin-3-yl]methyl}-1-methyl-1,2-dihydropyridin-2-one

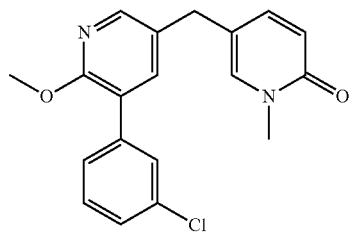 [SMILES: COc1ncc(Cc2ccc(=O)n(C)c2)cc1-c1cccc(Cl)c1]

¹H NMR (400 MHz, CD₃OD) δ 8.03 (d, J=2.0 Hz, 1H), 7.60-7.51 (m, 3H), 7.47-7.30 (m, 4H), 6.51 (d, J=9.4 Hz, 1H), 3.93 (s, 3H), 3.76 (s, 2H), 3.55 (s, 3H). [M+H]=341.19.

Example 53

3-(3-Chlorophenyl)-2-methoxy-5-(pyridin-4-ylmethyl)pyridine

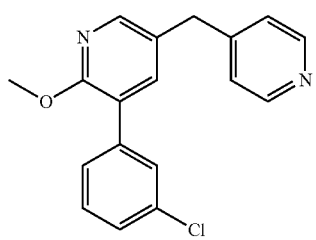 [SMILES: COc1ncc(Cc2ccncc2)cc1-c1cccc(Cl)c1]

¹H NMR (400 MHz, DMSO-d₆) δ 8.44 (d, J=4.70 Hz, 1H), 8.12 (s, 1H), 7.71 (s, 1H), 7.61-7.56 (m, 2H), 7.55-7.31 (m, 3H), 7.29 (d, J=4.70 Hz, 2H), 3.96 (s, 2H), 3.85 (s, 3H). [M+H]=311.13.

Example 54

5-{[5-(3-Chlorophenyl)-6-(difluoromethoxy)pyridin-3-yl]methyl}pyridine-2-carboxylic acid

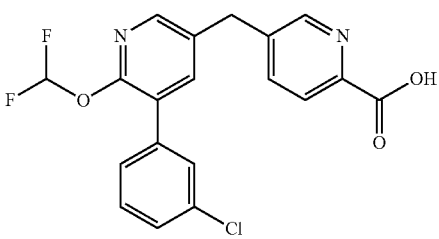

Example 54 was prepared in a manner analogous to Example 21, with the appropriate starting materials and reagent substitutions. ¹H NMR (400 MHz, DMSO-d₆) δ 8.61 (br s, 1H), 8.19 (br s, 1H), 8.12-7.94 (m, 1H), 7.93-7.75 (m, 2H), 7.72-7.57 (m, 3H), 7.56-7.39 (m, 3H), 4.10 (br. s., 2H). [M+H]=391.25.

Example 55

3-(3-Chlorophenyl)-2-methoxy-5-[(2-methoxypyrimidin-5-yl)methyl]pyrazine

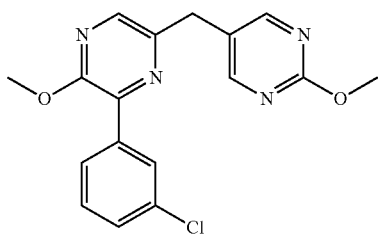

¹H NMR (400 MHz, DMSO-d₆) δ 8.58 (s, 2H), 8.23 (s, 1H), 8.03-7.86 (m, 2H), 7.50 (d, J=4.30 Hz, 2H), 4.09 (s, 2H), 3.96 (s, 3H), 3.85 (s, 3H). [M+H]=343.01.

Example 56

5-{[6-(3-Chlorophenyl)-5-methoxypyrazin-2-yl]methyl}-N-methylpyrimidin-2-amine

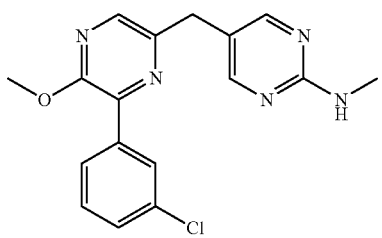

¹H NMR (400 MHz, CD₃OD) δ 8.48 (br s, 1H), 8.13 (s, 2H), 8.07-7.90 (m, 2H), 7.42 (d, J=5.09 Hz, 2H), 4.11-3.94 (m, 5H), 2.96 (s, 3H). [M+H]=342.05.

Example 57

5-{[6-(3-Chlorophenyl)-5-methoxypyrazin-2-yl]methyl}-N-cyclopropylpyrimidin-2-amine

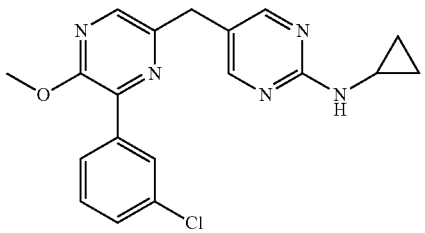 [SMILES: COc1ncc(Cc2cnc(NC3CC3)nc2)nc1-c1cccc(Cl)c1]

¹H NMR (400 MHz, CD₃OD) δ 8.12-8.18 (m, 1H), 7.93-8.05 (m, 2H), 7.59-7.70 (m, 1H), 7.50-7.55 (m, 1H), 7.41 (d, J=5.09 Hz, 2H), 4.09 (s, 2H), 4.03 (s, 3H), 2.68 (m, 1H), 0.84-0.97 (m, 2H), 0.61-0.71 (m, 2H). [M+H]=368.06.

Example 58

3-(3-Chlorophenyl)-2-methoxy-5-[(1-methyl-1H-pyrazol-4-yl)methyl]pyrazine

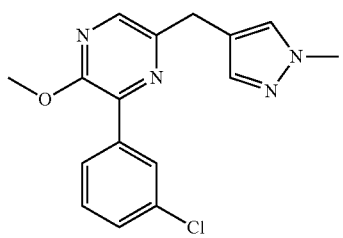

¹H NMR (400 MHz, CD₃OD) δ 8.10-7.92 (m, 3H), 7.55 (br s, 1H), 7.45-7.39 (m, 3H), 4.01 (s, 3H), 3.98 (s, 2H), 3.83 (s, 3H). [M+H]=315.01.

Example 59

(4-{[5-(3-Chlorophenyl)-6-methoxypyridin-3-yl]methyl}phenyl)methanamine

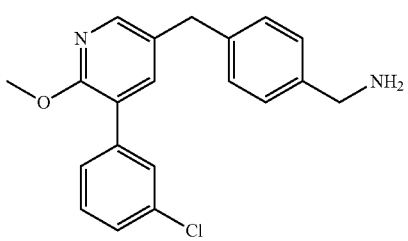

¹H NMR (400 MHz, CD₃OD) δ 7.99 (d, J=1.96 Hz, 2H), 7.47 (s, 2H), 7.44-7.14 (m, 6H), 3.94 (s, 2H), 3.91 (s, 3H). [M+H]=339.10.

Example 60

4-{[5-(3-Chlorophenyl)-6-methoxypyridin-3-yl]methyl}pyridin-2-amine

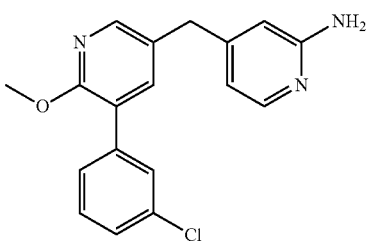 [SMILES: COc1ncc(Cc2ccnc(N)c2)cc1-c1cccc(Cl)c1]

¹H NMR (400 MHz, CD₃OD) δ 8.02 (d, J=1.96 Hz, 1H), 7.81-7.74 (m, 1H), 7.58-7.48 (m, 2H), 7.45-7.25 (m, 3H), 6.50 (d, J=5.48 Hz, 1H), 6.43 (s, 1H), 3.93 (s, 3H), 3.85 (s, 2H). [M+H]=326.01.

Example 61

3-(3-Chlorophenyl)-5-[(2,6-dimethylpyridin-4-yl)methyl]-2-methoxypyridine

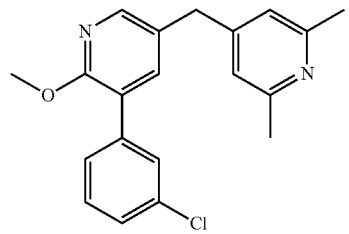

¹H NMR (400 MHz, CD₃OD) δ 8.02 (d, J=2.35 Hz, 1H), 7.59-7.48 (m, 2H), 7.47-7.25 (m, 3H), 6.97 (s, 2H), 3.98-3.86 (m, 5H), 2.43 (s, 6H). [M+H]=339.05.

Example 62

4-{[5-(3-Chlorophenyl)-6-methoxypyridin-3-yl]methyl}pyridine-2-carbonitrile

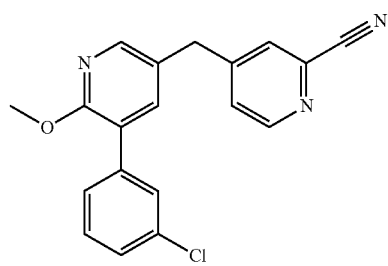 [SMILES: COc1ncc(Cc2ccnc(C#N)c2)cc1-c1cccc(Cl)c1]

¹H NMR (400 MHz, CD₃OD) δ 8.57 (d, J=5.09 Hz, 1H), 8.07 (d, J=2.35 Hz, 1H), 7.79 (s, 1H), 7.60 (d, J=2.35 Hz, 1H), 7.54 (d, J=1.96 Hz, 2H), 7.48-7.26 (m, 3H), 4.08 (s, 2H), 3.93 (s, 3H). [M+H]=336.14.

Example 63

4-{[5-(3-Chlorophenyl)-6-methoxypyridin-3-yl]methyl}pyridine-2-carboxamide

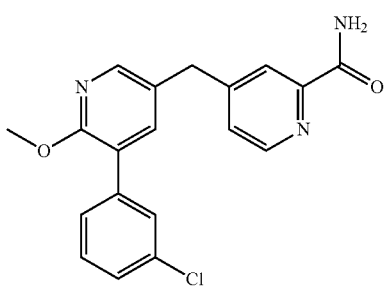 [SMILES: COc1ncc(Cc2ccnc(C(N)=O)c2)cc1-c1cccc(Cl)c1]

The title compound was made in a manner analogous to Example 23, from 4-{[5-(3-chlorophenyl)-6-methoxypyridin-3-yl]methyl}pyridine-2-carbonitrile (Example 62), reaction run at room temperature. ¹H NMR (400 MHz, DMSO-d₆) δ 8.49 (d, J=5.09 Hz, 1H), 8.15 (d, J=1.96 Hz, 1H), 8.05 (br s, 1H), 7.92 (s, 1H), 7.74 (d, J=1.96 Hz, 1H), 7.58 (d, J=1.57 Hz, 2H), 7.54-7.33 (m, 4H), 4.05 (s, 2H), 3.85 (s, 3H). [M+H]=354.15.

Example 64

3-(3-Chlorophenyl)-2-methoxy-5-(pyridin-3-ylmethyl)pyridine

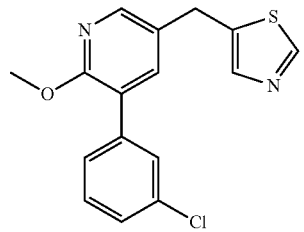 [SMILES: COc1ncc(Cc2cncs2)cc1-c1cccc(Cl)c1]

¹H NMR (400 MHz, DMSO-d₆) δ 8.55 (d, J=2.0 Hz, 1H), 8.39 (dd, J=1.2, 4.7 Hz, 1H), 8.13 (d, J=2.0 Hz, 1H), 7.72 (d, J=2.3 Hz, 1H), 7.70-7.66 (m, 1H), 7.58 (d, J=1.6 Hz, 1H), 7.52-7.37 (m, 3H), 7.29 (dd, J=4.7, 7.8 Hz, 1H), 3.96 (s, 2H), 3.85 (s, 3H). [M+H]=318.09.

Example 65

3-(3-Chlorophenyl)-2-methoxy-5-(1,3-thiazol-5-ylmethyl)pyridine

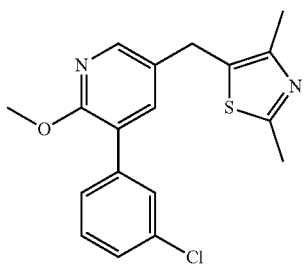 [SMILES: COc1ncc(Cc2sc(C)nc2C)cc1-c1cccc(Cl)c1]

¹H NMR (400 MHz, DMSO-d₆) δ 8.93 (s, 1H), 8.07-8.15 (m, 1H), 7.75 (s, 1H), 7.71 (d, J=2.35 Hz, 1H), 7.56-7.62 (m, 1H), 7.37-7.52 (m, 3H), 4.21 (s, 2H), 3.86 (s, 3H). [M+H]=318.15.

Example 66

3-(3-Chlorophenyl)-5-[(dimethyl-1,3-thiazol-5-yl)methyl]-2-methoxypyridine

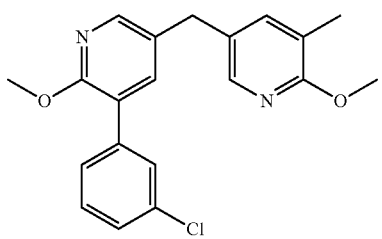

¹H NMR (400 MHz, DMSO-d₆) δ 8.06 (s, 1H), 7.63 (s, 1H), 7.57 (s, 1H), 7.50-7.40 (m, 3H), 4.03 (s, 2H), 3.85 (s, 3H), 2.48 (s, 3H), 2.28 (s, 3H). [M+H]=345.17.

Example 67

3-(3-Chlorophenyl)-2-methoxy-5-[(6-methoxy-5-methylpyridin-3-yl)methyl]pyridine

¹H NMR (400 MHz, DMSO-d₆) δ 8.09 (d, J=2.3 Hz, 1H), 7.99 (d, J=2.3 Hz, 1H), 7.94 (d, J=2.0 Hz, 1H), 7.69-7.62 (m,

1H), 7.59-7.52 (m, 1H), 7.51-7.36 (m, 3H), 3.87-3.84 (m, 6H), 3.82 (s, 2H), 3.81 (s, 3H). [M+H]=356.09.

Example 68

3-(3-Chlorophenyl)-2-(difluoromethoxy)-5-(1,3-thiazol-5-ylmethyl)pyridine

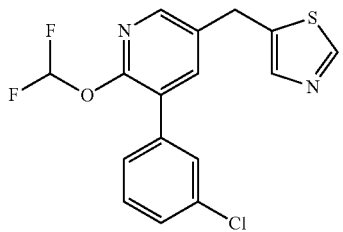 [SMILES: FC(F)Oc1ncc(Cc2cncs2)cc1-c1cccc(Cl)c1]

$^1$H NMR (400 MHz, DMSO-d$_6$) δ 8.94 (s, 1H), 8.22 (d, J=2.0 Hz, 1H), 7.94 (d, J=2.3 Hz, 1H), 7.77 (s, 1H), 7.69 (s, 1H), 7.59 (s, 1H), 7.53-7.45 (m, 3H), 4.29 (s, 2H). [M+H]=354.12.

Example 69

3-(3-Chlorophenyl)-2-(difluoromethoxy)-5-[(dimethyl-1,3-thiazol-5-yl)methyl]pyridine

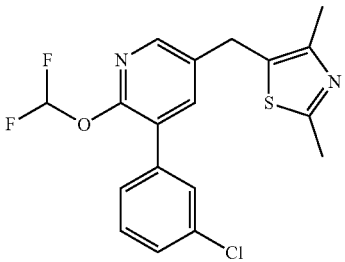 [SMILES: Cc1nc(C)c(Cc2cnc(OC(F)F)c(-c3cccc(Cl)c3)c2)s1]

$^1$H NMR (400 MHz, DMSO-d$_6$) δ 8.14 (d, J=2.0 Hz, 1H), 7.88-7.83 (m, 1H), 7.68 (s, 1H), 7.62-7.57 (m, 1H), 7.55-7.45 (m, 3H), 4.11 (s, 2H), 2.51 (s, 3H), 2.29 (s, 3H). [M+H]=381.15.

Example 70

5-{[5-(3-Chlorophenyl)-6-(difluoromethoxy)pyridin-3-yl]methyl}pyridine-3-carboxamide

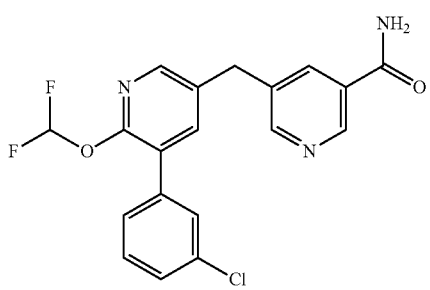 [SMILES: NC(=O)c1cncc(Cc2cnc(OC(F)F)c(-c3cccc(Cl)c3)c2)c1]

$^1$H NMR (400 MHz, DMSO-d$_6$) δ 8.86 (d, J=2.0 Hz, 1H), 8.70 (d, J=2.0 Hz, 1H), 8.26 (d, J=2.0 Hz, 1H), 8.10 (s, 2H), 7.98 (d, J=2.3 Hz, 1H), 7.60 (s, 1H), 7.55 (br s, 1H), 7.52-7.43 (m, 4H), 4.09 (s, 2H). [M+H]=391.05.

Example 71

(5-{[5-(3-Chlorophenyl)-6-(difluoromethoxy)pyridin-3-yl]methyl}pyridin-3-yl)methanamine

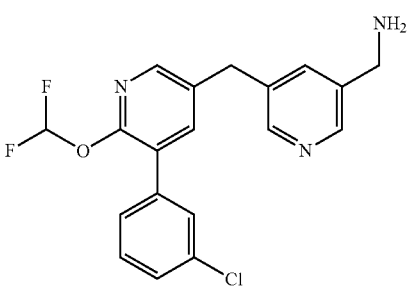 [SMILES: NCc1cncc(Cc2cnc(OC(F)F)c(-c3cccc(Cl)c3)c2)c1]

Step 1. tert-Butyl ((5-((5-(3-chlorophenyl)-6-(difluoromethoxy)pyridin-3-yl)methyl)pyridin-3-yl)methyl)carbamate. The title compound was prepared in a manner analogous to Example 1, with the appropriate starting material substitutions.

Step 2. (5-{[5-(3-Chlorophenyl)-6-(difluoromethoxy)pyridin-3-yl]methyl}pyridin-3-yl)methanamine. Purified compound from step 1, was treated with a solution of 20% trifluoroacetic acid in DCM and stirred at room temperature for 4 h. The solvent was removed under reduced pressure and the residue partitioned between EtOAc and saturated sodium bicarbonate. The organic layers were washed with brine, dried (Na$_2$SO$_4$) and concentrated under reduced pressure to afford the title compound. $^1$H NMR (400 MHz, DMSO-d$_6$) δ 8.61-8.47 (m, 1H), 8.31 (m, 2H), 8.22 (br s, 1H), 7.97-7.80 (m, 2H), 7.72-7.57 (m, 2H), 7.50 (br s, 2H), 4.12-4.03 (m, 2H), 4.00 (s, 2H), 3.15 (d, J=4.7 Hz, 2H). [M+H]=377.25.

Example 72

3-(3-Chlorophenyl)-2-(difluoromethoxy)-5-[(6-methylpyridin-3-yl)methyl]pyridine

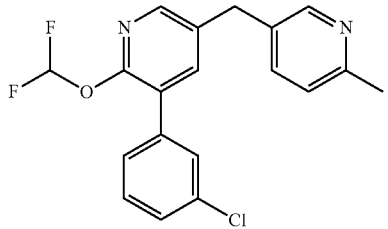 [SMILES: Cc1ccc(Cc2cnc(OC(F)F)c(-c3cccc(Cl)c3)c2)cn1]

$^1$H NMR (400 MHz, DMSO-d$_6$) δ 8.42 (s, 1H), 8.20 (d, J=2.0 Hz, 1H), 7.91 (d, J=2.0 Hz, 1H), 7.85 (s, 1H), 7.89-7.83

(m, 1H), 7.69-7.65 (m, 1H), 7.67 (s, 1H), 7.61-7.54 (m, 3H), 3.97 (s, 2H), 2.39 (s, 3H). [M+H]=361.06.

Example 73

3-(3-Chlorophenyl)-2-(difluoromethoxy)-5-[(2-methyl-1,3-thiazol-5-yl)methyl]pyridine

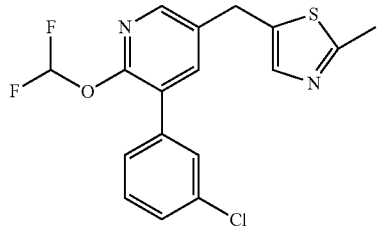 [SMILES: Cc1ncc(Cc2cnc(OC(F)F)c(-c3cccc(Cl)c3)c2)s1]

$^1$H NMR (400 MHz, DMSO-d$_6$) δ 8.20 (s, 1H), 7.94-7.84 (m, 1H), 7.69 (s, 1H), 7.59 (s, 1H), 7.53-7.42 (m, 4H), 4.19 (s, 2H), 2.55 (s, 3H). [M+H]=368.02.

Example 74

3-(3-Chlorophenyl)-2-(difluoromethoxy)-5-(1,3-thiazol-2-ylmethyl)pyridine

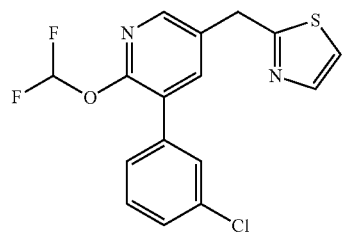 [SMILES: FC(F)Oc1ncc(Cc2nccs2)cc1-c1cccc(Cl)c1]

$^1$H NMR (400 MHz, DMSO-d$_6$) δ 8.27 (s, 1H), 8.01 (s, 1H), 7.74-7.64 (m, 1H), 7.63-7.56 (m, 2H), 7.55-7.41 (m, 4H), 4.43 (s, 2H). [M+H]=354.05.

Example 75

5-{[5-(3-Chlorophenyl)-6-methoxypyridin-3-yl]methyl}-2-methylpyrimidine

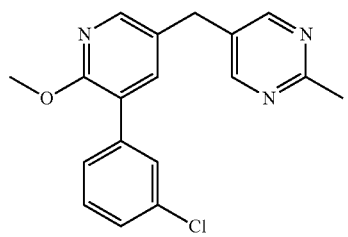

$^1$H NMR (400 MHz, DMSO-d$_6$) δ 8.55 (s, 2H), 8.13 (d, J=2.3 Hz, 1H), 7.72 (d, J=2.3 Hz, 1H), 7.63-7.56 (m, 1H), 7.53-7.34 (m, 3H), 4.02 (s, 2H), 3.80 (s, 3H), 3.85 (s, 3H). [M+H]=327.15.

Example 76

5-{[5-(3-Chlorophenyl)-6-methoxypyridin-3-yl]methyl}-2-methoxypyrimidine

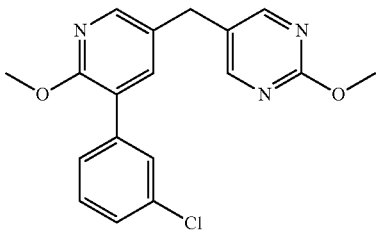

$^1$H NMR (400 MHz, DMSO-d$_6$) δ 8.55 (s, 2H), 8.13 (d, J=2.3 Hz, 1H), 7.72 (d, J=2.3 Hz, 1H), 7.63-7.56 (m, 1H), 7.53-7.34 (m, 3H), 4.02 (s, 2H), 3.80 (s, 3H), 3.85 (s, 3H). [M+H]=342.15.

Example 77

5-{[5-(3-Chlorophenyl)-6-methoxypyridin-3-yl]methyl}-N-(propan-2-yl)pyrimidin-2-amine

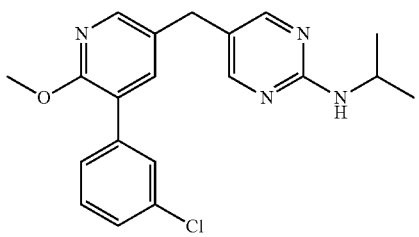 [SMILES: COc1ncc(Cc2cnc(NC(C)C)nc2)cc1-c1cccc(Cl)c1]

$^1$H NMR (400 MHz, DMSO-d$_6$) δ 8.30 (s, 2H), 8.11 (d, J=2.3 Hz, 1H), 7.70 (d, J=2.3 Hz, 1H), 7.58 (t, J=1.8 Hz, 1H), 7.53-7.36 (m, 3H), 7.35 (br s, 1H), 4.03-3.89 (m, 1H), 3.85 (s, 3H), 3.75 (s, 2H), 1.11 (d, J=6.3 Hz, 6H). [M+H]=370.05.

Example 78

5-{[5-(3-Chlorophenyl)-6-methoxypyridin-3-yl]methyl}pyrimidine

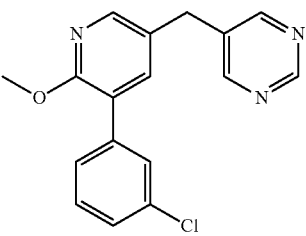

¹H NMR (400 MHz, DMSO-d₆) δ 9.02 (s, 1H), 8.77 (s, 2H), 8.16 (d, J=2.3 Hz, 1H), 7.76 (d, J=2.3 Hz, 1H), 7.65-7.36 (m, 4H), 3.98 (s, 2H), 3.30 (s, 3H). [M+H]=313.01.

Example 79

3-(3-Chlorophenyl)-2-methoxy-5-[(1-methyl-1H-pyrazol-4-yl)methyl]pyridine

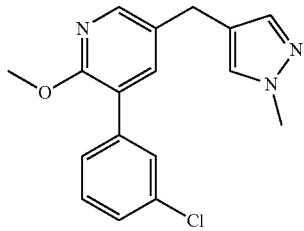 [SMILES: COc1ncc(Cc2cnn(C)c2)cc1-c1cccc(Cl)c1]

¹H NMR (400 MHz, DMSO-d₆) δ 8.05 (d, J=2.0 Hz, 1H), 7.61 (d, J=2.3 Hz, 1H), 7.57 (s, 1H), 7.52-7.38 (m, 4H), 7.28 (s, 1H), 3.84 (s, 3H), 3.75 (s, 2H), 3.65 (s, 3H). [M+H]=315.02.

Example 80

3-(3-Chlorophenyl)-2-methoxy-5-(1H-pyrazol-4-ylmethyl)pyridine

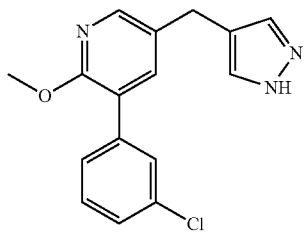 [SMILES: COc1ncc(Cc2cn[nH]c2)cc1-c1cccc(Cl)c1]

Step 1. tert-Butyl 4-((5-(3-chlorophenyl)-6-methoxypyridin-3-yl)methyl)-1H-pyrazole-1-carboxylate. The title compound was prepared in a manner analogous to Example 1, with the appropriate starting material substitutions.

Step 2. Purified compound from Step 1, was treated with a solution of 20% trifluoroacetic acid in DCM and stirred at room temperature for 4 h. The solvent was removed under reduced pressure and the residue partitioned between EtOAc and saturated sodium bicarbonate. The organic layers were washed with brine, dried (Na₂SO₄), and concentrated under reduced pressure to afford the title compound. ¹H NMR (400 MHz, DMSO-d₆) δ 8.05 (d, J=2.0 Hz, 1H), 7.62 (d, J=2.0 Hz, 1H), 7.58-7.54 (m, 3H), 7.50-7.36 (m, 4H), 3.84 (s, 3H), 3.72 (s, 2H). [M+H]=301.02.

Example 81

5-{[5-(3-Chlorophenyl)-6-methoxypyridin-3-yl]methyl}-N-methylpyrimidin-2-amine

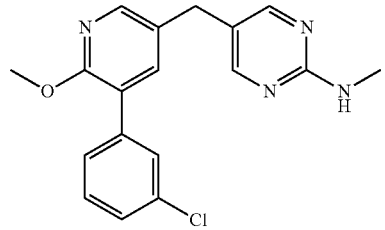

¹H NMR (400 MHz, DMSO-d₆) δ 8.34 (s, 2H), 8.11 (d, J=2.0 Hz, 1H), 7.84 (br s, 1H), 7.70 (d, J=2.0 Hz, 1H), 7.58 (t, J=1.8 Hz, 1H), 7.53-7.36 (m, 3H), 3.83 (s 3H), 3.80-3.75 (m, 3H), 3.73 (s, 2H). [M+H]=342.05.

Example 82

5-{[5-(3-Chlorophenyl)-6-methoxypyridin-3-yl]methyl}-N-cyclopropylpyrimidin-2-amine

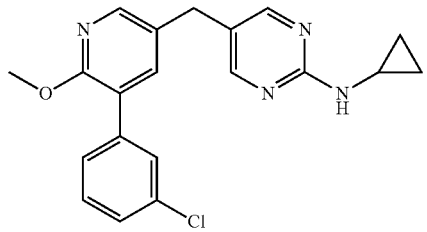

¹H NMR (400 MHz, DMSO-d₆) δ 8.34 (s, 2H), 8.11 (d, J=2.0 Hz, 1H), 7.84 (br s, 1H), 7.70 (d, J=2.0 Hz, 1H), 7.58 (t, J=1.8 Hz, 1H), 7.53-7.36 (m, 3H), 3.80 (s, 3H), 3.78 (s, 2H), 2.68-2.56 (m, 1H), 0.71-0.61 (m, 2H), 0.53-0.38 (m, 2H). [M+H]=368.02.

Example 83

5-{[5-(3-Chlorophenyl)-6-methoxypyridin-3-yl]methyl}-N,N-dimethylpyrimidin-2-amine

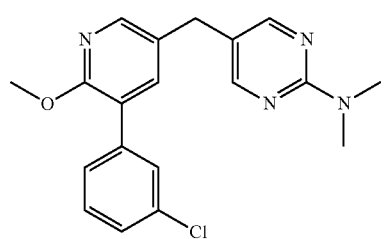

¹H NMR (400 MHz, DMSO-d₆) δ 8.38 (s, 2H), 8.16 (d, J=2.0 Hz, 1H), 7.72 (d, J=2.0 Hz, 1H), 7.56 (t, J=1.8 Hz, 1H), 7.50-7.36 (m, 3H), 3.86 (s 3H), 3.73 (s, 2H), 3.01 (s, 6H). [M+H]=355.18.

Example 84

5-{[5-(3-Chlorophenyl)-6-methoxypyridin-3-yl]methyl}-N-(2,2,2-trifluoroethyl)pyrimidin-2-amine

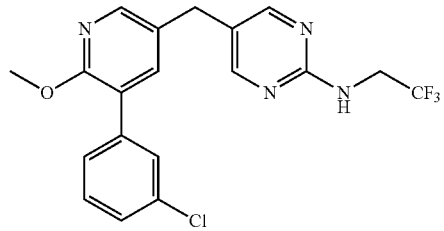 [SMILES: COc1ncc(Cc2cnc(NCC(F)(F)F)nc2)cc1-c1cccc(Cl)c1]

¹H NMR (400 MHz, DMSO-d₆) δ 8.38 (s, 2H), 8.16 (d, J=2.0 Hz, 1H), 7.84 (br s, 1H), 7.72 (d, J=2.0 Hz, 1H), 7.56 (t, J=1.8 Hz, 1H), 7.50-7.36 (m, 3H), 4.10-4.01 (m, 2H), 3.86 (s 3H), 3.73 (s, 2H). [M+H]=409.14.

Example 85

Methyl 4-{[6-(3-chlorophenyl)-5-methoxypyrazin-2-yl]methyl}benzoate

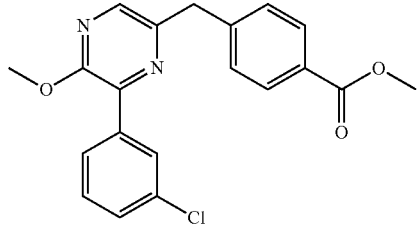

[M+H]=369.16

Example 86

4-{[6-(3-Chlorophenyl)-5-methoxypyrazin-2-yl]methyl}benzonitrile

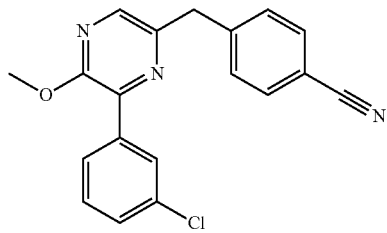 [SMILES: COc1ncc(Cc2ccc(C#N)cc2)nc1-c1cccc(Cl)c1]

[M+H]=336.6

Example 87

5-{[6-(3-Chlorophenyl)-5-methoxypyrazin-2-yl]methyl}pyrimidin-2-amine

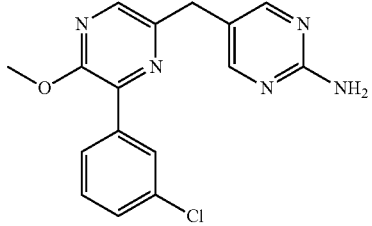

¹H NMR (400 MHz, CD₃OD) δ 8.29 (s, 1H), 8.09 (s, 1H), 8.04 (s, 1H), 7.98 (t, J=3.72 Hz, 1H), 7.69-7.52 (m, 1H), 7.41 (d, J=5.09 Hz, 2H), 4.03 (s, 3H), 3.98 (s, 2H). [M+H]=328.21.

Example 88

3-(3-Chlorophenyl)-5-[(4-fluorophenyl)methyl]-2-methoxypyridine

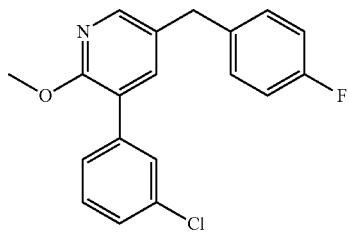 [SMILES: COc1ncc(Cc2ccc(F)cc2)cc1-c1cccc(Cl)c1]

¹H NMR (400 MHz, CD₃OD) δ 7.99 (d, J=2.3 Hz, 1H), 7.51 (t, J=2.5 Hz, 2H), 7.42-7.21 (m, 5H), 7.01 (t, J=8.8 Hz, 2H), 3.95 (s, 2H), 3.92 (s, 3H). [M+H]=328.26.

Example 89

5-{[5-(3-Chlorophenyl)-6-(difluoromethoxy)pyridin-3-yl]methyl}pyrimidin-2-amine

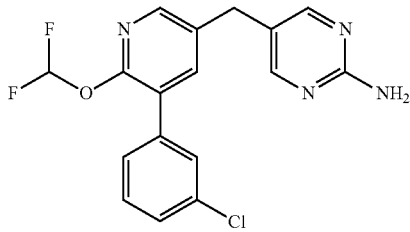 [SMILES: Nc1ncc(Cc2cnc(OC(F)F)c(-c3cccc(Cl)c3)c2)cn1]

¹H NMR (400 MHz, CD₃OD) δ 8.11 (s, 2H), 8.01 (d, J=2.3 Hz, 1H), 7.70-7.63 (m, 1H), 7.50 (s, 1H), 7.45 (s, 1H), 7.38-7.28 (m, 3H), 3.78 (s, 2H). [M+H]=363.30.

Example 90

5-{[6-(3-Chlorophenyl)-5-methoxypyrazin-2-yl]methyl}pyridine-2-carboxamide

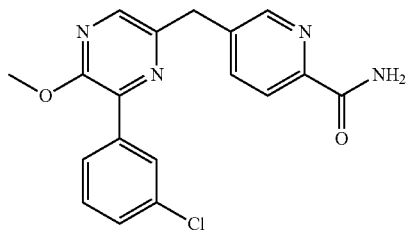

Step 1. Methyl 5-(6-(3-chlorophenyl)-5-methoxypyrazin-2-yl)methyl)picolinate. Prepared in a manner analogous to Example 1 from (6-(methoxycarbonyl)pyridin-3-yl)boronic acid and Intermediate 3, to affords 20 mg of the corresponding methyl ester as an orange oil. [M+H]=370.10.

Step 2. 5-{[6-(3-Chlorophenyl)-5-methoxypyrazin-2-yl]methyl}pyridine-2-carboxamide. A solution of 5-((6-(3-chlorophenyl)-5-methoxypyrazin-2-yl)methyl)picolinate (from Step 1) and ammonia (7N in methanol) was heated at 60° C. for 8 h, then concentrated under reduced pressure. Trituration with diethyl ether obtained the title compound (12 mg, 70%) as a yellow solid. ¹H NMR (400 MHz, CD₃OD) δ 8.66 (br s, 1H), 8.14 (s, 1H), 8.07 (d, J=7.83 Hz, 1H), 8.02 (s, 1H), 7.69-7.60 (m, 1H), 7.59-7.50 (m, 1H), 7.41 (d, J=4.70 Hz, 2H), 4.27 (s, 2H), 4.00-4.09 (m, 3H). [M+H]=355.10.

Example 91

5-{[5-(3-Chlorophenyl)-6-(difluoromethoxy)pyridin-3-yl}methyl]-N-cyclopropylpyrimidin-2-amine

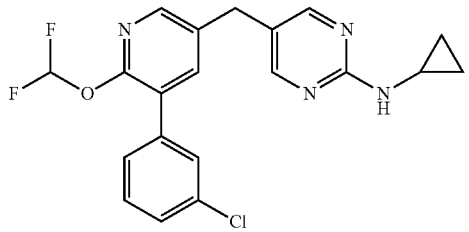 [SMILES: FC(F)Oc1ncc(Cc2cnc(NC3CC3)nc2)cc1-c1cccc(Cl)c1]

¹H NMR (400 MHz, CD₃OD) δ 8.25 (br s, 2H), 8.11 (br s, 1H), 7.75 (br s, 1H), 7.48-7.68 (m, 2H), 7.35-7.46 (m, 3H), 3.90 (br s, 2H), 2.63 (br s, 1H), 0.76 (d, J=6.26 Hz, 2H), 0.51 (br s, 2H). [M+H]=403.12.

Example 92

5-{[5-(3-Chlorophenyl)-6-(difluoromethoxy)pyridin-3-yl]methyl}-2-methoxypyrimidine

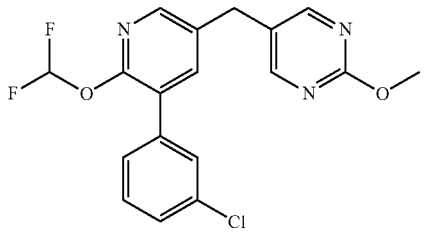 [SMILES: COc1ncc(Cc2cnc(OC(F)F)c(-c3cccc(Cl)c3)c2)cn1]

¹H NMR (400 MHz, CD₃OD) δ 8.49 (br s, 2H), 8.13 (br s, 1H), 7.78 (d, J=2.74 Hz, 1H), 7.63-7.49 (m, 2H), 7.47-7.31 (m, 3H), 4.07-3.81 (m, 5H). [M+H]=376.20.

Example 93

5-{[5-(3-Chlorophenyl)-6-(difluoromethoxy)pyridin-3-yl]methyl}-N-methylpyrimidin-2-amine

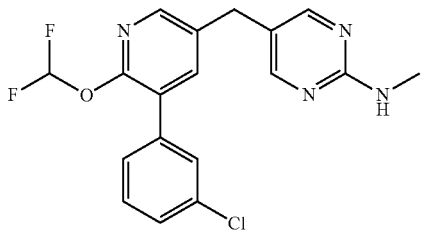 [SMILES: CNc1ncc(Cc2cnc(OC(F)F)c(-c3cccc(Cl)c3)c2)cn1]

¹H NMR (400 MHz, CD₃OD) δ 8.20 (br s, 2H), 8.10 (br s, 1H), 7.74 (br s, 2H), 7.68-7.49 (m, 1H), 7.46-7.27 (m, 3H), 3.87 (br s, 2H), 2.89 (br s, 3H). [M+H]=377.10.

Example 94

5-{[5-(3-Chlorophenyl)-6-(difluoromethoxy)pyridin-3-yl]methyl}-N-(2,2,2-trifluoroethyl)pyrimidin-2-amine

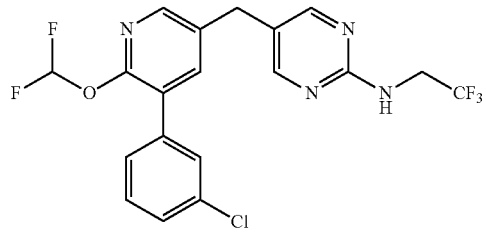 [SMILES: FC(F)Oc1ncc(Cc2cnc(NCC(F)(F)F)nc2)cc1-c1cccc(Cl)c1]

¹H NMR (400 MHz, CD₃OD) δ 8.27 (br s, 2H), 8.10 (br s, 1H), 7.80-7.68 (m, 1H), 7.61-7.49 (m, 1H), 7.47-7.31 (m, 4H), 4.19-4.02 (m, 2H), 3.90 (br s, 2H). [M+H]=445.10.

Example 95

3-(3-Chlorophenyl)-2-methoxy-5-(1,2-oxazol-4-ylmethyl)pyrazine

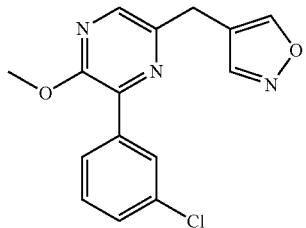 [SMILES: COc1ncc(Cc2cnoc2)nc1-c1cccc(Cl)c1]

¹H NMR (400 MHz, CD₃OD) δ 8.58 (s, 1H), 8.09 (s, 1H), 8.43 (s, 1H), 8.05 (s, 1H), 8.02-7.95 (m, 1H), 7.47-7.38 (m, 2H), 4.20-3.90 (m, 5H). [M+H]=302.10.

Example 96

3-(3-Chlorophenyl)-2-methoxy-5-(1,2-oxazol-4-ylmethyl)pyridine

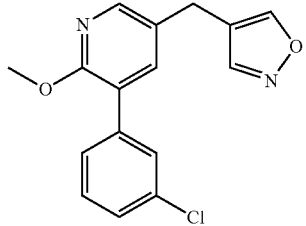 [SMILES: COc1ncc(Cc2cnoc2)cc1-c1cccc(Cl)c1]

¹H NMR (400 MHz, CD₃OD) δ 8.52 (s, 1H), 8.34 (s, 1H), 8.04 (s, 1H), 7.60-7.53 (m, 2H), 7.46-7.27 (m, 3H), 3.93 (s, 3H), 3.85 (s, 2H). [M+H]=301.10.

Example 97

3-(3-Chlorophenyl)-2-(difluoromethoxy)-5-(1,2-oxazol-4-ylmethyl)pyridine

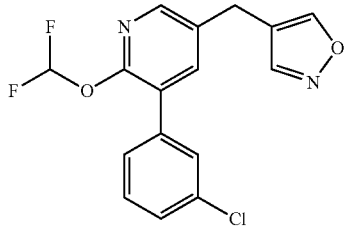 [SMILES: FC(F)Oc1ncc(Cc2cnoc2)cc1-c1cccc(Cl)c1]

Example 98

3-(3-Chlorophenyl)-5-[(dimethyl-1,2-oxazol-4-yl)methyl]-2-methoxypyrazine

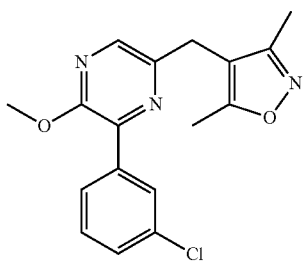 [SMILES: COc1ncc(Cc2c(C)noc2C)nc1-c1cccc(Cl)c1]

¹H NMR (400 MHz, CD₃OD) δ 8.07-7.88 (m, 2H), 7.46-7.30 (m, 3H), 4.03 (s, 3H), 3.89 (br s, 2H), 2.40 (br s, 3H), 2.21 (s, 3H). [M+H]=330.79.

Example 99

3-(3-Chlorophenyl)-2-(difluoromethoxy)-5-[(dimethyl-1,2-oxazol-4-yl)methyl]pyridine

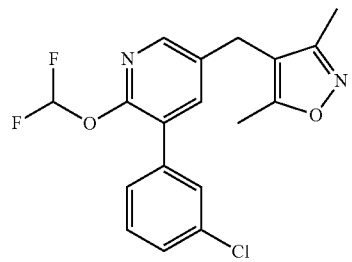 [SMILES: Cc1noc(C)c1Cc1cnc(OC(F)F)c(-c2cccc(Cl)c2)c1]

¹H NMR (400 MHz, CD₃OD) δ 8.01 (br s, 1H), 7.64 (br s, 1H), 7.58 (br s, 1H), 7.53 (br s, 1H), 7.47-7.31 (m, 3H), 3.81 (br s, 2H), 2.36 (br s, 3H), 2.12 (br s, 3H). [M+H]=365.20.

Example 100

Methyl 2-(4-{[5-(3-chlorophenyl)-6-(difluoromethoxy)pyridin-3-yl]methyl}phenyl)acetate

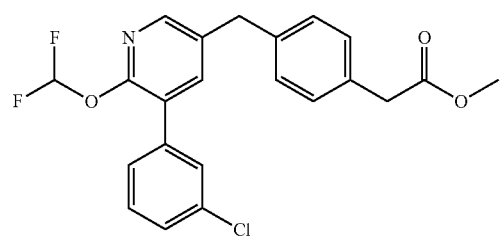 [SMILES: COC(=O)Cc1ccc(Cc2cnc(OC(F)F)c(-c3cccc(Cl)c3)c2)cc1]

¹H NMR (400 MHz, CD₃OD) δ 8.08 (d, J=2.35 Hz, 1H), 8.02 (d, J=2.35 Hz, 1H), 7.76 (s, 1H), 7.71-7.66 (m, 1H), 7.56-7.59 (m, 1H), 7.55 (s, 1H), 7.57-7.46 (m, 1H), 7.45-7.36 (m, 4H), 4.01 (s, 2H), 3.67 (s, 3H), 3.61 (s, 2H). [M+H]=418.29.

Example 101

Ethyl 1-(4-{[5-(3-chlorophenyl)-6-(difluoromethoxy)pyridin-3-yl]methyl}phenyl)cyclopropane-1-carboxylate

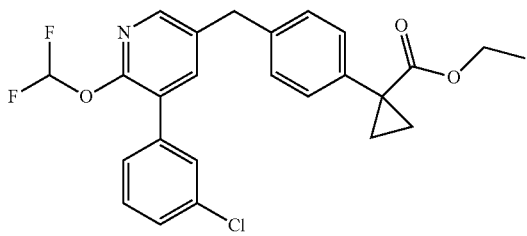 [SMILES: CCOC(=O)C1(c2ccc(Cc3cnc(OC(F)F)c(-c4cccc(Cl)c4)c3)cc2)CC1]

¹H NMR (400 MHz, CD₃OD) δ 8.08 (d, J=2.35 Hz, 1H), 7.76 (s, 1H), 7.68 (d, J=2.35 Hz, 1H), 7.59-7.52 (m, 1H), 7.52-7.47 (m, 2H), 7.45-7.36 (m, 4H), 7.31-7.27 (m, 1H), 4.10-4.05 (m, 4H), 4.03 (m, 1H), 4.00 (s, 2H), 1.55-1.49 (m, 2H), 1.14-1.19 (m, 3H). [M+H]=445.10.

Example 102

3-(3-Chlorophenyl)-5-{[6-(cyclopropylmethoxy)pyridin-3-yl]methyl}-2-(difluoromethoxy)pyridine

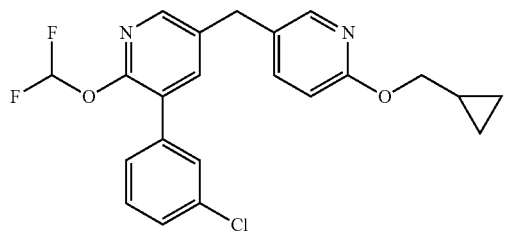 [SMILES: FC(F)Oc1ncc(Cc2ccc(OCC3CC3)nc2)cc1-c1cccc(Cl)c1]

¹H NMR (400 MHz, CD₃OD) δ 8.08-8.05 (m, 1H), 8.01-7.90 (m, 1H), 7.71 (d, J=2.35 Hz, 1H), 7.58 (s, 1H), 7.50-7.45 (m, 1H), 7.43-7.36 (m, 4H), 6.75-6.73 (m, 1H), 4.05 (d, J=7.04 Hz, 2H), 3.96 (s, 2H), 1.32-1.17 (m, 1H), 0.52-0.63 (m, 2H), 0.25-0.36 (m, 2H). [M+H]=417.33.

Example 103

5-{6-[3-(Difluoromethoxy)phenyl]-5-ethoxypyrazin-2-yl}methyl)pyridine-2-carbonitrile

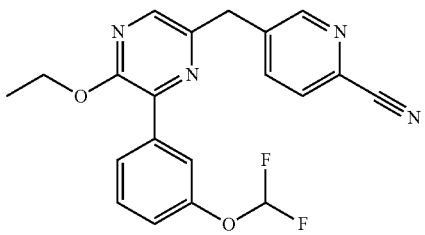 [SMILES: CCOc1ncc(Cc2ccc(C#N)nc2)nc1-c1cccc(OC(F)F)c1]

¹H NMR (400 MHz, CD₃OD) δ 8.73 (d, J=1.6 Hz, 1H), 8.13 (s, 1H), 8.01-7.90 (m, 2H), 7.86 (t, J=1.8 Hz, 1H), 7.80 (dd, J=0.8, 7.8 Hz, 1H), 7.46 (t, J=8.0 Hz, 1H), 7.19 (dd, J=2.0, 8.2 Hz, 1H), 7.05-6.59 (m, 1H), 4.48 (q, J=7.3 Hz, 2H), 4.27 (s, 2H), 1.43 (t, J=7.0 Hz, 3H). [M+H]=383.26.

Example 104

5-({6-[3-(Difluoromethoxy)phenyl]-5-ethoxypyrazin-2-yl}methyl)pyrimidin-2-amine

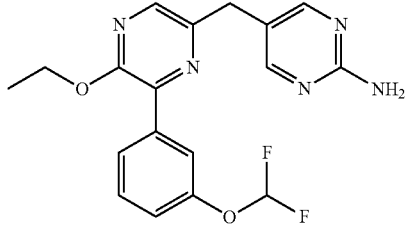 [SMILES: CCOc1ncc(Cc2cnc(N)nc2)nc1-c1cccc(OC(F)F)c1]

¹H NMR (400 MHz, CD₃OD) δ 8.52 (s, 2H), 8.13 (s, 1H), 7.95 (qd, J=0.9, 7.9 Hz, 1H), 7.89-7.85 (m, 1H), 7.47 (t, J=8.2 Hz, 1H), 7.20 (dd, J=3.3, 8.0 Hz, 1H), 7.05-6.62 (m, 1H), 4.49 (q, J=7.2 Hz, 2H), 4.07 (s, 2H), 1.43 (t, J=7.0 Hz, 3H). [M+H]=374.14.

Example 105

5-{[6-(3-Chlorophenyl)-5-ethoxypyrazin-2-yl]methyl}pyrimidin-2-amine

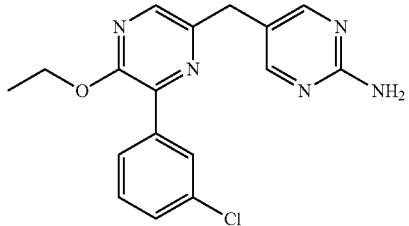 [SMILES: CCOc1ncc(Cc2cnc(N)nc2)nc1-c1cccc(Cl)c1]

¹H NMR (400 MHz, DMSO-d₆) δ 8.23-8.17 (m, 2H), 8.15 (s, 1H), 8.05-8.02 (m, 1H), 7.99 (ddd, J=1.6, 3.6, 5.4 Hz, 1H), 7.52-7.47 (m, 2H), 6.44 (s, 2H), 4.41 (q, J=7.0 Hz, 2H), 3.90 (s, 2H), 1.35 (t, J=7.0 Hz, 3H). [M+H]=342.15.

Example 106

5-{6-[3-(Difluoromethoxy)phenyl]-5-methoxy-pyrazin-2-yl}methyl)pyrimidin-2-amine

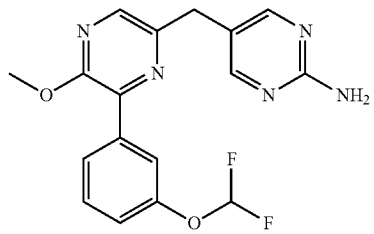 [SMILES: COc1ncc(Cc2cnc(N)nc2)nc1-c1cccc(OC(F)F)c1]

¹H NMR (400 MHz, DMSO-d₆) δ 8.23-8.14 (m, 3H), 7.88 (d, J=8.2 Hz, 1H), 7.77 (s, 1H), 7.52 (t, J=8.0 Hz, 1H), 7.29-7.21 (m, 1H), 7.09-5.70 (m, 3H), 3.95 (s, 3H), 3.90 (s, 2H). [M+H]=360.21.

Example 107

5-{6-[3-(Difluoromethoxy)phenyl]-5-methoxy-pyrazin-2-yl}methyl)pyrimidine-2-carbonitrile

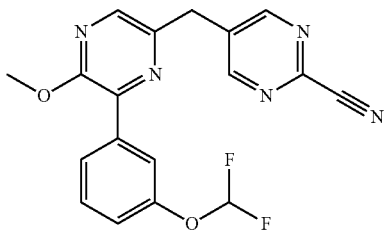 [SMILES: COc1ncc(Cc2cnc(C#N)nc2)nc1-c1cccc(OC(F)F)c1]

¹H NMR (400 MHz, CD₃OD) δ 8.94 (s, 2H), 8.19 (s, 1H), 7.90 (td, J=1.4, 7.8 Hz, 1H), 7.79 (t, J=2.2 Hz, 1H), 7.46 (t, J=8.0 Hz, 1H), 7.19 (dd, J=2.3, 8.2 Hz, 1H), 7.03-6.62 (m, 1H), 4.28 (s, 2H), 4.04 (s, 3H). M+H]=370.19.

Example 108

5-{[6-(3-Chlorophenyl)-5-ethoxypyrazin-2-yl]methyl}pyrimidine-2-carbonitrile

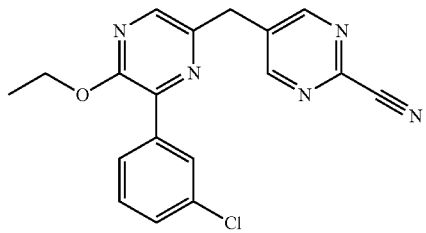 [SMILES: CCOc1ncc(Cc2cnc(C#N)nc2)nc1-c1cccc(Cl)c1]

¹H NMR (400 MHz, CD₃OD) δ 8.93 (s, 2H), 8.17 (s, 1H), 8.06-8.02 (m, 1H), 7.97 (ddd, J=1.6, 3.7, 5.3 Hz, 1H), 7.43-7.38 (m, 2H), 4.49 (q, J=7.0 Hz, 2H), 4.27 (s, 2H), 1.43 (t, J=7.0 Hz, 3H). [M+H]=352.26.

Example 109

3-(3-Chlorophenyl)-2-(difluoromethoxy)-5-(pyridin-2-ylmethyl)pyridine

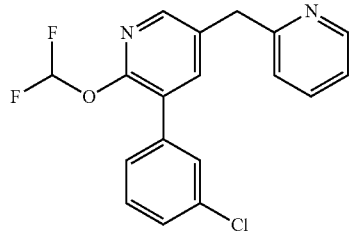 [SMILES: FC(F)Oc1ncc(Cc2ccccn2)cc1-c1cccc(Cl)c1]

Step 1. ((5-(3-Chlorophenyl)-6-(difluoromethoxy)pyridin-3-yl)methyl)zinc(II) bromide. To a suspension of zinc (42.77 mg, 0.65 mmol) in THF (1 mL) was added 1,2-dibromoethane (2.48 µL, 0.03 mmol). The resulting mixture was heated at 70° C. for 10 minutes before being cooled to room temperature. Once cooled, trimethylsilylchloride (2.92 µL, 0.02 mmol) was added and the solution was stirred at room temperature for an additional 30 min. To the activated zinc solution was added 5-(bromomethyl)-3-(3-chlorophenyl)-2-(difluoromethoxy)pyridine (Intermediate 12, 200 mg, 0.57 mmol) and the resulting mixture was heated at 70° C. for 8 h. The reaction mixture was cooled to room temperature and decanted from the solids to afford a ~0.5 M solution of the title compound.

Step 2. 3-(3-Chlorophenyl)-2-(difluoromethoxy)-5-(pyridin-2-ylmethyl)pyridine. To a solution of 2-bromopyridine (29.89 µL, 0.31 mmol) and tetrakis(triphenylphosphine)palladium(0) (9.88 mg, 0.01 mmol) in THF (3.00 mL) was added ((5-(3-chlorophenyl)-6-(difluoromethoxy)pyridin-3-yl)methyl)zinc(II) bromide (500.00 µL, 0.57 mol/L, 0.29 mmol, from step 1). The resulting solution was heated at 70° C. for 5 h. The solvent was removed, and the crude material was purified on the Shimadzu HPLC using the 5-95% gradient with TFA to obtain the title compound TFA salt as an oil (21 mg, 16%). ¹H NMR (400 MHz, DMSO-d₆) δ 8.72-8.78 (m, 1H), 8.46 (dt, J=1.57, 8.02 Hz, 1H), 8.23 (d, J=2.35 Hz, 1H), 7.84-7.93 (m, 3H), 7.39-7.83 (m, 5H), 4.50 (s, 2H). [M+H]=347.08.

Examples 110-111 were prepared in a manner analogous to Example 109, with the appropriate starting materials and reagent substitutions.

Example 110

2-{[5-(3-Chlorophenyl)-6-(difluoromethoxy)pyridin-3-yl]methyl}pyrazine

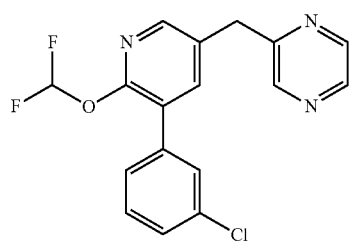 [SMILES: FC(F)Oc1ncc(Cc2cnccn2)cc1-c1cccc(Cl)c1]

$^1$H NMR (400 MHz, CD$_3$OD) δ 8.65 (d, J=1.57 Hz, 1H), 8.55 (dd, J=1.57, 2.74 Hz, 1H), 8.47 (d, J=2.74 Hz, 1H), 8.18 (d, J=2.35 Hz, 1H), 7.86 (d, J=2.35 Hz, 1H), 7.79-7.36 (m, 5H), 4.25 (s, 2H). [M+H]=348.06.

Example 111

6-{[5-(3-Chlorophenyl)-6-(difluoromethoxy)pyridin-3-yl]methyl}pyridazin-3-amine

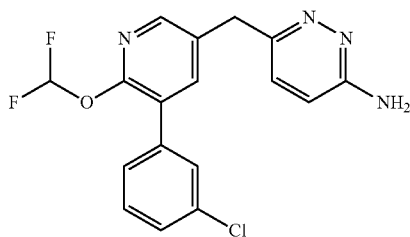 [SMILES: Nc1ccc(Cc2cnc(OC(F)F)c(-c3cccc(Cl)c3)c2)nn1]

$^1$H NMR (400 MHz, CD$_3$OD) δ 8.18 (d, J=2.35 Hz, 1H), 7.84 (d, J=2.35 Hz, 1H), 7.79 (d, J=2.35 Hz, 1H), 7.39-7.78 (m, 6H), 4.19 (s, 2H). [M+H]=363.16.

Example 112

3-(3-Chlorophenyl)-2-methoxy-6-methyl-5-(1H-1,2,4-triazol-1-ylmethyl)pyridine

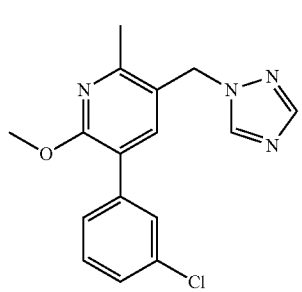 [SMILES: COc1nc(C)c(Cn2cncn2)cc1-c1cccc(Cl)c1]

To a solution of 3-(chloromethyl)-5-(3-chlorophenyl)-6-methoxy-2-methylpyridine (Intermediate 8, 87 mg, 0.31 mmol), in acetone (12 mL), was added 1H-1,2,4-triazole (32 mg, 0.46 mmol), and cesium carbonate (150 mg, 0.63 mmol). The reaction mixture stirred at room temperature for 2 h, then filtered and concentrated under reduced pressure. Purification (FCC, SiO$_2$, 0-100%, EtOAc/hexanes) afforded the title compound (82.4 mg, 84%). $^1$H NMR (400 MHz, CDCl$_3$) δ 8.03 (s, 1H), 7.98 (s, 1H), 7.52 (s, 1H), 7.45-7.37 (m, 2H), 7.37-7.29 (m, 2H), 5.34 (s, 2H), 3.98 (s, 3H), 2.52 (s, 3H). [M+H]=315.22.

Examples 113, 115, 117, 123, 125-126 were prepared in a manner analogous to Example 13, with the appropriate starting materials and reagent substitutions.

Example 113

4-{[6-(3-Chlorophenyl)-5-methoxypyrazin-2-yl]methyl}benzamide

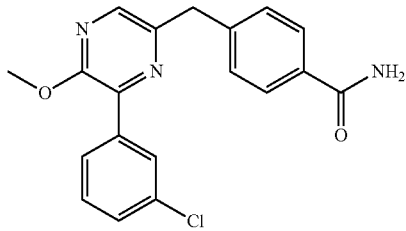 [SMILES: COc1ncc(Cc2ccc(C(N)=O)cc2)nc1-c1cccc(Cl)c1]

$^1$H NMR (400 MHz, CD$_3$OD) δ 8.02-8.08 (m, 2H), 7.98 (td, J=4.30, 1.57 Hz, 1H), 7.81 (d, J=8.22 Hz, 2H), 7.47-7.37 (m, 4H), 4.21 (s, 2H), 4.02 (s, 3H). [M+H]=354.20.

Example 114

5-{[5-(3-Chlorophenyl)-6-(difluoromethoxy)pyridin-3-yl]methyl}pyridine-2-carboxamide

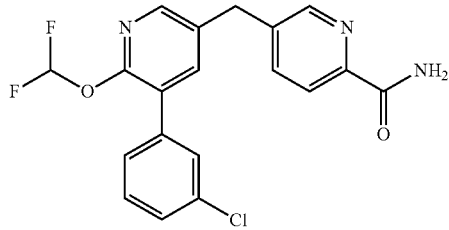 [SMILES: NC(=O)c1ccc(Cc2cnc(OC(F)F)c(-c3cccc(Cl)c3)c2)cn1]

The title compound was prepared in a manner analogous to Example 90, with the appropriate starting material substitutions. $^1$H NMR (400 MHz, CD$_3$OD) δ 8.49 (d, J=2.0 Hz, 1H), 8.05 (d, J=2.3 Hz, 1H), 7.95 (d, J=8.2 Hz, 1H), 7.75 (dd, J=2.0, 8.2 Hz, 1H), 7.71-7.27 (m, 6H), 4.07 (s, 2H). [M+H]=390.16.

Example 115

5-{[6-(Difluoromethoxy)-5-(3-methoxyphenyl)pyridin-3-yl]methyl}pyrimidine-2-carboxamide

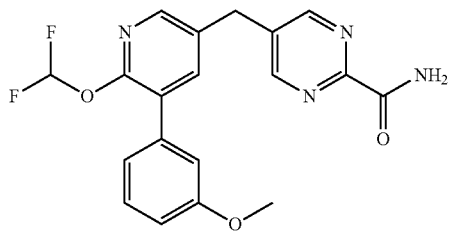 [SMILES: COc1cccc(-c2cc(Cc3cnc(C(N)=O)nc3)cnc2OC(F)F)c1]

$^1$H NMR (400 MHz, CD$_3$OD) δ 8.85 (s, 2H), 8.14 (d, J=2.35 Hz, 1H), 7.81 (d, J=2.35 Hz, 1H), 7.38-7.30 (m, 1H), 7.59 (s, 1H), 7.10-7.03 (m, 2H) 6.95 (dd, J=8.22, 1.57 Hz, 1H) 3.81 (s, 3H) 4.17 (s, 2H). [M+H]=387.32.

Example 116

5-{[5-(3-Chlorophenyl)-6-methoxypyridin-3-yl]methyl}pyridine-2-carboxamide

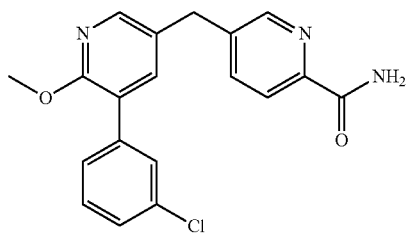 [SMILES: COc1ncc(Cc2ccc(C(N)=O)nc2)cc1-c1cccc(Cl)c1]

The title compound was prepared in a manner analogous to Example 90, with the appropriate starting material substitutions. $^1$H NMR (400 MHz, CD$_3$OD) δ 8.56 (d, J=1.6 Hz, 1H), 8.09-8.00 (m, 2H), 7.82 (dd, J=2.0, 8.2 Hz, 1H), 7.59 (d, J=2.3 Hz, 1H), 7.53 (s, 1H), 7.45-7.30 (m, 3H), 4.09 (s, 2H), 3.93 (s, 3H). [M+H]=354.20.

Example 117

5-{[5-(3-Chlorophenyl)-6-(difluoromethoxy)pyridin-3-yl]methyl}pyrimidine-2-carboxamide

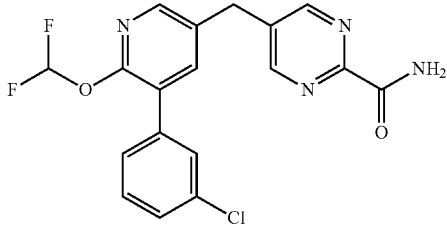 [SMILES: NC(=O)c1ncc(Cc2cnc(OC(F)F)c(-c3cccc(Cl)c3)c2)cn1]

$^1$H NMR (400 MHz, CD$_3$OD) δ 8.85 (s, 2H), 8.18 (d, J=2.3 Hz, 1H), 7.84 (d, J=2.3 Hz, 1H), 7.80-7.37 (m, 5H), 4.18 (s, 2H). [M+H]=391.16.

Example 118

5-{[5-(3-Fluorophenyl)-6-methoxypyridin-3-yl]methyl}pyrimidine-2-carboxamide

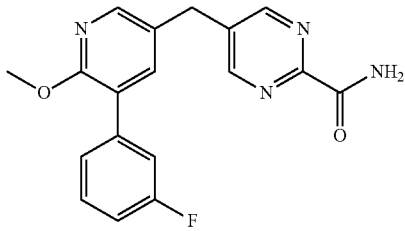 [SMILES: COc1ncc(Cc2cnc(C(N)=O)nc2)cc1-c1cccc(F)c1]

$^1$H NMR (400 MHz, CD$_3$OD) δ 8.83 (s, 2H), 8.11 (d, J=2.3 Hz, 1H), 7.65 (d, J=2.3 Hz, 1H), 7.45-7.26 (m, 3H), 7.10-7.02 (m, 1H), 4.12 (s, 2H), 3.94 (s, 3H). [M+H]=339.18.

Example 119

5-({5-[3-(Difluoromethoxy)phenyl]-6-ethoxypyridin-3-yl}methyl)pyrimidine-2-carboxamide

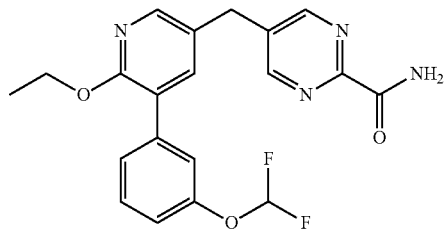 [SMILES: CCOc1ncc(Cc2cnc(C(N)=O)nc2)cc1-c1cccc(OC(F)F)c1]

$^1$H NMR (400 MHz, CD$_3$OD) δ 8.84 (s, 2H), 8.09 (d, J=2.3 Hz, 1H), 7.66 (d, J=2.3 Hz, 1H), 7.46-7.35 (m, 3H), 7.17-7.08

(m, 1H), 7.03-6.61 (m, 1H), 4.40 (q, J=7.0 Hz, 2H), 4.12 (s, 2H), 1.35 (t, J=7.0 Hz, 3H). [M+H]=401.27.

Example 120

5-({5-[2-(Difluoromethoxy)pyridin-4-yl]-6-methoxypyridin-3-yl}methyl)pyrimidine-2-carboxamide

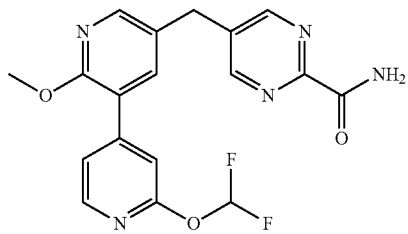 [SMILES: COc1ncc(Cc2cnc(C(N)=O)nc2)cc1-c1ccnc(OC(F)F)c1]

¹H NMR (400 MHz, DMSO-d₆) δ 8.91 (s, 2H), 8.33-8.27 (m, 2H), 8.12 (br s, 1H), 7.95 (d, J=2.3 Hz, 1H), 7.93-7.55 (m, 2H), 7.50 (dd, J=1.6, 5.5 Hz, 1H), 7.32-7.29 (m, 1H), 4.09 (s, 2H), 3.91 (s, 3H). [M+H]=388.24.

Example 121

5-({5-[3-(Difluoromethoxy)phenyl]-6-methoxypyridin-3-yl}methyl)pyrimidine-2-carboxamide

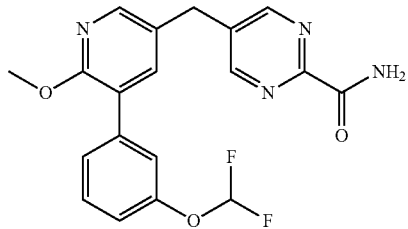 [SMILES: COc1ncc(Cc2cnc(C(N)=O)nc2)cc1-c1cccc(OC(F)F)c1]

¹H NMR (400 MHz, CD₃OD) δ 8.84 (s, 2H), 8.11 (d, J=2.3 Hz, 1H), 7.66 (d, J=2.3 Hz, 1H), 7.46-7.35 (m, 2H), 7.32 (t, J=1.8 Hz, 1H), 7.14-7.10 (m, 1H), 6.83 (t, J=1.0 Hz, 1H), 4.13 (s, 2H), 3.95 (s, 3H). [M+H]=387.25.

Example 122

5-({5-[2-(Difluoromethoxy)pyridin-4-yl]-6-ethoxypyridin-3-yl}methyl)pyrimidine-2-carboxamide

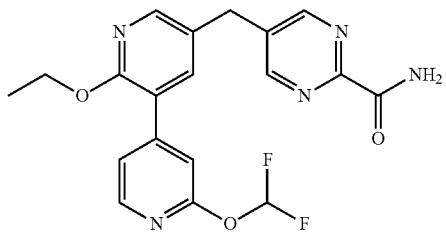 [SMILES: CCOc1ncc(Cc2cnc(C(N)=O)nc2)cc1-c1ccnc(OC(F)F)c1]

¹H NMR (400 MHz, CD₃OD) δ 8.84 (s, 2H), 8.23-8.15 (m, 2H), 7.79 (s, 1H), 7.75-7.36 (m, 2H), 7.22-7.20 (m, 1H), 4.44 (q, J=7.0 Hz, 2H), 4.13 (s, 2H), 1.37 (t, J=7.0 Hz, 3H). [M+H]=402.26.

Example 123

5-{[6-(3-Chlorophenyl)-5-methoxypyrazin-2-yl]methyl}pyrimidine-2-carboxamide

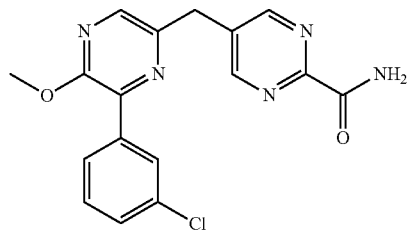 [SMILES: COc1ncc(Cc2cnc(C(N)=O)nc2)nc1-c1cccc(Cl)c1]

¹H NMR (400 MHz, CD₃OD) δ 8.94 (s, 2H), 8.20 (s, 1H), 8.02 (s, 1H), 7.99-7.91 (m, 1H), 7.41 (d, J=5.09 Hz, 2H), 4.28 (s, 2H), 4.04 (s, 3H). [M+H]=356.20.

Example 124

5-({6-[3-(Difluoromethoxy)phenyl]-5-ethoxypyrazin-2-yl}methyl)pyridine-2-carboxamide

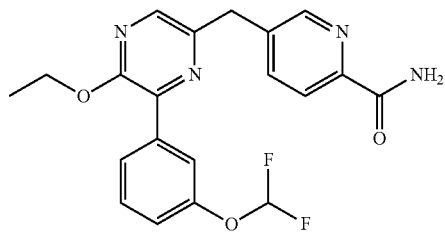 [SMILES: CCOc1ncc(Cc2ccc(C(N)=O)nc2)nc1-c1cccc(OC(F)F)c1]

The title compound was prepared in a manner analogous to Example 90, with the appropriate starting material substitutions. ¹H NMR (400 MHz, CD₃OD) δ 8.66-8.63 (m, 1H), 8.11 (s, 1H), 8.04 (dd, J=0.8, 7.8 Hz, 1H), 7.98-7.85 (m, 3H), 7.46 (t, J=8.2 Hz, 1H), 7.19 (dd, J=2.0, 8.2 Hz, 1H), 7.04-6.61 (m, 1H), 4.48 (q, J=7.0 Hz, 2H), 4.25 (s, 2H), 1.43 (t, J=7.0 Hz, 3H). [M+H]=401.25.

Example 125

5-({6-[3-(Difluoromethoxy)phenyl]-5-methoxy-pyrazin-2-yl}methyl)pyrimidine-2-carboxamide

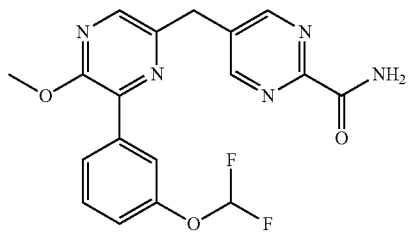 [SMILES: COc1ncc(Cc2cnc(C(N)=O)nc2)nc1-c1cccc(OC(F)F)c1]

$^1$H NMR (400 MHz, DMSO-d$_6$) δ 8.92 (s, 2H), 8.29 (s, 1H), 8.12 (br s, 1H), 7.88-7.82 (m, 1H), 7.74 (t, J=2.0 Hz, 1H), 7.71 (br s, 1H), 7.52 (t, J=8.0 Hz, 1H), 7.45-7.03 (m, 2H), 4.26 (s, 2H), 3.96 (s, 3H). [M+H]=388.15.

Example 126

5-{[6-(3-Chlorophenyl)-5-ethoxypyrazin-2-yl]methyl}pyrimidine-2-carboxamide

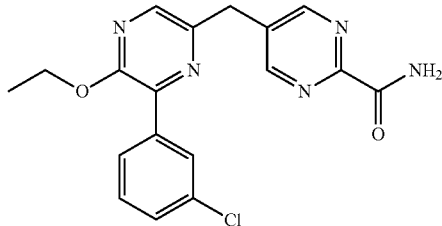 [SMILES: CCOc1ncc(Cc2cnc(C(N)=O)nc2)nc1-c1cccc(Cl)c1]

$^1$H NMR (400 MHz, DMSO-d$_6$) δ 8.92 (s, 2H), 8.27 (s, 1H), 8.13 (br s, 1H), 8.04-7.99 (m, 1H), 7.99-7.91 (m, 1H), 7.71 (br s, 1H), 7.52-7.45 (m, 2H), 4.48-4.37 (m, 2H), 4.25 (s, 2H), 1.40-1.28 (m, 3H). [M+H]=370.05.

Example 127

Methyl 1-{[6-(3-chlorophenyl)-5-methoxypyrazin-2-yl]methyl}-1H-1,2,4-triazole-3-carboxylate

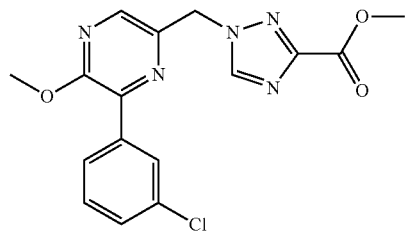

To a solution of 5-(bromomethyl)-3-(3-chlorophenyl)-2-methoxypyrazine (Intermediate 3, 200.00 mg, 0.64 mmol), in acetone (3.19 mL), was added methyl 1H-1,2,4-triazole-3-carboxylate (121.60 mg, 0.96 mmol) and potassium carbonate (264.44 mg, 1.91 mmol). The reaction was stirred at room temperature for 2 h. The LC/MS showed two peaks with [M+H] values consistent with the two major regioproducts. The mixture was diluted with DCM (5 mL), dried (Na$_2$SO$_4$) and concentrated under reduced pressure. Purification (FCC, SiO$_2$, 20-100% EtOAc/hexanes) afforded the title compound (100 mg; 44%). 1H NMR (400 MHz, CD$_3$OD) δ 8.79 (s, 1H), 8.26 (s, 1H), 8.01 (td, J=1.1, 2.1 Hz, 1H), 7.99-7.90 (m, 1H), 7.45-7.36 (m, 2H), 5.64 (s, 2H), 4.07 (s, 3H), 3.92 (s, 3H). [M+H]=360.24.

Examples 128-149, 151-197 were prepared in a manner analogous to Example 4 or Example 127 with the appropriate starting materials and reagent substitutions.

Example 128

3-(3-Chlorophenyl)-5-[(3-cyclopropyl-1H-1,2,4-triazol-1-yl)methyl]-2-(difluoromethoxy)pyridine

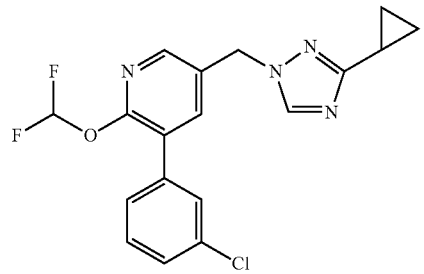 [SMILES: FC(F)Oc1ncc(Cn2cnc(C3CC3)n2)cc1-c1cccc(Cl)c1]

$^1$H NMR (400 MHz, CDCl$_3$) δ 7.96 (s, 1H), 7.71-7.63 (m, 1H), 7.50 (d, J=19.17 Hz, 1H), 7.39 (s, 2H), 7.26 (s, 2H), 5.26 (s, 2H), 3.70 (s, 1H), 2.04 (s, 1H), 1.55 (s, 1H), 0.95 (d, J=6.65 Hz, 3H). [M+H]=377.22.

Example 129

3-(3-Fluorophenyl)-2-methoxy-5-(1H-1,2,4-triazol-1-ylmethyl)pyridine

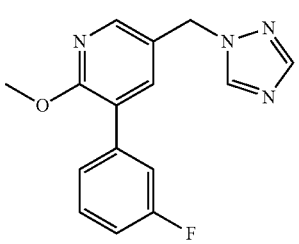 [SMILES: COc1ncc(Cn2cncn2)cc1-c1cccc(F)c1]

¹H NMR (400 MHz, CD₃OD) δ 8.60 (s, 1H), 8.19 (d, J=2.7 Hz, 1H), 8.00 (s, 1H), 7.75 (d, J=2.3 Hz, 1H), 7.45-7.38 (m, 1H), 7.34-7.26 (m, 2H), 7.12-7.05 (m, 1H), 5.44 (s, 2H), 3.95 (s, 3H). [M+H]=285.26.

Example 130

3-(3-Chlorophenyl)-2-methoxy-5-(1H-1,2,4-triazol-1-ylmethyl)pyrazine

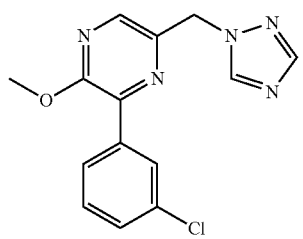

¹H NMR (400 MHz, CD₃OD) δ 8.68 (s, 1H), 8.20 (s, 1H), 8.01 (s, 2H), 7.98-7.92 (m, 1H), 7.44-7.39 (m, 2H), 5.58 (s, 2H), 4.06 (s, 3H). [M+H]=302.31.

Example 131

3-(3-Chlorophenyl)-2-(difluoromethoxy)-5-(1H-1,2,4-triazol-1-ylmethyl)pyridine

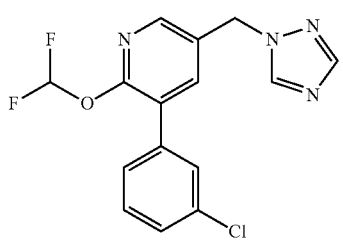 [SMILES: FC(F)Oc1ncc(Cn2cncn2)cc1-c1cccc(Cl)c1]

¹H NMR (400 MHz, CD₃OD) δ 8.63 (s, 1H), 8.25 (d, J=2.3 Hz, 1H), 8.02 (s, 1H), 7.92 (d, J=2.3 Hz, 1H), 7.83-7.61 (m, 1H), 7.56 (s, 1H), 7.50-7.39 (m, 3H), 5.51 (s, 2H). [M+H]=337.15.

Example 132

3-(3-Chlorophenyl)-2-methoxy-5-[(3-methyl-1H-1,2,4-triazol-1-yl)methyl]pyrazine

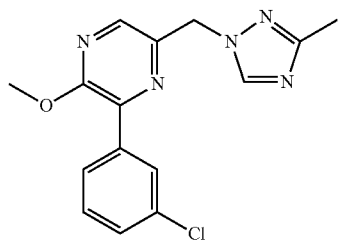

as a mixture

¹H NMR (400 MHz, CD₃OD) δ 8.54 (s, 2H), 8.18 (d, J=6.65 Hz, 2H), 7.90-8.05 (m, 4H), 7.85 (s, 2H), 7.37-7.47 (m, 4H), 5.50 (d, J=10.17 Hz, 4H), 4.07 (s, 6H), 2.27-2.69 (m, 6H). [M+H]=316.22.

Example 133

3-(3-Chlorophenyl)-5-[(3-cyclopropyl-1H-1,2,4-triazol-1-yl)methyl]-2-methoxypyrazine

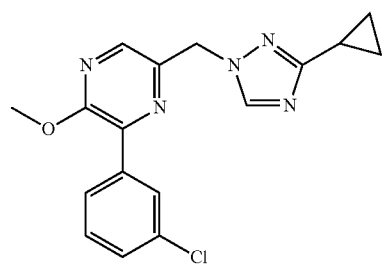

as a mixture

¹H NMR (400 MHz, CD₃OD) δ 8.47 (s, 1H), 8.16 (s, 2H), 8.01 (d, J=1.2 Hz, 4H), 7.78 (s, 1H), 7.44-7.39 (m, 4H), 5.62 (s, 2H), 5.45 (s, 2H), 4.06 (m, 6H), 2.43-2.33 (m, 1H), 2.04-1.94 (m, 1H), 1.20-0.84 (m, 8H). [M+H]=342.33.

Example 134

3-(3-Chlorophenyl)-2-methoxy-5-(1H-1,2,4-triazol-1-ylmethyl)pyridine

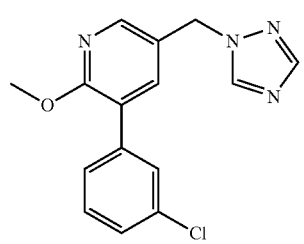 [SMILES: COc1ncc(Cn2cncn2)cc1-c1cccc(Cl)c1]

¹H NMR (400 MHz, CDCl₃) δ 8.16 (d, J=2.3 Hz, 1H), 8.12 (s, 1H), 7.98 (s, 1H), 7.55 (d, J=2.3 Hz, 1H), 7.51 (d, J=0.8 Hz, 1H), 7.43-7.32 (m, 3H), 5.33 (s, 2H), 3.98 (s, 3H). [M+H]=301.19.

Example 135

3-(3-Chlorophenyl)-2-(propan-2-yloxy)-5-(1H-1,2,4-triazol-1-ylmethyl)pyridine

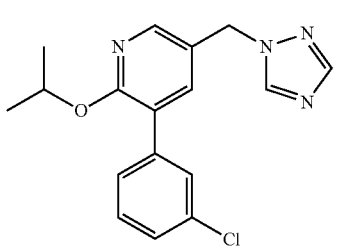 [SMILES: CC(C)Oc1ncc(Cn2cncn2)cc1-c1cccc(Cl)c1]

¹H NMR (400 MHz, CD₃OD) δ 8.63-8.57 (m, 1H), 8.16 (d, J=2.3 Hz, 1H), 8.00 (s, 1H), 7.73 (d, J=2.3 Hz, 1H), 7.56 (s, 1H), 7.49-7.31 (m, 3H), 5.44-5.40 (m, 3H), 1.31 (d, J=6.3 Hz, 6H). [M+H]=329.26.

Example 136

3-[2-Methoxy-5-(1H-1,2,4-triazol-1-ylmethyl)pyridin-3-yl]benzonitrile

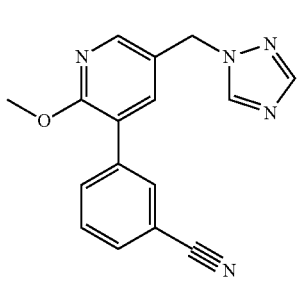 [SMILES: COc1ncc(Cn2cncn2)cc1-c1cccc(CN)c1]

¹H NMR (400 MHz, DMSO-d₆) δ 8.67 (s, 1H), 8.25 (d, J=2.3 Hz, 1H), 7.99 (m, 2H), 7.91-7.83 (m, 3H), 7.69-7.62 (m, 1H), 5.43 (s, 2H), 3.90 (s, 3H). [M+H]=292.26.

Example 137

2-Methoxy-5-(1H-1,2,4-triazol-1-ylmethyl)-3-[3-(trifluoromethoxy)phenyl]pyridine

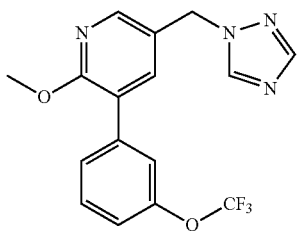 [SMILES: COc1ncc(Cn2cncn2)cc1-c1cccc(OC(F)(F)F)c1]

¹H NMR (400 MHz, CD₃OD) δ 8.60 (s, 1H), 8.21 (d, J=2.3 Hz, 1H), 8.00 (s, 1H), 7.77 (d, J=2.3 Hz, 1H), 7.54-7.45 (m, 3H), 7.27 (d, J=6.3 Hz, 1H), 5.45 (s, 2H), 3.96 (s, 3H). [M+H]=351.29.

Example 138

3-(3-Chlorophenyl)-2-methoxy-5-[(3-methyl-4H-1,2,4-triazol-4-yl)methyl]pyridine

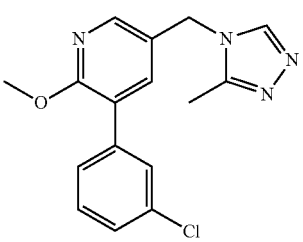 [SMILES: COc1ncc(Cn2cnnc2C)cc1-c1cccc(Cl)c1]

¹H NMR (400 MHz, CD₃OD) δ 8.52 (s, 1H), 8.13 (d, J=2.3 Hz, 1H), 7.66 (d, J=2.3 Hz, 1H), 7.55 (s, 1H), 7.47-7.33 (m, 3H), 5.27 (s, 2H), 3.96 (s, 3H), 2.45 (s, 3H). [M+H]=315.10.

Example 139

3-(3,5-Difluorophenyl)-2-methoxy-5-(1H-1,2,4-triazol-1-ylmethyl)pyridine

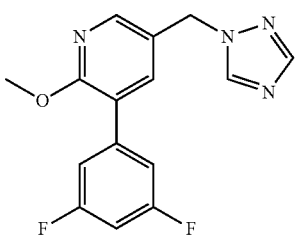 [SMILES: COc1ncc(Cn2cncn2)cc1-c1cc(F)cc(F)c1]

¹H NMR (400 MHz, CD₃OD) δ 8.60 (s, 1H), 8.22 (d, J=2.3 Hz, 1H), 8.00 (s, 1H), 7.80 (d, J=2.3 Hz, 1H), 7.18 (dd, J=2.0, 8.6 Hz, 2H), 7.00-6.89 (m, 1H), 5.44 (s, 2H), 3.97 (s, 3H). [M+H]=303.09.

Example 140

Methyl 1-{[5-(3-chlorophenyl)-6-methoxypyridin-3-yl]methyl}-1H-1,2,4-triazole-5-carboxylate

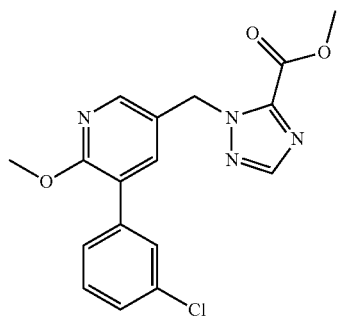

¹H NMR (400 MHz, CDCl₃) δ 8.31-8.23 (m, 1H), 8.00 (s, 1H), 7.70-7.63 (m, 1H), 7.52-7.45 (m, 1H), 7.41-7.29 (m, 3H), 5.79 (s, 2H), 4.05-3.92 (m, 6H). [M+H]=359.33.

Example 141

Methyl 1-{[5-(3-chlorophenyl)-6-methoxypyridin-3-yl]methyl}-1H-1,2,4-triazole-3-carboxylate

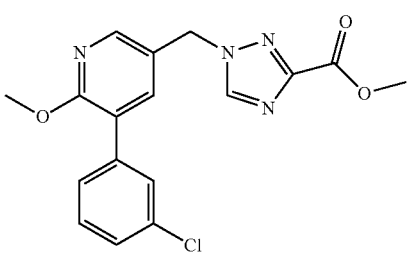

$^1$H NMR (400 MHz, CDCl$_3$) δ 8.21-8.18 (m, 1H), 8.18-8.15 (m, 1H), 7.56 (s, 1H), 7.50 (d, J=1.2 Hz, 1H), 7.38-7.33 (m, 3H), 5.41 (s, 2H), 3.99 (m, 6H). [M+H]=359.35.

Example 142

3-(4-Chlorothiophen-2-yl)-2-methoxy-5-(1H-1,2,4-triazol-1-ylmethyl)pyridine

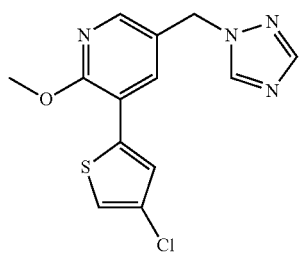 [SMILES: COc1ncc(Cn2cncn2)cc1-c1cc(Cl)cs1]

$^1$H NMR (400 MHz, CD$_3$OD) δ 8.58 (br s, 1H), 8.05 (d, J=2.0 Hz, 1H), 8.02-7.89 (m, 2H), 7.44 (d, J=1.2 Hz, 1H), 7.24 (d, J=1.2 Hz, 1H), 5.35 (s, 2H), 3.97 (s, 3H). [M+H]=307.12.

Example 143

3-(3-Chlorophenyl)-2-methoxy-5-[(3-methyl-1H-1,2,4-triazol-1-yl)methyl]pyridine

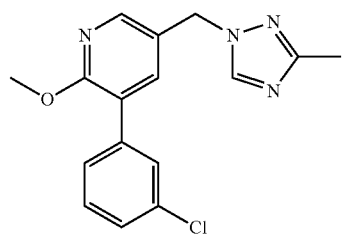

As a mixture $^1$H NMR (400 MHz, CDCl$_3$) δ 8.15 (d, J=2.0 Hz, 1H), 8.09 (d, J=2.3 Hz, 1H), 7.99 (s, 1H), 7.82 (s, 1H), 7.56-7.49 (m, 4H), 7.42-7.32 (m, 6H), 5.26 (m, 4H), 3.98 (m, 6H), 2.49 (s, 3H), 2.40 (s, 3H). [M+H]=315.22.

Example 144

3-[3-(Difluoromethyl)phenyl]-2-methoxy-5-(1H-1,2,4-triazol-1-ylmethyl)pyridine

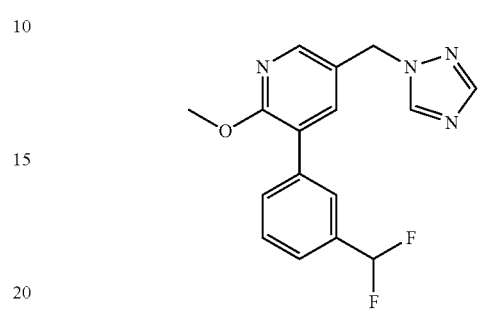

$^1$H NMR (400 MHz, DMSO-d$_6$) δ 8.65 (s, 1H), 8.21 (d, J=2.3 Hz, 1H), 7.95 (s, 1H), 7.79 (d, J=2.3 Hz, 1H), 7.73-7.62 (m, 2H), 7.62-7.51 (m, 2H), 7.23-6.90 (m, 1H), 5.42 (s, 2H), 3.86 (s, 3H). [M+H]=317.21.

Example 145

3-(3-Chlorophenyl)-2-methoxy-5-(1H-pyrazol-1-ylmethyl)pyridine

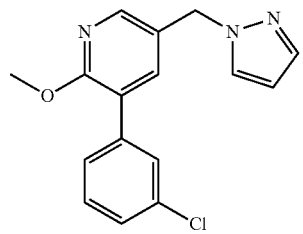 [SMILES: COc1ncc(Cn2cccn2)cc1-c1cccc(Cl)c1]

$^1$H NMR (400 MHz, CD$_3$OD) δ 8.08 (d, J=2.3 Hz, 1H), 7.76 (d, J=2.0 Hz, 1H), 7.61 (d, J=2.3 Hz, 1H), 7.52 (d, J=1.2 Hz, 2H), 7.45-7.31 (m, 3H), 6.33 (s, 1H), 5.35 (s, 2H), 3.94 (s, 3H). [M+H]=300.15.

Example 146

3-(3-Chlorophenyl)-2-methoxy-5-{[3-(trifluoromethyl)-1H-1,2,4-triazol-1-yl]methyl}pyridine

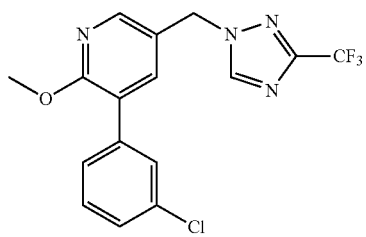 [SMILES: COc1ncc(Cn2cnc(C(F)(F)F)n2)cc1-c1cccc(Cl)c1]

$^1$H NMR (400 MHz, CD$_3$OD) δ 8.72 (s, 1H), 8.24 (d, J=2.0 Hz, 1H), 7.79 (d, J=2.3 Hz, 1H), 7.56 (s, 1H), 7.49-7.31 (m, 3H), 5.50 (s, 2H), 3.96 (s, 3H). [M+H]=369.17.

Example 147

3-(3-Chlorophenyl)-5-[(3-cyclopropyl-1H-1,2,4-triazol-1-yl)methyl]-2-methoxypyridine

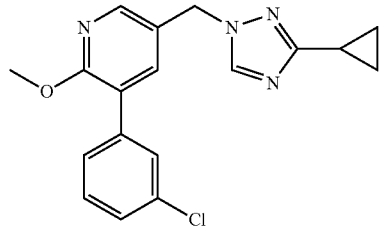

As a mixture $^1$H NMR (400 MHz, CD$_3$OD) δ 8.39 (s, 2H), 8.18-8.12 (m, 2H), 7.81-7.32 (m, 10H), 5.50 (s, 2H), 5.32 (s, 2H), 3.97-3.93 (m, 6H), 2.29-2.19 (m, 1H), 2.04-1.98 (m, 1H), 1.17-0.83 (m, 8H). [M+H]=341.23.

Example 148

3-(3-Chlorophenyl)-2-(difluoromethoxy)-5-[(3-methyl-1H-1,2,4-triazol-1-yl)methyl]pyridine

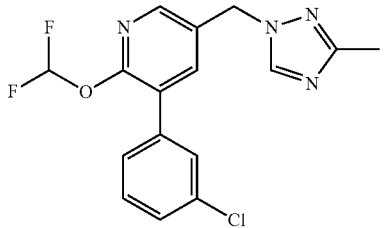

As a mixture $^1$H NMR (400 MHz, CD$_3$OD) δ 8.58-7.32 (m, 14H), 5.43 (d, J=13.3 Hz, 4H), 2.58-2.29 (m, 6H). [M+H]=351.17.

Example 149

3-(3-Chlorophenyl)-2-methoxy-5-{[4-(trifluoromethyl)-1H-imidazol-1-yl]methyl}pyridine

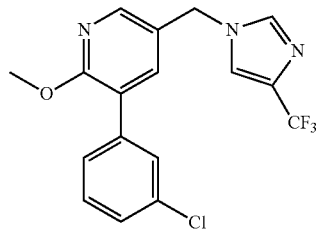 [SMILES: COc1ncc(Cn2cnc(C(F)(F)F)c2)cc1-c1cccc(Cl)c1]

$^1$H NMR (400 MHz, CD$_3$OD) δ 8.48 (br s, 1H), 8.24 (br s, 1H), 8.02 (m, 2H), 7.88-7.62 (m, 4H), 5.58 (m, 2H), 4.25 (s, 3H). [M+H]=368.10

Example 150

3-(3-Chlorophenyl)-2-(difluoromethoxy)-5-[1-(1H-1,2,4-triazol-1-yl)ethyl]pyridine

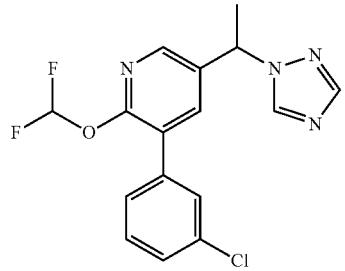 [SMILES: CC(c1cnc(OC(F)F)c(-c2cccc(Cl)c2)c1)n1cncn1]

Step 1. 1-(5-(3-chlorophenyl)-6-(difluoromethoxy)pyridin-3-yl)ethanol. A solution of 5-(3-chlorophenyl)-6-(difluoromethoxy)nicotinaldehyde (Example 36 product from Step 2., 287 mg, 1.0 mmol) in DCM (5 mL) was cooled to 0° C. and methylmagnesium bromide (1.5 mL of a 1M solution in toluene, 1.5 mmol) was added dropwise. The mixture was warmed to room temperature and stirred for 30 minutes. A saturated aqueous solution of ammonium chloride was added and the mixture was extracted into DCM. The combined extracts were dried (Na$_2$SO$_4$), filtered and solvent removed under reduced pressure. Purification (FCC, SiO$_2$, 0-60%, EtOAc/hexanes) gave 1-(5-(3-chlorophenyl)-6-(difluoromethoxy)pyridin-3-yl)ethanol (231 mg, 76%). [M+H]=300.1.

Step 2. A solution of 1-(5-(3-chlorophenyl)-6-(difluoromethoxy)pyridin-3-yl)ethanol (231 mg, 0.76 mmol) and N,N-diisopropylethylamine (196 mg, 1.52 mmol) in THF (5 mL) was cooled to 0° C. and methanesulfonyl chloride (108 mg, 0.92 mmol) was added. The mixture was warmed to room temperature and stirred for 1 hour. The LCMS confirmed the disappearance of the starting material. All solvents were removed in vacuo and the crude material purified (FCC, SiO$_2$, 0-60%, EtOAc/hexanes) to give the desired intermediate mesylate (205 mg, 70%) which was not characterized, and used directly in the next step.

Step 3. 3-(3-Chlorophenyl)-2-(difluoromethoxy)-5-[1-(1H-1,2,4-triazol-1-yl)ethyl]pyridine. The mesylate from the previous step (90 mg, 0.23 mmol) was reacted in a manner analogous to Example 127, with the appropriated starting material substitutions. Purification (FCC, SiO$_2$, 50-100%, EtOAc/hexanes) gave the title compound (56 mg, 69%). $^1$H NMR (400 MHz, CD$_3$OD) δ 8.64 (s, 1H), 8.24 (d, J=2.3 Hz, 1H), 8.02 (s, 1H), 7.91 (d, J=2.3 Hz, 1H), 7.82-7.59 (m, 1H), 7.54 (s, 1H), 7.48-7.40 (m, 3H), 5.86 (d, J=7.0 Hz, 1H), 1.96 (d, J=7.0 Hz, 3H). [M+H]=351.19.

Example 151

3-(3-Fluorophenyl)-2-methoxy-5-[(3-methyl-1H-1,2,4-triazol-1-yl)methyl]pyridine

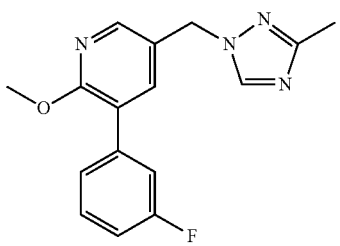

As a mixture $^1$H NMR (400 MHz, CD$_3$OD) δ 8.45 (s, 1H), 8.17 (d, J=2.3 Hz, 1H), 8.11 (d, J=2.3 Hz, 1H), 7.85 (s, 1H), 7.73 (d, J=2.3 Hz, 1H), 7.67 (d, J=2.3 Hz, 1H), 7.45-7.25 (m, 6H), 7.11-7.04 (m, 2H), 5.38 (s, 2H), 5.34 (s, 2H), 3.95 (m, 6H), 2.51 (s, 3H), 2.32 (s, 3H). [M+H]=299.16.

Example 152

3-(3-Chlorophenyl)-2-ethoxy-5-{[3-(trifluoromethyl)-1H-1,2,4-triazol-1-yl]methyl}pyridine

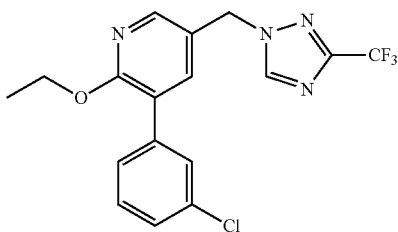 [SMILES: CCOc1ncc(Cn2cnc(C(F)(F)F)n2)cc1-c1cccc(Cl)c1]

$^1$H NMR (400 MHz, CD$_3$OD) δ 8.71 (s, 1H), 8.21 (d, J=2.3 Hz, 1H), 7.79 (d, J=2.3 Hz, 1H), 7.58 (s, 1H), 7.49-7.32 (m, 3H), 5.49 (s, 2H), 4.42 (d, J=7.0 Hz, 2H), 1.34 (t, J=7.0 Hz, 3H). [M+H]=383.18.

Example 153

3-(3-Chlorophenyl)-2-ethoxy-5-{[5-(trifluoromethyl)-1H-1,2,4-triazol-1-yl]methyl}pyridine

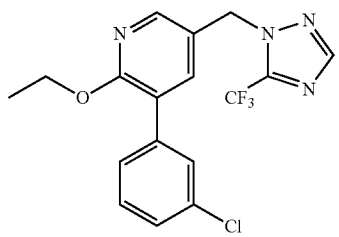 [SMILES: CCOc1ncc(Cn2ncnc2C(F)(F)F)cc1-c1cccc(Cl)c1]

$^1$H NMR (400 MHz, CD$_3$OD) δ 8.14-8.11 (m, 2H), 7.71 (d, J=2.3 Hz, 1H), 7.55 (s, 1H), 7.46-7.33 (m, 3H), 5.59 (s, 2H), 4.41 (d, J=7.0 Hz, 2H), 1.34 (t, J=7.2 Hz, 3H). [M+H]=383.18.

Example 154

3-(3-Chlorophenyl)-2-(difluoromethoxy)-5-[(4-methyl-1H-imidazol-1-yl)methyl]pyridine

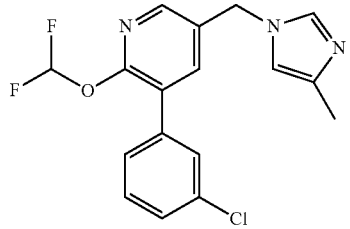 [SMILES: Cc1cn(Cc2cnc(OC(F)F)c(-c3cccc(Cl)c3)c2)cn1]

$^1$H NMR (400 MHz, DMSO-d$_6$) δ 8.25 (d, J=2.3 Hz, 1H), 7.99 (d, J=2.3 Hz, 1H), 7.67-7.43 (m, 6H), 6.93 (s, 1H), 5.14 (s, 2H), 2.02 (s, 3H). [M+H]=350.18.

Example 155

3-[3-(Difluoromethoxy)phenyl]-2-methoxy-5-[(3-methyl-1H-1,2,4-triazol-1-yl)methyl]pyridine

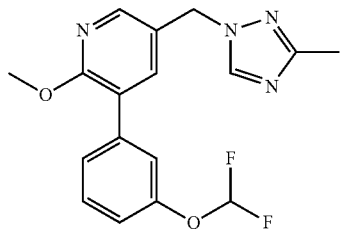

As a mixture $^1$H NMR (400 MHz, CD$_3$OD) δ 8.44 (s, 1H), 8.19-8.09 (m, 2H), 7.74-7.65 (m, 3H), 7.47-7.29 (m, 6H), 7.17-7.10 (m, 2H), 7.04-6.64 (m, 2H), 5.40-5.37 (m, 2H), 5.34 (s, 2H), 3.94 (m, 6H), 2.51 (s, 3H), 2.32 (s, 3H). [M+H]=347.23.

Example 156

1-{[5-(3-Chlorophenyl)-6-(difluoromethoxy)pyridin-3-yl]methyl}-1H-1,2,4-triazole-3-carbonitrile

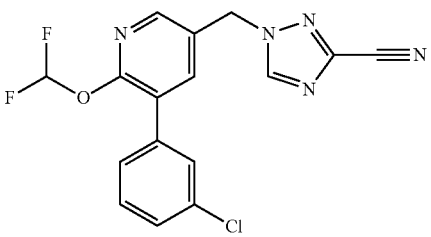 [SMILES: N#Cc1ncn(Cc2cnc(OC(F)F)c(-c3cccc(Cl)c3)c2)n1]

¹H NMR (400 MHz, CD₃OD) δ 8.76 (s, 1H), 8.29 (d, J=2.3 Hz, 1H), 7.97 (d, J=2.3 Hz, 1H), 7.82-7.40 (m, 5H), 5.58 (s, 2H). [M+H]=362.01.

Example 157

3-(3-Chlorophenyl)-2-(difluoromethoxy)-5-{[3-(methoxymethyl)-1H-1,2,4-triazol-1-yl]methyl}pyridine

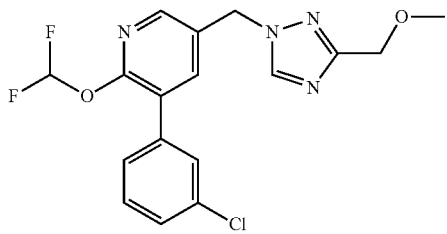 [SMILES: COCc1ncn(Cc2cnc(OC(F)F)c(-c3cccc(Cl)c3)c2)n1]

¹H NMR (400 MHz, CD₃OD) δ 8.58 (s, 1H), 8.25 (d, J=2.3 Hz, 1H), 7.91 (d, J=2.3 Hz, 1H), 7.80-7.40 (m, 5H), 5.48 (s, 2H), 4.46 (s, 2H), 3.36 (s, 3H). [M+H]=381.17.

Example 158

3-(3-Chlorophenyl)-2-(difluoromethoxy)-5-{[5-(methoxymethyl)-1H-1,2,4-triazol-1-yl]methyl}pyridine

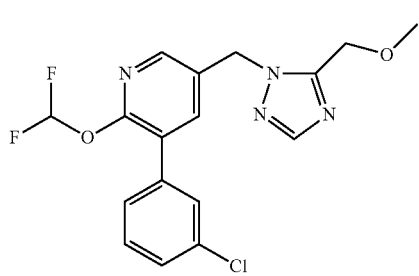 [SMILES: COCc1ncnn1Cc1cnc(OC(F)F)c(-c2cccc(Cl)c2)c1]

¹H NMR (400 MHz, CD₃OD) δ 8.23 (d, J=2.3 Hz, 1H), 7.94 (s, 1H), 7.90 (d, J=2.3 Hz, 1H), 7.80-7.40 (m, 5H), 5.51 (s, 2H), 4.71 (s, 2H), 3.37 (s, 3H). [M+H]=381.17.

Example 159

3-[3-(Difluoromethoxy)phenyl]-2-methoxy-5-{[3-(trifluoromethyl)-1H-1,2,4-triazol-1-yl]methyl}pyridine

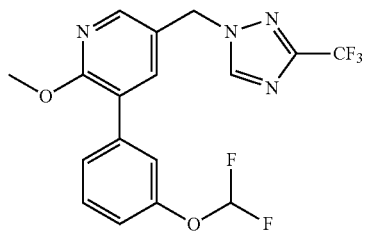 [SMILES: COc1ncc(Cn2cnc(C(F)(F)F)n2)cc1-c1cccc(OC(F)F)c1]

¹H NMR (400 MHz, CD₃OD) δ 8.71 (s, 1H), 8.24 (d, J=2.3 Hz, 1H), 7.79 (d, J=2.3 Hz, 1H), 7.47-7.36 (m, 2H), 7.33 (d, J=2.0 Hz, 1H), 7.17-7.11 (m, 1H), 7.03-6.64 (m, 1H), 5.50 (s, 2H), 3.96 (s, 3H). [M+H]=401.19.

Example 160

3-[3-(Difluoromethoxy)phenyl]-2-methoxy-5-{[5-(trifluoromethyl)-1H-1,2,4-triazol-1-yl]methyl}pyridine

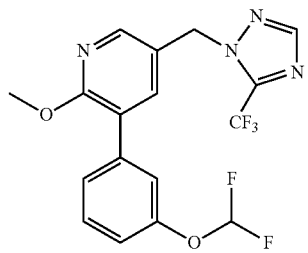 [SMILES: COc1ncc(Cn2ncnc2C(F)(F)F)cc1-c1cccc(OC(F)F)c1]

¹H NMR (400 MHz, CD₃OD) δ 8.15 (d, J=2.3 Hz, 1H), 8.12 (s, 1H), 7.72 (d, J=2.3 Hz, 1H), 7.43 (d, J=8.2 Hz, 1H), 7.37 (s, 1H), 7.30 (s, 1H), 7.16-7.11 (m, 1H), 7.03-6.65 (m, 1H), 5.60 (s, 2H), 3.95 (s, 3H). [M+H]=401.19.

Example 161

3-(3-Chlorophenyl)-2-(difluoromethoxy)-5-(1H-1,2,3,4-tetrazol-1-ylmethyl)pyridine

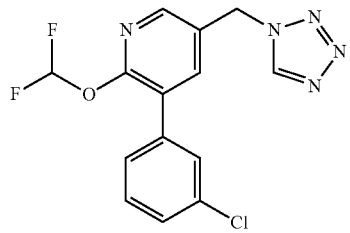 [SMILES: FC(F)Oc1ncc(Cn2cnnn2)cc1-c1cccc(Cl)c1]

$^1$H NMR (400 MHz, CDCl$_3$) δ 8.65 (s, 1H), 8.23 (d, J=2.3 Hz, 1H), 7.73 (d, J=2.3 Hz, 1H), 7.39 (s, 5H), 5.64 (s, 2H). [M+H]=338.15.

Example 162

3-(3-Chlorophenyl)-2-(difluoromethoxy)-5-(2H-1,2,3,4-tetrazol-2-ylmethyl)pyridine

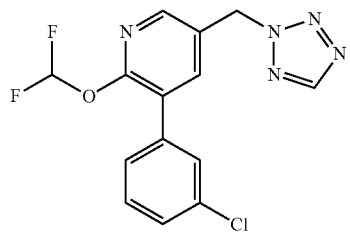 [SMILES: FC(F)Oc1ncc(Cn2ncnn2)cc1-c1cccc(Cl)c1]

$^1$H NMR (400 MHz, CDCl$_3$) δ 8.55 (s, 1H), 8.30 (d, J=2.3 Hz, 1H), 7.82 (d, J=2.7 Hz, 1H), 7.73-7.34 (m, 5H), 5.85 (s, 2H). [M+H]=338.15.

Example 163

3-[3-(Difluoromethoxy)phenyl]-2-ethoxy-5-{[3-(trifluoromethyl)-1H-1,2,4-triazol-1-yl]methyl}pyridine

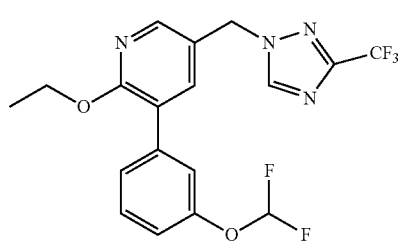 [SMILES: CCOc1ncc(Cn2cnc(C(F)(F)F)n2)cc1-c1cccc(OC(F)F)c1]

$^1$H NMR (400 MHz, CD$_3$OD) δ 8.72 (s, 1H), 8.21 (d, J=2.38 Hz, 1H), 7.81 (d, J=2.38 Hz, 1H), 7.48-7.35 (m, 3H), 7.18-7.06 (m, 1H), 7.06-6.60 (m, 1H), 5.50 (s, 2H), 4.42 (q, J=7.07 Hz, 2H), 1.35 (t, J=7.09 Hz, 3H). [M+H]=415.21.

Example 164

3-[3-(Difluoromethoxy)phenyl]-2-ethoxy-5-{[5-(trifluoromethyl)-1H-1,2,4-triazol-1-yl]methyl}pyridine

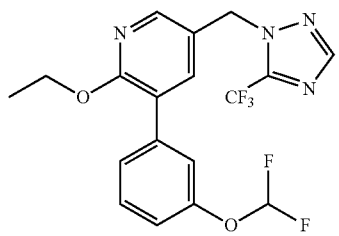 [SMILES: CCOc1ncc(Cn2ncnc2C(F)(F)F)cc1-c1cccc(OC(F)F)c1]

$^1$H NMR (400 MHz, CD$_3$OD) δ 8.13 (s, 2H), 7.74 (d, J=2.51 Hz, 1H), 7.49-7.42 (m, 1H), 7.40-7.34 (m, 2H), 7.14 (dd, J=7.40, 1.76 Hz, 1H), 7.05-6.63 (m, 1H) 5.60 (s, 2H), 4.41 (q, J=7.03 Hz, 2H), 1.35 (t, J=7.09 Hz, 3H). [M+H]=415.21.

Example 165

3-[3-(Difluoromethoxy)phenyl]-2-ethoxy-5-{[3-(methoxymethyl)-1H-1,2,4-triazol-1-yl]methyl}pyridine

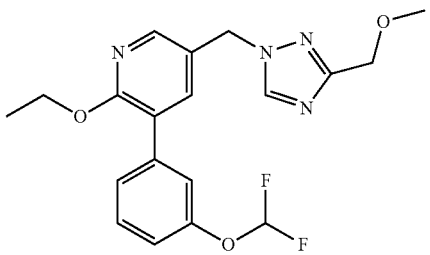 [SMILES: CCOc1ncc(Cn2cnc(COC)n2)cc1-c1cccc(OC(F)F)c1]

$^1$H NMR (400 MHz, CD$_3$OD) δ 8.56 (s, 1H), 8.17 (d, J=2.3 Hz, 1H), 7.76 (d, J=2.3 Hz, 1H), 7.49-7.35 (m, 3H), 7.13 (td,

J=2.0, 7.8 Hz, 1H), 7.04-6.63 (m, 1H), 5.41 (s, 2H), 4.47 (s, 2H), 4.41 (q, J=7.0 Hz, 2H), 3.37 (s, 3H), 1.35 (t, J=7.2 Hz, 3H). [M+H]=391.28.

Example 166

3-[3-(Difluoromethoxy)phenyl]-2-ethoxy-5-{[5-(methoxymethyl)-1H-1,2,4-triazol-1-yl]methyl}pyridine

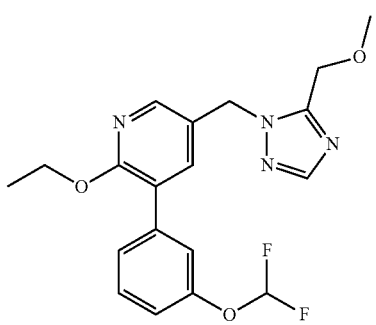 [SMILES: CCOc1ncc(Cn2ncnc2COC)cc1-c1cccc(OC(F)F)c1]

¹H NMR (400 MHz, CD₃OD) δ 8.15 (d, J=2.3 Hz, 1H), 7.93 (s, 1H), 7.75 (d, J=2.3 Hz, 1H), 7.49-7.33 (m, 3H), 7.12 (tdd, J=1.0, 2.1, 7.7 Hz, 1H), 7.04-6.60 (m, 1H), 5.44 (s, 2H), 4.70 (s, 2H), 4.40 (q, J=7.0 Hz, 2H), 3.38 (s, 3H), 1.34 (t, J=7.0 Hz, 3H). [M+H]=391.25.

Example 167

5-[(4-Chloro-1H-pyrazol-1-yl)methyl]-3-[3-(difluoromethoxy)phenyl]-2-methoxypyridine

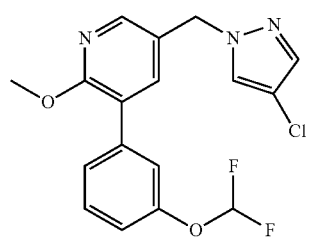 [SMILES: COc1ncc(Cn2cc(Cl)cn2)cc1-c1cccc(OC(F)F)c1]

¹H NMR (400 MHz, CD₃OD) δ 8.11 (d, J=2.7 Hz, 1H), 7.84 (s, 1H), 7.67 (d, J=2.3 Hz, 1H), 7.49-7.30 (m, 4H), 7.15-7.10 (m, 1H), 7.03-6.64 (m, 1H), 5.30 (s, 2H), 3.94 (s, 3H). [M+H]=366.16.

Example 168

1-{[5-(3-Chlorophenyl)-6-ethoxypyridin-3-yl]methyl}-1H-pyrazole-3-carboxamide

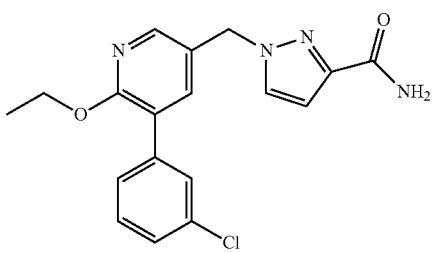 [SMILES: CCOc1ncc(Cn2ccc(C(N)=O)n2)cc1-c1cccc(Cl)c1]

¹H NMR (400 MHz, CD₃OD) δ 8.14 (d, J=2.3 Hz, 1H), 7.78 (d, J=2.3 Hz, 1H), 7.70 (d, J=2.3 Hz, 1H), 7.57 (s, 1H), 7.48-7.43 (m, 1H), 7.41-7.32 (m, 2H), 6.76 (d, J=2.3 Hz, 1H), 5.39 (s, 2H), 4.41 (q, J=7.0 Hz, 2H), 1.34 (t, J=7.0 Hz, 3H). [M+H]=357.29.

Example 169

Ethyl 1-{[5-(3-chlorophenyl)-6-methoxypyridin-3-yl]methyl}-1H-pyrazole-4-carboxylate

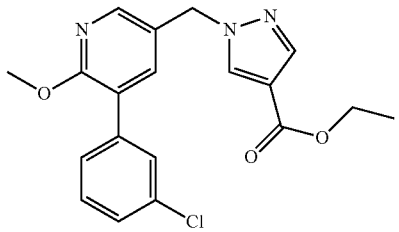 [SMILES: CCOC(=O)c1cnn(Cc2cnc(OC)c(-c3cccc(Cl)c3)c2)c1]

¹H NMR (400 MHz, DMSO-d₆) δ 8.48 (s, 1H), 8.20 (d, J=2.35 Hz, 1H), 7.87-7.76 (m, 2H), 7.57 (s, 1H), 7.56-7.32

(m, 3H), 5.35 (s, 2H), 4.18 (q, J=7.04 Hz, 2H), 3.87 (s, 3H), 1.23 (t, J=7.04 Hz, 3H). [M+H]=372.13.

Example 170

1-{[5-(3-Chlorophenyl)-6-methoxypyridin-3-yl]methyl}-1H-pyrazole-4-carbonitrile

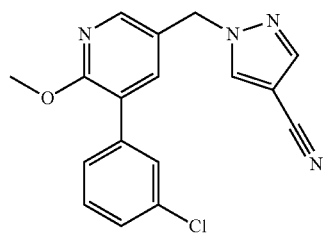 [SMILES: COc1ncc(Cn2cc(C#N)cn2)cc1-c1cccc(Cl)c1]

$^1$H NMR (400 MHz, DMSO-d$_6$) δ 8.67 (s, 1H), 8.20 (d, J=1.96 Hz, 1H), 8.05 (s, 1H), 7.81 (d, J=1.96 Hz, 1H), 7.61-7.31 (m, 4H), 5.39 (s, 2H), 3.87 (s, 3H). [M+H]=328.08.

Example 171

2-Methoxy-3-(pyridin-4-yl)-5-(1H-1,2,4-triazol-1-ylmethyl)pyridine

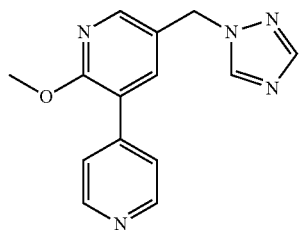 [SMILES: COc1ncc(Cn2cncn2)cc1-c1ccncc1]

$^1$H NMR (400 MHz, DMSO-d$_6$) δ 8.83 (d, J=3.91 Hz, 2H), 8.67 (s, 1H), 8.35 (s, 1H), 8.00 (dd, J=13.30, 7.83 Hz, 4H), 5.45 (s, 2H), 3.93 (s, 3H). [M+H]=298.15.

Example 172

N-(1-{[5-(3-Chlorophenyl)-6-methoxypyridin-3-yl]methyl}-1H-pyrazol-4-yl)acetamide

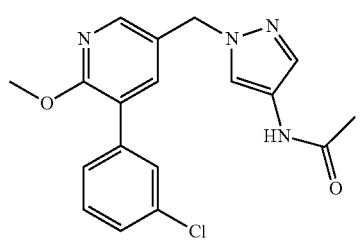 [SMILES: COc1ncc(Cn2cc(NC(C)=O)cn2)cc1-c1cccc(Cl)c1]

The title compound was isolated as a bi-product from Example 236. $^1$H NMR (400 MHz, CD$_3$OD) δ 8.04 (d, J=1.57 Hz, 1H), 7.95 (s, 1H), 7.57 (d, J=1.57 Hz, 1H), 7.47 (s, 1H), 7.44 (s, 1H), 7.34-7.29 (m, 3H), 5.22 (s, 2H), 3.88 (s, 3H), 2.01 (s, 3H). [M+H]=357.32.

Example 173

3-(3-Chlorophenyl)-5-(1H-imidazol-1-ylmethyl)-2-methoxypyridine

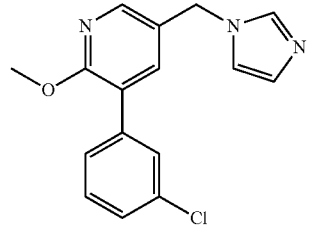 [SMILES: COc1ncc(Cn2ccnc2)cc1-c1cccc(Cl)c1]

$^1$H NMR (400 MHz, DMSO-d$_6$) δ 8.21 (d, J=2.3 Hz, 1H), 7.84-7.77 (m, 2H), 7.58 (d, J=0.8 Hz, 1H), 7.53-7.39 (m, 3H), 7.26 (s, 1H), 6.87 (s, 1H), 5.17 (s, 2H), 3.93-3.78 (m, 3H). [M+H]=301.12.

Example 174

2-(Difluoromethoxy)-3-(3-fluorophenyl)-5-(1H-1,2,4-triazol-1-ylmethyl)pyridine

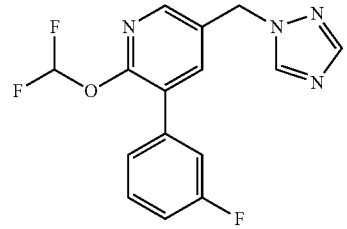 [SMILES: Fc1cccc(-c2cc(Cn3cncn3)cnc2OC(F)F)c1]

$^1$H NMR (400 MHz, DMSO-d$_6$) δ 8.73-8.62 (m, 1H), 8.32-8.20 (m, 1H), 8.06-7.96 (m, 1H), 7.93-7.85 (m, 1H), 7.75-7.66 (m, 1H), 7.60-7.49 (m, 1H), 7.44-7.33 (m, 1H), 7.28 (dt, J=2.3, 8.6 Hz, 1H), 5.49 (s, 1H), 5.44 (s, 2H). [M+H]=321.14.

Example 175

2-(Difluoromethoxy)-3-(3-methoxyphenyl)-5-(1H-1,2,4-triazol-1-ylmethyl)pyridine

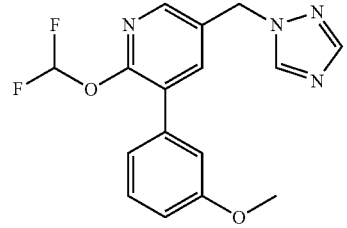 [SMILES: COc1cccc(-c2cc(Cn3cncn3)cnc2OC(F)F)c1]

¹H NMR (400 MHz, DMSO-d₆) δ 8.71-8.62 (m, 1H), 8.03-7.92 (m, 1H), 7.91-7.87 (m, 1H), 7.73-7.68 (m, 1H), 7.55-7.51 (m, 1H), 7.43-7.37 (m, 1H), 7.10-7.05 (m, 1H), 7.03-6.96 (m, 1H), 5.75 (s, 1H), 5.49 (s, 1H), 5.44 (s, 1H), 3.78 (s, 3H). [M+H]=333.24.

Example 176

2-(Difluoromethoxy)-5-(1H-1,2,4-triazol-1-ylmethyl)-3-[3-(trifluoromethoxy)phenyl]pyridine

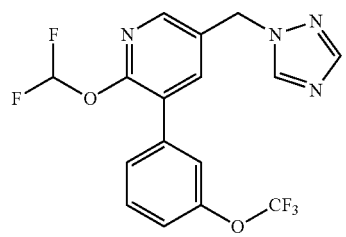 [SMILES: FC(F)Oc1ncc(Cn2cncn2)cc1-c1cccc(OC(F)(F)F)c1]

¹H NMR (400 MHz, DMSO-d₆) δ 8.67 (d, J=9.8 Hz, 1H), 8.33-8.19 (m, 2H), 8.04 (d, J=2.3 Hz, 1H), 7.98 (d, J=3.1 Hz, 1H), 7.88 (d, J=0.8 Hz, 1H), 7.70 (s, 1H), 7.67-7.39 (m, 2H), 5.50 (s, 1H), 5.44 (s, 1H). [M+H]=386.14.

Example 177

1-{[5-(3-Chlorophenyl)-6-methoxypyridin-3-yl]methyl}-1,2-dihydropyridin-2-one

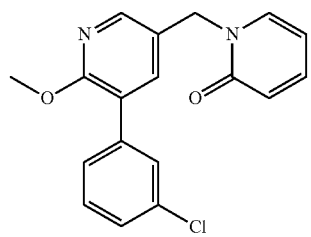 [SMILES: COc1ncc(Cn2ccccc2=O)cc1-c1cccc(Cl)c1]

¹H NMR (400 MHz, CDCl₃) δ 8.16 (d, J=1.96 Hz, 1H), 7.65 (d, J=1.96 Hz, 1H), 7.52 (s, 1H), 7.42-7.32 (m, 1H), 7.36-7.29 (m, 4H), 6.61 (d, J=9.00 Hz, 1H), 6.18 (t, J=6.46 Hz, 1H), 5.12 (s, 2H), 3.96 (s, 3H). [M+H]=327.17.

Example 178

5-[(4-Chloro-1H-pyrazol-1-yl)methyl]-3-(3-chlorophenyl)-2-methoxypyridine

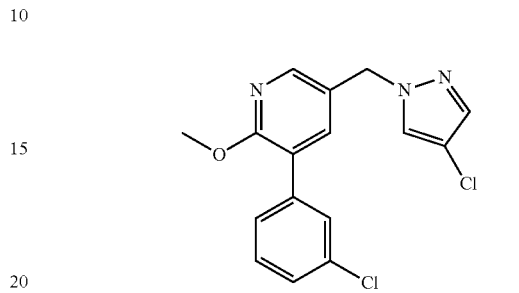

¹H NMR (400 MHz, DMSO-d₆) δ 8.20 (s, 1H), 8.10 (s, 1H), 7.80 (s, 1H), 7.60 (s, 1H), 7.55 (s, 1H), 7.50-7.40 (m, 3H), 5.24 (s, 2H), 3.86 (s, 3H). [M+H]=334.07,

Example 179

3-(3-Chlorophenyl)-2-methoxy-5-[(4-methyl-1H-pyrazol-1-yl)methyl]pyridine

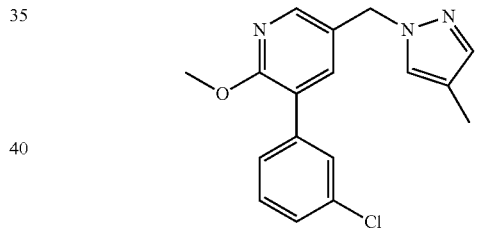

¹H NMR (400 MHz, DMSO-d₆) δ 8.15 (s, 1H), 7.67 (s, 1H), 7.61-7.58 (m, 1H), 7.54-7.36 (m, 4H), 7.10 (s, 1H), 5.14 (s, 2H), 3.85 (s, 3H), 3.60 (s, 3H). [M+H]=314.10.

Example 180

3-(3-Chlorophenyl)-2-methoxy-5-[(4-nitro-1H-pyrazol-1-yl)methyl]pyridine

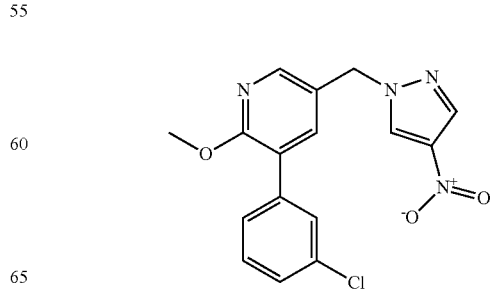

¹H NMR (400 MHz, DMSO-d₆) δ 9.05 (s, 1H), 8.06 (s, 1H), 7.61 (s, 1H), 7.57 (s, 1H), 7.52-7.38 (m, 4H), 5.54 (s, 2H), 3.85 (s, 3H). [M+H]=345.09.

Example 181

3-(3-Chlorophenyl)-2-methoxy-5-[(4-nitro-1H-pyrazol-1-yl)methyl]pyrazine

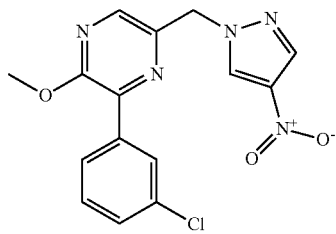 [SMILES: COc1ncc(Cn2cc([N+](=O)[O-])cn2)nc1-c1cccc(Cl)c1]

¹H NMR (400 MHz, CD₃OD) δ 8.76 (s, 1H), 8.19 (s, 1H), 8.13 (s, 1H), 8.02 (s, 1H), 8.01-7.91 (m, 1H), 7.45-7.35 (m, 2H), 5.52 (s, 2H), 4.06 (s, 3H). [M+H]=346.70.

Example 182

3-(3-Chlorophenyl)-2-methoxy-5-(1H-pyrazol-1-ylmethyl)pyrazine

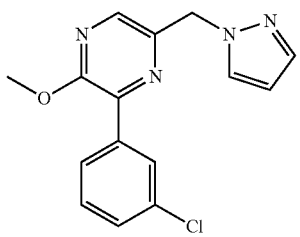 [SMILES: COc1ncc(Cn2cccn2)nc1-c1cccc(Cl)c1]

¹H NMR (400 MHz, CD₃OD) δ 8.76 (s, 1H), 8.19 (s, 1H), 8.13 (s, 1H), 8.02 (s, 1H), 8.01-7.91 (m, 2H), 7.45-7.35 (m, 2H), 5.52 (s, 2H), 4.06 (s, 3H). [M+H]=301.11.

Example 183

3-(3-Chlorophenyl)-5-(1H-imidazol-1-ylmethyl)-2-methoxypyrazine

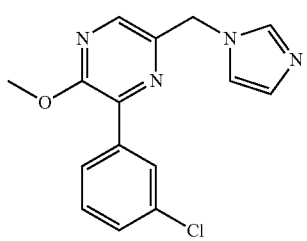 [SMILES: COc1ncc(Cn2ccnc2)nc1-c1cccc(Cl)c1]

¹H NMR (400 MHz, CD₃OD) δ 9.13 (br s, 1H), 8.33 (s, 1H), 8.05-7.89 (m, 2H), 7.73 (br s, 1H), 7.57 (br s, 1H), 7.48-7.35 (m, 2H), 5.60 (s, 2H), 4.09 (s, 3H). [M+H]=303.11.

Example 184

3-(3-Chlorophenyl)-2-methoxy-5-[(4-methyl-1H-pyrazol-1-yl)methyl]pyrazine

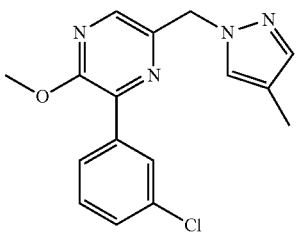 [SMILES: COc1ncc(Cn2cc(C)cn2)nc1-c1cccc(Cl)c1]

¹H NMR (400 MHz, CD₃OD) δ 8.07-7.96 (m, 2H), 7.94 (s, 1H), 7.58 (br s, 1H), 7.42 (d, J=3.91 Hz, 2H), 7.34 (s, 1H), 5.39 (s, 2H), 4.04 (s, 3H), 2.09 (s, 3H). [M+H]=315.10.

Example 185

3-[3-(Difluoromethoxy)phenyl]-2-ethoxy-5-[(3-methyl-1H-1,2,4-triazol-1-yl)methyl]pyrazine

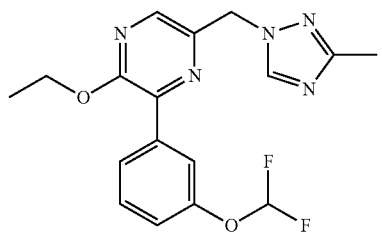

as a mixture

¹H NMR (400 MHz, CD₃OD) δ 8.53 (s, 1H), 8.15 (s, 1H), 8.14 (s, 1H), 7.96-7.90 (m, 2H), 7.86 (t, J=2.0 Hz, 1H), 7.85-7.82 (m, 2H), 7.46 (dt, J=1.6, 8.0 Hz, 2H), 7.21 (s, 1H), 7.19 (s, 1H), 7.04-6.64 (m, 2H), 5.50 (s, 2H), 5.47 (s, 2H), 4.57-4.45 (m, 4H), 2.63 (s, 3H), 2.32 (s, 3H), 1.44 (t, J=7.0 Hz, 6H). [M+H]=362.15.

Example 186

5-[(3-Cyclopropyl-1H-1,2,4-triazol-1-yl)methyl]-3-[3-(difluoromethoxy)phenyl]-2-ethoxypyrazine

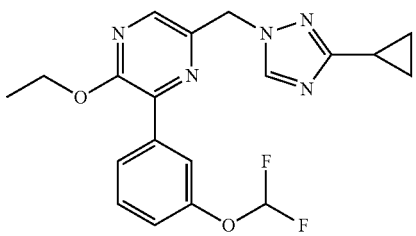

as a mixture

¹H NMR (400 MHz, CD₃OD) δ 8.46 (s, 1H), 8.14 (s, 2H), 7.99-7.92 (m, 2H), 7.89-7.85 (m, 2H), 7.78 (s, 2H), 7.48-7.44 (m, 2H), 7.21-7.18 (m, 1H), 7.04-6.62 (m, 2H), 5.61 (s, 2H), 5.45 (s, 2H), 4.58-4.46 (m, 4H), 2.41-2.30 (m, 1H), 1.99 (tt, J=5.2, 8.3 Hz, 1H), 1.45 (dt, J=1.6, 7.0 Hz, 6H), 1.17-1.09 (m, 2H), 1.07-1.01 (m, 2H), 0.98-0.90 (m, 2H), 0.90-0.85 (m, 2H). [M+H]=388.15.

Example 187

3-[3-(Difluoromethoxy)phenyl]-2-ethoxy-5-{[3-(trifluoromethyl)-1H-1,2,4-triazol-1-yl]methyl}pyrazine

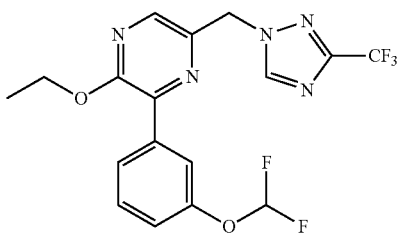 [SMILES: CCOc1ncc(Cn2cnc(C(F)(F)F)n2)nc1-c1cccc(OC(F)F)c1]

¹H NMR (400 MHz, CD₃OD) δ 8.80 (s, 1H), 8.23 (s, 1H), 7.93-7.90 (m, 1H), 7.86 (t, J=2.0 Hz, 1H), 7.46 (t, J=8.0 Hz, 1H), 7.20 (dd, J=2.0, 8.2 Hz, 1H), 7.03-6.62 (m, 1H), 5.64 (s, 2H), 4.52 (q, J=7.0 Hz, 2H), 1.45 (t, J=7.0 Hz, 3H). [M+H]=416.12.

Example 188

3-[3-(Difluoromethoxy)phenyl]-2-ethoxy-5-{[5-(trifluoromethyl)-1H-1,2,4-triazol-1-yl]methyl}pyrazine

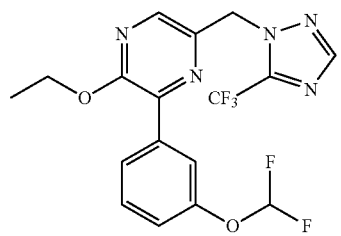 [SMILES: CCOc1ncc(Cn2ncnc2C(F)(F)F)nc1-c1cccc(OC(F)F)c1]

¹H NMR (400 MHz, CD₃OD) δ 8.19 (s, 1H), 8.12 (s, 1H), 7.95-7.87 (m, 1H), 7.83 (t, J=2.0 Hz, 1H), 7.44 (t, J=8.0 Hz, 1H), 7.19 (dd, J=2.2, 8.0 Hz, 1H), 7.02-6.59 (m, 1H), 5.74 (s, 2H), 4.52 (q, J=7.3 Hz, 2H), 1.45 (t, J=7.0 Hz, 3H). [M+H]=416.12.

Example 189

3-[3-(Difluoromethoxy)phenyl]-2-ethoxy-5-{[3-(methoxymethyl)-1H-1,2,4-triazol-1-yl]methyl}pyrazine

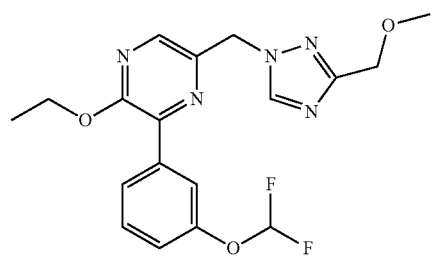 [SMILES: CCOc1ncc(Cn2cnc(COC)n2)nc1-c1cccc(OC(F)F)c1]

¹H NMR (400 MHz, CD₃OD) δ 8.63 (s, 1H), 8.18 (s, 1H), 7.96-7.91 (m, 1H), 7.85 (t, J=2.2 Hz, 1H), 7.45 (t, J=8.2 Hz, 1H), 7.20 (dd, J=2.0, 8.2 Hz, 1H), 7.05-6.62 (m, 1H), 5.54 (s, 2H), 4.51 (q, J=7.0 Hz, 2H), 4.46 (s, 3H), 4.30 (s, 2H), 1.44 (t, J=7.0 Hz, 3H). [M+H]=392.26.

Example 190

3-[3-(Difluoromethoxy)phenyl]-2-ethoxy-5-{[5-(methoxymethyl)-1H-1,2,4-triazol-1-yl]methyl}pyrazine

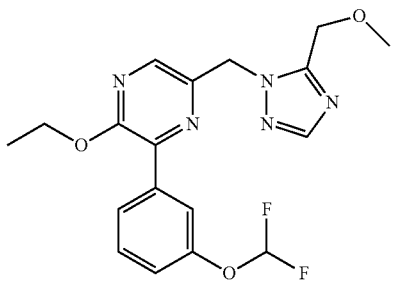 [SMILES: CCOc1ncc(Cn2ncnc2COC)nc1-c1cccc(OC(F)F)c1]

¹H NMR (400 MHz, CD₃OD) δ 8.14 (s, 1H), 7.95-7.91 (m, 2H), 7.84 (d, J=2.0 Hz, 1H), 7.46 (t, J=8.0 Hz, 1H), 7.20 (dd,

J=2.2, 8.0 Hz, 1H), 7.03-6.63 (m, 1H), 5.60 (s, 2H), 4.79 (s, 2H), 4.51 (q, J=7.0 Hz, 2H), 3.38 (s, 3H), 1.44 (t, J=7.0 Hz, 3H). [M+H]=392.15.

Example 191

Methyl 1-((6-(3-(difluoromethoxy)phenyl)-5-ethoxy-pyrazin-2-yl)methyl)-1H-1,2,4-triazole-3-carboxylate

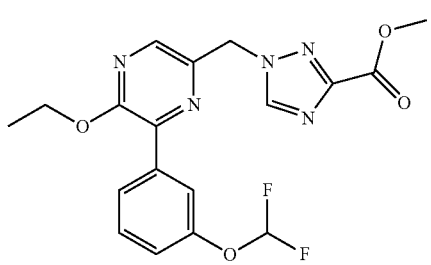 [SMILES: CCOc1ncc(Cn2cnc(C(=O)OC)n2)nc1-c1cccc(OC(F)F)c1]

$^1$H NMR (400 MHz, CD$_3$OD) δ 8.78 (s, 1H), 8.23 (s, 1H), 7.92 (td, J=1.4, 7.8 Hz, 1H), 7.84 (t, J=2.0 Hz, 1H), 7.45 (t, J=8.0 Hz, 1H), 7.19 (dd, J=2.3, 8.2 Hz, 1H), 7.03-6.63 (m, 1H), 5.63 (s, 2H), 4.51 (q, J=7.0 Hz, 2H), 3.91 (s, 3H), 1.44 (t, J=7.2 Hz, 3H). [M+H]=406.15.

Example 192

Methyl 1-((6-(3-(difluoromethoxy)phenyl)-5-ethoxy-pyrazin-2-yl)methyl)-1H-1,2,4-triazole-5-carboxylate

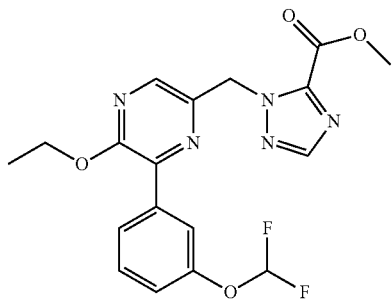 [SMILES: CCOc1ncc(Cn2ncnc2C(=O)OC)nc1-c1cccc(OC(F)F)c1]

$^1$H NMR (400 MHz, CD$_3$OD) δ 8.63 (s, 1H), 8.18 (s, 1H), 7.95-7.92 (m, 1H), 7.87-7.85 (m, 1H), 7.45 (t, J=8.2 Hz, 1H), 7.20 (dd, J=2.0, 8.2 Hz, 1H), 7.03-6.64 (m, 1H), 5.54 (s, 2H), 4.51 (q, J=7.0 Hz, 2H), 3.35 (s, 3H), 1.44 (t, J=7.0 Hz, 3H). [M+H]=406.26.

Example 193

3-(3-(Difluoromethoxy)phenyl)-2-ethoxy-5-((3-nitro-1H-1,2,4-triazol-1-yl)methyl)pyrazine

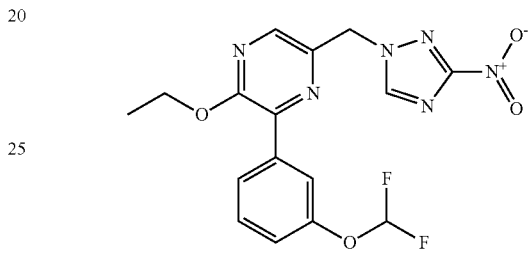

$^1$H NMR (400 MHz, CD$_3$OD) δ 8.82 (s, 1H), 8.28 (s, 1H), 7.92 (td, J=1.4, 7.8 Hz, 1H), 7.86 (t, J=2.0 Hz, 1H), 7.46 (t, J=8.0 Hz, 1H), 7.20 (dd, J=2.7, 8.2 Hz, 1H), 7.03-6.62 (m, 1H), 5.67 (s, 2H), 4.53 (q, J=7.0 Hz, 2H), 1.45 (t, J=7.0 Hz, 3H). [M+H]=393.15.

Example 194

3-(3-(Difluoromethoxy)phenyl)-2-ethoxy-5-((5-nitro-1H-1,2,4-triazol-1-yl)methyl)pyrazine

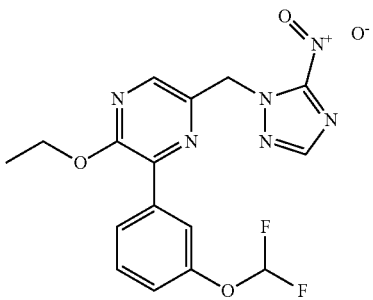

$^1$H NMR (400 MHz, CD$_3$OD) δ 8.23 (s, 1H), 8.10 (s, 1H), 7.80 (td, J=1.4, 7.8 Hz, 1H), 7.73 (t, J=2.3 Hz, 1H), 7.43 (t,

J=8.0 Hz, 1H), 7.18 (dd, J=2.0, 8.2 Hz, 1H), 7.02-6.61 (m, 1H), 6.01 (s, 2H), 4.51 (q, J=7.0 Hz, 2H), 1.44 (t, J=7.0 Hz, 3H). [M+H]=393.21.

Example 195

Methyl 1-{[6-(3-chlorophenyl)-5-methoxypyrazin-2-yl]methyl}-1H-1,2,4-triazole-5-carboxylate

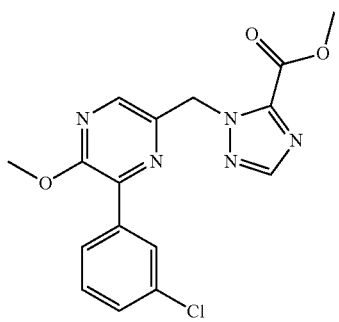

$^1$H NMR (400 MHz, CD$_3$OD) δ 8.19 (s, 1H), 8.09 (s, 1H), 7.94 (td, J=1.1, 2.1 Hz, 1H), 7.93-7.86 (m, 1H), 7.43-7.34 (m, 2H), 5.99 (s, 2H), 4.08-4.04 (m, 3H), 3.99-3.95 (m, 3H). [M+H]=360.18.

Example 196

Methyl 1-({6-[3-(difluoromethoxy)phenyl]-5-methoxypyrazin-2-yl}methyl)-1H-1,2,4-triazole-3-carboxylate

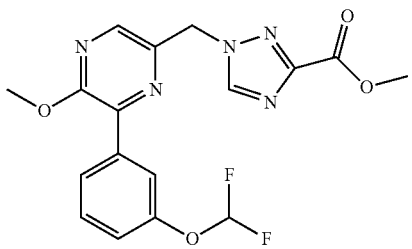

$^1$H NMR (400 MHz, DMSO-d$_6$) δ 8.88 (s, 1H), 8.35 (s, 1H), 7.83 (td, J=1.4, 7.8 Hz, 1H), 7.72-7.68 (m, 1H), 7.52 (t, J=8.0 Hz, 1H), 7.43-7.04 (m, 2H), 5.66 (s, 2H), 3.99 (s, 3H), 3.29 (s, 3H). [M+H]=392.16.

Example 197

Methyl 1-{[6-(3-chlorophenyl)-5-ethoxypyrazin-2-yl]methyl}-1H-1,2,4-triazole-3-carboxylate

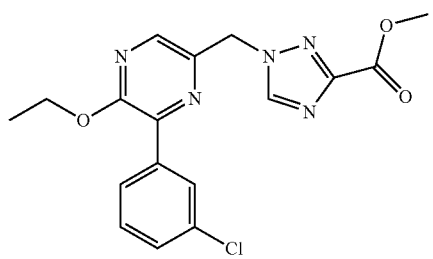 [SMILES: CCOc1ncc(Cn2cnc(C(=O)OC)n2)nc1-c1cccc(Cl)c1]

$^1$H NMR (400 MHz, DMSO-d$_6$) δ 8.89 (s, 1H), 8.32 (s, 1H), 7.99-7.96 (m, 1H), 7.96-7.90 (m, 1H), 7.52-7.46 (m, 2H), 5.64 (s, 2H), 4.45 (q, J=7.0 Hz, 2H), 3.83-3.77 (m, 3H), 1.39-1.34 (m, 3H). [M+H]=374.18.

Example 198

1-{[5-(3-Chlorophenyl)-6-(difluoromethoxy)pyridin-3-yl]methyl}-1H-imidazole-4-carboxamide

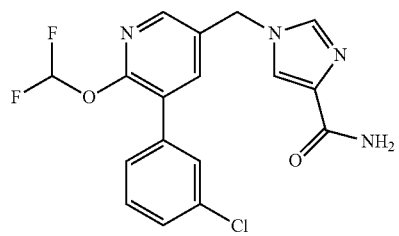 [SMILES: NC(=O)c1cn(Cc2cnc(OC(F)F)c(-c3cccc(Cl)c3)c2)cn1]

Step 1. Methyl 1-((5-(3-chlorophenyl)-6-(difluoromethoxy)pyridin-3-yl)methyl)-1H-imidazole-4-carboxylate was prepared in a manner analogous to Example 127.

Step 2. 1-{[5-(3-Chlorophenyl)-6-(difluoromethoxy)pyridin-3-yl]methyl}-1H-imidazole-4-carboxamide. To a solution of methyl 1-((5-(3-chlorophenyl)-6-(difluoromethoxy)pyridin-3-yl)methyl)-1H-imidazole-4-carboxylate in 7 N ammonia in MeOH (4 mL) was added NaCN (5 mg). Reaction mixture was heated 24 h at 130° C. LC-MS confirms the disappearance of starting material. The reaction mixture was concentrated under reduced pressure. Purification (FCC, SiO$_2$, 0-1%, EtOAc/MeOH) gave the title compound. $^1$H NMR (400 MHz, DMSO-d$_6$) δ 8.18 (d, J=2.3 Hz, 1H), 8.04 (s, 1H), 7.92 (d, J=2.3 Hz, 1H), 7.68 (s, 1H), 7.61 (s, 1H), 7.57-7.55 (m, 1H), 7.53-7.43 (m, 3H), 5.58 (s, 2H), 3.55 (s, 1H), 3.15 (d, J=5.1 Hz, 1H). [M+H]=379.15.

Example 199

(1-{[6-(3-Chlorophenyl)-5-methoxypyrazin-2-yl]methyl}-1H-1,2,4-triazol-3-yl)methanol

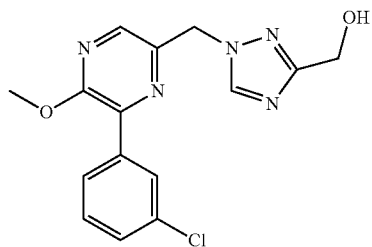 [SMILES: COc1ncc(Cn2cnc(CO)n2)nc1-c1cccc(Cl)c1]

To a solution of methyl 1-((6-(3-chlorophenyl)-5-methoxypyrazin-2-yl)methyl)-1H-1,2,4-triazole-3-carboxylate (Example 127, 77.00 mg, 0.21 mmol), in THF (1 mL) was added lithium borohydride (4.66 mg, 0.21 mmol). The mixture was stirred at room temperature for 3 hr. The mixture was diluted with water and extracted into DCM. The combined extracts were dried (Na$_2$SO$_4$) and concentrated under reduced pressure. Purification (FCC, SiO$_2$, 0-5% DCM/MeOH) afforded the title compound (50 mg; 70%). $^1$H NMR (400 MHz, CD$_3$OD) δ 8.61 (s, 1H), 8.21 (s, 1H), 8.02 (td, J=1.1, 2.1 Hz, 1H), 8.00-7.92 (m, 1H), 7.45-7.38 (m, 2H), 5.53 (s, 2H), 4.59 (s, 2H), 4.06 (s, 3H). [M+H]=332.15.

Examples 200-212 were prepared in a manner analogous to Example 199, with the appropriate starting materials and reagent substitutions.

Example 200

(1-{[5-(3-Chlorophenyl)-6-(difluoromethoxy)pyridin-3-yl]methyl}-1H-1,2,4-triazol-3-yl)methanol

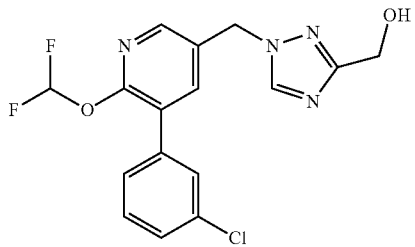 [SMILES: OCc1ncn(Cc2cnc(OC(F)F)c(-c3cccc(Cl)c3)c2)n1]

$^1$H NMR (400 MHz, CD$_3$OD) δ 8.55 (s, 1H), 8.26 (d, J=2.3 Hz, 1H), 7.93 (d, J=2.7 Hz, 1H), 7.82-7.38 (m, 5H), 5.46 (s, 2H), 4.59 (s, 2H). [M+H]=367.18.

Example 201

[1-({5-[3-(Difluoromethoxy)phenyl]-6-ethoxypyridin-3-yl}methyl)-1H-1,2,4-triazol-3-yl]methanol

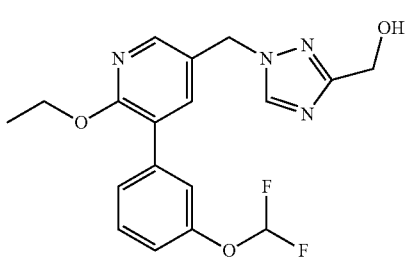 [SMILES: CCOc1ncc(Cn2cnc(CO)n2)cc1-c1cccc(OC(F)F)c1]

$^1$H NMR (400 MHz, CD$_3$OD) δ 8.52 (s, 1H), 8.17 (d, J=2.3 Hz, 1H), 7.76 (d, J=2.3 Hz, 1H), 7.49-7.34 (m, 3H), 7.13 (td, J=2.0, 7.8 Hz, 1H), 7.02-6.65 (m, 1H), 5.39 (s, 2H), 4.59 (s, 2H), 4.40 (q, J=7.2 Hz, 2H), 1.34 (t, J=7.0 Hz, 3H). [M+H]=377.25.

Example 202

[1-({5-[3-(Difluoromethoxy)phenyl]-6-methoxypyridin-3-yl}methyl)-1H-1,2,4-triazol-3-yl]methanol

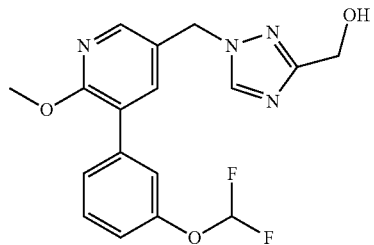 [SMILES: COc1ncc(Cn2cnc(CO)n2)cc1-c1cccc(OC(F)F)c1]

$^1$H NMR (400 MHz, CD$_3$OD) δ 8.53 (s, 1H), 8.20 (d, J=2.7 Hz, 1H), 7.76 (d, J=2.3 Hz, 1H), 7.48-7.35 (m, 2H), 7.32 (t,

J=1.8 Hz, 1H), 7.16-7.11 (m, 1H), 7.03-6.65 (m, 1H), 5.49 (s, 1H), 4.59 (s, 2H), 3.95 (s, 3H). [M+H]=363.23.

Example 203

(1-((5-(3-Chlorophenyl)-6-ethoxypyridin-3-yl)methyl)-1H-1,2,4-triazol-3-yl)methanol

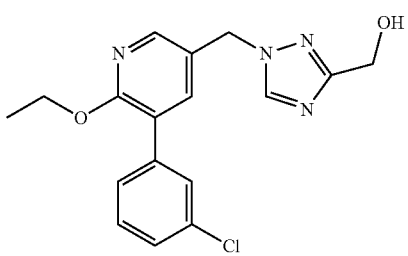 [SMILES: CCOc1ncc(Cn2cnc(CO)n2)cc1-c1cccc(Cl)c1]

$^1$H NMR (400 MHz, CD$_3$OD) δ 8.53 (s, 1H), 8.18 (d, J=2.7 Hz, 1H), 7.75 (d, J=2.7 Hz, 1H), 7.60-7.56 (m, 1H), 7.49-7.45 (m, 1H), 7.42-7.33 (m, 2H), 5.39 (s, 2H), 4.59 (s, 2H), 4.42 (q, J=7.0 Hz, 2H), 1.34 (t, J=7.0 Hz, 3H). [M+H]=345.22.

Example 204

(1-{[6-(Difluoromethoxy)-5-(3-ethoxyphenyl)pyridin-3-yl]methyl}-1H-1,2,4-triazol-3-yl)methanol

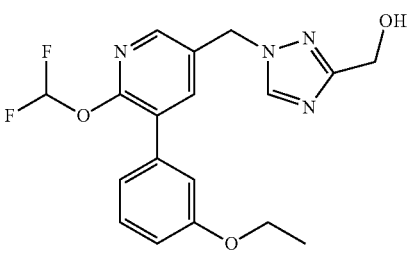 [SMILES: CCOc1cccc(-c2cc(Cn3cnc(CO)n3)cnc2OC(F)F)c1]

$^1$H NMR (400 MHz, CD$_3$OD) δ 8.56 (s, 1H), 8.22 (d, J=2.3 Hz, 1H), 7.89 (d, J=2.3 Hz, 1H), 7.61 (t, J=1.0 Hz, 1H), 7.38-7.31 (m, 1H), 7.10-7.03 (m, 2H), 6.95 (ddd, J=1.0, 2.4, 8.3 Hz, 1H), 5.46 (s, 2H), 4.59 (s, 2H), 4.07 (q, J=7.0 Hz, 2H), 1.40 (t, J=7.0 Hz, 3H). [M+H]=377.25.

Example 205

[1-({5-[2-(Difluoromethoxy)pyridin-4-yl]-6-methoxypyridin-3-yl}methyl)-1H-1,2,4-triazol-3-yl]methanol

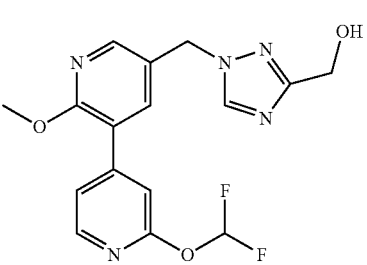 [SMILES: COc1ncc(Cn2cnc(CO)n2)cc1-c1ccnc(OC(F)F)c1]

$^1$H NMR (400 MHz, CD$_3$OD) δ 8.53 (s, 1H), 8.28 (d, J=2.3 Hz, 1H), 8.24-8.21 (m, 1H), 7.89 (d, J=2.3 Hz, 1H), 7.76-7.37 (m, 2H), 7.20-7.17 (m, 1H), 5.41 (s, 2H), 4.59 (s, 2H), 3.98 (s, 3H). [M+H]=364.22.

Example 206

[1-({5-[2-(Difluoromethoxy)pyridin-4-yl]-6-ethoxypyridin-3-yl}methyl)-1H-1,2,4-triazol-3-yl]methanol

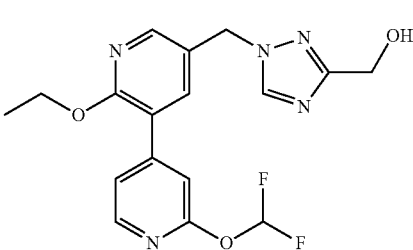 [SMILES: CCOc1ncc(Cn2cnc(CO)n2)cc1-c1ccnc(OC(F)F)c1]

$^1$H NMR (400 MHz, CD$_3$OD) δ 8.54 (s, 1H), 8.26 (d, J=2.3 Hz, 1H), 8.24 (dd, J=0.8, 5.5 Hz, 1H), 7.89 (d, J=2.3 Hz, 1H), 7.77-7.56 (m, 1H), 7.44-7.41 (m, 1H), 7.23-7.20 (m, 1H), 5.41 (s, 2H), 4.59 (s, 2H), 4.45 (q, J=7.0 Hz, 2H), 1.37 (t, J=7.0 Hz, 3H). [M+H]=378.20.

Example 207

(1-{[6-(Difluoromethoxy)-5-[2-(difluoromethoxy) pyridin-4-yl]pyridin-3-yl]methyl}-1H-1,2,4-triazol-3-yl)methanol

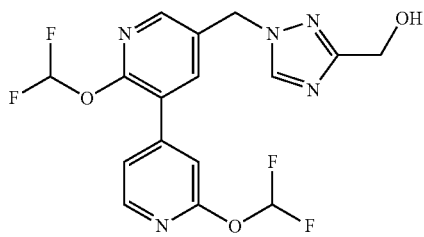 [SMILES: OCc1ncn(Cc2cnc(OC(F)F)c(-c3ccnc(OC(F)F)c3)c2)n1]

¹H NMR (400 MHz, CD₃OD) δ 8.56 (s, 1H), 8.35-8.28 (m, 2H), 8.05 (d, J=2.3 Hz, 1H), 7.83-7.41 (m, 2H), 7.41-7.39 (m, 1H), 7.19-7.17 (m, 1H), 5.49 (s, 2H), 4.59 (s, 2H). [M+H]= 400.21.

Example 208

[1-({6-[3-(Difluoromethoxy)phenyl]-5-ethoxy-pyrazin-2-yl}methyl)-1H-1,2,4-triazol-3-yl]methanol

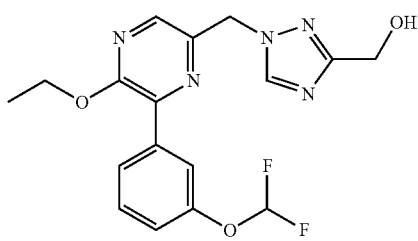 [SMILES: CCOc1ncc(Cn2cnc(CO)n2)nc1-c1cccc(OC(F)F)c1]

¹H NMR (400 MHz, CD₃OD) δ 8.60 (s, 1H), 8.18 (s, 1H), 7.93 (td, J=1.4, 7.8 Hz, 1H), 7.86 (t, J=2.0 Hz, 1H), 7.46 (t, J=8.0 Hz, 1H), 7.20 (dd, J=2.0, 8.2 Hz, 1H), 7.04-6.64 (m, 1H), 5.52 (s, 2H), 4.59 (s, 2H), 4.51 (q, J=7.3 Hz, 2H), 1.44 (t, J=7.0 Hz, 3H). [M+H]=378.25.

Example 209

[1-({6-[3-(Difluoromethoxy)phenyl]-5-ethoxy-pyrazin-2-yl}methyl)-1H-1,2,4-triazol-5-yl]methanol

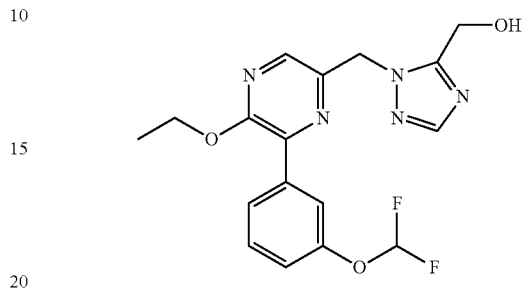

¹H NMR (400 MHz, CD₃OD) δ 8.14 (s, 1H), 7.90 (s, 1H), 7.93-7.89 (m, 1H), 7.83 (t, J=2.0 Hz, 1H), 7.46 (t, J=8.0 Hz, 1H), 7.19 (dd, J=2.7, 7.8 Hz, 1H), 7.05-6.62 (m, 1H), 5.65 (s, 2H), 4.91 (s, 2H), 4.50 (q, J=7.0 Hz, 2H), 1.44 (t, J=7.0 Hz, 3H). [M+H]=378.15.

Example 210

(1-{[6-(3-Chlorophenyl)-5-methoxypyrazin-2-yl] methyl}-1H-1,2,4-triazol-5-yl)methanol

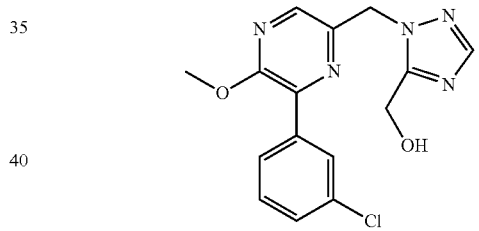

¹H NMR (400 MHz, CD₃OD) δ 8.16 (s, 1H), 8.02-7.99 (m, 1H), 7.94 (ddd, J=1.8, 3.5, 5.3 Hz, 1H), 7.92-7.89 (m, 1H), 7.44-7.39 (m, 2H), 5.66 (s, 2H), 4.90 (s, 2H), 4.06 (s, 3H). [M+H]=332.18.

Example 211

[1-({6-[3-(Difluoromethoxy)phenyl]-5-methoxy-pyrazin-2-yl}-methyl)-1H-1,2,4-triazol-3-yl]methanol

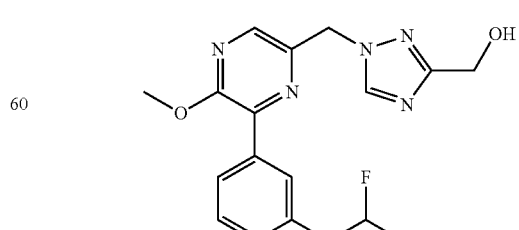

¹H NMR (400 MHz, DMSO-d₆) δ 8.59 (s, 1H), 8.27 (s, 1H), 7.88-7.83 (m, 1H), 7.76-7.71 (m, 1H), 7.53 (t, J=8.0 Hz, 1H), 7.45-7.06 (m, 2H), 5.50 (s, 2H), 5.16 (t, J=6.1 Hz, 1H), 4.36 (d, J=6.3 Hz, 2H), 3.98 (s, 3H). [M+H]=364.14.

Example 212

(1-{[6-(3-Chlorophenyl)-5-ethoxypyrazin-2-yl]methyl}-1H-1,2,4-triazol-3-yl)methanol

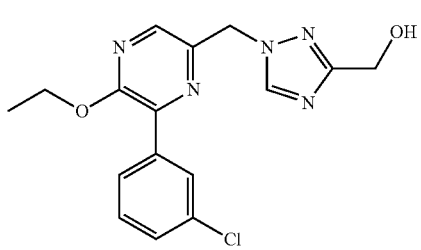 [SMILES: CCOc1ncc(Cn2cnc(CO)n2)nc1-c1cccc(Cl)c1]

¹H NMR (400 MHz, DMSO-d₆) δ 8.60 (s, 1H), 8.24 (s, 1H), 8.02-7.99 (m, 1H), 7.99-7.93 (m, 1H), 7.54-7.48 (m, 2H), 5.49 (s, 2H), 5.16 (t, J=6.1 Hz, 1H), 4.45 (q, J=7.0 Hz, 2H), 4.36 (d, J=5.9 Hz, 2H), 1.36 (t, J=7.0 Hz, 3H). [M+H]=346.25.

Example 213

3-(3-Chlorophenyl)-2-methoxy-5-[(3-methoxy-1H-1,2,4-triazol-1-yl)methyl]pyridine

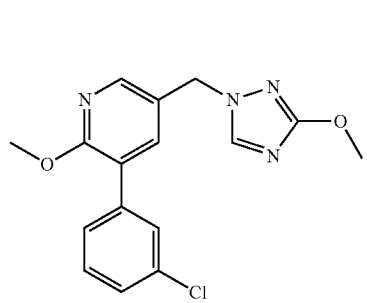

Step 1. 3-(3-Chlorophenyl)-2-methoxy-5-((3-nitro-1H-1,2,4-triazol-1-yl)methyl)pyridine. The title compound was prepared in a manner analogous to Example 127 with the appropriate starting material substitutions.

Step 2. 3-(3-Chlorophenyl)-2-methoxy-5-[(3-methoxy-1H-1,2,4-triazol-1-yl)methyl]pyridine. To a solution of 3-(3-chlorophenyl)-2-methoxy-5-((3-nitro-1H-1,2,4-triazol-1-yl)methyl)pyridine (135 mg, 0.39 mmol), in methanol (3 mL) was added sodium methoxide (63 mg, 1.17 mmol). The mixture was stirred at 60° C. for 16 h. The LC/MS showed approximately 70% conversion. All solvents removed under reduced pressure, the residue dissolved in DCM (50 mL) and water (50 mL), the layers shaken and separated and the aqueous layer extracted into DCM (3×50 mL). The combined extracts were dried (MgSO₄), filtered and solvent removed under reduced pressure. Purification (FCC, SiO₂, 0-100% EtOAc/DCM) afforded the title compound (72 mg, 56%). ¹H NMR (400 MHz, DMSO-d₆) δ 8.33 (s, 1H), 8.19 (d, J=2.0 Hz, 1H), 7.79 (d, J=2.3 Hz, 1H), 7.58 (s, 1H), 7.52-7.38 (m, 3H), 5.23 (s, 2H), 3.87 (s, 3H), 3.79 (s, 3H). [M+H]=331.21.

Examples 214-216 were prepared in a manner analogous to Example 213, with the appropriate starting materials and reagent substitutions.

Example 214

3-(3-Chlorophenyl)-2-(difluoromethoxy)-5-[(3-methoxy-1H-1,2,4-triazol-1-yl)methyl]pyridine

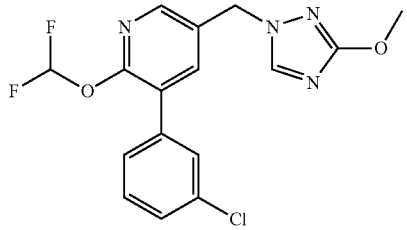 [SMILES: COc1ncn(Cc2cnc(OC(F)F)c(-c3cccc(Cl)c3)c2)n1]

¹H NMR (400 MHz, CD₃OD) δ 8.27 (s, 1H), 8.24 (d, J=2.3 Hz, 1H), 7.91 (d, J=2.3 Hz, 1H), 7.82-7.61 (m, 1H), 7.57 (s, 1H), 7.49-7.40 (m, 3H), 5.32 (s, 2H), 3.92 (s, 3H). [M+H]=367.16.

Example 215

3-(3-Chlorophenyl)-2-(difluoromethoxy)-5-[(5-methoxy-1H-1,2,4-triazol-1-yl)methyl]pyridine

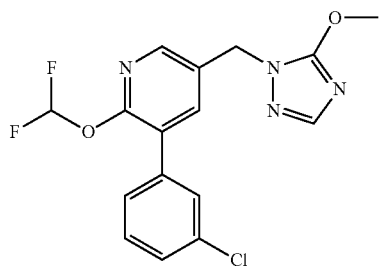 [SMILES: COc1ncnn1Cc1cnc(OC(F)F)c(-c2cccc(Cl)c2)c1]

¹H NMR (400 MHz, CD₃OD) δ 8.17 (d, J=2.0 Hz, 1H), 7.84 (d, J=2.3 Hz, 1H), 7.61-7.39 (m, 6H), 5.21 (s, 2H), 4.12 (s, 3H). [M+H]=367.16.

Example 216

3-(3-Chlorophenyl)-2-(difluoromethoxy)-5-[(3-ethoxy-1H-1,2,4-triazol-1-yl)methyl]pyridine

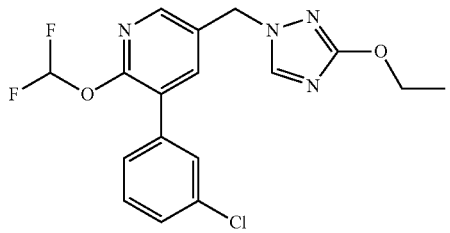 [SMILES: CCOc1ncn(Cc2cnc(OC(F)F)c(-c3cccc(Cl)c3)c2)n1]

¹H NMR (400 MHz, CD₃OD) δ 8.28-8.21 (m, 2H), 7.91 (d, J=2.3 Hz, 1H), 7.84-7.60 (m, 1H), 7.56 (s, 1H), 7.49-7.40 (m, 3H), 5.31 (s, 2H), 4.26 (q, J=7.0 Hz, 2H), 1.35 (t, J=7.0 Hz, 3H). [M+H]=380.18.

Example 217

1-({5-[3-(Difluoromethoxy)phenyl]-6-methoxypyridin-3-yl}methyl)-1H-1,2,4-triazol-3-amine

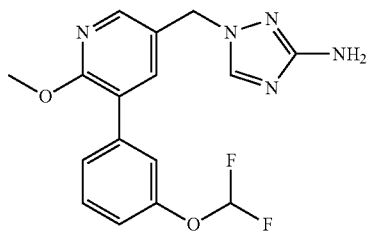

Step 1. 3-(3-(Difluoromethoxy)phenyl)-2-methoxy-5-((3-nitro-1H-1,2,4-triazol-1-yl)methyl)pyridine. The title compound was prepared in a manner analogous to Example 127 with the appropriate starting material substitutions.

Step 2. 1-({5-[3-(Difluoromethoxy)phenyl]-6-methoxypyridin-3-yl}methyl)-1H-1,2,4-triazol-3-amine. To a solution of 3-(3-(difluoromethoxy)phenyl)-2-methoxy-5-((3-nitro-1H-1,2,4-triazol-1-yl)methyl)pyridine (331.00 mg, 0.88 mmol) in AcOH (6 mL), and water (2 mL) was added zinc (573.57 mg, 8.77 mmol). The mixture was stirred at 50° C. for 1 hr. The solvent was removed under reduced pressure to afford a white solid. The crude solid was dissolved in DCM (50 mL), sonicated and filtered (repeated twice). The combined DCM extracts were washed with a saturated aqueous solution of sodium bicarbonate and the layers separated. The organic layers were combined, dried (Na₂SO₄) and concentrated under reduced pressure. The resulting solid was triturated with hexanes to give the title compound (287 mg, 94%). ¹H NMR (400 MHz, CD₃OD) δ 8.15 (d, J=2.7 Hz, 1H), 8.13 (s, 1H), 7.71 (d, J=2.3 Hz, 1H), 7.47-7.36 (m, 2H), 7.33 (t, J=1.8 Hz, 1H), 7.16-7.11 (m, 1H), 7.04-6.65 (m, 1H), 5.19 (s, 2H), 3.95 (s, 3H). [M+H]=348.22.

Examples 218-237 were prepared in a manner analogous to Example 217, with the appropriate starting materials and reagent substitutions.

Example 218

1-{[5-(3-Chlorophenyl)-6-methoxypyridin-3-yl]methyl}-1H-1,2,4-triazol-3-amine

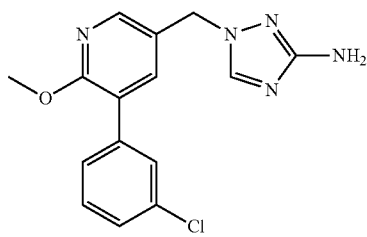

¹H NMR (400 MHz, DMSO-d₆) δ 8.17 (d, J=2.3 Hz, 1H), 8.09 (s, 1H), 7.76 (d, J=2.3 Hz, 1H), 7.58 (d, J=1.6 Hz, 1H), 7.51-7.42 (m, 3H), 5.26 (s, 2H), 5.11 (s, 2H), 3.88 (s, 3H). [M+H]=316.21.

Example 219

1-{[5-(3-Chlorophenyl)-6-(difluoromethoxy)pyridin-3-yl]methyl}-1H-1,2,4-triazol-3-amine

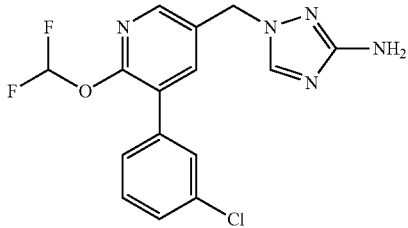 [SMILES: Nc1ncn(Cc2cnc(OC(F)F)c(-c3cccc(Cl)c3)c2)n1]

¹H NMR (400 MHz, CD₃OD) δ 8.11 (d, J=2.3 Hz, 1H), 8.06 (s, 1H), 7.78 (d, J=2.3 Hz, 1H), 7.73-7.50 (m, 1H), 7.47 (s, 1H), 7.41-7.30 (m, 3H), 5.15 (s, 2H). [M+H]=352.17.

Example 220

1-{[5-(3-Fluorophenyl)-6-methoxypyridin-3-yl]methyl}-1H-1,2,4-triazol-3-amine

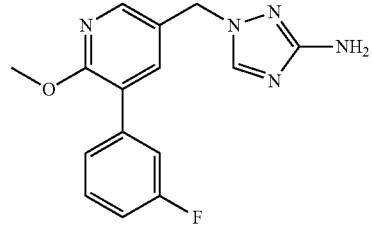

Step 1. 3-Bromo-2-methoxy-5-((3-nitro-1H-1,2,4-triazol-1-yl)methyl)pyridine. Title compound was prepared in a manner analogous to Intermediate 5 with the appropriate starting materials and reagent substitutions. [M+H]=314.24/316.25.

Step 2. 1-((5-(3-Fluorophenyl)-6-methoxypyridin-3-yl)methyl)-1H-1,2,4-triazol-3-amine. To a solution of 3-bromo-2-methoxy-5-((3-nitro-1H-1,2,4-triazol-1-yl)methyl)pyridine (60 mg, 0.191 mmol) in AcOH (3 mL), and water (1 mL) was added zinc (124 mg, 1.91 mmol). The mixture was stirred at 50° C. for 1 hr. The solvent was removed under reduced pressure to afford a white solid. The crude solid was dissolved in DCM (50 mL), sonicated and filtered (repeated twice). The combined DCM extracts were washed with a saturated aqueous solution of sodium bicarbonate and the layers separated. The organic layers were combined, dried (Na₂SO₄) and concentrated under reduced pressure. The crude intermediate and (3-fluorophenyl) boronic (42 mg, 0.3 mmol) dissolved in mixture of water (2 mL), and ACN (4 mL) were added [1,1'-bis(diphenylphosphino)ferrocene]dichloropalladium(II) (8 mg, 0.01 mmol) followed by sodium carbonate (53 mg, 0.5 mmol). The mixture was irradiated under microwaves for 15 minutes at 100° C. The reaction mixture was diluted with water and extracted with DCM (3×5 mL). The combined organic phase was dried (Na₂SO₄), filtered, and concentrated under reduced pressure. Purification (FCC, SiO₂, 0-10% DCM/MeOH) afforded the title compound (49.7 mg, 89%). ¹H NMR (400 MHz, CD₃OD) δ 8.13 (br s, 1H), 7.71 (br s, 1H), 7.63-7.23 (m, 4H), 7.08 (br s, 1H), 5.19 (m, 2H), 3.95 (s, 3H). [M+H]=300.27.

Examples 221-223 were prepared in a manner analogous to Example 220, with the appropriate starting material and reagent substitutions.

Example 221

1-{[6-Methoxy-5-(3-methoxyphenyl)pyridin-3-yl]methyl}-1H-1,2,4-triazol-3-amine

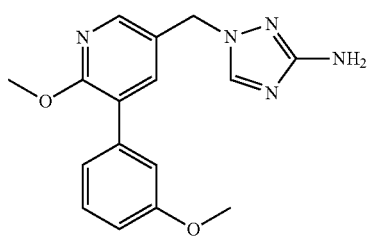 [SMILES: COc1cccc(-c2cc(Cn3cnc(N)n3)cnc2OC)c1]

¹H NMR (400 MHz, CD₃OD) δ 8.12 (s, 2H), 7.67 (d, J=2.3 Hz, 1H), 7.31 (dd, J=8.2 Hz, 1H), 7.10-7.04 (m, 2H), 6.91 (dd, J=1.6, 8.2 Hz, 1H), 5.18 (s, 2H), 3.94 (s, 3H), 3.82 (s, 3H). [M+H]=312.28.

Example 222

1-{[6-Methoxy-5-(3-methylphenyl)pyridin-3-yl]methyl}-1H-1,2,4-triazol-3-amine

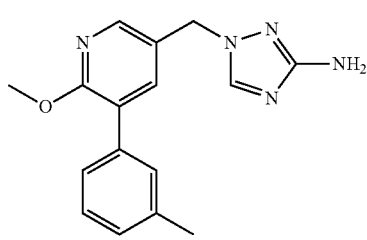 [SMILES: COc1ncc(Cn2cnc(N)n2)cc1-c1cccc(C)c1]

¹H NMR (400 MHz, CD₃OD) δ 8.12 (m, 2H), 7.64-7.29 (m, 4H), 7.16 (br s, 1H), 5.17 (br s, 2H), 3.94 (s, 3H), 2.37 (s, 3H). [M+H]=296.29.

Example 223

3-{5-[(3-Amino-1H-1,2,4-triazol-1-yl)methyl]-2-methoxypyridin-3-yl}benzonitrile

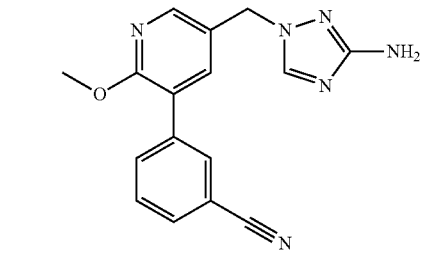 [SMILES: COc1ncc(Cn2cnc(N)n2)cc1-c1cccc(C#N)c1]

¹H NMR (400 MHz, CD₃OD) δ 8.19 (br s, 1H), 8.13 (br s, 1H), 7.92-7.68 (m, 4H), 7.61 (d, J=7.8 Hz, 1H), 5.19 (br s, 2H), 3.96 (s, 3H). [M+H]=307.26.

Example 224

1-{[5-(3-Ethoxyphenyl)-6-methoxypyridin-3-yl]methyl}-1H-1,2,4-triazol-3-amine

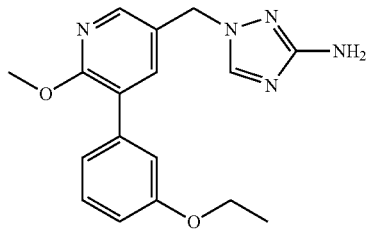 [SMILES: CCOc1cccc(-c2cc(Cn3cnc(N)n3)cnc2OC)c1]

¹H NMR (400 MHz, CD₃OD) δ 8.13-8.09 (m, 2H), 7.66 (d, J=2.3 Hz, 1H), 7.31-7.25 (m, 1H), 7.07-7.03 (m, 2H), 6.91-6.87 (m, 1H), 5.17 (s, 2H), 4.05 (d, J=7.0 Hz, 2H), 3.93 (s, 3H), 1.39 (t, J=7.0 Hz, 3H). [M+H]=326.26.

Example 225

1-{[5-(3-Cyclopropoxyphenyl)-6-methoxypyridin-3-yl]methyl}-1H-1,2,4-triazol-3-amine

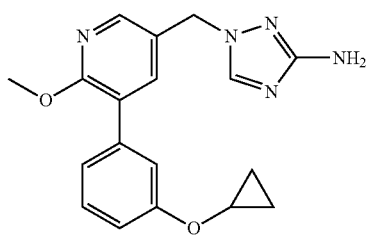 [SMILES: COc1ncc(Cn2cnc(N)n2)cc1-c1cccc(OC2CC2)c1]

¹H NMR (400 MHz, CD₃OD) δ 8.16-8.09 (m, 2H), 7.66 (d, J=2.38 Hz, 1H), 7.36-7.16 (m, 2H), 7.11-7.02 (m, 2H), 5.18 (s, 2H), 3.94 (s, 3H), 3.80 (tt, J=6.01, 2.96 Hz, 1H), 0.82-0.67 (m, 4H). [M+H]=338.27.

Example 226

1-({5-[3-(Difluoromethoxy)phenyl]-6-ethoxypyridin-3-yl}methyl)-1H-1,2,4-triazol-3-amine

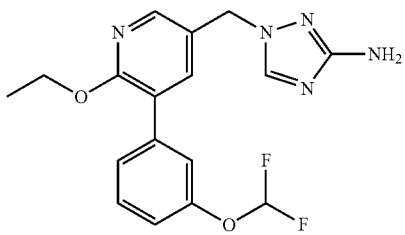

¹H NMR (400 MHz, CD₃OD) δ 8.18-8.07 (m, 2H), 7.71 (d, J=2.3 Hz, 1H), 7.50-7.34 (m, 3H), 7.17-7.09 (m, 1H), 7.06-6.62 (m, 1H), 5.18 (s, 2H), 4.41 (q, J=7.0 Hz, 2H), 1.35 (t, J=7.0 Hz, 3H). [M+H]=362.24.

Example 227

1-{[6-(Difluoromethoxy)-5-(3-methoxyphenyl)pyridin-3-yl]methyl}-1H-1,2,4-triazol-3-amine

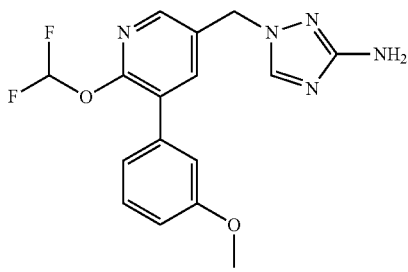 [SMILES: COc1cccc(-c2cc(Cn3cnc(N)n3)cnc2OC(F)F)c1]

¹H NMR (400 MHz, CD₃OD) δ 8.22-8.11 (m, 2H), 7.84 (d, J=2.3 Hz, 1H), 7.80-7.39 (m, 1H), 7.35 (t, J=8.0 Hz, 1H), 7.10-7.05 (m, 2H), 6.97 (dd, J=2.5, 8.4 Hz, 1H), 5.24 (s, 2H), 3.82 (s, 3H). [M+H]=348.22.

Example 228

1-{[5-(5-Chloropyridin-3-yl)-6-methoxypyridin-3-yl]methyl}-1H-1,2,4-triazol-3-amine

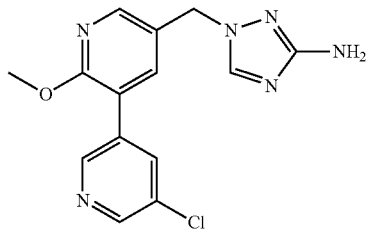 [SMILES: COc1ncc(Cn2cnc(N)n2)cc1-c1cncc(Cl)c1]

¹H NMR (400 MHz, CD₃OD) δ 9.28 (s, 1H), 8.78 (d, J=1.76 Hz, 1H), 8.66 (d, J=2.13 Hz, 1H), 8.38 (d, J=2.26 Hz, 1H), 8.31 (t, J=2.01 Hz, 1H), 8.01 (d, J=2.26 Hz, 1H), 5.38 (s, 2H), 4.02 (s, 3H). [M+H]=317.21.

Example 229

1-({5-[2-(Difluoromethoxy)pyridin-4-yl]-6-methoxypyridin-3-yl}methyl)-1H-1,2,4-triazol-3-amine

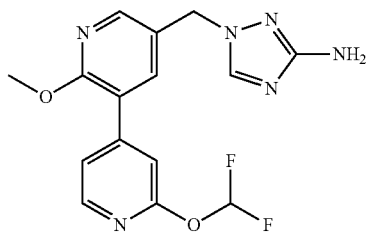 [SMILES: COc1ncc(Cn2cnc(N)n2)cc1-c1ccnc(OC(F)F)c1]

¹H NMR (400 MHz, CD₃OD) δ 8.25-8.19 (m, 2H), 8.13 (s, 1H), 7.84 (d, J=2.3 Hz, 1H), 7.76-7.55 (m, 1H), 7.44-7.36 (m, 1H), 7.18 (d, J=0.8 Hz, 1H), 5.19 (s, 2H), 3.98 (s, 3H). [M+H]=349.25.

Example 230

1-({5-[2-(Difluoromethoxy)pyridin-4-yl]-6-ethoxypyridin-3-yl}methyl)-1H-1,2,4-triazol-3-amine

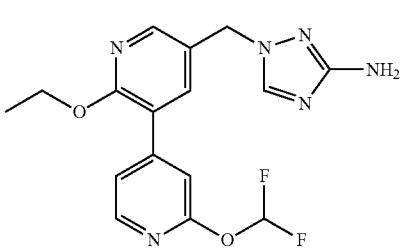 [SMILES: CCOc1ncc(Cn2cnc(N)n2)cc1-c1ccnc(OC(F)F)c1]

¹H NMR (400 MHz, CD₃OD) δ 8.24 (dd, J=0.8, 5.1 Hz, 1H), 8.21 (d, J=2.3 Hz, 1H), 8.14 (s, 1H), 7.85 (d, J=2.7 Hz, 1H), 7.77-7.57 (m, 1H), 7.43 (dd, J=1.6, 5.5 Hz, 1H), 7.22 (dd, J=0.8, 1.6 Hz, 1H), 5.20 (s, 2H), 4.47 (q, J=7.0 Hz, 2H), 1.37 (t, J=7.0 Hz, 3H). [M+H]=363.19.

Example 231

1-{[6-(Difluoromethoxy)-5-[2-(difluoromethoxy) pyridin-4-yl]pyridin-3-yl]methyl}-1H-1,2,4-triazol-3-amine

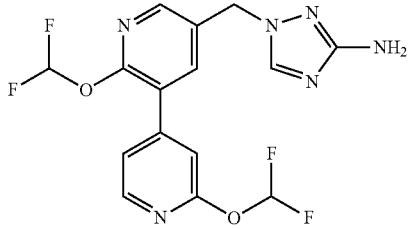 [SMILES: Nc1ncn(Cc2cnc(OC(F)F)c(-c3ccnc(OC(F)F)c3)c2)n1]

¹H NMR (400 MHz, CD₃OD) δ 8.32-8.27 (m, 2H), 8.16 (s, 1H), 7.99 (d, J=2.3 Hz, 1H), 7.84-7.38 (m, 3H), 7.19-7.16 (m, 1H), 5.27 (s, 2H). [M+H]=385.20.

Example 232

1-({5-[3-(Difluoromethoxy)phenyl]-6-methoxypyridin-3-yl}methyl)-1H-pyrazol-3-amine

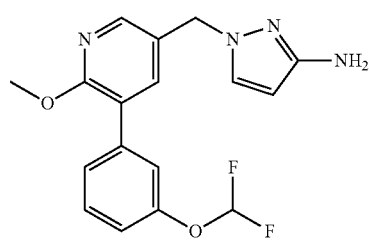 [SMILES: COc1ncc(Cn2ccc(N)n2)cc1-c1cccc(OC(F)F)c1]

Example 233

1-({5-[3-(Difluoromethoxy)phenyl]-6-methoxypyridin-3-yl}methyl)-1H-pyrazol-5-amine

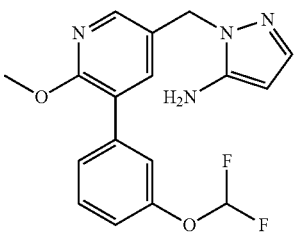 [SMILES: COc1ncc(Cn2nccc2N)cc1-c1cccc(OC(F)F)c1]

¹H NMR (400 MHz, CD₃OD) δ 8.04 (d, J=2.3 Hz, 1H), 7.58 (d, J=2.3 Hz, 1H), 7.46-7.30 (m, 4H), 7.14-7.09 (m, 1H), 7.02-6.64 (m, 1H), 5.64 (d, J=2.3 Hz, 1H), 5.10 (s, 2H), 3.93 (s, 3H). [M+H]=347.37.

¹H NMR (400 MHz, CD₃OD) δ 7.99 (d, J=2.3 Hz, 1H), 7.55 (d, J=2.7 Hz, 1H), 7.44-7.33 (m, 2H), 7.30 (t, J=2.0 Hz, 1H), 7.22 (d, J=2.0 Hz, 1H), 7.13-7.09 (m, 1H), 7.02-6.63 (m, 1H), 5.50 (d, J=2.3 Hz, 1H), 5.16 (s, 2H), 3.92 (s, 3H). [M+H]=347.37.

Example 234

4-Chloro-1-{[5-(3-chlorophenyl)-6-ethoxypyridin-3-yl]methyl}-1H-pyrazol-3-amine

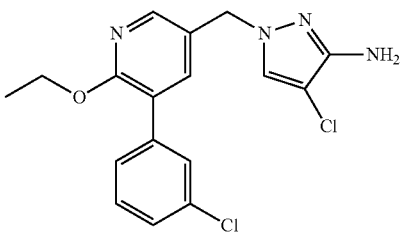 [SMILES: CCOc1ncc(Cn2cc(Cl)c(N)n2)cc1-c1cccc(Cl)c1]

¹H NMR (400 MHz, CD₃OD) δ 8.05 (d, J=2.7 Hz, 1H), 7.62 (d, J=2.3 Hz, 1H), 7.59-7.56 (m, 2H), 7.48-7.44 (m, 1H), 7.41-7.32 (m, 2H), 5.06 (s, 2H), 4.40 (q, J=7.0 Hz, 2H), 1.38-1.30 (t, J=7.0 Hz, 3H). [M+H]=363.30.

Example 235

4-Chloro-1-{[5-(3-chlorophenyl)-6-ethoxypyridin-3-yl]methyl}-1H-pyrazol-5-amine

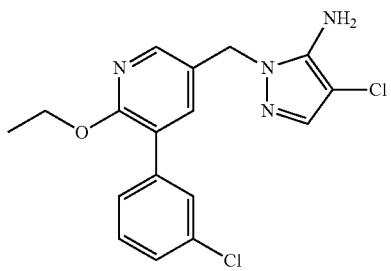 [SMILES: CCOc1ncc(Cn2ncc(Cl)c2N)cc1-c1cccc(Cl)c1]

¹H NMR (400 MHz, CD₃OD) δ 7.99 (d, J=2.3 Hz, 1H), 7.60-7.55 (m, 2H), 7.47-7.43 (m, 1H), 7.41-7.32 (m, 2H), 7.25 (s, 1H), 5.16 (s, 2H), 4.39 (q, J=7.4 Hz, 2H), 1.34 (t, J=7.0 Hz, 4H). [M+H]=363.30.

Example 236

1-{[6-(3-Chlorophenyl)-5-methoxypyrazin-2-yl]methyl}-1H-pyrazol-4-amine

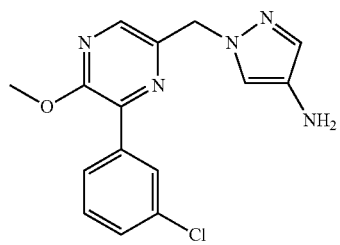 [SMILES: COc1ncc(Cn2cc(N)cn2)nc1-c1cccc(Cl)c1]

The title compound was prepared in a manner analogous to Example 217, two products were formed. ¹H NMR (400 MHz, CD₃OD) δ 8.14 (s, 1H), 8.07 (s, 1H), 8.03 (s, 1H), 7.98 (d, J=4.30 Hz, 1H), 7.61 (s, 1H), 7.47-7.39 (m, 2H), 5.49 (s, 2H), 4.06 (s, 3H). [M+H]=316.10.

Example 237

1-((6-(3-(Difluoromethoxy)phenyl)-5-ethoxypyrazin-2-yl)methyl)-1H-1,2,4-triazol-3-amine

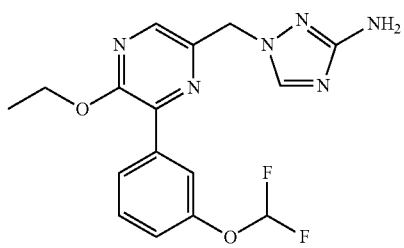 [SMILES: CCOc1ncc(Cn2cnc(N)n2)nc1-c1cccc(OC(F)F)c1]

¹H NMR (400 MHz, CD₃OD) δ 8.64-8.50 (m, 1H), 8.18 (s, 1H), 7.93 (td, J=1.4, 7.8 Hz, 1H), 7.86 (t, J=2.0 Hz, 1H), 7.46 (t, J=8.0 Hz, 1H), 7.20 (dd, J=2.0, 8.2 Hz, 1H), 7.05-6.60 (m, 1H), 5.52 (s, 2H), 4.51 (q, J=7.3 Hz, 2H), 1.44 (t, J=7.0 Hz, 3H). [M+H]=363.14.

Example 238

1-{[5-(3-Chlorophenyl)-6-(difluoromethoxy)pyridin-3-yl]methyl}-N-methyl 1H-1,2,4-triazol-3-amine

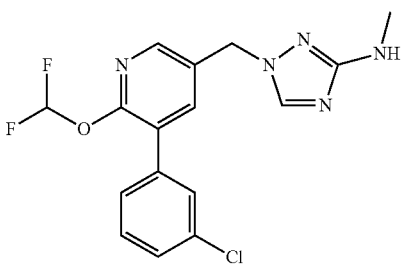 [SMILES: CNc1ncn(Cc2cnc(OC(F)F)c(-c3cccc(Cl)c3)c2)n1]

To a solution of 1-((5-(3-chlorophenyl)-6-(difluoromethoxy)pyridin-3-yl)methyl)-1H-1,2,4-triazol-3-amine (Example 219, 120 mg, 0.34 mmol) in DCM (2 mL), was added formaldehyde (26 μL of 37 wt % solution, 0.35 mmol), sodium triacetoxyborohydride (145 mg, 0.68 mmol) and a few drops of AcOH. The mixture was stirred at room temperature for 16 h. Purification by reverse-phase PREP-HPLC gave the title compound (25 mg, 20%). ¹H NMR (400 MHz, CD₃OD) δ 8.19-8.11 (m, 1H), 7.82 (d, J=2.0 Hz, 1H), 7.71 (s, 1H), 7.53 (s, 1H), 7.47 (s, 1H), 7.41-7.28 (m, 3H), 5.21 (s, 2H), 2.72 (s, 3H). [M+H]=366.21.

Example 239

1-{[5-(3-Chlorophenyl)-6-(difluoromethoxy)pyridin-3-yl]methyl}-N,N-dimethyl-1H-1,2,4-triazol-3-amine

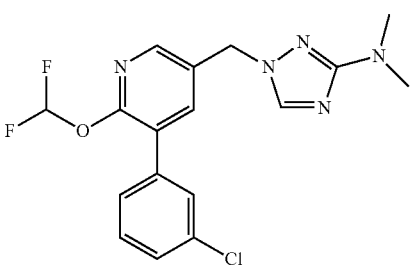 [SMILES: CN(C)c1ncn(Cc2cnc(OC(F)F)c(-c3cccc(Cl)c3)c2)n1]

Prepared as a product of the reaction from procedure as Example 238. Purification by reverse-phase PREP-HPLC gave the title compound (41 mg, 32%). ¹H NMR (400 MHz, CD₃OD) δ 8.57 (s, 1H), 8.25 (d, J=2.0 Hz, 1H), 7.93 (d, J=2.3

Hz, 1H), 7.84-7.61 (m, 1H), 7.57 (s, 1H), 7.50-7.39 (m, 3H), 5.32 (s, 2H), 2.96 (s, 6H). [M+H]=380.24.

Example 240

(1-{[5-(3-Chlorophenyl)-6-(difluoromethoxy)pyridin-3-yl]methyl}-1H-1,2,4-triazol-3-yl)methanamine

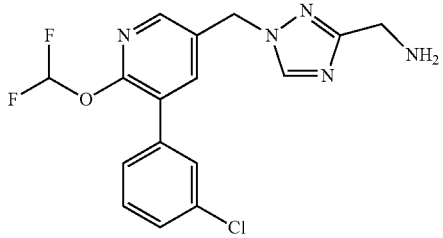 [SMILES: NCc1ncn(Cc2cnc(OC(F)F)c(-c3cccc(Cl)c3)c2)n1]

To a cooled solution, −78° C., of 1-((5-(3-chlorophenyl)-6-(difluoromethoxy)pyridin-3-yl)methyl)-1H-1,2,4-triazole-3-carbonitrile (Example 156, 345 mg, 0.95 mmol) in DCM (5 mL) was slowly added diisobutylaluminum hydride (135.64 mg, 0.95 mmol). The mixture was stirred at −78° C. for 1 h. The reaction was quenched with wet sodium sulphate and stirred at room temperature for 30 min. The white aluminum precipitate was filtered and the filtrate concentrated under reduced pressure. Purification (FCC, SiO$_2$, 40-100% EtOAc/DCM, followed by 0-10% MeOH/DCM) afforded the title compound (37 mg, 10%). $^1$H NMR (400 MHz, CD$_3$OD) δ 8.54 (s, 1H), 8.25 (d, J=2.3 Hz, 1H), 7.92 (d, J=2.3 Hz, 1H), 7.81-7.40 (m, 5H), 5.45 (s, 2H), 3.85-3.82 (m, 2H). [M+H]=366.20.

Example 241

1-{[5-(3-Chlorophenyl)-6-methoxypyridin-3-yl]methyl}-1H-1,2,4-triazole-3-carboxamide

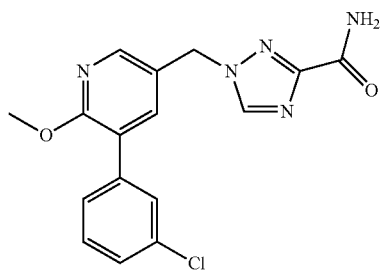 [SMILES: COc1ncc(Cn2cnc(C(N)=O)n2)cc1-c1cccc(Cl)c1]

To a solution of methyl 1-((5-(3-chlorophenyl)-6-methoxypyridin-3-yl)methyl)-1H-1,2,4-triazole-3-carboxylate (Example 141, 103 mg, 0.28 mmol) in methanol (2 mL) was added ammonia in methanol (2 mL of 7N solution, 14 mmol). The mixture was heated using microwave irradiation at 130° C. for 20 min. The LC/MS showed incomplete conversion. To the reaction mixture was added more ammonia in methanol (2 mL, 14 mmol) and irradiated in a microwave at 120° C. for an additional 20 min. The solvent was removed under reduced pressure. Purification (FCC, SiO$_2$, 0-5% MeOH/DCM) afforded the title compound (77 mg, 77%). $^1$H NMR (400 MHz, DMSO-d$_6$) δ 8.74 (s, 1H), 8.25 (d, J=2.3 Hz, 1H), 7.85 (d, J=2.3 Hz, 1H), 7.78-7.70 (m, 1H), 7.62-7.40 (m, 5H), 5.45 (s, 2H), 3.87 (s, 3H). [M+H]=354.18.

Example 242

2-Methoxy-3-(1H-pyrazol-4-yl)-5-(1H-1,2,4-triazol-1-ylmethyl)pyridine

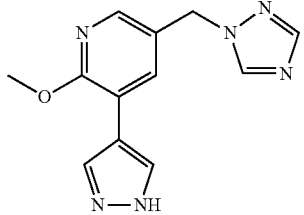 [SMILES: COc1ncc(Cn2cncn2)cc1-c1cn[nH]c1]

The title compound was prepared in a manner analogous to Example 4, from Intermediate 13 and the appropriate pyrazole boronic acid. $^1$H NMR (400 MHz, DMSO-d$_6$) δ 8.69 (s, 1H), 8.07 (s, 1H), 8.01 (q, J=2.3 Hz, 2H), 7.99 (s, 1H), 5.37 (s, 1H), 3.94 (s, 3H), 2.52 (s, 1H). [M+H]=257.26.

Examples 243-246 were prepared in a manner analogous to Example 90, with the appropriate starting materials and reagent substitutions.

Example 243

4-{[5-(3-Chlorophenyl)-6-methoxypyridin-3-yl]methyl}-N-(oxetan-3-yl)benzamide

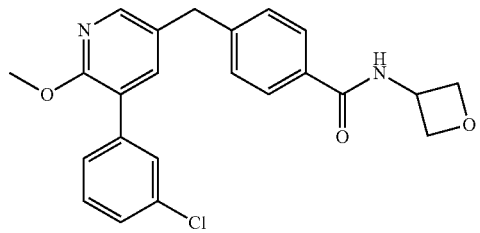 [SMILES: COc1ncc(Cc2ccc(C(=O)NC3COC3)cc2)cc1-c1cccc(Cl)c1]

$^1$H NMR (400 MHz, CD$_3$OD) δ 7.94 (d, J=2.3 Hz, 1H), 7.71 (d, J=8.2 Hz, 2H), 7.47-7.39 (m, 2H), 7.34-7.19 (m, 5H), 5.07-4.97 (m, 1H), 4.81 (d, J=7.4 Hz, 2H), 4.60 (t, J=6.5 Hz, 2H), 3.94 (s, 2H), 3.83 (s, 3H). [M+H]=409.24.

Example 244

5-{[5-(3-Chlorophenyl)-6-(difluoromethoxy)pyridin-3-yl]methyl}-N-methylpyridine-2-carboxamide

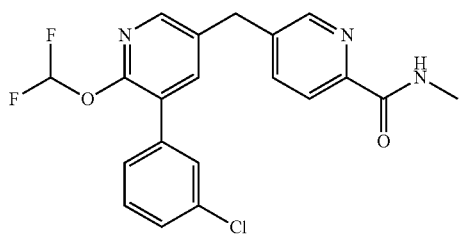 [SMILES: CNC(=O)c1ccc(Cc2cnc(OC(F)F)c(-c3cccc(Cl)c3)c2)cn1]

The title compound was prepared in a manner analogous to Example 90 with the appropriate starting material substitutions. $^1$H NMR (400 MHz, CD$_3$OD) δ 8.57 (d, J=1.6 Hz, 1H), 8.14 (d, J=2.0 Hz, 1H), 8.01 (d, J=7.8 Hz, 1H), 7.83 (dd, J=2.0, 8.2 Hz, 1H), 7.78 (d, J=2.3 Hz, 1H), 7.59 (s, 1H), 7.54 (s, 1H), 7.47-7.38 (m, 3H), 4.15 (s, 2H), 2.94 (s, 3H). [M+H]=404.17.

Example 245

1-(4-{[5-(3-Chlorophenyl)-6-(difluoromethoxy)pyridin-3-yl]methyl}phenyl)cyclopropane-1-carboxamide

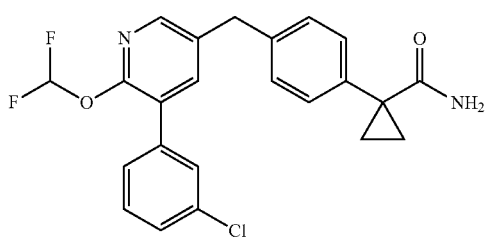 [SMILES: NC(=O)C1(c2ccc(Cc3cnc(OC(F)F)c(-c4cccc(Cl)c4)c3)cc2)CC1]

$^1$H NMR (400 MHz, CD$_3$OD) δ 8.10 (d, J=2.35 Hz, 1H), 7.76 (s, 1H), 7.73 (d, J=2.35 Hz, 1H), 7.58 (s, 1H), 7.53-7.49 (m, 1H), 7.46-7.30 (m, 4H), 7.30-7.21 (m, 2H), 4.04 (s, 2H), 1.47 (q, J=3.65 Hz, 1H), 1.09-1.00 (m, 2H) 0.90-0.80 (m, 2H). [M+H]=429.10.

Example 246

2-(4-{[5-(3-Chlorophenyl)-6-(difluoromethoxy)pyridin-3-yl]methyl}phenyl)acetamide

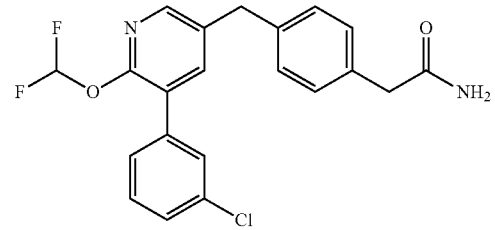 [SMILES: NC(=O)Cc1ccc(Cc2cnc(OC(F)F)c(-c3cccc(Cl)c3)c2)cc1]

$^1$H NMR (400 MHz, CD$_3$OD) δ 8.08 (d, J=2.35 Hz, 1H), 7.76 (s, 1H), 7.67 (d, J=2.35 Hz, 1H), 7.57 (s, 1H), 7.50 (m, 1H), 7.34-7.44 (m, 2H), 7.17-7.28 (m, 4H), 4.01 (s, 2H), 3.47 (s, 2H). [M+H]=403.29.

Example 247

2-(1-{[5-(3-Chlorophenyl)-6-methoxypyridin-3-yl]methyl}-1H-1,2,4-triazol-3-yl)propan-2-ol

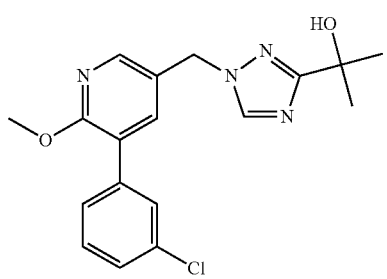 [SMILES: COc1ncc(Cn2cnc(C(C)(C)O)n2)cc1-c1cccc(Cl)c1]

To a solution of 1-((5-(3-chlorophenyl)-6-methoxypyridin-3-yl)methyl)-1H-1,2,4-triazole-3-carboxylate (Example 141, 104 mg, 0.28 mmol) in DCM (2 mL) was added methylmagnesium bromide in diethyl ether (0.28 mL of 3M solution, 0.84 mmol). The mixture was stirred at room temperature for 20 min. The mixture was carefully quenched with wet sodium sulfate, diluted with DCM, filtered and concentrated under reduced pressure. Purification (FCC, SiO$_2$, 50-100% EtOAc/hexanes) afforded the title compound (67 mg, 67%). $^1$H NMR (400 MHz, CDCl$_3$) δ 8.15 (d, J=2.0 Hz, 1H), 8.00 (s, 1H), 7.59-7.48 (m, 2H), 7.42-7.31 (m, 3H), 5.28 (s, 2H), 3.98 (s, 3H), 3.70 (s, 1H), 1.62 (s, 6H). [M+H]=359.09.

Example 248

2-Methoxy-3-(1-methyl-1H-pyrazol-4-yl)-5-(1H-1,2,4-triazol-1-ylmethyl)pyridine

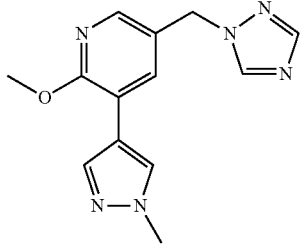 [SMILES: COc1ncc(Cn2cncn2)cc1-c1cnn(C)c1]

The title compound was prepared in a manner analogous to Example 4, from Intermediate 13 and the appropriate pyrazole boronic acid. (400 MHz, DMSO-$d_6$) δ 8.67 (s, 1H), 8.14 (s, 1H), 8.01 (d, J=2.0 Hz, 1H), 7.98 (d, J=2.7 Hz, 2H), 7.90 (s, 1H), 5.37 (s, 2H), 3.94 (s, 3H), 3.86 (s, 3H). [M+H]=271.15.

Examples 249-252 were prepared in a manner analogous to Example 247, with the appropriate starting materials and reagent substitutions.

Example 249

2-(1-{[5-(3-Chlorophenyl)-6-methoxypyridin-3-yl]methyl}-1H-1,2,4-triazol-5-yl)propan-2-ol

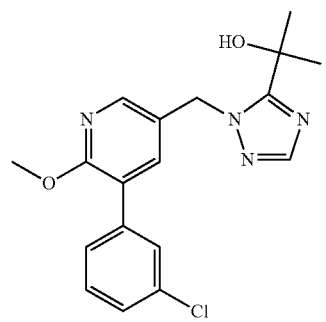 [SMILES: COc1ncc(Cn2ncnc2C(C)(C)O)cc1-c1cccc(Cl)c1]

$^1$H NMR (400 MHz, CDCl$_3$) δ 8.15 (d, J=2.0 Hz, 1H), 7.79 (s, 1H), 7.64 (d, J=2.0 Hz, 1H), 7.51 (s, 1H), 7.41-7.29 (m, 3H), 5.63 (s, 2H), 3.96 (s, 3H), 2.11 (s, 1H), 1.70 (s, 6H). [M+H]=359.09.

Example 250

2-(4-{[5-(3-Chlorophenyl)-6-methoxypyridin-3-yl]methyl}phenyl)propan-2-ol

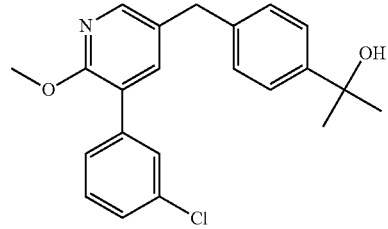

$^1$H NMR (400 MHz, CD$_3$OD) δ 7.99 (d, J=2.0 Hz, 1H), 7.49 (d, J=1.6 Hz, 2H), 7.45-7.27 (m, 5H), 7.19 (d, J=8.2 Hz, 2H), 3.94 (s, 2H), 3.65 (s, 3H), 1.50 (s, 6H). [M+H]=368.23.

Example 251

2-(5-{[5-(3-Chlorophenyl)-6-methoxypyridin-3-yl]methyl}pyridin-2-yl)propan-2-ol

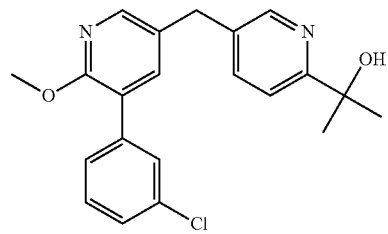 [SMILES: COc1ncc(Cc2ccc(C(C)(C)O)cc2)cc1-c1cccc(Cl)c1]

$^1$H NMR (400 MHz, CD$_3$OD) δ 8.39 (s, 1H), 8.04 (d, J=2.0 Hz, 1H), 7.70-7.58 (m, 2H), 7.57-7.48 (m, 2H), 7.43-7.28 (m, 3H), 3.99 (s, 2H), 3.92 (s, 3H), 1.51 (s, 6H). [M+H]=369.23.

Example 252

2-(5-{[5-(3-Chlorophenyl)-6-(difluoromethoxy)pyridin-3-yl]methyl}pyridin-2-yl)propan-2-ol

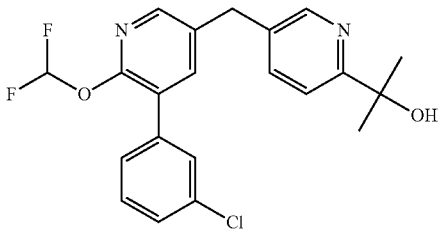 [SMILES: CC(C)(O)c1ccc(Cc2cnc(OC(F)F)c(-c3cccc(Cl)c3)c2)cn1]

¹H NMR (400 MHz, CD₃OD) δ 8.41 (d, J=2.0 Hz, 1H), 8.12 (d, J=2.3 Hz, 1H), 7.78-7.57 (m, 4H), 7.52 (d, J=1.6 Hz, 1H), 7.46-7.36 (m, 3H), 4.07 (s, 2H), 1.51 (s, 6H). [M+H]=405.22.

Example 253

3-[3-(Difluoromethoxy)phenyl]-5-{[3-(fluoromethyl)-1H-1,2,4-triazol-1-yl]methyl}-2-methoxypyridine

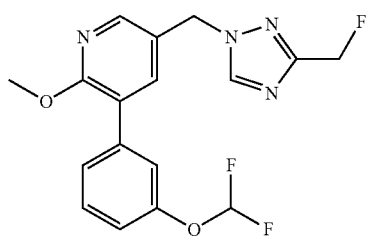 [SMILES: COc1ncc(Cn2cnc(CF)n2)cc1-c1cccc(OC(F)F)c1]

To a solution of (1-((5-(3-(difluoromethoxy)phenyl)-6-methoxypyridin-3-yl)methyl)-1H-1,2,4-triazol-3-yl)methanol (Example 202, 40.0 mg, 0.11 mmol) in DCM (3 mL) was added Deoxo-Fluor® (36.64 mg, 0.17 mmol). The mixture was stirred at room temperature for 2 h. The material was adsorbed on silica and purified (FCC, SiO₂, 20-100% EtOAc/hexanes) to afford the title compound (11 mg, 27%). ¹H NMR (400 MHz, CD₃OD) δ 8.61 (s, 1H), 8.21 (d, J=2.3 Hz, 1H), 7.77 (d, J=2.3 Hz, 1H), 7.49-7.36 (m, 2H), 7.33 (t, J=2.2 Hz, 1H), 7.16-7.11 (m, 1H), 7.04-6.65 (m, 1H), 5.44 (s, 2H), 5.41-5.28 (m, 2H), 3.96 (s, 3H). [M+H]=365.21.

Examples 254-258 were prepared in a manner analogous to Example 253, with the appropriate starting materials and reagent substitutions.

Example 254

3-[3-(Difluoromethoxy)phenyl]-2-ethoxy-5-{[4-(fluoromethyl)-1H-1,2,3-triazol-1-yl]methyl}pyridine

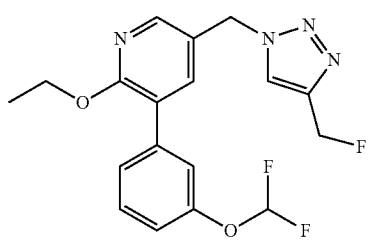 [SMILES: CCOc1ncc(Cn2cc(CF)nn2)cc1-c1cccc(OC(F)F)c1]

¹H NMR (400 MHz, CD₃OD) δ 8.23-8.18 (m, 2H), 7.76 (d, J=2.3 Hz, 1H), 7.48-7.36 (m, 3H), 7.17-7.11 (m, 1H), 7.03-6.65 (m, 1H), 5.64 (s, 2H), 5.42 (d, J=48 Hz, 2H), 4.42 (q, J=7.0 Hz, 2H), 1.35 (t, J=7.2 Hz, 3H). [M+H]=379.23.

Example 255

2-(Difluoromethoxy)-3-(3-ethoxyphenyl)-5-{[3-(fluoromethyl)-1H-1,2,4-triazol-1-yl]methyl}pyridine

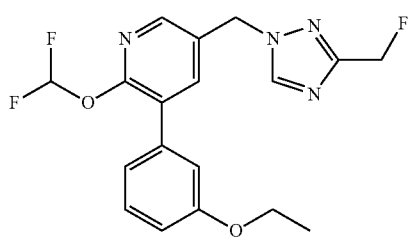 [SMILES: CCOc1cccc(-c2cc(Cn3cnc(CF)n3)cnc2OC(F)F)c1]

¹H NMR (400 MHz, CD₃OD) δ 8.63 (s, 1H), 8.23 (d, J=2.3 Hz, 1H), 7.90 (d, J=2.3 Hz, 1H), 7.81-7.42 (m, 1H), 7.38-7.31 (m, 1H), 7.10-7.03 (m, 2H), 6.96 (ddd, J=1.0, 2.5, 8.2 Hz, 1H), 5.53-5.27 (m, 4H), 4.16-4.00 (q, J=7.0 Hz, 2H), 1.47-1.35 (t, J=7.0 Hz, 3H). [M+H]=379.27.

Example 256

3-[2-(Difluoromethoxy)pyridin-4-yl]-5-{[3-(fluoromethyl)-1H-1,2,4-triazol-1-yl]methyl}-2-methoxypyridine

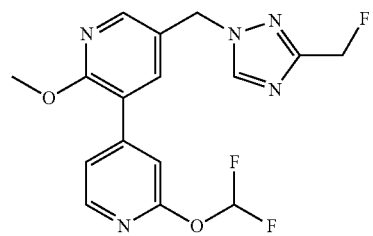 [SMILES: COc1ncc(Cn2cnc(CF)n2)cc1-c1ccnc(OC(F)F)c1]

¹H NMR (400 MHz, CD₃OD) δ 8.61 (s, 1H), 8.29 (d, J=2.3 Hz, 1H), 8.26-8.21 (m, 1H), 7.90 (d, J=2.3 Hz, 1H), 7.76-7.39 (m, 2H), 7.19 (dd, J=0.8, 1.6 Hz, 1H), 5.48-5.27 (m, 4H), 4.00 (s, 3H). [M+H]=366.23.

Example 257

3-[3-(Difluoromethoxy)phenyl]-2-ethoxy-5-{[3-(fluoromethyl)-1H-1,2,4-triazol-1-yl]methyl}pyrazine

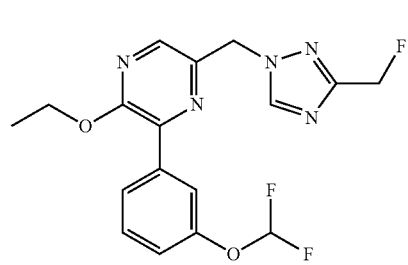 [SMILES: CCOc1ncc(Cn2cnc(CF)n2)nc1-c1cccc(OC(F)F)c1]

¹H NMR (400 MHz, CD₃OD) δ 8.77-8.66 (m, 1H), 8.24 (s, 1H), 8.03-7.92 (m, 1H), 7.87 (d, J=10.6 Hz, 1H), 7.57-7.41 (m, 1H), 7.25 (dd, J=2.7, 8.2 Hz, 1H), 7.17-6.71 (m, 1H), 5.61 (s, 2H), 5.58-5.54 (m, 1H), 5.45-5.29 (m, 1H), 4.61-4.47 (m, 2H), 1.52-1.43 (m, 3H). [M+H]=380.13.

Example 258

3-(3-Chlorophenyl)-5-{[3-(fluoromethyl)-1H-1,2,4-triazol-1-yl]methyl}-2-methoxypyrazine

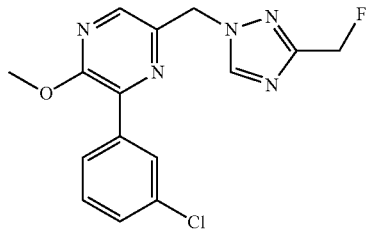 [SMILES: COc1ncc(Cn2cnc(CF)n2)nc1-c1cccc(Cl)c1]

¹H NMR (400 MHz, DMSO-d₆) δ 8.76 (s, 1H), 8.31 (s, 1H), 8.00-7.86 (m, 2H), 7.58-7.45 (m, 2H), 5.58 (s, 2H), 5.38 (s, 1H), 5.26 (s, 1H), 3.99 (s, 3H). [M+H]=334.16.

Example 259

3-(3-Chlorophenyl)-2-(difluoromethoxy)-5-{[3-(difluoromethyl)-1H-1,2,4-triazol-1-yl]methyl}pyridine

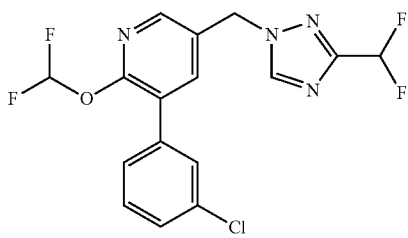 [SMILES: FC(F)Oc1ncc(Cn2cnc(C(F)F)n2)cc1-c1cccc(Cl)c1]

Step 1. Methyl 1-((5-(3-chlorophenyl)-6-(difluoromethoxy)pyridin-3-yl)methyl)-1H-1,2,4-triazole-3-carboxylate. The title compound was prepared in a manner analogous to Example 127 with the appropriate starting material substitutions.

Step 2. 1-((5-(3-Chlorophenyl)-6-(difluoromethoxy)pyridin-3-yl)methyl)-1H-1,2,4-triazole-3-carbaldehyde. To a cooled solution, −78° C., of methyl 1-((5-(3-chlorophenyl)-6-(difluoromethoxy)pyridin-3-yl)methyl)-1H-1,2,4-triazole-3-carboxylate (146 mg, 0.37 mmol) in DCM (5 mL) was added diisobutylaluminum hydride (52.6 mg, 0.37 mmol) slowly. The mixture was stirred at −78° C. for 1 h. The reaction was quenched with wet sodium sulphate and stirred at room temperature for 30 min. The white aluminum salt precipitate obtained was filtered and (the filtrate) concentrated under reduced pressure. The crude product was purified (FCC, SiO₂, 40-100% EtOAc/DCM followed by 0-5% MeOH/DCM) to afford the title compound (69 mg; 51%).

Step 3. 3-(3-Chlorophenyl)-2-(difluoromethoxy)-5-{[3-(difluoromethyl)-1H-1,2,4-triazol-1-yl]methyl}pyridine. To a solution of ((5-(3-chlorophenyl)-6-(difluoromethoxy)pyridin-3-yl)methyl)-1H-1,2,4-triazole-3-carbaldehyde (69 mg, 0.19 mmol) in DCM (5 mL) was added Deoxo-Fluor® (104.6 mg, 0.47 mmol). The mixture was stirred at room temperature for 16 h. The LC/MS suggested the presence of the title compound. The material was adsorbed on silica and purified (FCC, SiO₂, 10-100% EtOAc/hexanes) to afford the title compound (13 mg, 18%). ¹H NMR (400 MHz, CD₃OD) δ 8.69 (s, 1H), 8.28 (d, J=2.3 Hz, 1H), 7.95 (d, J=2.3 Hz, 1H), 7.81-7.39 (m, 5H), 6.94-6.65 (m, 1H), 5.54 (s, 2H). [M+H]=387.17.

Examples 260-261 were prepared in a manner analogous to Example 259, with the appropriate starting materials and reagent substitutions.

Example 260

3-[3-(Difluoromethoxy)phenyl]-5-{[3-(difluoromethyl)-1H-1,2,4-triazol-1-yl]methyl}-2-ethoxypyridine

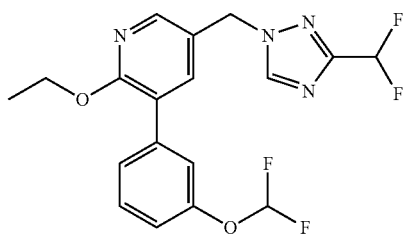 [SMILES: CCOc1ncc(Cn2cnc(C(F)F)n2)cc1-c1cccc(OC(F)F)c1]

¹H NMR (400 MHz, CD₃OD) δ 8.67 (s, 1H), 8.20 (d, J=2.3 Hz, 1H), 7.79 (d, J=2.3 Hz, 1H), 7.51-7.35 (m, 3H), 7.18-7.10 (m, 1H), 7.04-6.63 (m, 2H), 5.47 (s, 2H), 4.42 (q, J=7.0 Hz, 2H), 1.35 (t, J=7.0 Hz, 3H). [M+H]=397.24.

Example 261

3-[2-(Difluoromethoxy)pyridin-4-yl]-5-{[3-(difluoromethyl)-1H-1,2,4-triazol-1-yl]methyl}-2-methoxypyridine

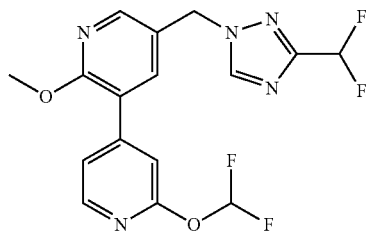 [SMILES: COc1ncc(Cn2cnc(C(F)F)n2)cc1-c1ccnc(OC(F)F)c1]

¹H NMR (400 MHz, CD₃OD) δ 8.67 (s, 1H), 8.30 (d, J=2.3 Hz, 1H), 8.23 (d, J=5.1 Hz, 1H), 7.92 (d, J=2.3 Hz, 1H), 7.77-7.55 (m, 1H), 7.41-7.39 (m, 1H), 7.21-7.17 (m, 1H), 6.95-6.63 (m, 1H), 5.49 (s, 2H), 3.99 (s, 3H). [M+H]=384.21.

Example 262

3-(3-Chlorophenyl)-2-methoxy-5-(1H-1,2,3-triazol-1-ylmethyl)pyridine

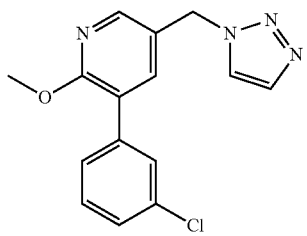 [SMILES: COc1ncc(Cn2ccnn2)cc1-c1cccc(Cl)c1]

Step 1. 5-(Azidomethyl)-3-(3-chlorophenyl)-2-methoxypyridine. To a solution of 5-(bromomethyl)-3-(3-chlorophenyl)-2-methoxypyridine (Intermediate 2, 160 mg, 0.51 mmol) in DMF (5 mL) was added sodium azide (0.05 g, 0.77 mmol) and potassium carbonate (0.14 g, 1.02 mmol). The mixture was stirred at room temperature for 16 h. The mixture was diluted with a saturated aqueous solution of sodium chloride and extracted into diethyl ether. All solvents were removed under reduced pressure to affore the title compound, which was used in the next step without further purification.

Step 2. 3-(3-Chlorophenyl)-2-methoxy-5-((4-(trimethylsilyl)-1H-1,2,3-triazol-1-yl)methyl)pyridine. To a solution of 5-(azidomethyl)-3-(3-chlorophenyl)-2-methoxypyridine (directly used from previous reaction) and ethynyltrimethylsilane (75.1 mg, 0.77 mmol) in THF (3 mL), water (1 mL), was added copper (I) iodide (19.4 mg, 0.10 mmol) and diisopropylethylamine (132 mg, 1.02 mmol). The mixture was stirred at room temperature for 2 h. The mixture was diluted with water and extracted in to DCM. The organic layers were combined, dried (Na₂SO₄), filtered and concentrated under reduced pressure. Purification (FCC, SiO₂, 0-50% EtOAc/hexanes) afforded the title compound (92 mg, 48%). [M+H]=373.2.

Step 3. 3-(3-Chlorophenyl)-2-methoxy-5-(1H-1,2,3-triazol-1-ylmethyl)pyridine. To a solution of 3-(3-chlorophenyl)-2-methoxy-5-((4-(trimethylsilyl)-1H-1,2,3-triazol-1-yl)methyl)pyridine (92.0 mg, 0.25 mmol) in THF (3 mL) was added tetrabutylammonium fluoride (129 mg, 0.49 mmol). The mixture was stirred at room temperature for 16 h. The mixture was diluted with water and extracted in to DCM. The DCM extracts were combined, dried (Na₂SO₄), filtered and concentrated under reduced pressure. Purification (FCC, SiO₂, 0-80% EtOAc/DCM) afforded the title compound (44 mg, 59%). ¹H NMR (400 MHz, CD₃OD) δ 8.10 (br s, 1H), 7.95 (s, 1H), 7.65-7.59 (m, 2H), 7.42 (br s, 1H), 7.35-7.21 (m, 3H), 5.54 (s, 2H), 3.85 (s, 3H). [M+H]=301.17.

Examples 263-268 were prepared in a manner analogous to Example 262, with the appropriate starting materials and reagent substitutions.

Example 263

[1-({5-[3-(Difluoromethoxy)phenyl]-6-ethoxypyridin-3-yl}methyl)-1H-1,2,3-triazol-4-yl]methanol

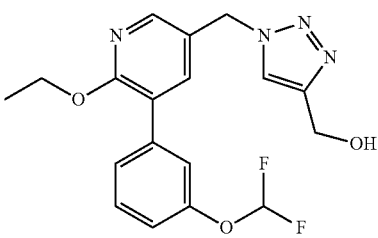 [SMILES: CCOc1ncc(Cn2cc(CO)nn2)cc1-c1cccc(OC(F)F)c1]

¹H NMR (400 MHz, CD₃OD) δ 8.19 (d, J=2.7 Hz, 1H), 7.98 (s, 1H), 7.74 (d, J=2.3 Hz, 1H), 7.47-7.35 (m, 3H), 7.14 (dd, J=1.2, 2.0 Hz, 1H), 7.03-6.64 (m, 1H), 5.60 (s, 2H), 4.73-4.60 (m, 2H), 4.41 (d, J=7.0 Hz, 2H), 1.34 (t, J=7.0 Hz, 3H). [M+H]=377.25.

Example 264

(1-((6-(Difluoromethoxy)-5-(3-ethoxyphenyl)pyridin-3-yl)methyl)-1H-1,2,3-triazol-4-yl)methanol

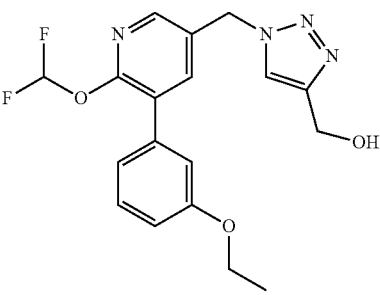 [SMILES: CCOc1cccc(-c2cc(Cn3cc(CO)nn3)cnc2OC(F)F)c1]

¹H NMR (400 MHz, CD₃OD) δ 8.23 (d, J=2.3 Hz, 1H), 8.00 (s, 1H), 7.86 (d, J=2.3 Hz, 1H), 7.61 (t, J=1.0 Hz, 1H), 7.37-7.31 (m, 1H), 7.05 (ddd, J=1.2, 2.5, 3.7 Hz, 2H), 6.95

(ddd, J=1.0, 2.4, 8.3 Hz, 1H), 5.67 (s, 2H), 4.66 (s, 2H), 4.07 (q, J=6.8 Hz, 2H), 1.40 (t, J=7.0 Hz, 3H). [M+H]=377.25.

Example 265

[1-({6-[3-(Difluoromethoxy)phenyl]-5-ethoxy-pyrazin-2-yl}methyl)-1H-1,2,3-triazol-4-yl]methanol

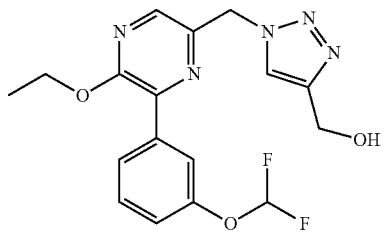 [SMILES: CCOc1ncc(Cn2cc(CO)nn2)nc1-c1cccc(OC(F)F)c1]

$^1$H NMR (400 MHz, CD$_3$OD) δ 8.19 (s, 1H), 8.05 (s, 1H), 7.98-7.93 (m, 1H), 7.88 (t, J=2.0 Hz, 1H), 7.47 (t, J=8.0 Hz, 1H), 7.21 (dd, J=3.5, 8.2 Hz, 1H), 7.05-6.65 (m, 1H), 5.73 (s, 2H), 4.67 (s, 2H), 4.51 (q, J=7.0 Hz, 2H), 1.44 (t, J=7.2 Hz, 3H). [M+H]=378.24.

Example 266

(1-{[6-(3-Chlorophenyl)-5-methoxypyrazin-2-yl]methyl}-1H-1,2,3-triazol-4-yl)methanol

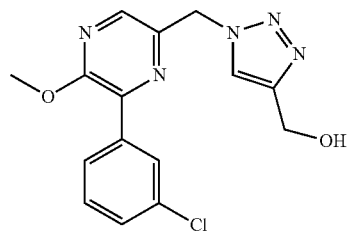 [SMILES: COc1ncc(Cn2cc(CO)nn2)nc1-c1cccc(Cl)c1]

$^1$H NMR (400 MHz, CD$_3$OD) δ 8.22 (s, 1H), 8.06-8.02 (m, 2H), 7.99 (ddd, J=1.6, 3.6, 5.4 Hz, 1H), 7.44-7.40 (m, 2H), 5.74 (s, 2H), 4.67 (s, 2H), 4.06 (s, 3H). [M+H]=332.15.

Example 267

[1-({6-[3-(Difluoromethoxy)phenyl]-5-methoxy-pyrazin-2-yl}methyl)-1H-1,2,3-triazol-4-yl]methanol

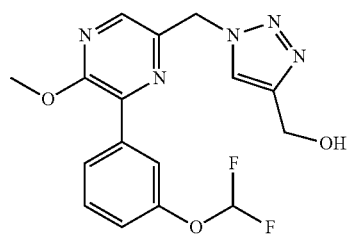 [SMILES: COc1ncc(Cn2cc(CO)nn2)nc1-c1cccc(OC(F)F)c1]

$^1$H NMR (400 MHz, DMSO-d$_6$) δ 8.31-8.29 (m, 1H), 8.05 (s, 1H), 7.88-7.84 (m, 1H), 7.76-7.72 (m, 1H), 7.53 (t, J=8.0 Hz, 1H), 7.45-7.05 (m, 2H), 5.72 (s, 2H), 5.16-5.05 (m, 1H), 4.49 (d, J=5.1 Hz, 2H), 3.98 (s, 3H). [M+H]=364.24.

Example 268

(1-{[6-(3-Chlorophenyl)-5-ethoxypyrazin-2-yl]methyl}-1H-1,2,3-triazol-4-yl)methanol

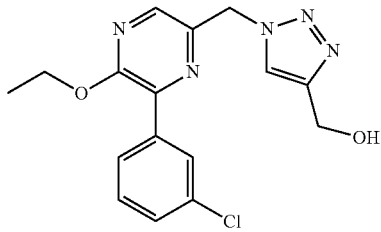 [SMILES: CCOc1ncc(Cn2cc(CO)nn2)nc1-c1cccc(Cl)c1]

$^1$H NMR (400 MHz, DMSO-d$_6$) δ 8.28 (s, 1H), 8.05 (s, 1H), 8.03-8.00 (m, 1H), 7.99-7.94 (m, 1H), 7.53-7.49 (m, 2H), 5.71 (s, 2H), 5.16-5.08 (m, 1H), 4.50-4.41 (m, 4H), 1.39-1.32 (m, 3H). [M+H]=346.18.

Example 269

3-[3-(Difluoromethoxy)phenyl]-5-{[4-(difluoromethyl)-1H-1,2,3-triazol-1-yl]methyl}-2-ethoxypyridine

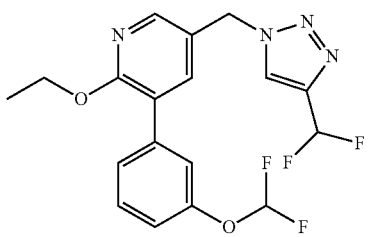 [SMILES: CCOc1ncc(Cn2cc(C(F)F)nn2)cc1-c1cccc(OC(F)F)c1]

Step 1. 1-((5-(3-(Difluoromethoxy)phenyl)-6-ethoxypyridin-3-yl)methyl)-1H-1,2,3-triazole-4-carbaldehyde. To a solution of [1-({5-[3-(difluoromethoxy)phenyl]-6-ethoxypyridin-3-yl}methyl)-1H-1,2,3-triazol-4-yl]methanol (Example 263, 115 mg, 0.31 mmol), in DCM (5 mL) was added Dess-Martin Reagent® (1.22 mL, 0.30 mol/L, 0.37 mmol). The reaction mixture was allowed to stir at room temperature for 3 hr. The reaction was quenched with wet sodium sulphate. The reaction mixture was extracted into DCM, filtered and solvent removed under reduced pressure. Purification (FCC, SiO$_2$, 10-100% EtOAc/hexanes) afforded the title compound (90 mg, 79%).

Step 2. 3-[3-(Difluoromethoxy)phenyl]-5-{[4-(difluoromethyl)-1H-1,2,3-triazol-1-yl]methyl}-2-ethoxypyridine. To a solution of 1-((5-(3-(difluoromethoxy)phenyl)-6-ethoxypyridin-3-yl)methyl)-1H-1,2,3-triazole-4-carbaldehyde (90 mg, 0.24 mmol) in DCM (5 mL) was added Deoxo-Fluor® (133 mg, 0.60 mmol). The mixture was stirred at room temperature for 4 h. The material was adsorbed on silica. Purification (FCC, SiO$_2$, 0-80% EtOAc/hexanes) afforded the title compound (53 mg, 56%). $^1$H NMR (400 MHz, CD$_3$OD) δ 8.36 (t, J=1.4 Hz, 1H), 8.20 (d, J=2.3 Hz, 1H), 7.77 (d, J=2.7

Hz, 1H), 7.47-7.36 (m, 3H), 7.16-7.10 (m, 1H), 7.07-6.63 (m, 2H), 5.66 (s, 2H), 4.41 (q, J=7.0 Hz, 2H), 1.34 (t, J=7.2 Hz, 3H). [M+H]=397.24.

Example 270

1-{[5-(3-Chlorophenyl)-6-methoxypyridin-3-yl]methyl}-1H-pyrazole-4-carboxylic acid

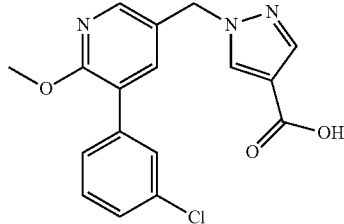 [SMILES: COc1ncc(Cn2cc(C(=O)O)cn2)cc1-c1cccc(Cl)c1]

To a solution of ethyl 1-((5-(3-chlorophenyl)-6-methoxypyridin-3-yl)methyl)-1H-pyrazole-4-carboxylate (Example 169, 25.00 mg, 0.07 mmol) in THF (2 mL), methanol (2 mL) was added lithium hydroxide (1.00 mL, 1.00 mol/L, 1.00 mmol). The mixture was stirred at room temperature for 2 h. The solvents were removed under reduced pressure and the crude residue dissolved in water. The aqueous reaction mixture was acidified with 1 N HCl (5 mL), and extracted into ethyl acetate. The combined organic layers were dried (Na$_2$SO$_4$), filtered and concentrated under reduced pressure to afford the title compound (20 mg, 87%). $^1$H NMR (400 MHz, DMSO-d$_6$) δ 12.30 (br s, 1H), 8.39 (br s, 1H), 8.19 (br s, 1H), 7.80 (br s, 2H), 7.68-7.26 (m, 4H), 5.34 (br s, 2H), 3.87 (br s, 3H). [M+H]=344.31.

Example 271

1-{[5-(3-Chlorophenyl)-6-methoxypyridin-3-yl]methyl}-1H-pyrazole-4-carboxamide

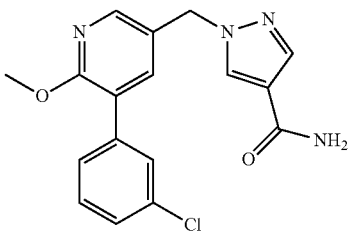 [SMILES: COc1ncc(Cn2cc(C(N)=O)cn2)cc1-c1cccc(Cl)c1]

A solution of 1-((5-(3-chlorophenyl)-6-methoxypyridin-3-yl)methyl)-1H-pyrazole-4-carbonitrile (Example 170, 25.00 mg, 0.08 mmol) in MeOH (1.54 mL) was heated to 50° C., until the starting material dissolved. Sodium hydroxide (0.23 mL, 1.00 mol/L, 0.23 mmol) and hydrogen peroxide (0.23 mL, 1.00 mol/L, 0.23 mmol) were added and the reaction stirred at 50° C. for 2 h. Water was added (5 mL), and the mixture was filtered and washed with water (3×5 mL) to afford the title compound as a solid (25.0 mg, 95%). $^1$H NMR (400 MHz, DMSO-d$_6$) δ 8.20 (d, J=13.69 Hz, 2H), 7.80 (d, J=14.48 Hz, 2H), 7.65-7.37 (m, 5H), 6.95 (br s, 1H), 5.32 (br s, 2H), 3.87 (br s, 3H). [M+H]=343.33.

Example 272

[1-({5-[3-(Difluoromethoxy)phenyl]-6-methoxypyridin-3-yl}methyl)-1H-pyrazol-4-yl]methanol

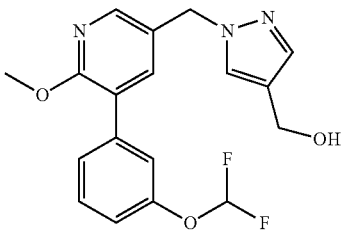 [SMILES: COc1ncc(Cn2cc(CO)cn2)cc1-c1cccc(OC(F)F)c1]

Step 1. 1-((5-(3-(Difluoromethoxy)phenyl)-6-methoxypyridin-3-yl)methyl)-1H-pyrazole-4-carbaldehyde. The title compound was prepared in a manner analogous to Example 127, with the appropriate starting material substitutions.

Step 2. [1-({5-[3-(Difluoromethoxy)phenyl]-6-methoxypyridin-3-yl}methyl)-1H-pyrazol-4-yl]methanol. To a solution of 1-((5-(3-(difluoromethoxy)phenyl)-6-methoxypyridin-3-yl)methyl)-1H-pyrazole-4-carbaldehyde (99 mg, 0.27 mmol) in methanol (5 mL) was added sodium borohydride (14.3 mg, 0.38 mmol). The mixture was stirred at room temperature for 10 min. The mixture was quenched with water (0.5 mL), diluted with DCM (10 mL), dried (Na$_2$SO$_4$), filtered and concentrated under reduced pressure. Purification (FCC, SiO$_2$, 20-100% EtOAc/hexanes) afforded the title compound (100 mg, 100%). $^1$H NMR (400 MHz, CD$_3$OD) δ 8.10 (d, J=2.3 Hz, 1H), 7.74-7.70 (m, 1H), 7.63 (d, J=2.3 Hz, 1H), 7.50 (s, 1H), 7.45-7.34 (m, 2H), 7.30 (t, J=2.3 Hz, 1H), 7.13 (s, 1H), 7.03-6.64 (m, 1H), 5.31 (s, 2H), 4.49 (s, 2H), 3.94 (s, 3H). [M+H]=362.21.

Examples 273-278 were prepared in a manner analogous to Example 272, with the appropriate starting materials and reagent substitutions.

Example 273

(1-{[5-(3-Chlorophenyl)-6-(difluoromethoxy)pyridin-3-yl]methyl}-1H-imidazol-5-yl)methanol

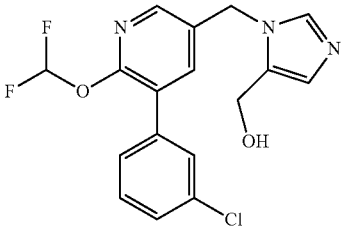 [SMILES: OCc1cncn1Cc1cnc(OC(F)F)c(-c2cccc(Cl)c2)c1]

$^1$H NMR (400 MHz, DMSO-d$_6$) δ 8.08-8.30 (m, 1H), 7.92 (d, J=2.35 Hz, 1H), 7.77 (s, 1H), 7.57-7.62 (m, 1H), 7.43-7.54

(m, 3H), 6.81 (s, 1H), 5.27 (s, 2H), 5.16 (t, J=5.28 Hz, 1H), 4.41 (d, J=5.09 Hz, 2H), 3.49-3.59 (m, 2H). [M+H]=366.20.

Example 274

(1-{[5-(3-Chlorophenyl)-6-(difluoromethoxy)pyridin-3-yl]methyl}-1H-imidazol-4-yl)methanol

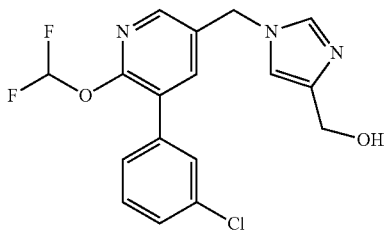 [SMILES: OCc1cn(Cc2cnc(OC(F)F)c(-c3cccc(Cl)c3)c2)cn1]

¹H NMR (400 MHz, DMSO-d₆) δ 8.19-8.40 (m, 1H), 8.05 (d, J=2.35 Hz, 1H), 7.83-7.46 (m, 6H), 7.13 (s, 1H), 5.20 (s, 2H), 4.28 (s, 2H), 3.55 (s, 1H). [M+H]=366.20.

Example 275

[1-({5-[3-(Difluoromethoxy)phenyl]-6-methoxypyridin-3-yl}methyl)-1H-pyrazol-3-yl]methanol

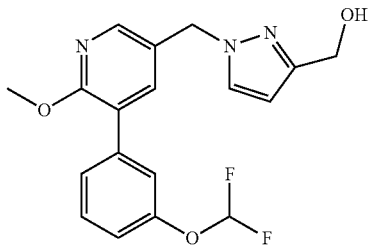 [SMILES: COc1ncc(Cn2ccc(CO)n2)cc1-c1cccc(OC(F)F)c1]

¹H (400 MHz, CD₃OD) δ 8.04 (d, J=2.3 Hz, 1H), 7.47-7.27 (m, 4H), 7.13-7.08 (m, 1H), 7.03-6.63 (m, 1H), 6.29 (d, J=2.0 Hz, 1H), 5.40 (s, 2H), 4.65 (s, 2H), 3.92 (s, 3H). [M+H]=362.17.

Example 276

(1-{[5-(3-Chlorophenyl)-6-ethoxypyridin-3-yl]methyl}-1H-pyrazol-4-yl)methanol

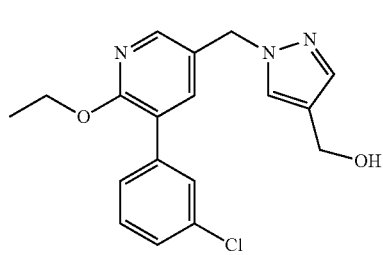 [SMILES: CCOc1ncc(Cn2cc(CO)cn2)cc1-c1cccc(Cl)c1]

¹H NMR (400 MHz, CD₃OD) δ 8.08 (d, J=2.3 Hz, 1H), 7.72 (s, 1H), 7.63 (d, J=2.3 Hz, 1H), 7.55 (t, J=1.6 Hz, 1H), 7.50 (s, 1H), 7.46-7.42 (m, 1H), 7.40-7.31 (m, 2H), 5.30 (s, 2H), 4.49 (s, 2H), 4.39 (q, J=7.0 Hz, 2H), 1.33 (t, J=7.0 Hz, 3H). [M+H]=344.33.

Example 277

(4-Chloro-1-{[5-(3-chlorophenyl)-6-ethoxypyridin-3-yl]methyl}-1H-pyrazol-3-yl)methanol

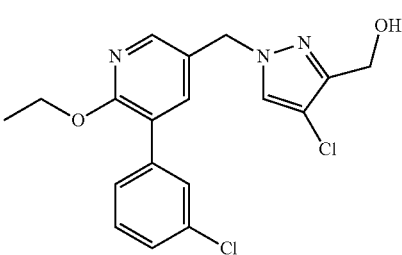 [SMILES: CCOc1ncc(Cn2cc(Cl)c(CO)n2)cc1-c1cccc(Cl)c1]

¹H NMR (400 MHz, CD₃OD) δ 8.10 (d, J=2.3 Hz, 1H), 7.80 (s, 1H), 7.68 (d, J=2.3 Hz, 1H), 7.56 (s, 1H), 7.47-7.43 (m, 1H), 7.40-7.31 (m, 2H), 5.25 (s, 2H), 4.53 (s, 2H), 4.39 (q, J=7.0 Hz, 2H), 1.33 (t, J=7.0 Hz, 3H). [M+H]=378.27.

Example 278

(4-Chloro-1-{[5-(3-chlorophenyl)-6-ethoxypyridin-3-yl]methyl}-1H-pyrazol-5-yl)methanol

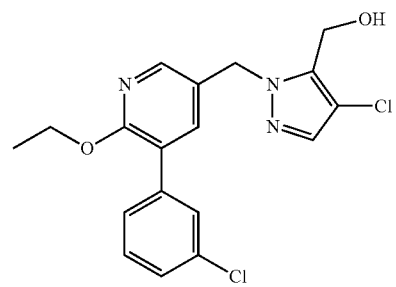 [SMILES: CCOc1ncc(Cn2ncc(Cl)c2CO)cc1-c1cccc(Cl)c1]

¹H NMR (400 MHz, CD₃OD) δ 8.08 (d, J=2.3 Hz, 1H), 7.68 (d, J=2.3 Hz, 1H), 7.56 (s, 1H), 7.47 (s, 1H), 7.46-7.42

(m, 1H), 7.40-7.31 (m, 2H), 5.40 (s, 2H), 4.67 (s, 2H), 4.40 (q, J=7.0 Hz, 2H), 1.33 (t, J=7.0 Hz, 4H). [M+H]=378.27.

Example 279

3-(4-Chloro-1H-pyrazol-1-yl)-2-methoxy-5-(1H-1,2,4-triazol-1-ylmethyl)pyridine

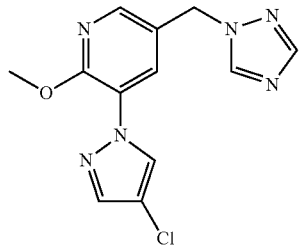 [SMILES: COc1ncc(Cn2cncn2)cc1-n1cc(Cl)cn1]

5-((1H-1,2,4-Triazol-1-yl)methyl)-3-(4-chloro-1H-Pyrazol-1-yl)-2-methoxypyridine. To a solution of 5-((1H-1,2,4-triazol-1-yl)methyl)-3-Bromo-2-methoxypyridine (Intermediate 13), (100 mg, 0.37 mmol), in toluene (5 mL) was added tris(dibenzylideneacetone)dipalladium(0) (34.1 mg, 0.04 mmol), sodium tert-butoxide (71.6 mg, 0.74 mmol), (2-dicyclohexylphosphino-2'-(N,N-dimethylamino)biphenyl (29.3 mgs, 0.07 mmol) and 4-chloro-1H-pyrazole (37.3 mg, 0.37 mmol). The mixture was heated at 100° C. for 30 min. The mixture was quenched with water (0.5 mL), diluted with ethyl acetate (10 mL), dried (Na$_2$SO$_4$), filtered and concentrated under reduced pressure. Purification (FCC, SiO$_2$, 20-100% EtOAc/hexanes) afforded the title compound (50 mg, 46%). $^1$H NMR (400 MHz, DMSO-d$_6$) δ 8.69 (s, 1H), 8.07 (s, 2H), 8.01 (q, J=2.3 Hz, 2H), 7.99 (s, 1H), 5.37 (s, 2H), 3.94 (s, 3H), 2.52 (s, 1H). [M+H]=292.12.

Example 280

4-{[5-(3-Chlorophenyl)-6-(difluoromethoxy)pyridin-3-yl]methyl}benzoic acid

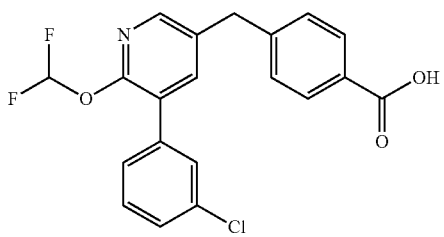 [SMILES: O=C(O)c1ccc(Cc2cnc(OC(F)F)c(-c3cccc(Cl)c3)c2)cc1]

The title compound was prepared in a manner analogous to Example 21, with the appropriated starting material and reagent substitutions. $^1$H NMR (400 MHz, CD$_3$OD) δ 8.01 (d, J=2.3 Hz, 1H), 7.87 (d, J=8.2 Hz, 2H), 7.63 (d, J=2.3 Hz, 1H), 7.49 (s, 1H), 7.43 (s, 1H), 7.35-7.24 (m, 5H), 4.01 (s, 2H). [M+H]=390.09.

PHARMACOLOGICAL EXAMPLES

The present disclosure will be further illustrated by the following pharmacological examples. These examples are understood to be exemplary only and are not intended to limit the scope of the invention disclosed herein.

Enzymatic Assay

An IMAP TR-FRET based PDE assay was developed using the PDE4D3 isoform. IMAP technology is based on high-affinity binding of phosphate by immobilized metal (MIII) coordination complexes on nanoparticles. The IMAP "binding reagent" recognizes phosphate groups on AMP or GMP generated from cAMP or cGMP in a PDE reaction. The cyclic nucleotides that carry a phosphodiester bond and not a free phosphate are not recognized by the binding reagent. The time resolved fluorescence resonance energy transfer (TR-FRET) is afforded by a Terbium (Tb)-Donor prebound to the nanoparticles. FRET can occur when fluorescent-labeled AMP or GMP product of a PDE reaction binds comes into close proximity of the Tb-Donor complex. Due to the long lifetime of Tb fluorescence, detection can be run in time-resolved mode to eliminate interference from autofluorescent compounds.

The IMAP TR-FRET PDE4D3 FAM-cAMP assay was performed in 1536-well white plates 15 pg per well GST-tagged PDE4D3 was dispensed in 2.5 μL IMAP assay buffer consisting of 10 mM Tris pH 7.2, 10 mM MgCl$_2$, 1 mM DTT, 0.1% fatty acid free BSA and 0.01% Tween-20. 30 nL of compound was then added from 1 mM stock in DMSO using the Kalypsys 1536 10 nL pintool. Plates were incubated for 5 min at RT before dispensing 1.5 μL of 533 nM FAM-cAMP for a final concentration of 200 nM. Plates were incubated 30 min at RT after a brief centrifugation. The assay was terminated by adding 5 μL IMAP binding reagent Tb complex to each well, prepared according to manufacturer's recommendations. Plates were incubated an additional 90 minutes at RT and read on a Viewlux plate reader. Compounds were solvated at 10 mM in DMSO and tested in 11-point dose-response in the PDE4D3 assay.

Pharmacological Example 1

PDE4 Inhibition

Representative compounds of the invention were evaluated in the PDE4 enzymatic assay. Typically, the compounds of the invention show PDE4 inhibitory properties at a concentration of 0.1 to 10 μM, typically at 5-100%.

As depicted in the following Table, these inhibitory properties were mirrored by pEC$_{50}$ values ranging from less than 5 ($10^{-5}$ M or 10 μM) to greater than 7 ($10^{-7}$ M or 0.1 μM).

| PD4d3 pEC$_{50}$ | Example Numbers |
|---|---|
| >7 | 1, 13, 25, 27, 28, 29, 30, 32, 33, 36, 38, 40, 46, 47, 48, 55, 56, 58, 65, 66, 68, 69, 71, 72, 73, 76, 78, 79, 80, 82, 84, 87, 89, 92, 93, 95, 100, 103, 104, 105, 106, 107, 110, 119, 122, 123, 124, 125, 126, 131, 134, 143, 144, 145, 148, 151, 153, 155, 162, 163, 165, 168, 173, 174, 183, 185, 201, 202, 203, 204, 205, 206, 217, 219, 226, 229, 230, 232, 246, 253, 256, 260, 261, 262, 263, 264, 272, 274, 275, 276 |
| 6-7 | 2, 5, 7, 12, 14, 20, 21, 24, 26, 34, 37, 41, 43, 44, 45, 49, 51, 53, 57, 59, 60, 64, 67, 74, 75, 81, 83, 85, 86, 88, 90, 91, 94, 96, 97, 102, 108, 109, 111, 112, 113, 114, 115, 116, 117, 118, 120, 121, 128, 129, 130, 132, 136, 137, 139, 141, 142, 146, 147, 150, 152, 154, 157, 159, 160, 161, 164, 166, 167, 170, 171, 176, 178, 179, 180, 188, 189, 191, 200, 207, 208, 211, 212, 213, 214, 216, 218, 220, 221, 222, 223, 224, 227, 231, 233, 234, 238, 239, 244, 245, 250, 251, 252, 254, 255, 259, 265, 266, 267, 268, 269, 271, 277, 278 |

-continued

| PD4d3 pEC$_{50}$ | Example Numbers |
|---|---|
| 5-6 | 3, 8, 15, 16, 17, 18, 19, 23, 31, 35, 39, 42, 50, 52, 54, 61, 62, 63, 70, 77, 98, 99, 101, 127, 133, 135, 138, 149, 156, 158, 169, 172, 177, 181, 182, 184, 186, 187, 190, 192, 193, 194, 195, 196, 197, 198, 199, 209, 210, 215, 225, 228, 235, 237, 240, 241, 243, 247, 248, 257, 258, 273, 280 |
| <5 | 4, 6, 9, 10, 11, 22, 140, 175, 236, 242, 249, 270, 279 |

BIOLOGICAL EXAMPLES

The present disclosure will be further illustrated by the following biological examples. These examples are understood to be exemplary only and are not intended to limit the scope of the invention disclosed herein.

Behavioral Assays

Numerous behavioral assays are available to assess the ability of a candidate compound to enhance memory formation, including contextual conditioning (e.g., fear conditioning), temporal conditioning (e.g., trace conditioning), and object recognition. Other non-limiting examples of appropriate assays to assess memory include those that incorporate or relate to multiple training sessions, spaced training sessions, contextual fear training with single or multiple trials, trace fear conditioning with single or multiple trials, contextual memory generally, temporal memory, spatial memory, episodic memory, passive avoidance memory, active avoidance memory, food preference memory, conditioned taste avoidance, and social recognition memory.

The behavioral assays can also be used in accordance with the present invention, as will be understood by those of ordinary skill in the art. These assays can be directed towards the evaluation of, without limitation, hippocampus-, cortex-, and/or amygdala-dependent memory formation or cognitive performance.

Biological Example 1

Effect of PDE4 Inhibitors on Contextual Memory
Rationale

Contextual fear conditioning is a form of associative learning in which animals learn to recognize a training environment (conditioned stimulus, CS) that has been previously paired with an aversive stimulus such as foot shock (unconditioned stimulus, US). When exposed to the same context at a later time, conditioned animals show a variety of conditional fear responses, including freezing behavior. The percent of time during the test that the animal exhibits such freezing provides a quantitative measure of the contextual associative memory (e.g., Fanselow, Behav. Neurosci. 1984, 98, 269-277; Fanselow, Behav. Neurosci. 1984, 98, 79-95; and Phillips and LeDoux, Behav. Neurosci. 1992, 106, 274-285).

Contextual conditioning has been extensively used to investigate the neural substrates mediating fear-motivated learning (e.g., Phillips and LeDoux, Behav. Neurosci. 1992, 106, 274-285; Kim et al., Behav. Neurosci. 1993, 107, 1093-1098; and Bourtchouladze et al., Learn. Mem. 1998, 5, 365-374). Studies in mice and rats provided evidence for functional interaction between hippocampal and nonhippocampal systems during contextual conditioning training (e.g., Maren et al., Behav. Brain Res. 1997, 88, 261-274; Maren et al., Neurobiol. Learn. Mem. 1997, 67, 142-149; and Frankland et al., Behav. Neurosci. 1998, 112, 863-874). Specifically, post-training lesions of the hippocampus (but not pre-training lesions) greatly reduced contextual fear, implying that: 1) the hippocampus is essential for contextual memory but not for contextual learning per se and 2) in the absence of the hippocampus during training, non-hippocampal systems can support contextual conditioning.

Contextual conditioning has been extensively used to study the impact of various mutations on hippocampus-dependent learning, as well as strain and genetic background differences in mice (e.g., Bourtchouladze et al., Cell 1994, 79, 59-68; Bourtchouladze et al., Learn Mem. 1998, 5, 365-374; Kogan et al., Current Biology 1997, 7, 1-11; Silva et al., Current Biology 1996, 6, 1509-1518; Abel et al., Cell 1997, 88, 615-626; Giese et al., Science 1998, 279, 870-873; Logue et al., Neuroscience 1997, 80, 1075-1086; Chen et al., Behav. Neurosci. 1996, 110, 1177-1180; and Nguyen et al., Learn Mem. 2000, 7, 170-179).

Because robust learning can be triggered with a few minutes training session, contextual conditioning has been especially useful to study the biology of temporally distinct processes of short- and long-term memory (e.g., Kim et al., Behav. Neurosci. 1993, 107, 1093-1098; Bourtchouladze et al., Cell 1994, 79, 59-68; Abel et al., Cell 1997, 88, 615-626; Logue et al., Behav. Neurosci. 1997, 111, 104-113; Bourtchouladze et al., Learn. Mem. 1998, 5, 365-374; and Nguyen et al., Learn. Mem. 2000, 7, 170-179). As such, contextual conditioning provides an excellent model to evaluate the effects of novel drug compounds on hippocampal-dependent memory formation.

Procedures

Previous investigations have established that training with 1× or 2×CS-US pairings induces sub-maximal (weak) memory in wild-type mice (e.g., U.S.2009/0053140; Tully et al., Nat. Rev. Drug Discov. 2003, 2, 267-77; and Bourtchouladze et al. Learn. Mem. 1998, 5, 365-374). Accordingly, contextual conditioning in this study was performed as described by Bourtchouladze et al., Cell 1994, 79, 59-68.

Young-adult (10-12 weeks old) C57BL/6 male mice and Sprague Dawley male rats were used. Mice and rats were group-housed in standard laboratory and maintained on a 12:12 light-dark cycle. The experiments were always conducted during the light phase of the cycle. With the exception of testing times, the mice had ad libidum access to food and water. To assess contextual memory, a modified contextual fear conditioning task originally developed for evaluation of memory in CREB knock-out mice was used (Bourtchouladze et al., 1994). Training sessions are comprised of a baseline period in the conditioning chamber (Med Associates, Inc.) followed by presentation of unconditioned stimuli (1-5 foot-shocks each at 0.2-1.0 mA for 2-sec) spaced at 60-sec intervals. Thirty seconds following the last shock, the animal is returned to the home cage. One to 7 days later, the animals are returned to the chamber and freezing behavior is scored. Freezing (complete immobility except respiration) is scored by Video Freeze software (Med Associates, Inc.) over an 8 minute test period. Treatment with cognition enhancers are expected to significantly increase freezing when compared with controls.

All experiments were designed and performed in a counterbalanced fashion. In each experiment, the experimenter was unaware (blind) to the treatment of the subjects during training and testing. Training and test sessions were recorded as digital video files. Data were analyzed by one-way ANOVA with appropriate post-hoc tests using GraphPad Prism software package.

Results

Exemplary compounds were found to enhance contextual memory in the fear conditioning assay. Significant enhancing effects are seen at several concentrations, including 0.01 mg/kg, 0.03 mg/kg, and 1.0 mg/kg.

Biological Example 2

Effect of PDE4 Inhibitors on Novel Object Recognition Rationale

Novel Object Recognition (NOR) is an assay of recognition learning and memory retrieval, and it takes advantage of the spontaneous preference of rodents to investigate a novel object compared with a familiar one. It is an ethologically relevant task, which in contrast to fear conditioning, does not result from negative reinforcement (foot shock)(e.g., Ennaceur and Delacour, Behav. Brain Res. 1988, 31, 47-59).

The NOR test has been employed extensively to assess the potential cognitive-enhancing properties of novel compounds derived from high-throughput screening. Object recognition the task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one (Bourtchouladze et. al., Proc. Natl. Acad. Sci. USA 2003, 100, 10518-10522).

Neuroimaging, pharmacological, and lesion studies have demonstrated that the hippocampus and adjacent perirhinal cortex are critical for object recognition memory in rodents, monkeys, and humans (e.g., Mitchell, Behav. Brain Res. 1998, 97, 107-113; Teng et al., J. Neurosci. 2000, 20, 3853-3863; Mumby, Brain Res. 2001, 127, 159-181; Eichenbaum et al., Annu. Rev. Neurosci. 2007, 30, 127-152; Squire et al., Nat. Rev. Neurosci. 2007, 8, 872-883; and Vann and Alabasser, Curr. Opin. Neurobiol 2011, 21, 440-445). Hence, object recognition provides an excellent behavioral model to evaluate drug-compound effects on cognitive tasks associated with function of the hippocampus and cortex.

Procedures

Object recognition was tested in young adult mice and rats using the following protocol. Animals are briefly handled by the experimenter 2-5 days prior to training. Each compound was administered between 15 minutes and 24-hours prior to, or following, training. Habituation sessions (duration 1-20 min, over 1-3 days) were conducted to familiarize the animal to the arena. During training trials (duration of 1-20 min) the animals were allowed to explore two identical objects. A test trial (duration of 1-20 min) was then performed 1-96 hrs later.

For novel object recognition, one object is replaced with one that is novel. All combinations and locations of objects are used in a balanced manner to reduce potential biases attributable to preference for particular locations or objects. Training and test trials are recorded and scored by video-tracking software (e.g. Noldus Ethovision). An animal is scored as exploring an object when its head was oriented toward the object within a distance of 1 cm (rat)/2 cm (mouse) or when the nose is touching the object. Turning around, climbing, or sitting on an object was not considered as exploration. If the animal generates a long-term memory for the familiar object, it will spend significantly more time exploring the novel object compared to the familiar object during the retention test (Cognitive enhancers are therefore expected to facilitate this discrimination between the familiar and novel object).

A discrimination index was calculated as previously described (Bourtchouladze et al., Proc. Natl. Acad. Sci. USA 2003, 100, 10518-10522). In each experiment, the experimenter was unaware (blind) to the treatment of the subjects during training and testing. Data were analyzed by one-way ANOVA with appropriate post-hoc tests using GraphPad Prism software package.

Results

Exemplary compounds of Formula (I) are found to significantly enhance 24 hour memory. Significant effects were seen at several concentrations, including 1.0 mg/kg and 3 mg/kg.

The specification, including the examples, is intended to be exemplary only, and it will be apparent to those skilled in the art that various modifications and variations can be made in the present invention without departing from the scope or spirit of the invention as defined by the appended claims.

Furthermore, while certain details in the present disclosure are provided to convey a thorough understanding of the invention as defined by the appended claims, it will be apparent to those skilled in the art that certain embodiments may be practiced without these details. Moreover, in certain instances, well-known methods, procedures, or other specific details have not been described to avoid unnecessarily obscuring aspects of the invention defined by the appended claims.

What is claimed is:

1. A compound selected from the groups consisting of:

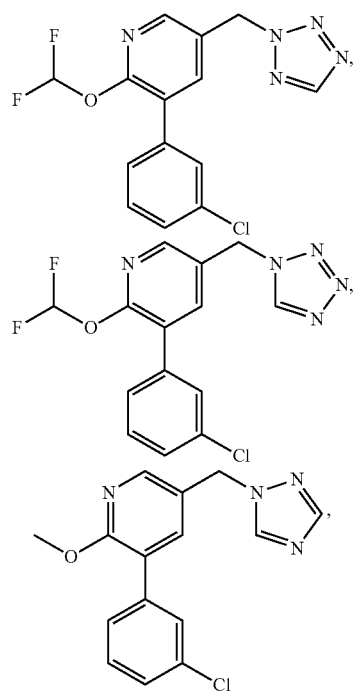

201
-continued
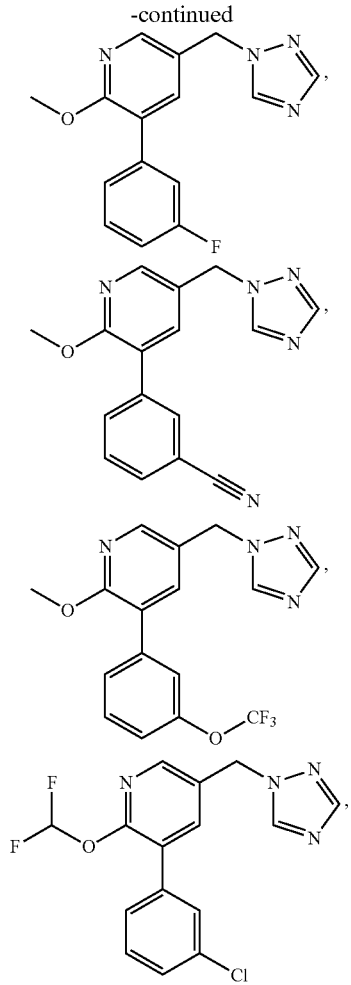
202
-continued
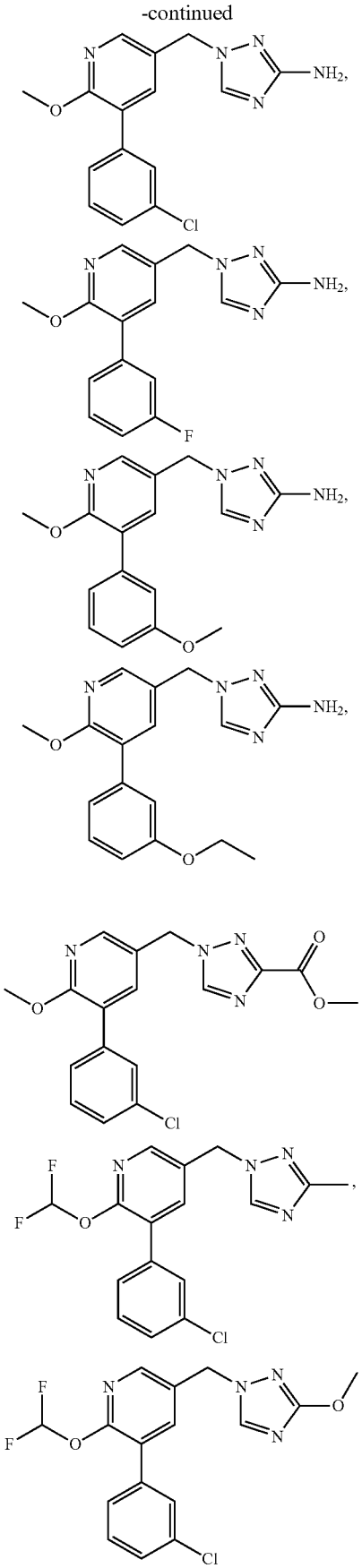

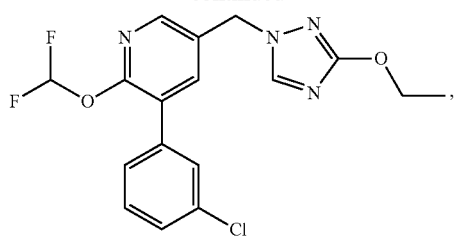
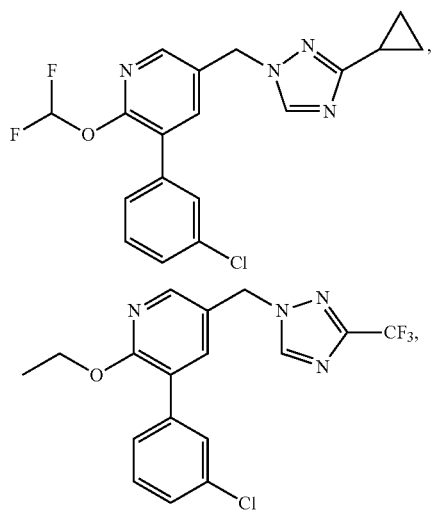
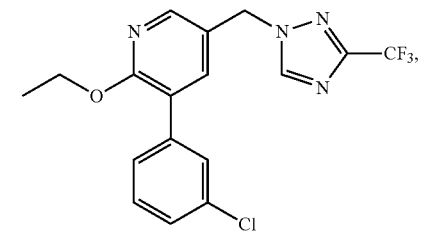
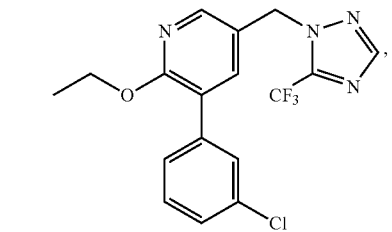
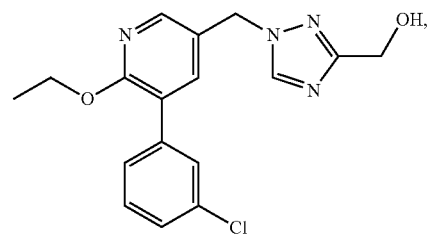
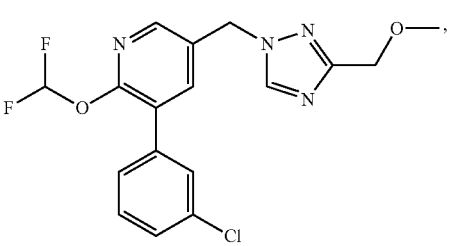
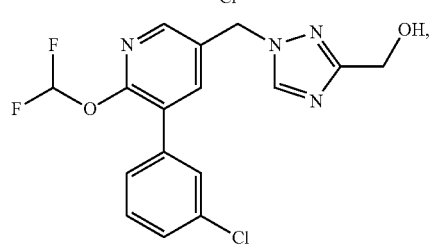
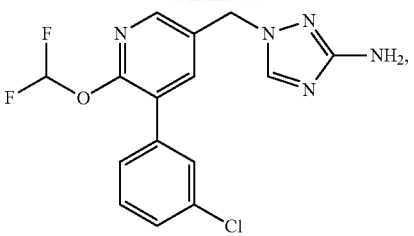
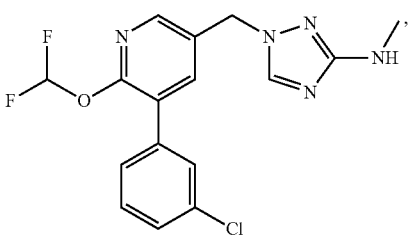
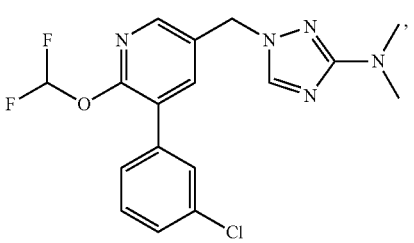
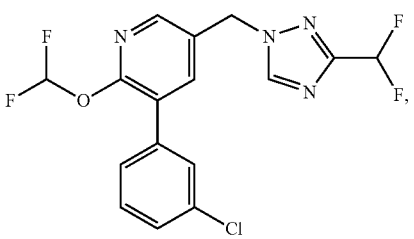
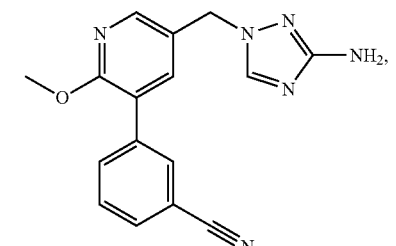
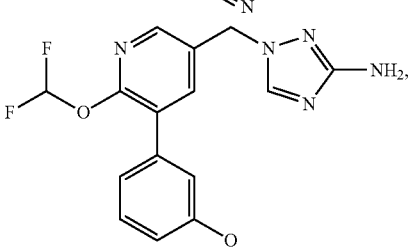
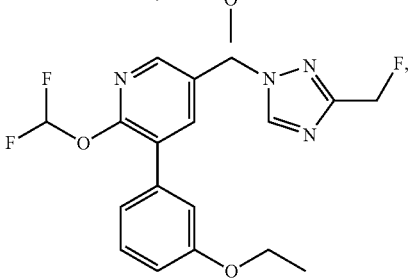

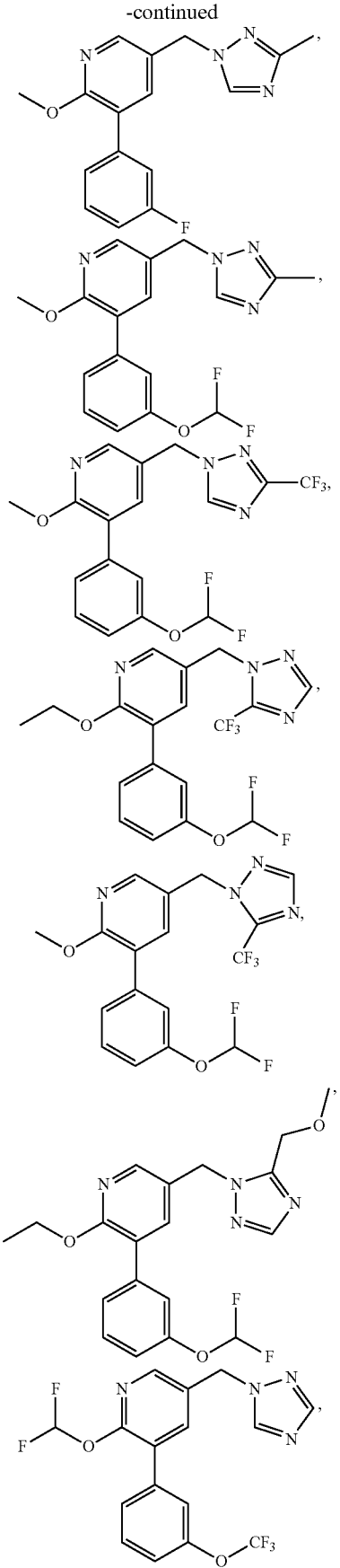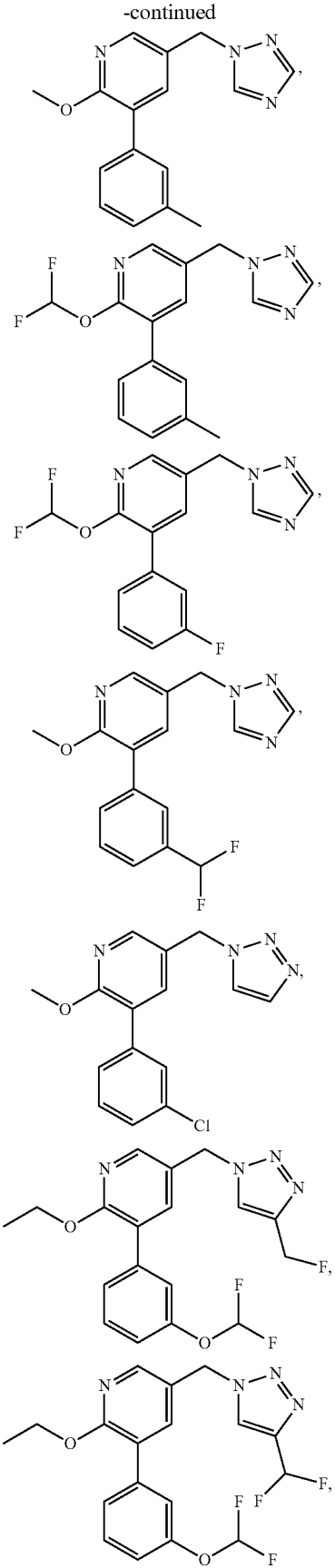

207
-continued
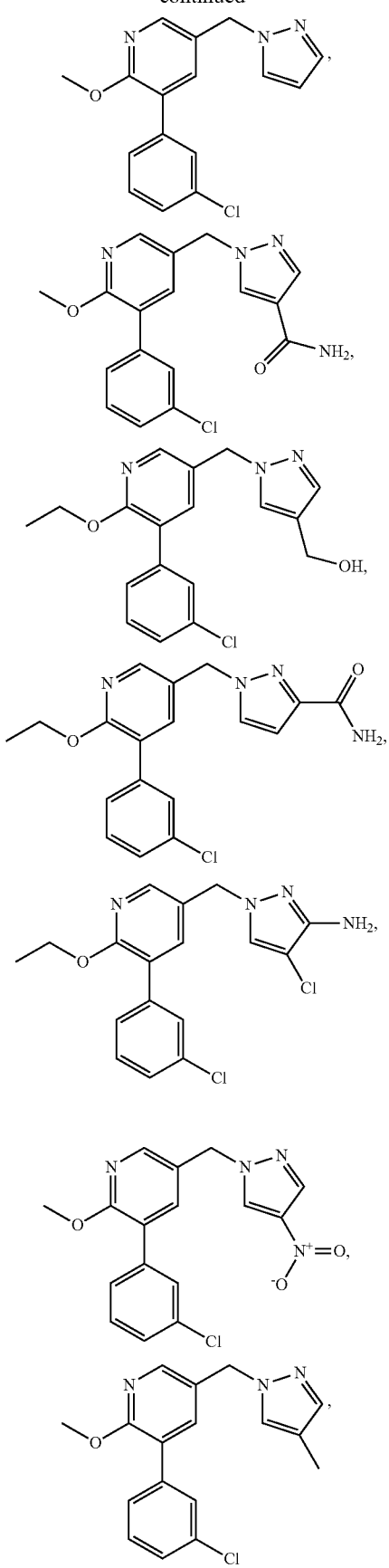
208
-continued
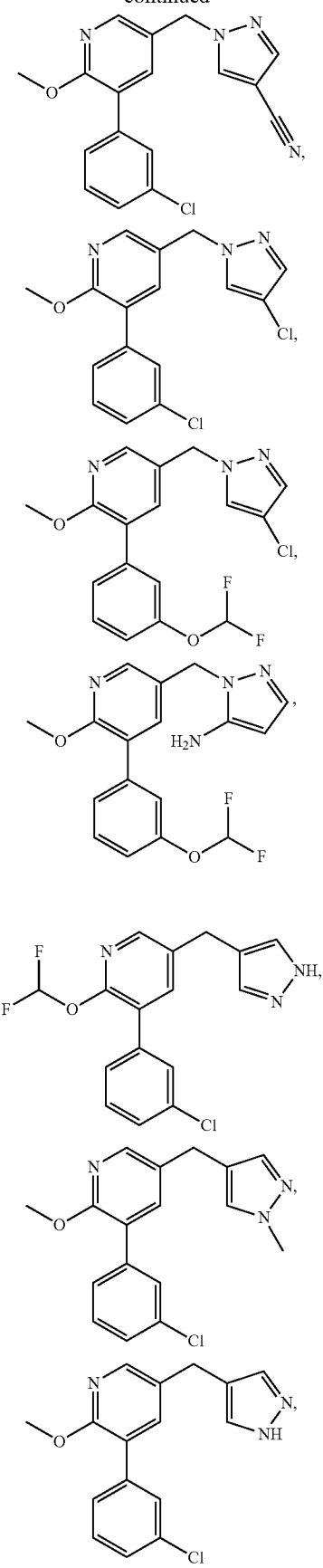

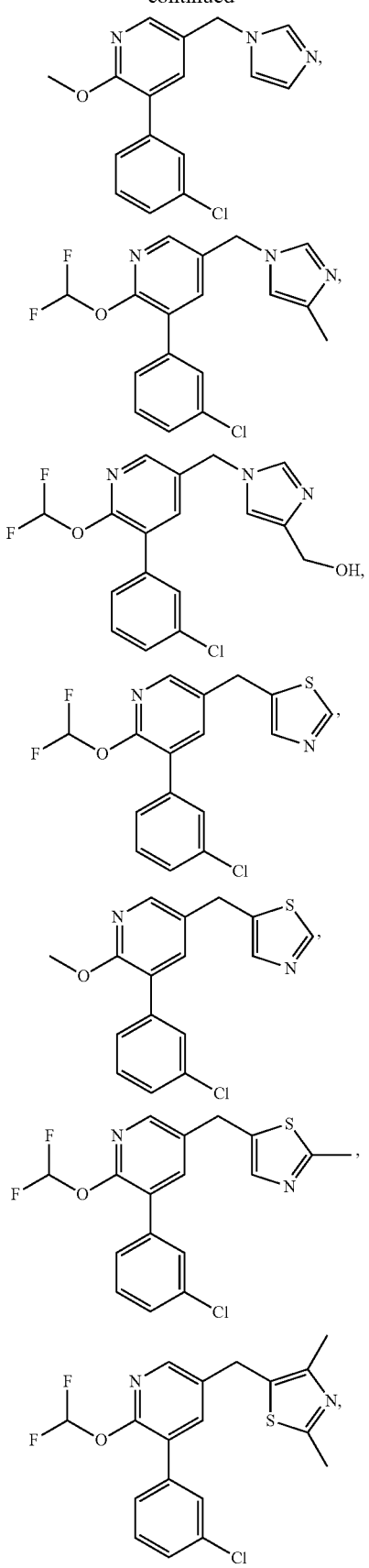
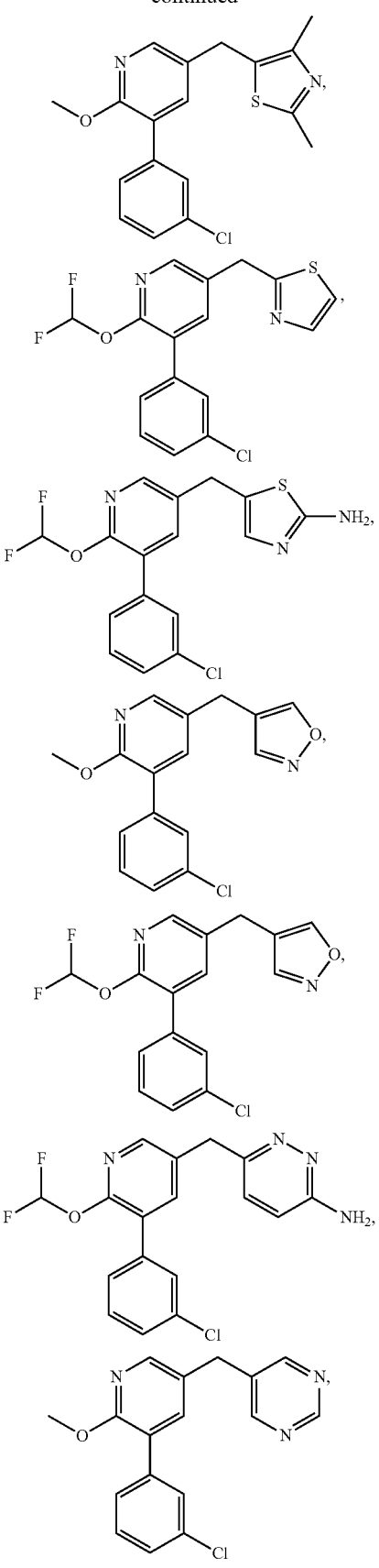

211
-continued
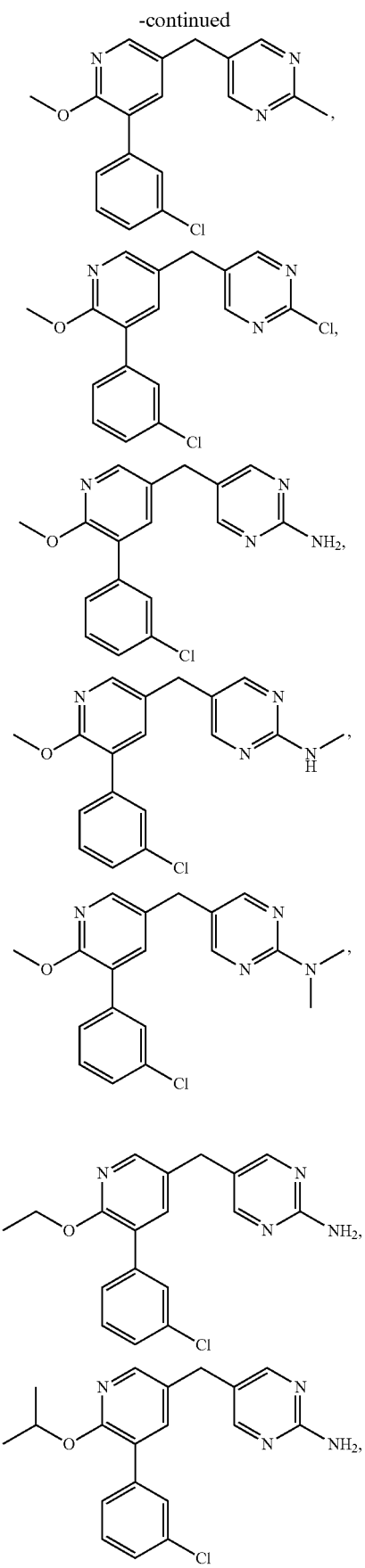
212
-continued
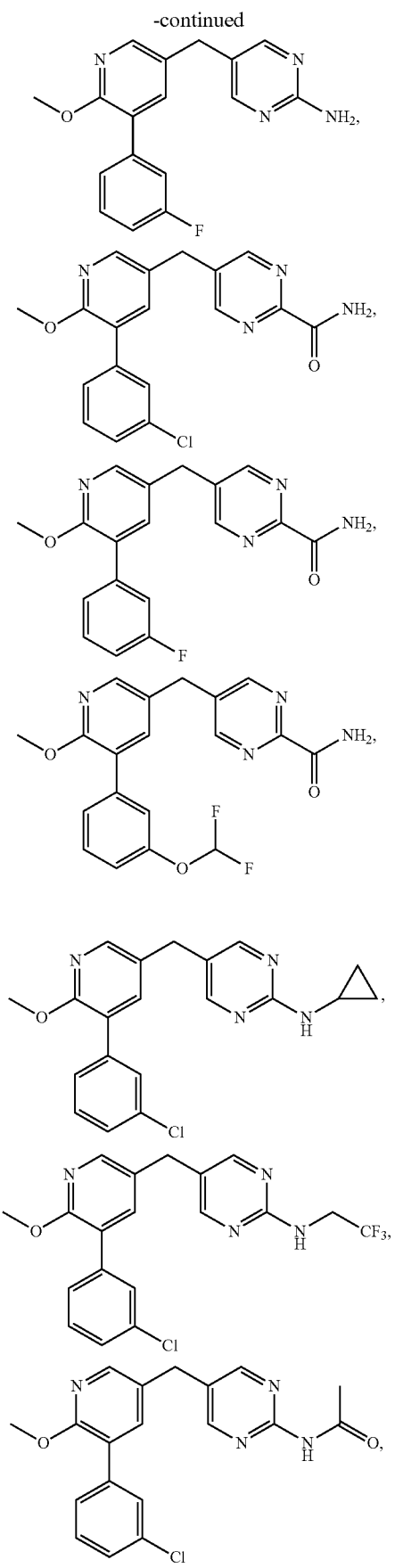

213
-continued
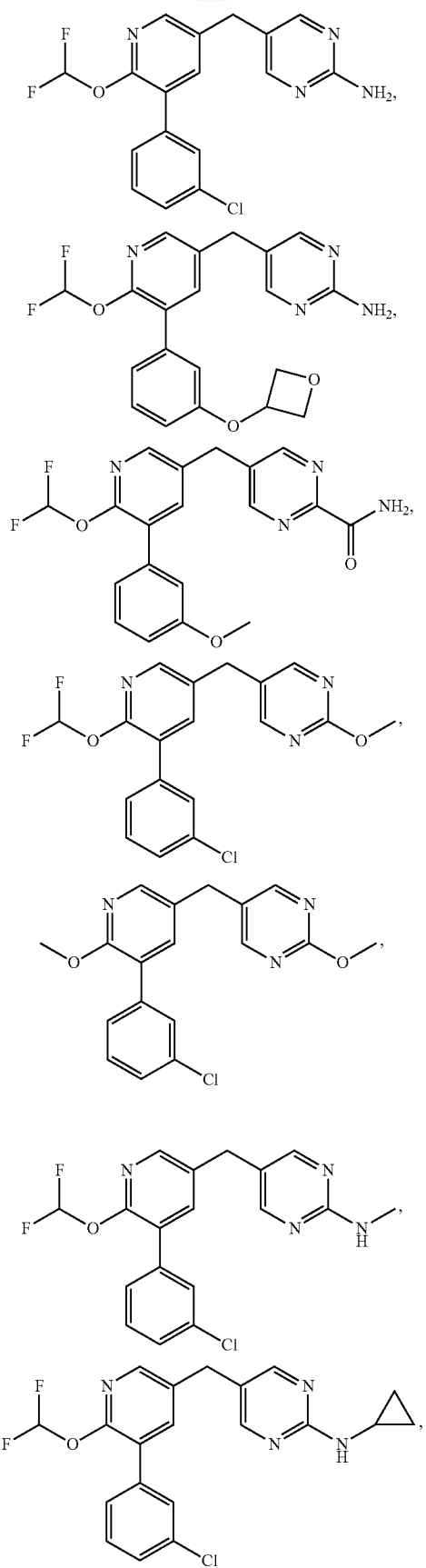
214
-continued
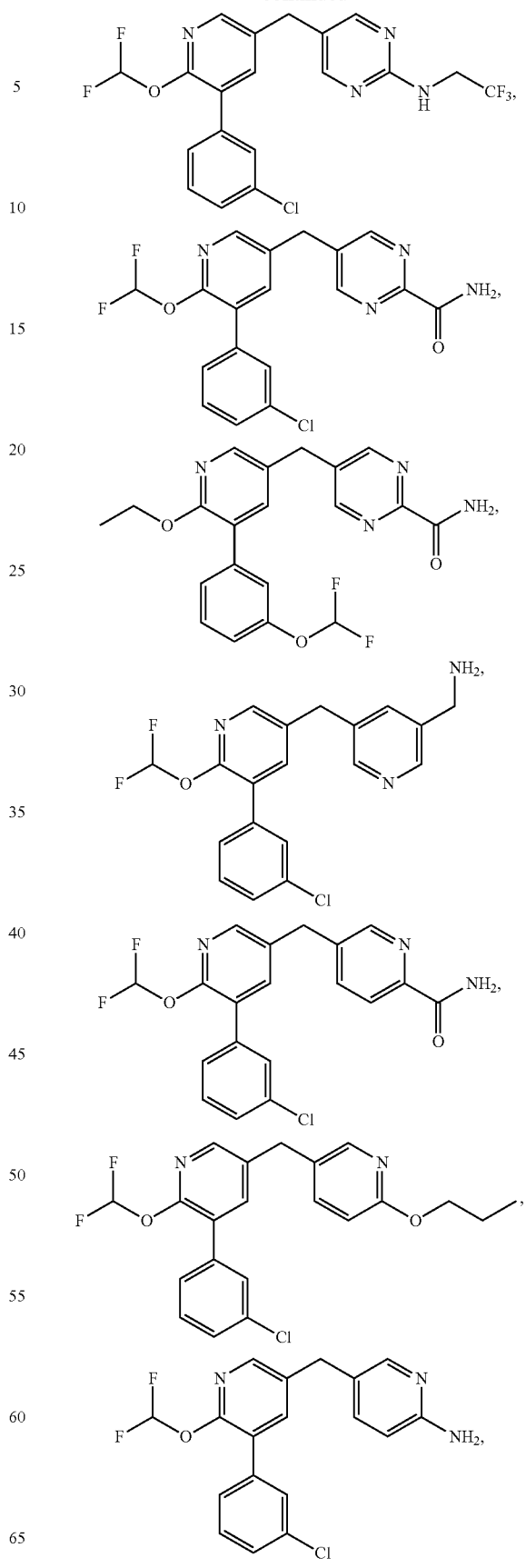

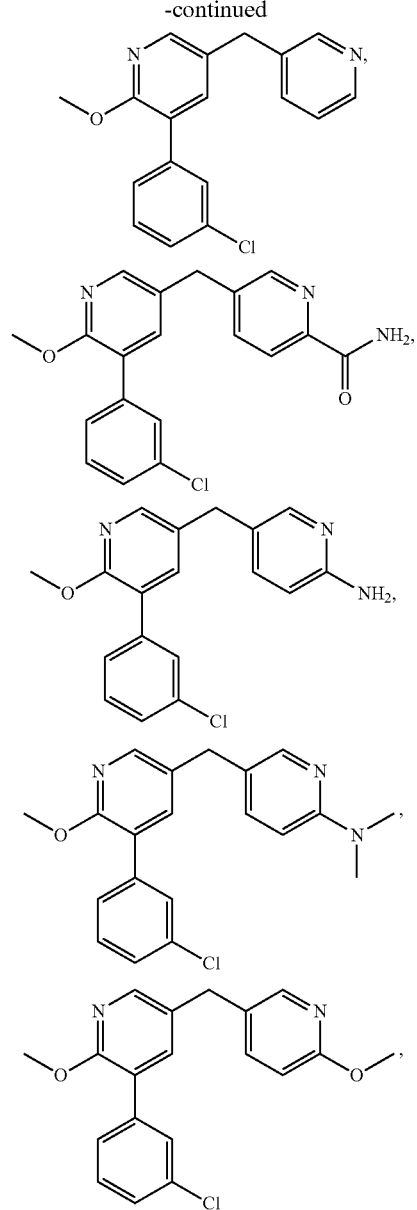
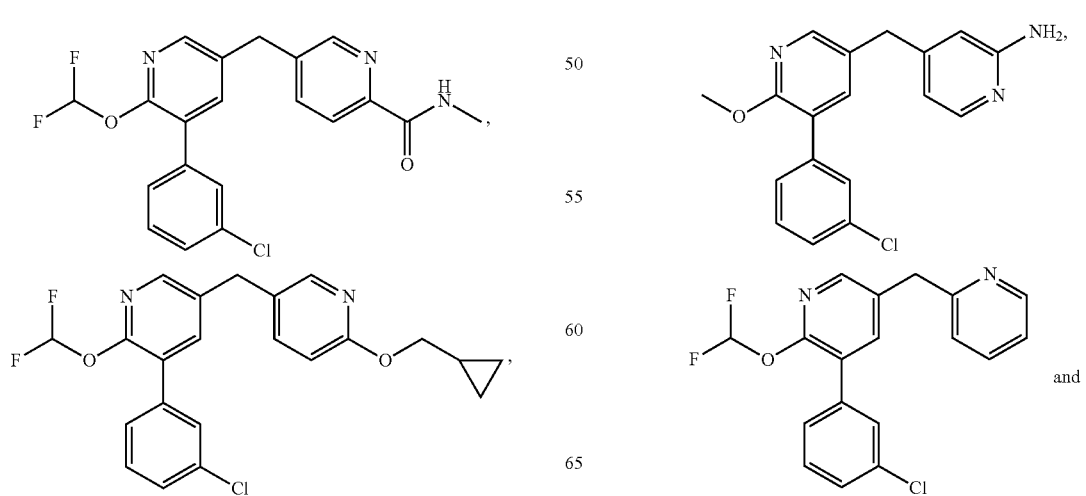

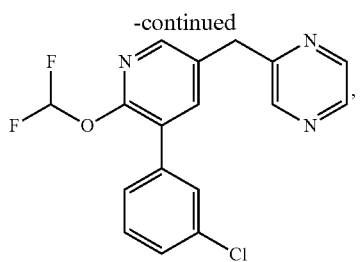
and pharmaceutically acceptable salts thereof.
* * * * *